US008685737B2

(12) United States Patent
Serber et al.

(10) Patent No.: US 8,685,737 B2
(45) Date of Patent: Apr. 1, 2014

(54) METHODS FOR GENOMIC MODIFICATION

(75) Inventors: Zach Serber, Emeryville, CA (US); Andrew Horwitz, Emeryville, CA (US)

(73) Assignee: Amyris, Inc., Emeryville, CA (US)

( * ) Notice: Subject to any disclaimer, the term of this patent is extended or adjusted under 35 U.S.C. 154(b) by 0 days.

(21) Appl. No.: 13/459,034

(22) Filed: Apr. 27, 2012

(65) Prior Publication Data

US 2012/0277120 A1 Nov. 1, 2012

Related U.S. Application Data

(60) Provisional application No. 61/479,821, filed on Apr. 27, 2011, provisional application No. 61/500,741, filed on Jun. 24, 2011, provisional application No. 61/539,389, filed on Sep. 26, 2011.

(51) Int. Cl.
*C12N 15/90* (2006.01)
*C40B 50/00* (2006.01)

(52) U.S. Cl.
USPC .......... 435/471; 506/23

(58) Field of Classification Search
None
See application file for complete search history.

(56) References Cited

U.S. PATENT DOCUMENTS

| | | | | |
|---|---|---|---|---|
| 5,888,732 | A | 3/1999 | Hartley et al. | |
| 6,140,466 | A | 10/2000 | Barbas, III et al. | |
| 6,453,242 | B1 | 9/2002 | Eisenberg et al. | |
| 6,503,712 | B1 | 1/2003 | Thukral | |
| 6,511,808 | B2 | 1/2003 | Wolffe et al. | |
| 7,314,712 | B2 | 1/2008 | Storici et al. | |
| 7,919,605 | B1 | 4/2011 | Benjamin | |
| 2003/0059767 | A1 | 3/2003 | Barbas, III et al. | |
| 2003/0108880 | A1 | 6/2003 | Rebar et al. | |
| 2008/0274523 | A1 * | 11/2008 | Renninger et al. | 435/157 |
| 2009/0205083 | A1 * | 8/2009 | Gupta et al. | 800/298 |
| 2011/0145940 | A1 | 6/2011 | Voytas et al. | |

FOREIGN PATENT DOCUMENTS

| | | | |
|---|---|---|---|
| EP | 2 180 058 | | 4/2010 |
| WO | WO 99/25821 | | 5/1999 |
| WO | WO 99/25840 | | 5/1999 |
| WO | WO 99/25841 | | 5/1999 |
| WO | WO 99/25851 | | 5/1999 |
| WO | WO 00/42219 | A1 | 7/2000 |
| WO | WO 01/07572 | A2 | 2/2001 |
| WO | WO 01/11058 | A1 | 2/2001 |
| WO | WO 01/23545 | A1 | 4/2001 |
| WO | WO 02/42459 | A2 | 5/2002 |
| WO | WO 02/099084 | A3 | 12/2002 |
| WO | WO 03/008045 | A2 | 1/2003 |

(Continued)

OTHER PUBLICATIONS

Basso et al. (2008) "Yeast selection for fuel ethanol production in Brazil" FEMS Yeast Res 8:1151-1163.*

(Continued)

*Primary Examiner* — Tracy Vivlemore
*Assistant Examiner* — Karen S Weiler
(74) *Attorney, Agent, or Firm* — Squire Sanders (US) LLP

(57) ABSTRACT

Provided herein are methods of integrating one or more exogenous nucleic acids into one or more selected target sites of a host cell genome. In certain embodiments, the methods comprise contacting the host cell genome with one or more integration polynucleotides comprising an exogenous nucleic acid to be integrated into a genomic target site, and a nuclease capable of causing a double-strand break near or within the genomic target site.

78 Claims, 8 Drawing Sheets

(56) References Cited

FOREIGN PATENT DOCUMENTS

Figure 1:
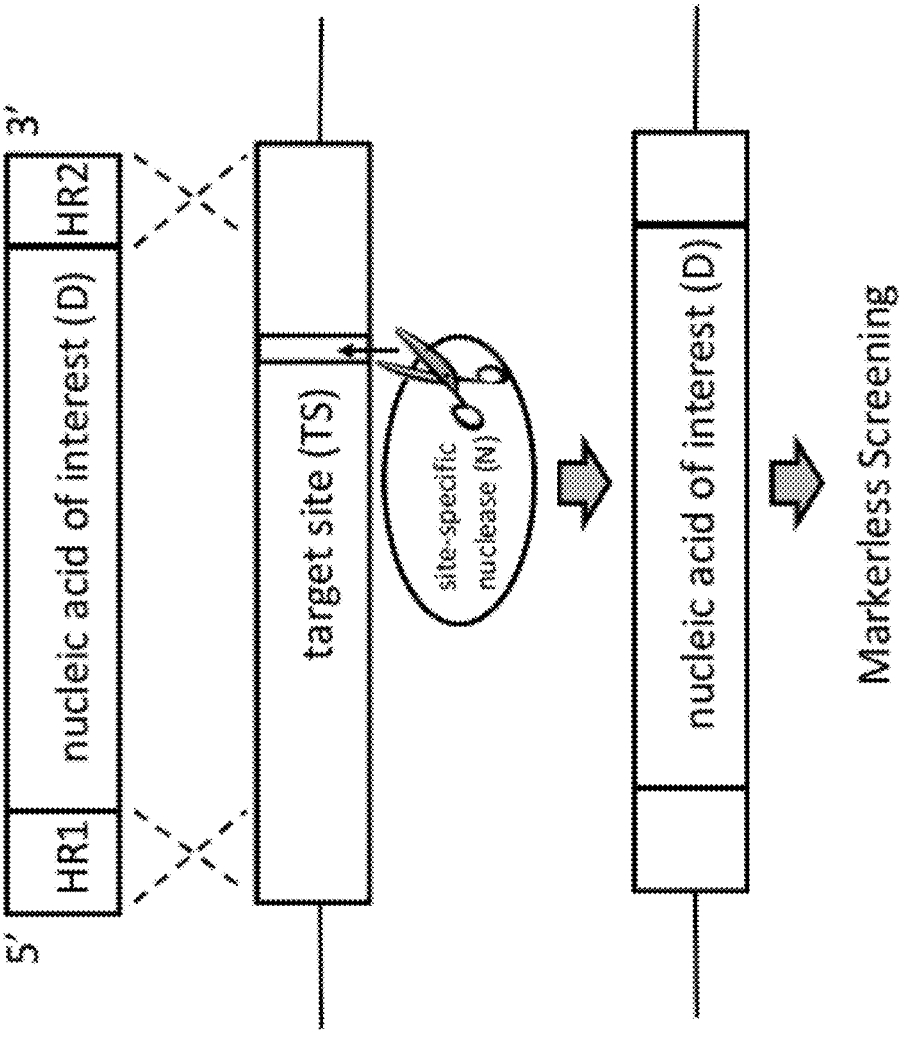

| | | | |
|---|---|---|---|
| WO | WO 03/062455 | A2 | 7/2003 |
| WO | WO 03/078619 | A1 | 9/2003 |
| WO | WO 03/080809 | A2 | 10/2003 |
| WO | WO 2004/031346 | A2 | 4/2004 |
| WO | WO 2004/067736 | A2 | 8/2004 |
| WO | WO 2004/067753 | | 8/2004 |
| WO | WO 2004/067753 | A2 | 8/2004 |
| WO | WO 2005/014791 | A2 | 2/2005 |
| WO | WO 2005/084190 | A2 | 9/2005 |
| WO | WO 2005/105989 | A1 | 11/2005 |
| WO | WO 2006/097784 | A1 | 9/2006 |
| WO | WO 2006/097853 | A1 | 9/2006 |
| WO | WO 2006/097854 | A1 | 9/2006 |
| WO | WO 2007/034262 | A1 | 3/2007 |
| WO | WO 2007/049095 | A1 | 5/2007 |
| WO | WO 2007/049156 | A2 | 5/2007 |
| WO | WO 2007/057781 | A2 | 5/2007 |
| WO | WO 2007/060495 | A2 | 5/2007 |
| WO | WO 2008/021207 | A2 | 2/2008 |
| WO | WO 2008/152524 | A2 | 12/2008 |
| WO | WO 2009/001159 | A1 | 12/2008 |
| WO | WO 2009/042186 | A2 | 4/2009 |
| WO | WO 2009/054985 | A1 | 4/2009 |
| WO | WO 2009/095742 | A1 | 8/2009 |
| WO | WO 2009/095793 | A1 | 8/2009 |
| WO | WO 2010/001189 | A1 | 1/2010 |
| WO | WO 2010/015899 | A2 | 2/2010 |
| WO | WO 2010/046786 | A1 | 4/2010 |
| WO | W O2010/065123 | A1 | 6/2010 |
| WO | W O2010/079430 | A1 | 7/2010 |

OTHER PUBLICATIONS

Abremski & Hoess, Evidence for a second conserved arginine residue in the integrase family of recombination proteins. *Protein Eng.* (1992) 5:87-91.

Albert et al., Site-specific integration of DNA into wild-type and mutant *lox* sites placed in the plant genome. *Plant J.*( (1995) 7:649-659.

Arnold et al., Mutants of Tn3 resolvase which do not require accessory binding sites for recombination activity. *EMBO J.* (1999) 18:1407-1414.

Bayer et al., Synthesis of methyl halides from biomass using engineered microbes. *J Am Chem Soc.* (2009) 131:6508-6515.

Beerli & Barbas, Engineering polydactyl zinc-finger transcription factors. *Nat Biotechnol.* (2002) 20:135-41.

Boch et al., Breaking the code of DNA binding specificity of TAL-type III effectors. *Science.* (2009) 326:1509-1512.

Buchholz & Stewart, Alteration of Cre recombinase site specificity by substrate-linked protein evolution. *Nat Biotechnol.* (2001) 19:1047-1052.

Capecchi, Altering the genome by homologous recombination. *Science.* (1989) 244:1288-1292.

Carroll et al., Design, construction and in vitro testing of zinc finger nucleases. *Nature Protocols.* (2006) 1:1329-1341.

Chames et al., In vivo selection of engineered homing endonucleases using double-strand break induced homologous recombination. *Nucleic Acids Res.* (2005) 33:e178.

Chen & Zhao, A highly sensitive selection method for directed evolution of homing endonucleases. *Nucleic Acids Res.* (2005) 33:el 54.

Chevalier et al., Design, activity, and structure of a highly specific artificial endonuclease. *Mol. Cell.* (2002) 10:895-905.

Christ & Dröge, Alterations in the directionality of λ site-specific recombination catalyzed by mutant integrases in vivo. *J Mol Biol.* (1998) 288:825-836.

Chu et al, Characterization of the intron in the phage T4 thymidylate synthase gene and evidence for its self-excision from the primary transcript, *Cell.* (1986) 45:157-166,.

Colleaux et al., The apocytochrome *b* gene of *Chlamydomonas smithii* contains a mobile intron related to both *Saccharomyces* and *Neurospora* introns. *Mol. Gen. Genet.* (1990) 223:288-296.

De Jonckheere, Evidence for the ancestral origin of group I introns in the SSUrDNA of *Naegleria* spp. *J. Eukaryot. Microbiol.* (1994) 41:457-463.

Dorgai et al., Identifying determinants of recombination specificity: construction and characterization of mutant bacteriophage integrases. (1995) *J Mol Biol.* 252:178-188.

Dorgai et al., Recognition of core binding sites by bacteriophage integrases. (1998) *J Mol Biol.* 277:1059-1070.

Dreier et al., Development of zinc finger domains for recognition of the 5'-ANN-3' family of DNA sequences and their use in the construction of artificial transcription factors. *J Biol Chem.* (2001) 276:29466-29478.

Dreier et al., Development of zinc finger domains for recognition of the 5'-CNN-3' family DNA sequences and their use in the construction of artificial transcription factors. *J Biol Chem* (2005) 280:35588-35597.

Dreier et al., Insights into the molecular recognition of the 5'-GNN-3' family of DNA sequences by zinc finger domains. *J Mol Biol* (2000) 303:489-502.

Durai et al., Zinc finger nucleases: custom-designed molecular scissors for genome engineering of plant and mammalian cells. *Nucleic Acids Res.* (2005) 33:5978-5990.

Eddy & Gold, the phage T4 *nrdB* intron: a deletion mutant of a version found in the wild. *Genes Dev.* (1991) 5: 1032-1041.

Elde et al., I-*Nja*I, a nuclear intron-encoded homing endonuclease from *Naegleria,* generates a pentanucleotide 3' cleavage-overhang within a 19 base-pair partially symmetric DNA recognition site. *Eur. J. Biochem.* (1999) 259:281-288.

Epinat et al., A novel engineered meganuclease induces homologous recombination in yeast and mammalian cells. *Nucleic Acids Res.* (2003) 31:2952-2962.

Esposito & Scocca, The integrase family of tyrosine recombinases: evolution of a conserved active site domain. *Nucleic Acids Res.* (1997) 25:3605-3614.

Foury et al., The complete sequence of the mitochondrial genome of *Saccharomyces cerevisiae. FEBS Lett.* (1998) 440:325-331.

Fujisawa et al., Sequence of the T4 recombination gene, *uvsX,* and its comparison with that of the *recA* gene of *Escherichia coli. Nucleic Acids Res.* (1985)13:7473-7481.

Gimble et al., Assessing the plasticity of DNA target site recognition of the PI-*Sce*I homing endonuclease using a bacterial two-hybrid selection system. *Mol Biol.* (2003) 334:993-1008.

Gloor et al., Targeted gene replacement in *Drosophila* via P element-induced gap repair. *Science.* (1991) 253:1110-1117.

Goodrich-Blair et al., A self-splicing group I intron in the DNA polymerase gene of *Bacillus subtilis* bacteriophage SPO1. *Cell.* (1990) 63:417-424.

Goodrich-Blair & Shub, Beyond homing: competition between intron endonucleases confers a selective advantage on flanking genetic markers. *Cell.* (1996) 84:211-221.

Griggs & Johnston, Regulated expression of the *GAL4* activator gene in yeast provides a sensitive genetic switch for glucose repression. *Proc. Natl. Acad. Sci.* (1991) 88:8597-8601.

Gruen, et al., An in vivo selection system for homing endonuclease activity. *Nucleic Acids Res.* (2002) 30:e29.

Gu et al., *R* gene expression induced by a type-III effector triggers disease resistance in rice. *Nature.* (2005) 435:1122-1125.

Guan et al., Heritable endogenous gene regulation in plants with designed polydactyl zinc finger transcription factors. *Proc Nati Acad Sci USA*, (2002) 99:13296-13301.

Guhan & Muniyappa, Structural and functional characteristics of homing endonucleases. *Crit Rev Biochem Mol Biol.* (2003) 38:199-248.

Hasty et al., The length of homology required for gene targeting in embryonic stem cells, *Mol Cell Biol.* (1991) 11:5586-5591.

Hirata et al., Molecular structure of a gene, *VMA1*, encoding the catalytic subunit of H(+)-translocating adenosine triphosphatase from vacuolar membranes of *Saccharomyces cerevisiae. J. Biol. Chem.* (1990) 265:6726-6733.

Hoess et al., The role of the *loxP* spacer region in P1 site-specific recombination. *Nucleic Acids Res.* (1986) 14:2287-2300.

Huang et al., A bacterial model system for chromosomal targeting. *Nucleic Acids Res.* (1991) 19:443-448.

(56) References Cited

OTHER PUBLICATIONS

Jamieson et al., Drug discovery with engineered zinc-finger proteins. *Nature Rev Drug Discov*. (2003) 2:361-368.
Jasin, Genetic manipulation of genomes with rare-cutting endonucleases. *Trends Genet.* (1996) 12(6):224-228.
Johansen & Vogt, An intron in the nuclear ribosomal DNA of Didymium iridis codes for a group I ribozyme and a novel ribozyme that cooperate in self-splicing, *Cell*. (1994) 76:725-734.
Johansen et al., A family of nuclear homing endonucleases. *Nucleic Acids Res.* (1993) 21:4405.
Jurica & Stoddard, Homing endonucleases: structure, function and evolution. *Cell Mol Life Sci.* (1999) 55:1304-1326.
Kaliman et al., The nucleotide sequence of the region of bacteriophage T4 inh(lip)-hoc genes. *Nucleic Acids. Res.* (1990) 18:4277.
Kay et al., A bacterial effector acts as a plant transcription factor and induces a cell size regulator. *Science.* (2007) 318:648-651.
Kim et al. Hybrid restriction enzymes: zinc finger fusions to *Fok* I cleavage domain. *Proc. Natl. Acad. Sci. USA*. (1996) 93:1156-1160.
Klippel et al., Isolation and characterization of unusual *gin* mutants. *EMBO J.* (1988) 7:3983-3989.
Kodumal et al., Total synthesis of long DNA sequences: synthesis of a contiguous 32-kb polyketide synthase gene cluster. *Proc Natl Acad Sci USA*. (2004) 101:15573-15578.
Kuhlman & Cox, Site-specific chromosomal integration of large synthetic constructs. *Nucleic Acids Res.* (2010) 38:e92.
Lange-Gustafson & Nash, Purification and properties of Int-h, a variant protein involved in site-specific recombination of bacteriophage λ. *J Biol Chem*. (1984) 259:12724-12732.
Lee & Saito, Role of nucleotide sequences of *loxP* spacer region in Cre-mediated recombination. *Gene*. (1998) 216:55-65.
Liu et al., Validated zinc finger protein designs for all 16 GNN DNA triplet targets. *J Biol Chem*. (2002) 277:3850-3856.
Lorbach et al., Site-specific recombination in human cells catalyzed by phage λ integrase mutants. *J Mol Biol.* (2000) 296:1175-1181.
Lucas et al., Rapid evolution of the DNA-binding site in LAGLIDADG homing endonucleases. *Nucleic Acids Res*. (2001) 29:960-969.
Ma et al., Complete reconstitution of a highly reducing iterative polyketide synthase. *Science.* (2009) 326:589-592.
Malphettes et al., Highly efficient deletion of *FUT8* in CHO cell lines using zinc-finger nucleases yields cells that produce completely nonfucosylated antibodies. *Biotechnol Bioeng*. (2010) 106(5):774-783.
Martin et al., Engineering a mevalonate pathway in *Escherichia coli* for production of terpenoids. *Nat Biotechnol.* (2003) 21:796-802.
Miller et al., *int*-h: an *int* mutation of phage λ that enhances ste-specfc recombinaton. *Cell*. (1980) 20:721-729.
Moran et al., Intron 5α of the *COXI* gene of yeast mitochondrial DNA is a mobile group I intron. *Nucleic Acids Res*. (1992) 20:4069-4076.
Moscou & Bogdanove, A simple cipher governs DNA recognition by TAL effectors. Science. (2009) 326:1501.
Moure, et al., Crystal structure of the intein homing endonuclease PI-*Sce*I bound to its recognition sequence. *Nat Struct Biol.* (2002) 9:764.
Muscarella et al., Characterization of I-*Ppo*, an intron-encoded endonuclease that mediates homing of a group I intron in the ribosomal DNA of *Physarum polycephalum*. *Mol. Cell. Biol.* (1990) 10:3386-3396.
Ordiz et al., Regulation of transgene expression in plants with polydactyl zinc finger transcription factors. *Proc Natl Aced Sci USA*. (2002) 99:13290-13295.
Pabo et al., Design and selection of novel $Cys_2His_2$ zinc finger proteins. *Ann Rev Biochem.* (2001) 70:313-340.
Porteus & Carroll, Gene targeting using zinc finger nucleases. *Nat Biotechnol.* (2005) 23:967-973.
Reyon et al., ZFNGenome: a comprehensive resource for locating zinc finger nuclease target sites in model organisms. *BMC Genomics.* (2011) 12:83.
Rochaix et al., The chloroplast ribosomal intron of *Chlamydomonas reinhardii* codes for a polypeptide related to mitochondrial maturases. *Nucleic Acids Res.* (1985) 13: 975-984.
Römer et al., Plant pathogen recognition mediated by promoter activation of the pepper *Bs3* resistance gene. *Science.* (2007) 318:645-648.
Rosen et al., Homing endonuclease I-Crel derivatives with novel DNA target specificities. *Nucleic Acids Res.* (2006) 34:4791-4800.
Sadowski, Site-specific genetic recombination: hops, flips, and flops. FASEB. (1993) 7:760-7.
Sanjana et al., A transcription activator-like effector toolbox for genome engineering. *Nature Protocols.* (2012) 7:171-192.
Santoro & Schultz, Directed evolution of the site specificity of Cre recombinase. *Proc Natl Acad Sci.* USA (2002) 99:4185-4190.
Sauer, Site-specific recombination: developments and applications. *Curr Op Biotechnol*. (1994) 5:521-527.
Saves et al., Identification of the first eubacterial endonuclease coded by an intein allele in the *pps1* gene of mycobacteria. *Nucleic Acids Res.* (2001) 29:4310-4318.
Schlake & Bode, Use of mutated FLP recognition target (FRT) sites for the exchange of expression cassettes at defined chromosomal loci. *Biochemistry.* (1994) 33:12746-12751.
Sclimenti et al., Directed evolution of a recombinase for improved genomic integration at a native human sequence. *Nucleic Acids Res.* (2001) 29:5044-5051.
Segal & Barbas, Custom DNA-binding proteins come of age: polydactyl zinc-finger proteins. *Curr Opin Biotechnol.* (2001) 12:632-637.
Segal, The use of zinc finger peptides to study the role of specific factor binding sites in the chromatin environment. *Methods.* (2002) 26:76-83.
Segal et al., Evaluation of a modular strategy for the construction of novel polydactyl zinc finger DNA-binding proteins. *Biochemistry.* (2003) 42:2137-2148.
Seligman et al., Mutations altering the cleavage specificity of a homing endonuclease. *Nucleic Acids Res.* (2002) 30:3870-3879.
Seibler & Bode, Double-reciprocal crossover mediated by FLP-recombinase: a concept and an assay. *Biochemistry.* (1997) 36:1740-1747.
Smith et al., A combinatorial approach to create artificial homing endonucleases cleaving chosen sequences. *Nucleic Acids Res.* (2006) 34:e149.
Steen et al., Microbial production of fatty-acid-derived fuels and chemicals from plant biomass. *Nature,* (2010) 463:559-562.
Stoddard, Homing endonuclease structure and function. *Q Rev Biophys.* (2006) 38:49-95.
Sugio et al., Two type III effector genes of *Xanthomonas oryzae* pv. *oryzae* control the induction of the host genes *OsTFIIAγ1* and *OsTFX1* during bacterial blight of rice. *Proc. Natl. Acad. Sci. USA.* (2007) 104:10720-10725.
Sussman et al., Isolation and characterization of new homing endonuclease specificities at individual target site positions. *J Mol Biol.* (2004) 342:31-41.
Thomson et al., Mutational analysis of *LoxP* sites for efficient Cre-mediated insertion into genomic DNA. *Genesis.* (2003) 36:162-167.
Thyagarajan et al., Site-specific genomic integration in mammalian cells mediated by phage ψC31 integrase. *Mol Cell Biol.* (2001) 21:3926-3934.
Tomaschewski & Rüger, Nucleotide sequence and primary structures of gene products coded for by the T4 genome between map positions 48.266 kb and 39.166 kb. *Nucleic Acids Res.* (1987) 15:3632-3633.
Turmel et al., Six group I introns and three internal transcribed spacers in the chloroplast large subunit ribosomal RNA gene of the green alga *Chlamydomonas eugametos*. *J .Mol. Biol.* (1991) 218:293-311.
Umlauf & Cox, The functional significance of DNA sequence structure in a site-specific genetic recombination reaction. *EMBO J.* (1988) 7:1845-1852.
Urnov et al., Highly efficient endogenous human gene correction using designed zinc-finger nucleases. *Nature.* (2005) 435:646-651.
Urnov et al., Genome editing with engineered zinc finger nucleases. *Nat Rev Genet.* (2010) 11:636-646.

(56) References Cited

OTHER PUBLICATIONS

Vergunst et al., VirB/D4-dependent protein translocation from *Agrobacterium* into plant cells. *Science.* (2000) 290:979-982.
Voziyanov et al., A dual reporter screening system identifies the amino acid at position 82 in Flp site-specific recombinase as a determinant for target specificity. *Nucleic Acids Res.* (2002) 30:1656-1663.
Voziyanov et al., Stepwise manipulation of DNA specificity in Flp recombinase: progressively adapting Flp to individual and combinatorial mutations in its target site. *J Mol Biol.* (2003) 326:65-76.
Wolfe et al., DNA recognition by $Cys_2His_2$ zinc finger proteins. *Ann Rev Biophys Biomol Struct.* (2000) 29:183-212.
Wright et al., High-frequency homologous recombination in plants mediated by zinc-finger nucleases. *Plant J.* (2005) 44:693-705.
Yagil et al., Identifying determinants of recombination specificity: construction and characterization of chimeric bacteriophage integrases. *J Mol Biol.* (1995) 252:163-177.
Yang et al., *Os8N3* is a host disease-susceptibility gene for bacterial blight of rice. *Proc. Natl. Acad. Sci. USA*. (2006) 103:10503-10508.
Zeng et al., A free-standing homing endonuclease targets an intron insertion site in the *psbA* gene of cyanophages. *Curr. Biol.* (2009) 19:218-222.
International Search Report for PCT/US2012/035657 mailed Aug. 8, 2012, 6 pgs.
Li et al., "Modularly assembled designer TAL effector nucleases for targeted gene knockout and gene replacement in eukaryotes", *Nucleic Acids Res.* vol. 39, No. 14, pp. 6315-6325 (2011).
Takahashi et al., "Metabolic Engineering of Sesquiterpene Metabolism in Yeast", Biotechnology and Bioengineering vol. 97, No. 1 pp. 170-181 (2007).

* cited by examiner

METHODS FOR GENOMIC MODIFICATION

1. CROSS REFERENCE TO RELATED APPLICATIONS

This application claims benefit of priority of U.S. Provisional Application No. 61/479,821, filed on Apr. 27, 2011; U.S. Provisional Application No. 61/500,741, filed on Jun. 24, 2011; and U.S. Provisional Application No. 61/539,389, filed on Sep. 26, 2011, the contents of which are hereby incorporated by reference in their entireties.

2. FIELD OF THE INVENTION

The methods and compositions provided herein generally relate to the fields of molecular biology and genetic engineering.

3. BACKGROUND

Genetic engineering techniques to introduce and integrate exogenous nucleic acids into a host cell genome are needed in a variety of fields. For example, in the field of synthetic biology, the fabrication of a genetically modified strain requires the insertion of customized DNA sequences into a chromosome of the host cell, and commonly, industrial scale production requires the introduction of dozens of genes into the host organism. Optimized designs for the industrial strain are arrived at empirically, requiring construction and in vivo testing of many DNA assemblies, alone and/or in concert with other biosynthetic pathway components.

Genetic engineering is highly reliant on gene targeting, which utilizes an extrachromosomal fragment of donor template DNA and invokes a cell's homologous recombination (HR) machinery to exchange a chromosomal sequence with an exogenous donor sequence. See, e.g., Capecchi, *Science* 244:1288-1292 (1989). Gene targeting is limited in its efficiency; in plant and mammalian cells, only ~1 in $10^6$ cells provided with excess template sequences undergo the desired gene modification. Yeast demonstrates an increased capacity for homologous recombination. However, the successful incorporation of exogenous DNA into yeast genomes is still a comparatively rare event (~1 in $10^5$), and requires the use of a selectable marker to screen for recombinant cells which usually comprise only a single genomic modification. In addition, since only a limited cache of selectable markers are available for use in yeast, selectable marker(s) must be removed from a recombinant strain to allow for additional genomic modifications using the same markers, and in some instances, prior to releasing the host cell in a manufacturing or natural environment. Thus, independent of the efficiency at which integration can be achieved at any single locus, the one-at-a-time serial nature of genomic engineering requires that making changes at multiple loci requires as many engineering cycles as there are loci to be modified.

The efficiency of gene targeting can be improved when combined with a targeted genomic double-stranded break (DSB) introduced near the intended site of integration. See e.g., Jasin, M., *Trends Genet* 12(6):224-228 (1996); and Urnov et al., *Nature* 435(7042):646-651 (2005). So called "designer nucleases" are enzymes that can be tailored to bind to a specific "target" sequence of DNA in vivo and introduce a double-strand break thereto. Such targeted double-strand breaks can be effected, for instance, by transforming a host cell with a plasmid containing a gene that encodes the designer nuclease. The host cell repairs these double-strand breaks by either homology-directed DNA repair or non-homologous end joining In the course of the repair, either mechanism may be utilized to incorporate an exogenous donor DNA at the target site. If the nuclease is introduced into the cell at the same time as the donor DNA is introduced, the cell can integrate the donor DNA at the target loci.

The advent of designer nucleases has enabled the introduction of transgenes into particular target loci in crops (Wright et al., *Plant J* 44:693-705 (2005)), to improve mammalian cell culture lines expressing therapeutic antibodies (Malphettes et al., *Biotechnol Bioeng* 106(5):774-783 (2010)), and even to edit the human genome to evoke resistance to HIV (Urnov et al., *Nat Rev Genet* 11(9):636-646 (2010)). While impactful, DSB-mediated HR has yet to be exploited to reduce the multiple rounds of engineering needed to integrate multiple DNA assemblies, for example, towards the construction of functional metabolic pathways in industrial microbes.

Thus, there exists a need for methods and compositions that allow for the simultaneous integration of a plurality of exogenous nucleic acids into specific regions of a host cell genome.

4. SUMMARY

Provided herein are methods and compositions for integrating one or more exogenous nucleic acids into specified genomic loci of a host cell. In some embodiments, a plurality of exogenous nucleic acids is simultaneously integrated with a single transformation reaction. In some embodiments, the methods comprise the introduction of one or more nucleases and one or more donor DNA assemblies into the cell to facilitate integration of the donor DNA at specified locations in the genome. The methods and compositions utilize the native homologous recombination machinery of the host cell, which recombination is further enhanced by inducing targeted double-strand breaks in the host cell's genome at the intended sites of integration.

Thus, in one aspect, provided herein is a method for integrating a plurality of exogenous nucleic acids into a host cell genome, the method comprising:

(a) contacting a host cell with:

(i) a plurality of exogenous nucleic acids, wherein each exogenous nucleic acid $(ES)_x$ comprises a first homology region $(HR1)_x$ and a second homology region $(HR2)_x$, wherein $(HR1)_x$ and $(HR2)_x$ are capable of initiating host cell mediated homologous recombination of $(ES)_x$ at a target site $(TS)_x$ of said host cell genome; and (ii) for each said target site $(TS)_x$, a nuclease $(N)_x$ capable of cleaving at $(TS)_x$, whereupon said cleaving results in homologous recombination of $(ES)_x$ at $(TS)_x$; and (b) recovering a host cell wherein each selected exogenous nucleic acid $(ES)_x$ has integrated at each selected target sequence $(TS)_x$, wherein x is any integer from 1 to n wherein n is at least 2.

In some embodiments, $(HR1)_x$ is homologous to a 5' region of $(TS)_x$, and $(HR2)_x$, is homologous to a 3' region of $(TS)_x$.

In some embodiments, $(N)_x$ is capable of cleaving at a region positioned between said 5' and 3' regions of $(TS)_x$.

In some embodiments, a single nuclease is capable of cleaving each $(TS)_x$.

In some embodiments, n=3, 4, 5, 6, 7, 8, 9 or 10. In some embodiments, n>10.

In some embodiments, said recovering does not require integration of a selectable marker. In some embodiments, said recovering occurs at a higher frequency as compared to not contacting the host cell with a nuclease capable of cleaving at said target site. In some embodiments, said recovering occurs at a frequency of about one every 10, 9, 8, 7, 6, 5, 4, 3, or 2 contacted host cells, or clonal populations thereof, screened. In some embodiments, said recovering comprises identifying said integrations by at least one method selected from the group consisting of PCR, Southern blot, restriction mapping, and DNA sequencing.

In some embodiments, $(N)_x$ is capable of cleaving an endogenous host genomic sequence, e.g., a native loci within $(TS)_x$. In some embodiments, $(N)_x$ is capable of cleaving an exogenous sequence, e.g., an introduced loci within $(TS)_x$.

In some embodiments, $(ES)_x$ further comprises a nucleic acid of interest $(D)_x$ positioned 3' of $(HR1)_x$ and 5' of $(HR2)_x$. In some embodiments, $(D)_x$ is selected from the group consisting of a promoter, a nucleic acid sequence encoding an epitope tag, a gene of interest, a reporter gene, and a nucleic acid sequence encoding a termination codon.

In some embodiments, $(ES)_x$ is linear. In some embodiments, $(N)_x$ is provided as an expression vector comprising the nucleic acid sequence encoding $(N)_x$. In some embodiments, $(N)_x$ is transformed into the host cell as a purified protein. In some embodiments, $(N)_x$ is transformed into the host cell as purified RNA.

In some embodiments, the host cell comprises one or more heterologous nucleotide sequences encoding one or more enzymes of a biosynthetic pathway. In some embodiments, the one or more heterologous nucleotide sequences encoding one or more enzymes of a biosynthetic pathway are genomically integrated. In some embodiments, each exogenous nucleic acid $(ES)_x$ comprises a nucleic acid of interest $(D)_x$ positioned 3' of $(HR1)_x$ and 5' of $(HR2)_x$, encoding an enzyme of a biosynthetic pathway. In some embodiments, $(D)_x$ is a member of a library $(L)_x$ comprising a plurality of nucleic acid molecules that encode variants of an enzyme of a biosynthetic pathway.

In some embodiments, the host cell comprises one or more heterologous nucleotide sequences encoding one or more enzymes of a mevalonate (MEV) pathway for making isopentenyl pyrophosphate. In some embodiments, the one or more enzymes of the mevaloante pathway are selected from acetyl-CoA thiolase, HMG-CoA synthase, HMG-CoA reductase, mevalonate kinase, phosphomevalonate kinase and mevalonate pyrophosphate decarboxylase. In some embodiments, the host cell comprises a plurality of heterologous nucleic acids encoding all of the enzymes of a MEV pathway. In other words, the plurality of heterologous nucleic acids, taken together, encodes at least one enzyme of each class of enzymes of the MEV pathway listed above. In some embodiments, each exogenous nucleic acid $(ES)_x$ comprises a nucleic acid of interest $(D)_x$ positioned 3' of $(HR1)_x$ and 5' of $(HR2)_x$, encoding a terpene synthase. In some embodiments, the terpene synthase is selected from the group consisting of a monoterpene synthase, a diterpene synthase, a sesquiterpene synthase, a sesterterpene synthase, a triterpene synthase, a tetraterpene synthase, and a polyterpene synthase.

In some embodiments, $(N)_x$ is selected from the group consisting of an endonuclease, e.g., a meganuclease, a zinc finger nuclease, a TAL-effector DNA binding domain-nuclease fusion protein (TALEN), a transposase, and a site-specific recombinase, wherein x is 1 or any integer from 1 to n. In some embodiments, the zinc finger nuclease is a fusion protein comprising the cleavage domain of a TypeIIS restriction endonuclease fused to an engineered zinc finger binding domain. In some embodiments, the TypeIIS restriction endonuclease is selected from the group consisting of HO endonuclease and Fok I endonuclease. In some embodiments, the zinc finger binding domain comprises 3, 5 or 6 zinc fingers. In some embodiments, the endonuclease is a homing endonuclease selected from the group consisting of: an LAGLIDADG homing endonuclease, an HNH homing endonuclease, a His-Cys box homing endonuclease, a GIY-YIG homing endonuclease, and a cyanobacterial homing endonuclease. In some embodiments, the endonuclease is selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, i-UarAP, i-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, or PI-TliII. In particular embodiments, the endonuclease is Fcph-I.

In some embodiments, the endonuclease is modified to specifically bind an endogenous host cell genomic sequence, wherein the modified endonuclease no longer binds to its wild type endonuclease recognition sequence. In some embodiments, the modified endonuclease is derived from a homing endonuclease selected from the group consisting of: an LAGLIDADG homing endonuclease, an HNH homing endonuclease, a His-Cys box homing endonuclease, a GIY-YIG homing endonuclease, and a cyanobacterial homing endonuclease. In some embodiments, the modified endonuclease is derived from an endonuclease selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, i-UarAP, i-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, or PI-TliII.

In some embodiments, the host cell is a fungal cell, a bacterial cell, a plant cell, an animal cell, or a human cell. In particular embodiments, the host cell is a yeast cell. In some embodiments, the yeast cell is a haploid yeast cell. In some embodiments, the yeast cell is a *Saccharomyces cerevisiae* cell. In some embodiments, the *Saccharomyces cerevisiae* cell is of the Baker's yeast, Mauri, Santa Fe, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1 or AL-1 strain.

In another aspect, provided herein is a method for markerless integration of an exogenous nucleic acid into a target site of a yeast cell genome, the method comprising:

(a) contacting a host yeast cell with:

(i) an exogenous nucleic acid (ES) comprising a first homology region (HR1) and a second homology region (HR2), wherein (HR1) and (HR2) are capable of initiating host cell mediated homologous recombination at said target site (TS); and (ii) a nuclease (N) capable of cleaving at (TS), whereupon said cleaving results in homologous recombination of (ES) at (TS); and (b) recovering a host cell having (ES) integrated at (TS), wherein said recovering does not require integration of a selectable marker.

In another aspect, provided herein is a modified host cell generated by any of the methods of genomically integrating one or more exogenous nucleic acids described herein. In some embodiments, the modified host cell comprises:

(a) a plurality of exogenous nucleic acids, wherein each exogenous nucleic acid $(ES)_x$ comprises a first homology region $(HR1)_x$ and a second homology region $(HR2)_x$, wherein $(HR1)_x$ and $(HR2)_x$ are capable of initiating host cell mediated homologous recombination of $(ES)_x$ at a target site $(TS)_x$ of said host cell genome; and (b) for each said target site $(TS)_x$ a nuclease $(N)_x$ capable of cleaving at $(TS)_x$ whereupon said cleaving results in homologous recombination of $(ES)_x$ at $(TS)_x$;

wherein x is any integer from 1 to n wherein n is at least 2.

In some embodiments, the modified host cell is a yeast cell and comprises:

(a) an exogenous nucleic acid (ES) comprising a first homology region (HR1) and a second homology region (HR2), wherein (HR1) and (HR2) are capable of initiating host cell mediated homologous recombination at a target site (TS) of the host cell genome; and (b) a nuclease (N) capable of cleaving at (TS), whereupon said cleaving results in homologous recombination of (ES) at (TS);

wherein (ES) does not comprise a selectable marker.

In another aspect, provided herein is a composition comprising:

(a) a yeast cell;

(b) a plurality of exogenous nucleic acids, wherein each exogenous nucleic acid $(ES)_x$ comprises:

(i) a first homology region $(HR1)_x$ and a second homology region $(HR2)_x$, wherein $(HR1)_x$ and $(HR2)_x$ are capable of initiating host cell mediated homologous recombination of $(ES)_x$ at a selected target site $(TS)_x$ of a yeast cell genome; and (ii) a nucleic acid of interest $(D)_x$ positioned 3' of $(HR1)_x$ and 5' of $(HR2)_x$;

(c) a plurality of nucleases, wherein each nuclease $(N)_x$ capable of cleaving at $(TS)_x$, whereupon said cleaving results in homologous recombination of $(ES)_x$ at $(TS)_x$;

wherein x is any integer from 1 to n wherein n is at least 2.

In another aspect, provided herein is a kit useful for performing the methods for genomically integrating one or more exogenous nucleic acids described herein. In some embodiments, the kit comprises:

(a) a plurality of exogenous nucleic acids, wherein each exogenous nucleic acid $(ES)_x$ comprises:

(i) a first homology region $(HR1)_x$ and a second homology region $(HR2)_x$, wherein $(HR1)_x$ and $(HR2)_x$ are capable of initiating host cell mediated homologous recombination of $(ES)_x$ at a selected target site $(TS)_x$ of a yeast cell genome; and (ii) a nucleic acid of interest $(D)_x$ positioned 3' of $(HR1)_x$ and 5' of $(HR2)_x$;

(b) a plurality of nucleases, wherein each nuclease $(N)_x$ capable of cleaving at $(TS)_x$, whereupon said cleaving results in homologous recombination of $(ES)_x$ at $(TS)_x$;

wherein x is any integer from 1 to n wherein n is at least 2.

In some embodiments, $(D)_x$ is selected from the group consisting of a selectable marker, a promoter, a nucleic acid sequence encoding an epitope tag, a gene of interest, a reporter gene, and a nucleic acid sequence encoding a termination codon. In some embodiments, the kit further comprises a plurality of primer pairs $(P)_x$, wherein each primer pair is capable of identifying integration of $(ES)_x$ at $(TS)_x$ by PCR. In some embodiments, $(ES)_x$ is linear. In some embodiments, $(ES)_x$ is circular.

In a particular embodiment, the kit enables site-specific integration of an exogenous nucleic acid at a unique target site within any of the approximately 6000 genetic loci of the yeast genome. In these embodiments, n≥6000, wherein each $(TS)_x$ is unique to a specific locus of the yeast cell genome.

5. BRIEF DESCRIPTION OF THE FIGURES

FIG. 1 provides an exemplary embodiment of markerless genomic integration of an exogenous nucleic acid using a site-specific nuclease.

Figure 2:
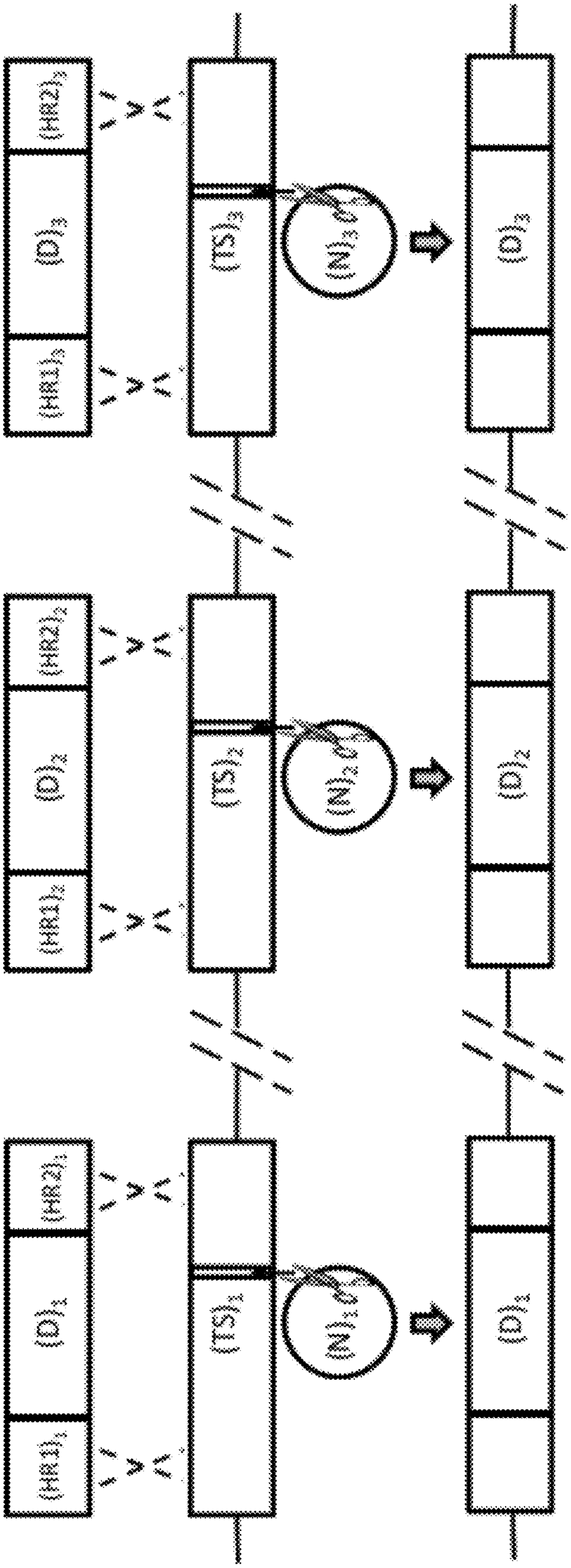

FIG. 2 provides an exemplary embodiment of simultaneous genomic integration of a plurality of exogenous nucleic acids using a plurality of site-specific nucleases. HR1—upstream homology region; HR2—downstream homology region; TS—target site; N—site-specific nuclease; D—nucleic acid of interest.

Figure 3:
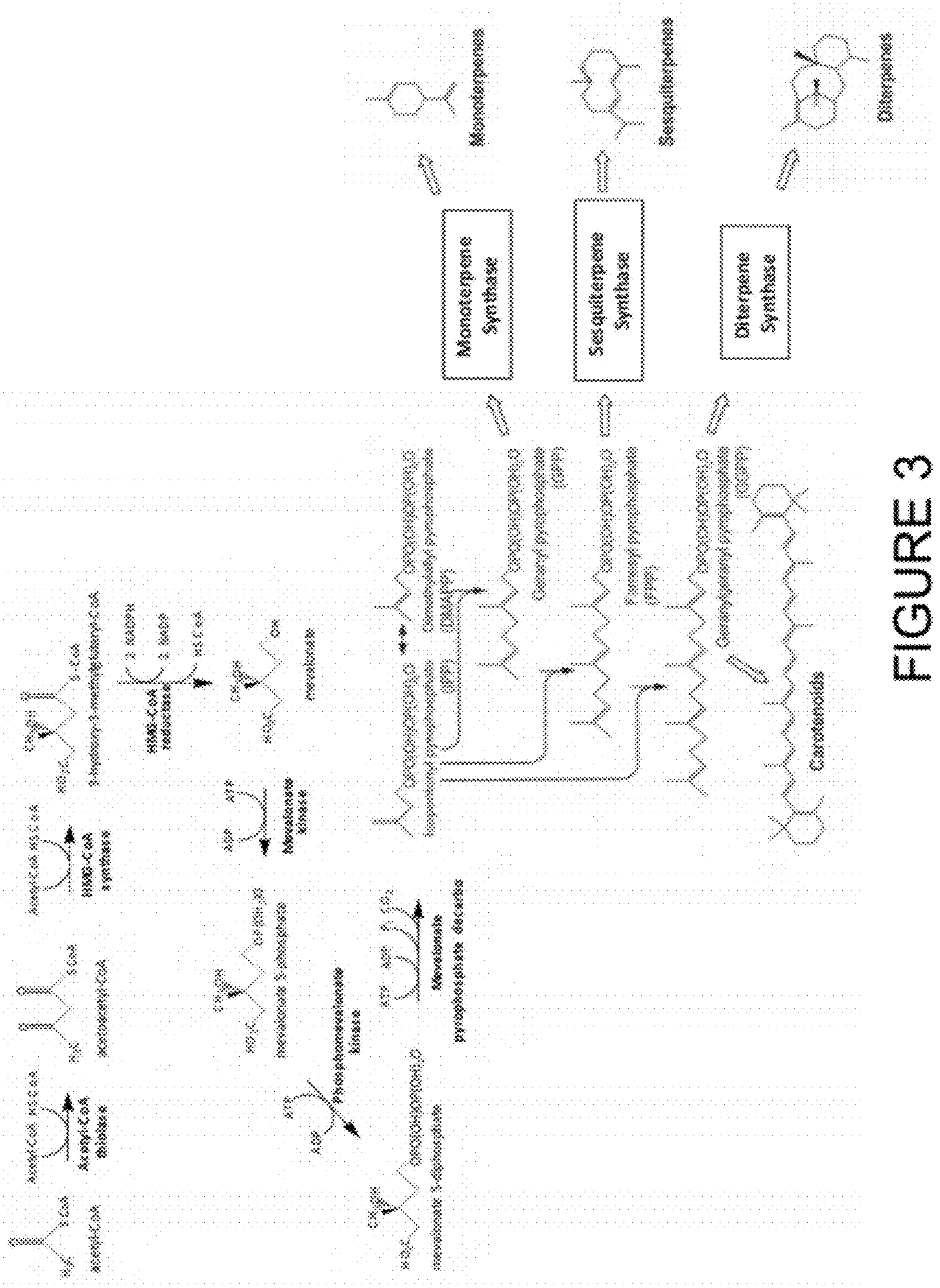

FIG. 3 provides a schematic representation of the MEV pathway for isoprenoid production.

Figure 4:
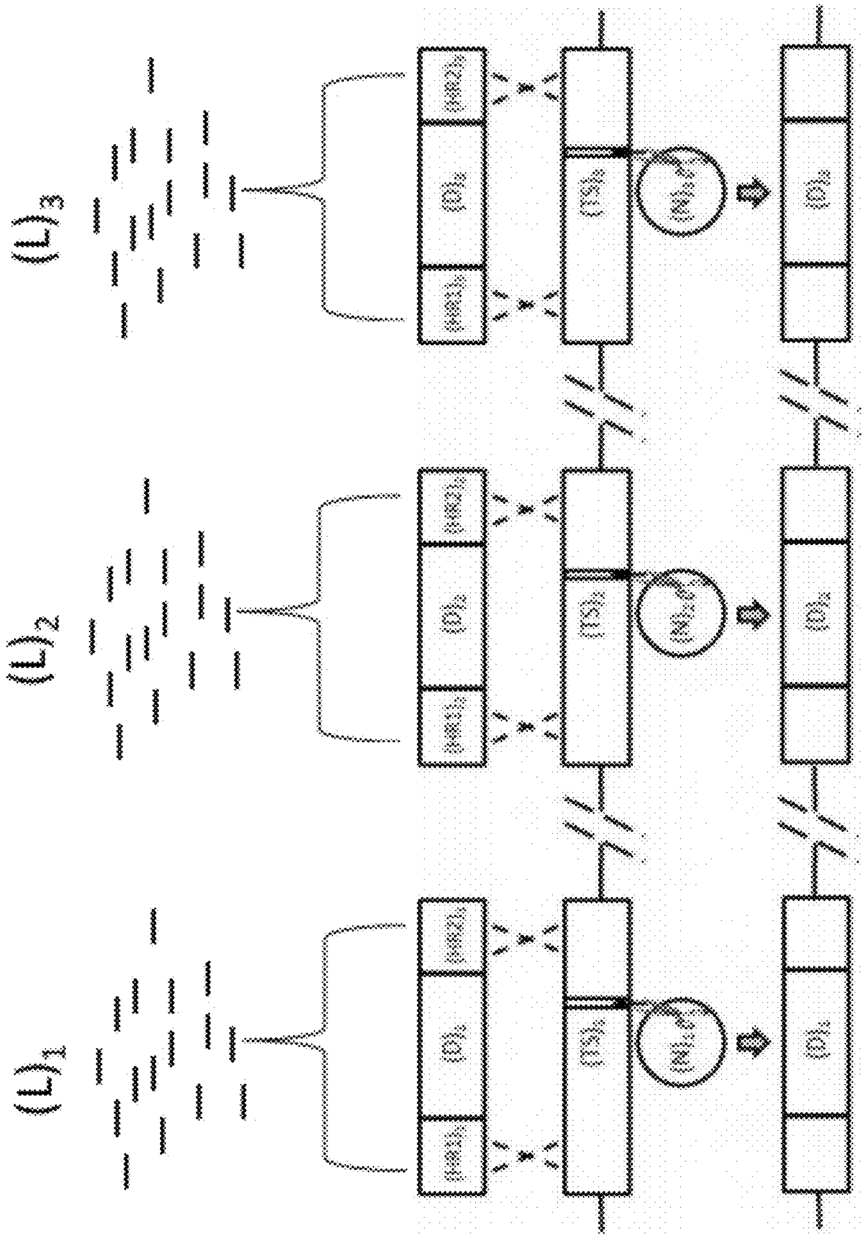

FIG. 4 provides an exemplary embodiment of the methods of generating combinatorial integration libraries provided herein. The hatch marks represent individual exogenous nucleic acid members of each library $(L)_x$.

Figure 5:
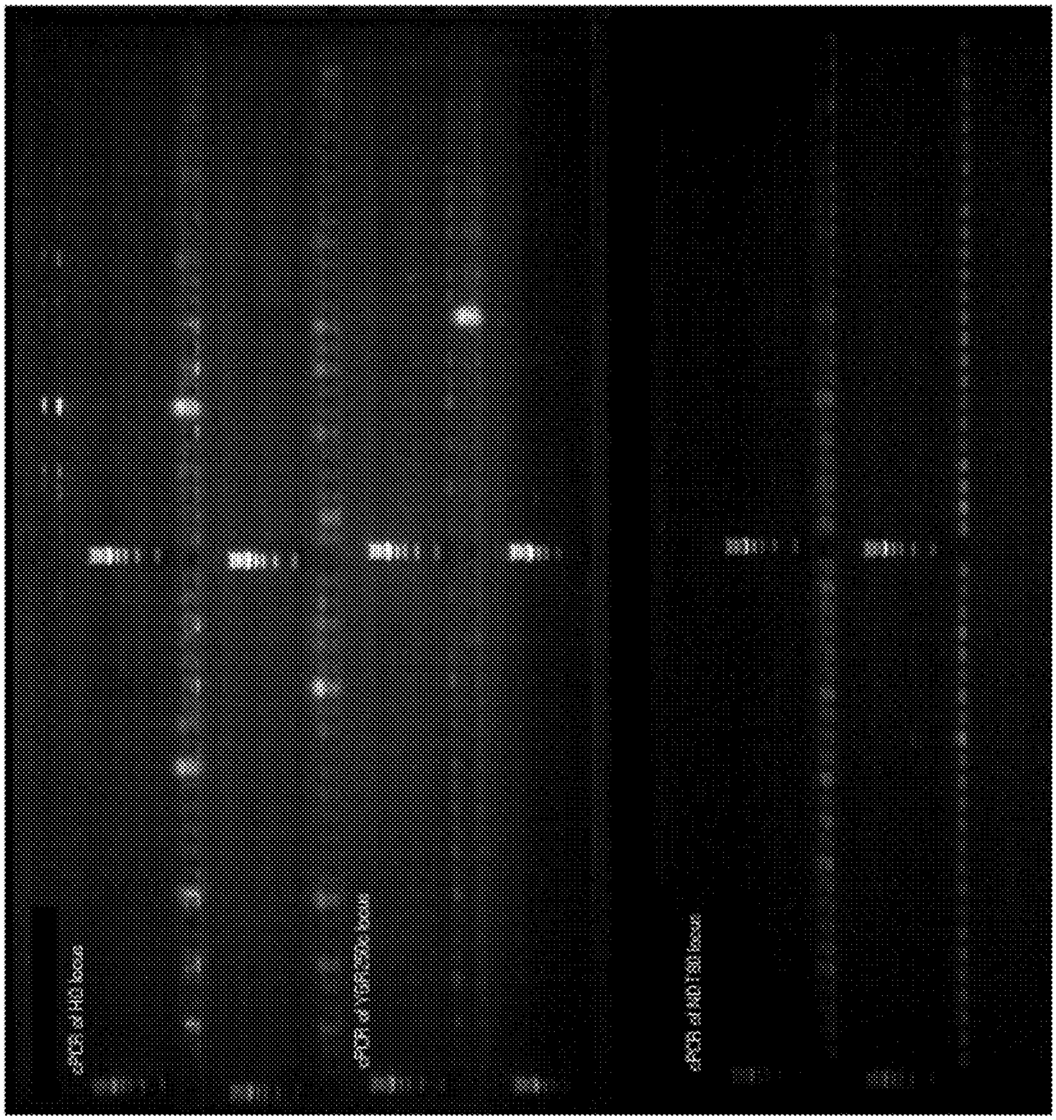

FIG. 5 provides results of colony PCR of 96 colonies of yeast cells transformed with empty vector DNA and linear "donor" DNA encoding functional EmGFP. The yeast cells comprised copies of "target" nucleic acid encoding a truncated, non-functional EmGFP genomically integrated at each of the HO, YGR250c, and NDT80 loci. Separate PCR reactions were performed to probe the HO, YGR250c, and NDT80 loci with primers specific to nucleic acid encoding functional EmGFP. No PCR products were observed, indicating that no replacements of the target nucleic acid encoding non-functional EmGFP with donor nucleic acid encoding functional EmGFP occurred.

Figure 6:
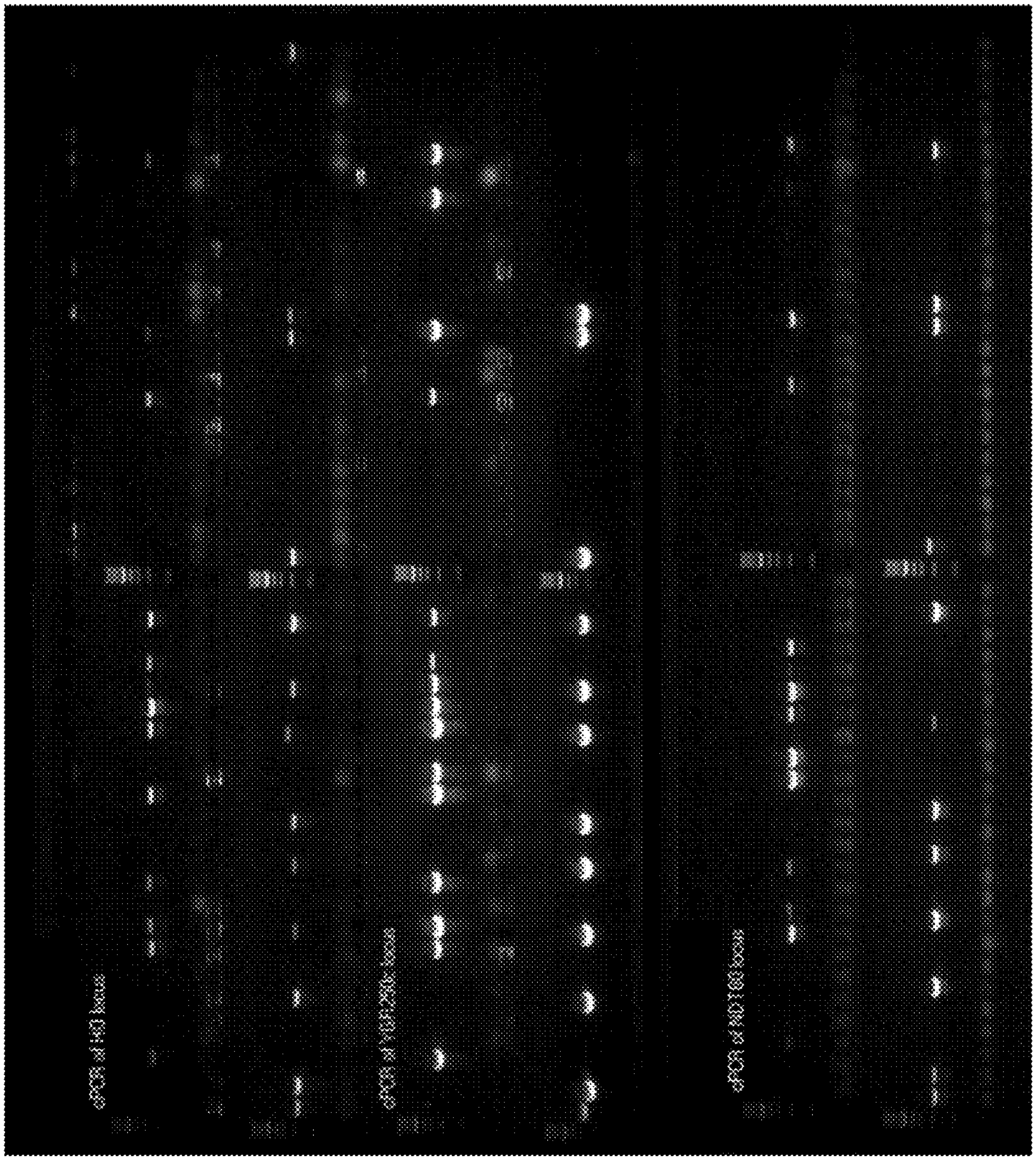

FIG. 6 provides results of colony PCR of 96 colonies of yeast cells transformed with pZFN.gfp DNA and linear "donor" DNA encoding functional EmGFP. The yeast cells comprised copies of "target" nucleic acid encoding a truncated, non-functional EmGFP genomically integrated at each of the HO, YGR250c, and NDT80 loci. pZFN.gfp encodes a zinc finger nuclease which recognizes and cleaves a nucleic acid sequence specific to the non-functional EmGFP coding sequence. Separate PCR reactions were performed to probe the HO, YGR250c, and NDT80 loci with primers specific to nucleic acid encoding functional EmGFP. Numerous PCR products were observed, indicating successful replacement of the non-functional EmGFP integrations with DNA expressing functional EmGFP. 23 colonies have all 3 loci replaced.

Figure 7:
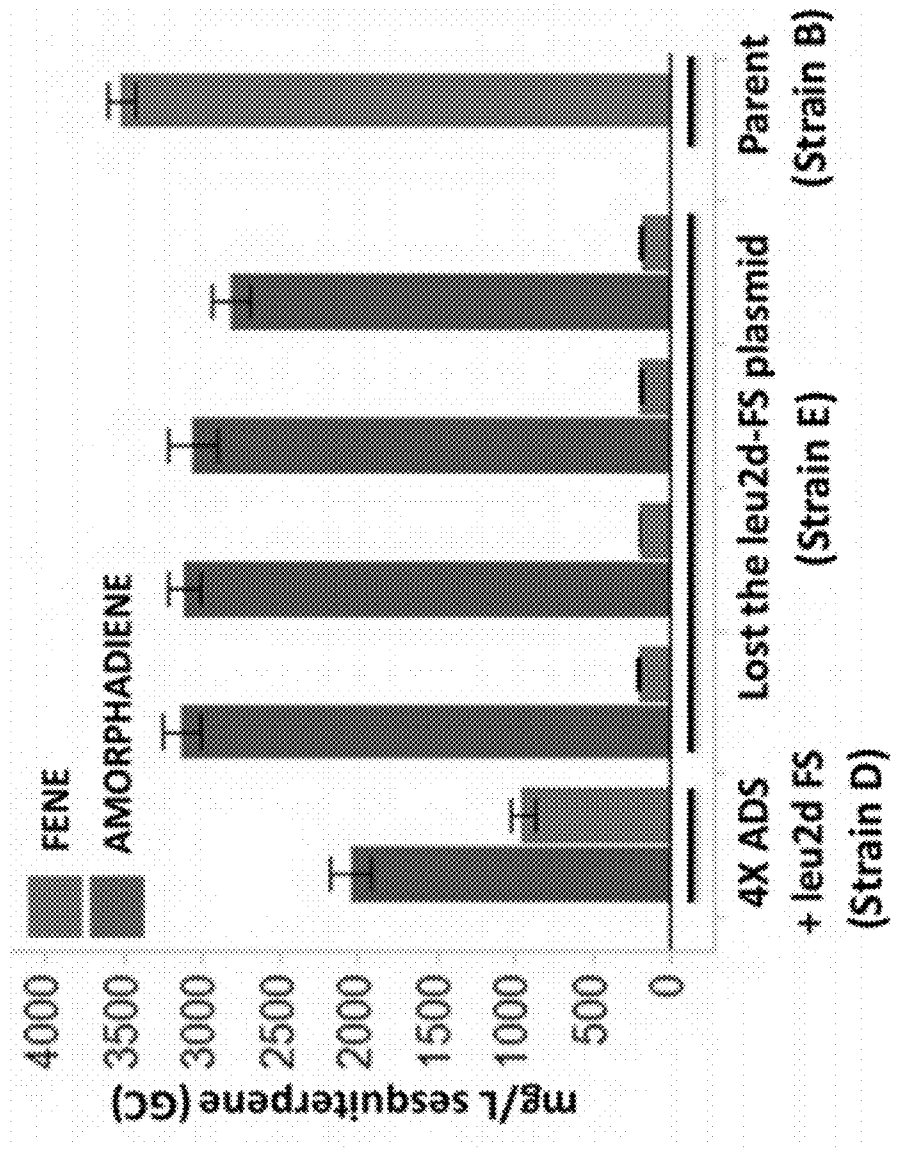

FIG. 7 provides the sequiterpene titers of Strain B, a parental farnesene-producing yeast strain comprising enzymes of the mevalonate pathway and a plasmid encoding farnesene synthase (FS); Strain D, a derivative strain of Strain B in which 4 copies of amorphadiene synthase (ADS) have been genomically integrated; and Strain E, a derivative strain of Strain D in which the plasmid encoding FS has been lost.

Nearly 100% of the sesquiterpene capacity of parental Strain B is maintained in Strains D and E with only the addition of multiple copies of ADS.

Figure 8:
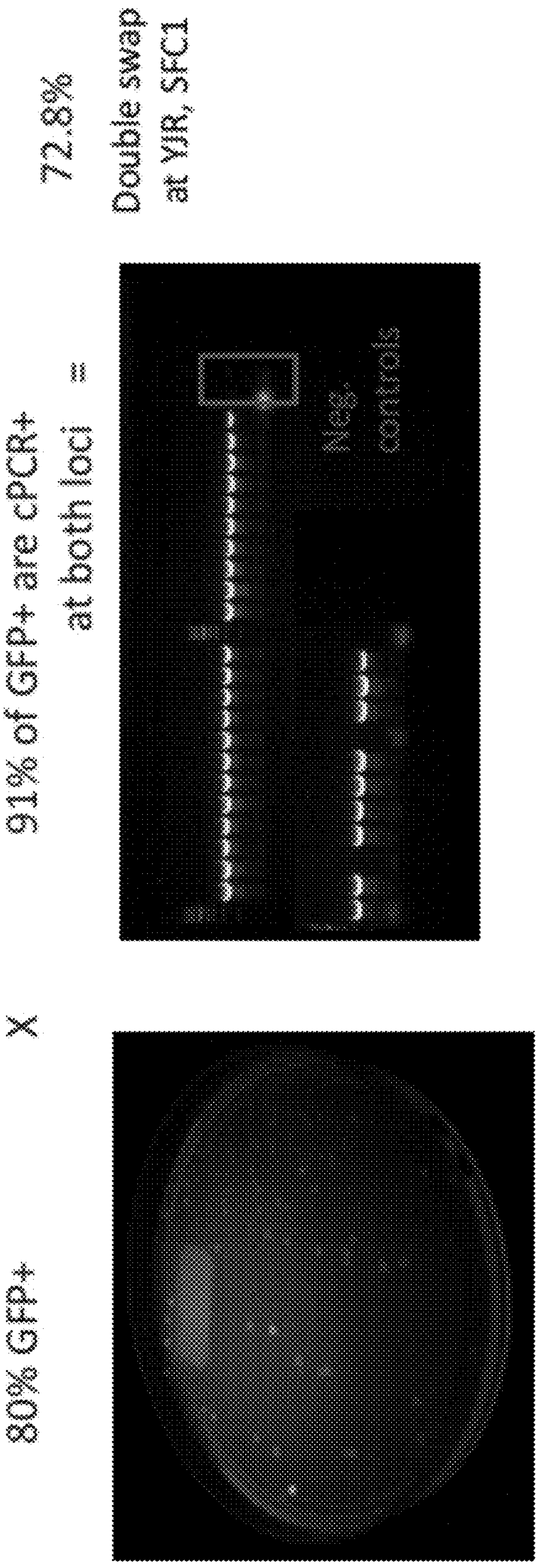

FIG. 8, provides results for cells co-transformed with linear donor DNAs for the SFC1 (GFP donor DNA) and YJR030c (ADE2 donor DNA) loci, the YJR030c endonuclease plasmid (pCUT006) and SFC1 endonuclease plasmid (pCUT058). 80% of colonies selected on URA dropout+Kan agar plates were GFP positive. Of these colonies, 91% were positive for ADE2 integration. In total, 72.8% of colonies had successfully integrated the markerless donor DNA at both loci.

6. DETAILED DESCRIPTION OF THE EMBODIMENTS

6.1 Definitions

As used herein, the terms "cleaves," "cleavage" and/or "cleaving" with respect to a nuclease, e.g. a homing endonuclease, zinc-finger nuclease or TAL-effector nuclease, refer to the act of creating a double-stranded break (DSB) in a particular nucleic acid. The DSB can leave a blunt end or sticky end (i.e., 5' or 3' overhang), as understood by those of skill in the art.

As used herein, the term "engineered host cell" refers to a host cell that is generated by genetically modifying a parent cell using genetic engineering techniques (i.e., recombinant technology). The engineered host cell may comprise additions, deletions, and/or modifications of nucleotide sequences to the genome of the parent cell.

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus.

As used herein, the term "homology" refers to the identity between two or more nucleic acid sequences, or two or more amino acid sequences. Sequence identity can be measured in terms of percentage identity (or similarity or homology); the higher the percentage, the more near to identical the sequences are to each other. Homologs or orthologs of nucleic acid or amino acid sequences possess a relatively high degree of sequence identity when aligned using standard methods. Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. Biosc.* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

As used herein, the term "markerless" refers to integration of a donor DNA into a target site within a host cell genome without accompanying integration of a selectable marker. In some embodiments, the term also refers to the recovery of such a host cell without utilizing a selection scheme that relies on integration of selectable marker into the host cell genome. For example, in certain embodiments, a selection marker that is episomal or extrachromasomal may be utilized to select for cells comprising a plasmid encoding a nuclease capable of cleaving a genomic target site. Such use would be considered "markerless" so long as the selectable marker is not integrated into the host cell genome.

As used herein, the term "polynucleotide" refers to a polymer composed of nucleotide units as would be understood by one of skill in the art. Preferred nucleotide units include but are not limited to those comprising adenine (A), guanine (G), cytosine (C), thymine (T), and uracil (U). Useful modified nucleotide units include but are not limited to those comprising 4-acetylcytidine, 5-(carboxyhydroxylmethyl)uridine, 2-O-methylcytidine, 5-carboxymethylaminomethyl-2-thiouridine, 5-carboxymethylamino-methyluridine, dihydrouridine, 2-O-methylpseudouridine, 2-O-methylguanosine, inosine, N6-isopentyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, 5-methoxyuridine, 5-methoxycarbonylmethyl-2-thiouridine, 5-methoxycarbonylmethyluridine, 2-methylthio-N6-isopentyladenosine, uridine-5-oxyacetic acid-methylester, uridine-5-oxyacetic acid, wybutoxosine, wybutosine, pseudouridine, queuosine, 2-thiocytidine, 5-methyl-2-thiouridine, 2-thiouridine, 4-thiouridine, 5-methyluridine, 2-O-methyl-5-methyluridine, 2-O-methyluridine, and the like. Polynucleotides include naturally occurring nucleic acids, such as deoxyribonucleic acid ("DNA") and ribonucleic acid ("RNA"), as well as nucleic acid analogs. Nucleic acid analogs include those that include non-naturally occurring bases, nucleotides that engage in linkages with other nucleotides other than the naturally occurring phosphodiester bond or that include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

As used herein, the term "simultaneous," when used with respect to multiple integration, encompasses a period of time beginning at the point at which a host cell is co-transformed with a nuclease, e.g. a plasmid encoding a nuclease, and more than one donor DNA to be integrated into the host cell genome, and ending at the point at which the transformed host cell, or clonal populations thereof, is screened for successful integration of the donor DNAs at their respective target loci. In some embodiments, the period of time encompassed by "simultaneous" is at least the amount of time required for the nuclease to bind and cleave its target sequence within the host cell's chromosome(s). In some embodiments, the period of time encompassed by “simultaneous” is at least 6, 12, 24, 36, 48, 60, 72, 96 or more than 96 hours, beginning at the point at which the a host cell is co-transformed with a nuclease, e.g. a plasmid encoding a nuclease, and more than one donor DNA.

6.2 Methods of Integrating Exogenous Nucleic Acids

Provided herein are methods of integrating one or more exogenous nucleic acids into one or more selected target sites of a host cell genome. In certain embodiments, the methods comprise contacting the host cell with one or more integration polynucleotides, i.e., donor DNAs, comprising an exogenous nucleic acid to be integrated into the genomic target site, and one or more nucleases capable of causing a double-strand break near or within the genomic target site. Cleavage near or within the genomic target site greatly increases the frequency of homologous recombination at or near the cleavage site.

In a particular aspect, provided herein is a method for markerless integration of an exogenous nucleic acid into a target site of a host cell genome, the method comprising:

(a) contacting a host cell with:

(i) an exogenous nucleic acid (ES) comprising a first homology region (HR1) and a second homology region (HR2), wherein (HR1) and (HR2) are capable of initiating host cell mediated homologous recombination at said target site (TS); and (ii) a nuclease (N) capable of cleaving at (TS), whereupon said cleaving results in homologous recombination of (ES) at (TS); and (b) recovering a host cell having (ES) integrated at (TS), wherein said recovering does not require integration of a selectable marker.

FIG. 1 provides an exemplary embodiment of markerless genomic integration of an exogenous nucleic acid using a site-specific nuclease. A donor polynucleotide is introduced to a host cell, wherein the polynucleotide comprises a nucleic acid of interest (D) flanked by a first homology region (HR1) and a second homology region (HR2). HR1 and HR2 share homology with 5' and 3' regions, respectively, of a genomic target site (TS). A site-specific nuclease (N) is also introduced to the host cell, wherein the nuclease is capable of recognizing and cleaving a unique sequence within the target site. Upon induction of a double-stranded break within the target site by the site-specific nuclease, endogenous homologous recombination machinery integrates the nucleic acid of interest at the cleaved target site at a higher frequency as compared to a target site not comprising a double-stranded break. This increased frequency of integration obviates the need to co-integrate a selectable marker in order to select transformants having undergone a recombination event. By eliminating the need for selectable markers, for example, during construction of an engineered microbe, the time needed to build a strain comprising a complete and functional biosynthetic pathway is greatly reduced. In addition, engineering strategies are no longer limited by the need to recycle selectable markers due to there being a limited cache of markers available for a given host organism.

In some embodiments, markerless recovery of a transformed cell comprising a successfully integrated exogenous nucleic acid occurs within a frequency of about one every 1000, 900, 800, 700, 600, 500, 400, 300, 200 or 100 contacted host cells, or clonal populations thereof, screened. In particular embodiments, markerless recovery of a transformed cell comprising a successfully integrated exogenous nucleic acid occurs within a frequency of about one every 90, 80, 70, 60, 50, 40, 30, 20, or 10 contacted host cells, or clonal populations thereof, screened. In more particular embodiments, markerless recovery of a transformed cell comprising a successfully integrated exogenous nucleic acid occurs within a frequency of about one every 9, 8, 7, 6, 5, 4, 3, or 2 contacted host cells, or clonal populations thereof, screened. In more particular embodiments, the host cell is a yeast cell, and the increased frequency of integration derives from yeast's increased capacity for homologous recombination relative to other host cell types.

A variety of methods are available to identify those cells having an altered genome at or near the target site without the use of a selectable marker. In some embodiments, such methods seek to detect any change in the target site, and include but are not limited to PCR methods, sequencing methods, nuclease digestion, e.g., restriction mapping, Southern blots, and any combination thereof In another aspect, provided herein is a method for integrating a plurality of exogenous nucleic acids into a host cell genome, the method comprising:

(a) contacting a host cell with:

(i) a plurality of exogenous nucleic acids, wherein each exogenous nucleic acid $(ES)_x$ comprises a first homology region $(HR1)_x$ and a second homology region $(HR2)_x$, wherein $(HR1)_x$ and $(HR2)_x$ are capable of initiating host cell mediated homologous recombination of $(ES)_x$ at a target site $(TS)_x$ of said host cell genome; and (ii) for each said target site $(TS)_x$, a nuclease $(N)_x$ capable of cleaving at $(TS)_x$, whereupon said cleaving results in homologous recombination of $(ES)_x$ at $(TS)_x$; and (b) recovering a host cell wherein each selected exogenous nucleic acid $(ES)_x$ has integrated at each selected target sequence $(TS)_x$, wherein x is any integer from 1 to n wherein n is at least 2.

FIG. 2 provides an exemplary embodiment of simultaneous genomic integration of a plurality of exogenous nucleic acids using a plurality of site-specific nucleases. In this example, three polynucleotides are introduced to a host cell, wherein each polynucleotide comprises an exogenous nucleic acid $(ES)_x$ comprising a nucleic acid of interest $(D)_x$, wherein x=1, 2 or 3. Each $(D)_x$ is flanked by a first homology region $(HR1)_x$ and a second homology region $(HR2)_x$. $(HR1)_x$ and $(HR2)_x$ share homology with 5' and 3' regions, respectively, of a selected target site $(TS)_x$, of three total unique target sites in the genome. A plurality of site-specific nucleases $(N)_x$ is also introduced to the host cell, wherein each $(N)_x$ is capable of recognizing and cleaving a unique sequence within its corresponding target site, $(TS)_x$. Upon cleavage of a target site $(TS)_x$ by its corresponding site-specific nuclease $(N)_x$, endogenous homologous recombination machinery facilitates integration of the corresponding nucleic acid interest $(D)_x$ at $(TS)_x$.

In particular embodiments, each exogenous nucleic acid $(ES)_x$, optionally comprising a nucleic acid of interest $(D)_x$, is integrated into its respective genomic target site $(TS)_x$ simultaneously, i.e., with a single transformation of the host cell with the plurality of integration polynucleotides and plurality of nucleases. In some embodiments, the methods are useful to simultaneously integrate any plurality of exogenous nucleic acids $(ES)_x$, that is, where x is any integer from 1 to n wherein n is at least 2, in accordance with the variables recited for the above described method. In some embodiments, the method of simultaneous integration provided herein is useful to simultaneously integrate up to 10 exogenous nucleic acids $(ES)_x$ into 10 selected target sites $(TS)_x$, that is, where x is any integer from 1 to n wherein n=2, 3, 4, 5, 6, 7, 8, 9, or 10. In some embodiments, the method of simultaneous integration provided herein is useful to simultaneously integrate up to 20 exogenous nucleic acids $(ES)_x$ into 20 selected target sites $(TS)_x$, that is, where x is any integer from 1 to n wherein n=2, 3, 4, 5, 6, 7, 8, 9, 10, 11, 12, 13, 14, 15, 16, 17, 18, 19 or 20.

In some embodiments, n=2. In some embodiments, n=3. In some embodiments, n=4. In some embodiments, n=5. In some embodiments, n=6. In some embodiments, n=7. In some embodiments, n=8. In some embodiments, n=9. In some embodiments, n=10. In some embodiments, n=11. In some embodiments, n=12. In some embodiments, n=13. In some embodiments, n=14. In some embodiments, n=15. In some embodiments, n=16. In some embodiments, n=17. In some embodiments, n=18. In some embodiments, n=19. In some embodiments, n=20. In some embodiments, the method of simultaneous integration provided herein is useful to simultaneously integrate more than 20 exogenous nucleic acids.

As with integration of a single exogenous nucleic acid at a single target site, the simultaneous multiple integration of a plurality of exogenous nucleic acids occurs at a substantially higher frequency as compared to not contacting the target sites with a nuclease capable of inducing a double-stranded break. In some embodiments, during the simultaneous integration of a plurality of exogenous nucleic acids at multiple loci, i.e., in the presence of multiple nucleases, the frequency of integration at any single loci is substantially higher compared to the frequency of integration at the same locus during a single integration event, i.e., in the presence of a single nuclease. Such an advantage is demonstrated in Example 6 (Section 7.5.2) below. Without being bound by theory, it is believed that the presence and activity of multiple nucleases, creating double-strand breaks (DSBs) at a plurality of target sites, enriches for transformants that successfully repair the DSBs by integrating donor DNA(s) at the cut site, and/or selects against transformants unable to repair the DSBs. Since DSBs are toxic to cells, it is believed that an increased number of nucleases leads to more DSBs, and correspondingly, an enrichment for cells able to repair the DSBs through HR-mediated integration of donor DNA(s).

In some embodiments, this increased frequency of integration obviates the requirement for co-integration of one or more selectable markers for the identification of the plurality of recombination events. In some embodiments, markerless recovery of a transformed cell comprising a plurality of successfully integrated exogenous nucleic acid occurs within a frequency of about one every 1000, 900, 800, 700, 600, 500, 400, 300, 200 or 100 contacted host cells, or clonal populations thereof, screened. In particular embodiments, markerless recovery occurs within a frequency of about one every 90, 80, 70, 60, 50, 40, 30, 20, or 10 contacted host cells, or clonal populations thereof, screened. In more particular embodiments, markerless recovery occurs within a frequency of about one every 9, 8, 7, 6, 5, 4, 3, or 2 contacted host cells, or clonal populations thereof, screened. In more particular embodiments, the host cell is a yeast cell, and the increased frequency of integration derives from yeast's increased capacity for homologous recombination relative to other host cell types.

6.2.1. Methods for Metabolic Pathway Engineering

The methods and compositions described herein provide particular advantages for constructing recombinant organisms comprising optimized biosynthetic pathways, for example, towards the conversion of biomass into biofuels, pharmaceuticals or biomaterials. Functional non-native biological pathways have been successfully constructed in microbial hosts for the production of precursors to the anti-malarial drug artemisinin (see, e.g., Martin et al., *Nat Biotechnol* 21:796-802 (2003); fatty acid derives fuels and chemicals (e.g., fatty esters, fatty alcohols and waxes; see, e.g., Steen et al., *Nature* 463:559-562 (2010); methyl halide-derived fuels and chemicals (see, e.g., Bayer et al., *J Am Chem Soc* 131:6508-6515 (2009); polyketide synthases that make cholesterol lowering drugs (see, e.g., Ma et al., *Science* 326:589-592 (2009); and polyketides (see, e.g., Kodumal, *Proc Natl Acad Sci USA* 101:15573-15578 (2004).

Traditionally, metabolic engineering, and in particular, the construction of biosynthetic pathways, has proceeded in a one-at-a-time serial fashion whereby pathway components have been introduced, i.e., integrated into the host cell genome at a single loci at a time. The methods of integration provided herein can be utilized to reduce the time typically required to engineer a host cell, for example, a microbial cell, to comprise one or more heterologous nucleotide sequences encoding enzymes of a new metabolic pathway, i.e., a metabolic pathway that produces a metabolite that is not endogenously produced by the host cell. In other particular embodiments, the methods of integration provided herein can be used to efficiently engineer a host cell to comprise one or more heterologous nucleotide sequences encoding enzymes of a metabolic pathway that is endogenous to the host cell, i.e., a metabolic pathway that produces a metabolite that is endogenously produced by the host cell. In one example, a design strategy may seek to replace three native genes of a host cell with a complementary exogenous pathway. Modifying these three endogenous loci using the current state of the art requires three separate transformations. By contrast, the methods of simultaneous multiple integration provided herein enables all three integrations to be performed in a single transformation, thus reducing the rounds of engineering needed by three-fold. Moreover, the methods enable the porting of DNA assemblies, comprising optimized pathway components integrated at multiple sites in one host cell chassis, to analogous sites in a second host cell chassis. By reducing the number of rounds needed to engineer a desired genotype, the pace of construction of metabolic pathways is substantially increased.

6.2.1.1 Isoprenoid Pathway Engineering

In some embodiments, the methods provided herein can be utilized to simultaneously introduce or replace one or more components of a biosynthetic pathway to modify the product profile of an engineered host cell. In some embodiments, the biosynthetic pathway is the isoprenoid pathway.

Terpenes are a large class of hydrocarbons that are produced in many organisms. When terpenes are chemically modified (e.g., via oxidation or rearrangement of the carbon skeleton) the resulting compounds are generally referred to as terpenoids, which are also known as isoprenoids. Isoprenoids play many important biological roles, for example, as quinones in electron transport chains, as components of membranes, in subcellular targeting and regulation via protein prenylation, as photosynthetic pigments including carotenoids, chlorophyll, as hormones and cofactors, and as plant defense compounds with various monoterpenes, sesquiterpenes, and diterpenes. They are industrially useful as antibiotics, hormones, anticancer drugs, insecticides, and chemicals.

Terpenes are derived by linking units of isoprene ($C_5H_8$), and are classified by the number of isoprene units present. Hemiterpenes consist of a single isoprene unit. Isoprene itself is considered the only hemiterpene. Monoterpenes are made of two isoprene units, and have the molecular formula $C_{10}H_{16}$. Examples of monoterpenes are geraniol, limonene, and terpineol. Sesquiterpenes are composed of three isoprene units, and have the molecular formula $C_{15}H_{24}$. Examples of sesquiterpenes are farnesenes and farnesol. Diterpenes are made of four isoprene units, and have the molecular formula $C_{20}H_{32}$. Examples of diterpenes are cafestol, kahweol, cembrene, and taxadiene. Sesterterpenes are made of five isoprene units, and have the molecular formula $C_{25}H_{40}$. An example of a sesterterpenes is geranylfarnesol. Triterpenes consist of six isoprene units, and have the molecular formula $C_{30}H_{48}$. Tetraterpenes contain eight isoprene units, and have the molecular formula $C_{40}H_{64}$. Biologically important tetraterpenes include the acyclic lycopene, the monocyclic gamma-carotene, and the bicyclic alpha- and beta-carotenes. Polyterpenes consist of long chains of many isoprene units. Natural rubber consists of polyisoprene in which the double bonds are cis.

Terpenes are biosynthesized through condensations of isopentenyl pyrophosphate (isopentenyl diphosphate or IPP) and its isomer dimethylallyl pyrophosphate (dimethylallyl diphosphate or DMAPP). Two pathways are known to generate IPP and DMAPP, namely the mevalonate-dependent (MEV) pathway of eukaryotes (FIG. 3), and the mevalonate-independent or deoxyxylulose-5-phosphate (DXP) pathway of prokaryotes. Plants use both the MEV pathway and the DXP pathway. IPP and DMAPP in turn are condensed to polyprenyl diphosphates (e.g., geranyl disphosphate or GPP, farnesyl diphosphate or FPP, and geranylgeranyl diphosphate or GGPP) through the action of prenyl disphosphate synthases (e.g., GPP synthase, FPP synthase, and GGPP synthase, respectively). The polyprenyl diphosphate intermediates are converted to more complex isoprenoid structures by terpene synthases.

Terpene synthases are organized into large gene families that form multiple products. Examples of terpene synthases include monoterpene synthases, which convert GPP into monoterpenes; diterpene synthases, which convert GGPP into diterpenes; and sesquiterpene synthases, which convert FPP into sesquiterpenes. An example of a sesquiterpene synthase is farnesene synthase, which converts FPP to farnesene. Terpene synthases are important in the regulation of pathway flux to an isoprenoid because they operate at metabolic branch points and dictate the type of isoprenoid produced by the cell. Moreover, the terpene synthases hold the key to high yield production of such terpenes. As such, one strategy to improve pathway flux in hosts engineered for heterologous isoprenoid production is to introduce multiple copies of nucleic acids encoding terpene synthases. For example, in engineered microbes comprising the MEV pathway where the production of sesquiterpenes such as farnesene is desired, a sesquiterpene synthase, e.g., a farnesene synthase is utilized as the terminal enzyme of the pathway, and multiple copies of farnesene synthase genes may be introduced into the host cell towards the generation of a strain optimized for farnesene production.

Because the biosynthesis of any isoprenoid relies on the same pathway components upstream of the prenyl disphosphate synthase and terpene synthase, these pathway components, once engineered into a host "platform" strain, can be utilized towards the production of any sesquiterpene, and the identity of the sesquiterpene can be dictated by the particular sesquiterpene synthase introduced into the host cell. Moreover, where production of terpenes having different isoprene units is desired, for example a monoterpene instead of a sesquiterpene, both the prenyl diphosphate synthase and the terpene synthase can be replaced to produce the different terpene while still utilizing the upstream components of the pathway.

Accordingly, the methods and compositions provided herein can be utilized to efficiently modify a host cell comprising an isoprenoid producing pathway, e.g., the MEV pathway to produce a desired isoprenoid. In some embodiments, the host cell comprises the MEV pathway, and the methods of simultaneous multiple integration provided herein can be utilized to simultaneously introduce multiple copies of a prenyl diphosphate synthase and/or a terpene synthase to define the terpene product profile of the host cell. In some embodiments, the prenyl diphosphate synthase is GPP synthase and the terpene synthase is a monoterpene synthase. In some embodiments, the prenyl diphosphate synthase is FPP synthase and the terpene synthase is a sesquiterpene synthase. In some embodiments, the prenyl diphosphate synthase is GGPP synthase and the terpene synthase is a diterpene synthase. In other embodiments, the host cell comprises the MEV pathway and a prenyl diphosphate synthase and/or a terpene synthase for the production of a first type of terpene, for example, farnesene, and the methods of simultaneous multiple integration provided herein can be utilized to simultaneously replace one or more copies of the prenyl diphosphate synthase and/or a terpene synthase to produce a second type of terpene, for example, amorphadiene. These embodiments are exemplified in Examples 3 and 4 below. The methods provided herein can be similarly utilized towards the construction and/or modification of any biosynthetic pathway which utilizes multiple copies of pathway components, and are particularly useful for engineering host cells whose product profile can be readily modified with the addition or exchange of multiple copies of a single pathway component.

6.2.1.2 Methods of Generating Combinatorial Integration Libraries

Once biosynthetic pathways are constructed, the expression levels of all the components need to be orchestrated to optimize metabolic flux and achieve high product titers. Common approaches for optimizing flux include varying the identity of the pathway component gene, the codon optimization of the gene, the use of solubility tags, the use of truncations or known mutations, and the expression context of the gene (i.e. promoter and terminator choice). To sample this variability in the course of building a strain using traditional methods requires generating and archiving an impractically large number of strains. For example, if a strain engineer plans to integrate constructs at three loci, and has devised 10 variants for each locus, 1,000 strains would need to be generated to fully sample the combinatorial diversity. Since pathway genes work in concert, and not all metabolite intermediates can easily be screened for, it is often impossible to evaluate the individual contribution of the pathway genes after each integration cycle. Thus, strain engineers routinely make choices that severely limit the design space that they sample when constructing a novel metabolic pathway.

To better identify the optimal pathway design, the methods of genomic modification provided herein can be utilized to generate strains comprising combinatorial libraries of rationally designed integration constructs. The methods rely on the introduction of one or more nucleases and one or more donor DNA assemblies into the cell to facilitate multiple simultaneous integration of donor DNA at specified locations in the genome. However, to generate a diversity of engineered strains, the methods comprise co-transforming a library of donor DNAs, i.e., a mixture of integration constructs for each targeted locus, such that combinatorial integration libraries of host strains can be generated (FIG. 4). The high frequency of multiple integrations achieved means that the resultant strains can reasonably be screened directly for product without extensive genomic quality control, and the identity of top strains can be determined after screening, for example, by sequencing. This method removes the burden of individual strain generation, quality control and archiving, and allows the engineer to generate diverse integration combinations in a single tube, and sort out the best performing strains by screening, e.g., for the terminal product of the pathway.

Thus, in some embodiments, the methods for integrating a plurality of exogenous nucleic acids into a host cell genome provided herein comprise:

(d) contacting a host cell with:

(i) a plurality of libraries, wherein each library (L)x comprises a plurality of exogenous nucleic acids, wherein a selected exogenous nucleic acid comprises, in a 5' to 3' orientation, a first homology region $(HR1)_x$, any nucleic acid of interest selected from the group $(D)_x$, and a second homology region $(HR2)_x$, wherein $(HR1)_x$ and $(HR2)_x$ are capable of initiating host cell mediated homologous recombination of said selected exogenous nucleic acid at a target site $(TS)_x$ of said host cell genome; and (ii) for each said target site $(TS)_x$, a nuclease $(N)_x$ capable of cleaving at $(TS)_x$, whereupon said cleaving results in homologous recombination of said selected exogenous nucleic acid at $(TS)_x$;

and (e) recovering a host cell wherein an exogenous nucleic acid from each library $(L)_x$ has integrated at each selected target sequence $(TS)_x$, wherein x is any integer from 1 to n wherein n is at least 2.

A schematic representation of this method is provided in FIG. 4.

Also provided herein is a host cell comprising:

(a) a plurality of libraries, wherein each library (L)x comprises a plurality of exogenous nucleic acids, wherein a selected exogenous nucleic acid comprises, in a 5' to 3' orientation, a first homology region $(HR1)_x$, any nucleic acid of interest selected from the group $(D)_x$, and a second homology region $(HR2)_x$, wherein $(HR1)_x$ and $(HR2)_x$ are capable of initiating host cell mediated homologous recombination of said selected exogenous nucleic acid at a target site $(TS)_x$ of said host cell genome; and (b) for each said target site $(TS)_x$, a nuclease $(N)_x$ capable of cleaving at $(TS)_x$, whereupon said cleaving results in homologous recombination of said selected exogenous nucleic acid at $(TS)_x$, wherein x is any integer from 1 to n wherein n is at least 2.

In some embodiments, each library $(L)_x$ comprises exogenous nucleic acids encoding enzymes of a common biosynthetic pathway. In some embodiments, the group $(D)_x$ comprises at least $10^1$, $10^2$, $10^3$, $10^4$, $10^5$, $10^6$, or more than $10^6$ unique nucleic acids of interest. In some embodiments, each library $(L)_x$ comprises a plurality of exogenous nucleic acids encoding variants of an enzyme of a biosynthetic pathway. As used herein, the term "variant" refers to an enzyme of a biosynthetic pathway that compared to a selected enzyme has a different nucleotide or amino acid sequence. For example, in some embodiments, a library $(L)_x$ comprises sesquiterpene synthase variants, and compared to the wild-type version of the selected sesquiterpene synthase, the sesquiterpene synthase variant may comprise nucleotide additions, deletions, and/or substitutions that may or may not result in changes to the corresponding amino acid sequence. In other embodiments, the enzyme variant comprises amino acid additions, deletions and/or substitutions relative to a reference enzyme, e.g., the wild-type version.

In some embodiments, the host cell comprises one or more heterologous nucleotide sequences encoding one or more enzymes of a biosynthetic pathway prior to said contacting. In some embodiments, the one or more heterologous nucleotide sequences encoding one or more enzymes of a biosynthetic pathway are genomically integrated.

6.3 Integration Polynucleotides

Advantageously, an integration polynucleotide, i.e., donor DNA, facilitates integration of one or more exogenous nucleic acid constructs into a selected target site of a host cell genome. In preferred embodiments, an integration polynucleotide comprises an exogenous nucleic acid $(ES)_x$ comprising a first homology region $(HR1)_x$ and a second homology region $(HR2)_x$, and optionally a nucleic acid of interest positioned between $(HR1)_x$ and $(HR2)_x$. In some embodiments, the integration polynucleotide is a linear DNA molecule. In other embodiments, the integration polynucleotide is a circular DNA molecule.

The integration polynucleotide can be generated by any technique apparent to one skilled in the art. In certain embodiments, the integration polynucleotide is generated using polymerase chain reaction (PCR) and molecular cloning techniques well known in the art. See, e.g., *PCR Technology: Principles and Applications for DNA Amplification*, ed. H A Erlich, Stockton Press, New York, N.Y. (1989); Sambrook et al., 2001, *Molecular Cloning—A Laboratory Manual, 3rd* edition, Cold Spring Harbor Laboratory, Cold Spring Harbor, N.Y.; *PCR Technology: Principles and Applications for DNA Amplification*, ed. H A Erlich, Stockton Press, New York, N.Y. (1989); U.S. Pat. No. 8,110,360.

6.3.1. Genomic Integration Sequences

In preferred embodiments, an integration polynucleotide comprises an exogenous nucleic acid $(ES)_x$ comprising a first homology region $(HR1)_x$ and a second homology region $(HR2)_x$, wherein $(HR1)_x$ and $(HR2)_x$ are capable of initiating host cell mediated homologous recombination at a selected target site $(TS)_x$ within the host cell genome. To integrate an exogenous nucleic acid into the genome by homologous recombination, the integration polynucleotide preferably comprises $(HR1)_x$ at one terminus and $(HR2)_x$ at the other terminus. In some embodiments, $(HR1)_x$ is homologous to a 5' region of the selected genomic target site $(TS)_x$, and $(HR2)_x$, is homologous to a 3' region of the selected target site $(TS)_x$. In some embodiments, $(HR1)_x$ is about 70%, 75%, 80%, 85%, 90%, 95% or 100% homologous to a 5' region of the selected genomic target site $(TS)_x$. In some embodiments, $(HR2)_x$, is about 70%, 75%, 80%, 85%, 90%, 95% or 100% homologous to a 3' region of the selected target site $(TS)_x$.

In certain embodiments, $(HR1)_x$ is positioned 5' to a nucleic acid of interest $(D)_x$. In some embodiments, $(HR1)_x$ is positioned immediately adjacent to the 5' end of $(D)_x$. In some embodiments, $(HR1)_x$ is positioned upstream to the 5' of $(D)_x$. In certain embodiments, $(HR2)_x$ is positioned 3' to a nucleic acid of interest $(D)_x$. In some embodiments, $(HR2)_x$ is positioned immediately adjacent to the 3' end of $(D)_x$. In some embodiments, $(HR2)_x$ is positioned downstream to the 3' of $(D)_x$.

Properties that may affect the integration of an integration polynucleotide at a particular genomic locus include but are not limited to: the lengths of the genomic integration sequences, the overall length of the excisable nucleic acid construct, and the nucleotide sequence or location of the genomic integration locus. For instance, effective heteroduplex formation between one strand of a genomic integration sequence and one strand of a particular locus in a host cell genome may depend on the length of the genomic integration sequence. An effective range for the length of a genomic integration sequence is 50 to 5,000 nucleotides. For a discussion of effective lengths of homology between genomic integration sequences and genomic loci. See, Hasty et al., *Mol Cell Biol* 11:5586-91 (1991).

In some embodiments, $(HR1)_x$ and $(HR2)_x$ can comprise any nucleotide sequence of sufficient length and sequence identity that allows for genomic integration of the exogenous nucleic acid $(ES)_x$ at any yeast genomic locus. In certain embodiments, each of $(HR1)_x$ and $(HR2)_x$ independently consists of about 50 to 5,000 nucleotides. In certain embodiments, each of $(HR1)_x$ and $(HR2)_x$ independently consists of about 100 to 2,500 nucleotides. In certain embodiments, each of $(HR1)_x$ and $(HR2)_x$ independently consists of about 100 to 1,000 nucleotides. In certain embodiments, each of $(HR1)_x$ and $(HR2)_x$ independently consists of about 250 to 750 nucleotides. In certain embodiments, each of $(HR1)_x$ and $(HR2)_x$ independently consists of about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900 or 5,000 nucleotides. In some embodiments, each of $(HR1)_x$ and $(HR2)_x$ independently consists of about 500 nucleotides.

6.3.2. Nucleic Acids of Interest

In some embodiments, the integration polynucleotide further comprises a nucleic acid of interest $(D)_x$. The nucleic acid of interest can be any DNA segment deemed useful by one of skill in the art. For example, the DNA segment may comprise a gene of interest that can be "knocked in" to a host genome. In other embodiments, the DNA segment functions as a "knockout" construct that is capable of specifically disrupting a target gene upon integration of the construct into the target site of the host cell genome, thereby rendering the disrupted gene non-functional. Useful examples of a nucleic acid of interest $(D)_x$ include but are not limited to: a protein-coding sequence, reporter gene, fluorescent marker coding sequence, promoter, enhancer, terminator, transcriptional activator, transcriptional repressor, transcriptional activator binding site, transcriptional repressor binding site, intron, exon, poly-A tail, multiple cloning site, nuclear localization signal, mRNA stabilization signal, integration loci, epitope tag coding sequence, degradation signal, or any other naturally occurring or synthetic DNA molecule. In some embodiments, $(D)_x$ can be of natural origin. Alternatively, $(D)_x$ can be completely of synthetic origin, produced in vitro. Furthermore, $(D)_x$ can comprise any combination of isolated naturally occurring DNA molecules, or any combination of an isolated naturally occurring DNA molecule and a synthetic DNA molecule. For example, $(D)_x$ may comprise a heterologous promoter operably linked to a protein coding sequence, a protein coding sequence linked to a poly-A tail, a protein coding sequence linked in-frame with a epitope tag coding sequence, and the like. The nucleic acid of interest $(D)_x$ may be obtained by standard procedures known in the art from cloned DNA (e.g., a DNA "library"), by chemical synthesis, by cDNA cloning, or by the cloning of genomic DNA, or fragments thereof, purified from the desired cell, or by PCR amplification and cloning. See, for example, Sambrook et al., *Molecular Cloning, A Laboratory Manual,* 3d. ed., Cold Spring Harbor Laboratory Press, Cold Spring Harbor, N.Y. (2001); Glover, D. M. (ed.), *DNA Cloning: A Practical Approach,* 2d. ed., MRL Press, Ltd., Oxford, U.K. (1995).

In particular embodiments, the nucleic acid of interest $(D)_x$ does not comprise nucleic acid encoding a selectable marker. In these embodiments, the high efficiency of integration provided by the methods described herein allows for the screening and identification of integration events without the requirement for growth of transformed cells on selection media. However, in other embodiments where growth on selective media is nonetheless desired, the nucleic acid of interest $(D)_x$ can comprise a selectable marker that may be used to select for the integration of the exogenous nucleic acid into a host genome.

A wide variety of selectable markers are known in the art (see, for example, Kaufman, *Meth. Enzymol.,* 185:487 (1990); Kaufman, *Meth. Enzymol.,* 185:537 (1990); Srivastava and Schlessinger, *Gene,* 103:53 (1991); Romanos et al., in *DNA Cloning* 2: *Expression Systems,* 2nd Edition, pages 123-167 (IRL Press 1995); Markie, *Methods Mol. Biol.,* 54:359 (1996); Pfeifer et al., *Gene,* 188:183 (1997); Tucker and Burke, *Gene,* 199:25 (1997); Hashida-Okado et al., FEBS Letters, 425:117 (1998)). In some embodiments, the selectable marker is a drug resistant marker. A drug resistant marker enables cells to detoxify an exogenous drug that would otherwise kill the cell. Illustrative examples of drug resistant markers include but are not limited to those which confer resistance to antibiotics such as ampicillin, tetracycline, kanamycin, bleomycin, streptomycin, hygromycin, neomycin, Zeocin™, and the like. In other embodiments, the selectable marker is an auxotrophic marker. An auxotrophic marker allows cells to synthesize an essential component (usually an amino acid) while grown in media that lacks that essential component. Selectable auxotrophic gene sequences include, for example, hisD, which allows growth in histidine free media in the presence of histidinol. Other selectable markers include a bleomycin-resistance gene, a metallothionein gene, a hygromycin B-phosphotransferase gene, the AURI gene, an adenosine deaminase gene, an aminoglycoside phosphotransferase gene, a dihydrofolate reductase gene, a thymidine kinase gene, a xanthine-guanine phosphoribosyltransferase gene, and the like. In other embodiments, the selectable marker is a marker other than one which rescues an auxotophic mutation. For example, the host cell strain can comprise mutations other than auxotrophic mutations, for example, mutations that are not lethal to the host and that also do not cause adverse effects on the intended use of the strain, e.g., industrial fermentation, so long as the mutations can be identified by a known selection method.

Host cell transformants comprising a chromosomally integrated polynucleotide can also be identified by selecting host cell transformants exhibiting other traits encoded by individual DNA segments or by combinations of DNA segments, e.g., expression of peptides that emit light, or by molecular analysis of individual host cell colonies, e.g., by restriction enzyme mapping, PCR amplification, or sequence analysis of isolated assembled polynucleotides or chromosomal integration sites.

6.4 Nucleases

In some embodiments of the methods described herein, a host cell genome is contacted with one or more nucleases capable of cleaving, i.e., causing a double-stranded break at a designated region within a selected target site. In some embodiments, a double-strand break inducing agent is any agent that recognizes and/or binds to a specific polynucleotide recognition sequence to produce a break at or near the recognition sequence. Examples of double-strand break inducing agents include, but are not limited to, endonucleases, site-specific recombinases, transposases, topoisomerases, and zinc finger nucleases, and include modified derivatives, variants, and fragments thereof.

In some embodiments, each of the one or more nucleases is capable of causing a double-strand break at a designated region within a selected target site $(TS)_x$. In some embodiments, the nuclease is capable of causing a double-strand break at a region positioned between the 5' and 3' regions of $(TS)_x$ with which $(HR1)_x$ and $(HR2)_x$ share homology, respectively. In other embodiments, the nuclease is capable of causing a double-strand break at a region positioned upstream or downstream of the 5' and 3' regions of $(TS)_x$.

A recognition sequence is any polynucleotide sequence that is specifically recognized and/or bound by a double-strand break inducing agent. The length of the recognition site sequence can vary, and includes, for example, sequences that are at least 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length.

In some embodiments, the recognition sequence is palindromic, that is, the sequence on one strand reads the same in the opposite direction on the complementary strand. In some embodiments, the nick/cleavage site is within the recognition sequence. In other embodiments, the nick/cleavage site is outside of the recognition sequence. In some embodiments, cleavage produces blunt end termini. In other embodiments, cleavage produces single-stranded overhangs, i.e., "sticky ends," which can be either 5' overhangs, or 3' overhangs.

In some embodiments, the recognition sequence within the selected target site can be endogenous or exogenous to the host cell genome. When the recognition site is an endogenous sequence, it may be a recognition sequence recognized by a naturally-occurring, or native double-strand break inducing agent. Alternatively, an endogenous recognition site could be recognized and/or bound by a modified or engineered double-strand break inducing agent designed or selected to specifically recognize the endogenous recognition sequence to produce a double-strand break. In some embodiments, the modified double-strand break inducing agent is derived from a native, naturally-occurring double-strand break inducing agent. In other embodiments, the modified double-strand break inducing agent is artificially created or synthesized. Methods for selecting such modified or engineered double-strand break inducing agents are known in the art. For example, amino acid sequence variants of the protein(s) can be prepared by mutations in the DNA. Methods for mutagenesis and nucleotide sequence alterations include, for example, Kunkel, (1985) *Proc Natl Acad Sci USA* 82:488-92; Kunkel, et al., (1987) *Meth Enzymol* 154:367-82; U.S. Pat. No. 4,873,192; Walker and Gaastra, eds. (1983) *Techniques in Molecular Biology* (MacMillan Publishing Company, New York) and the references cited therein. Guidance regarding amino acid substitutions not likely to affect biological activity of the protein is found, for example, in the model of Dayhoff, et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double strand break inducing activity are known and generally measure the overall activity and specificity of the agent on DNA substrates containing recognition sites.

In some embodiments of the methods provided herein, one or more of the nucleases is an endonuclease. Endonucleases are enzymes that cleave the phosphodiester bond within a polynucleotide chain, and include restriction endonucleases that cleave DNA as specific sites without damaging the bases. Restriction endonucleases include Type I, Type II, Type III, and Type IV endonucleases, which further include subtypes. Restriction endonucleases are further described and classified, for example in the REBASE database (webpage at rebase.neb.com; Roberts, et al., (2003) *Nucleic Acids Res* 31:418-20), Roberts, et al., (2003) *Nucleic Acids Res* 31:1805-12, and Belfort, et al., (2002) in *Mobile DNA II*, pp. 761-783, Eds. Craigie, et al., ASM Press, Washington, D.C.

As used herein, endonucleases also include homing endonucleases, which like restriction endonucleases, bind and cut at a specific recognition sequence. However the recognition sites for homing endonucleases are typically longer, for example, about 18 bp or more. Homing endonucleases, also known as meganucleases, have been classified into the following families based on conserved sequence motifs: an LAGLIDADG (SEQ ID NO: 50) homing endonuclease, an HNH homing endonuclease, a His-Cys box homing endonuclease, a GIY-YIG (SEQ ID NO: 51) homing endonuclease, and a cyanobacterial homing endonuclease. See, e.g., Stoddard, *Quarterly Review of Biophysics* 38(1): 49-95 (2006). These families differ greatly in their conserved nuclease active-site core motifs and catalytic mechanisms, biological and genomic distributions, and wider relationship to non-homing nuclease systems. See, for example, Guhan and Muniyappa (2003) *Crit Rev Biochem Mol Biol* 38:199-248; Lucas, et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure, et al., (2002) *Nat Struct Biol* 9:764. Examples of useful specific homing endonucleases from these families include, but are not limited to: I-CreI (see, Rochaix et al., *Nucleic Acids Res.* 13: 975-984 (1985), I-MsoI (see, Lucas et al., *Nucleic Acids Res.* 29: 960-969 (2001), I-SceI (see, Foury et al., *FEBS Lett.* 440: 325-331 (1998), I-SceIV (see, Moran et al., *Nucleic Acids Res.* 20: 4069-4076 (1992), H-DreI (see, Chevalier et al., *Mol. Cell* 10: 895-905 (2002), I-HmuI (see, Goodrich-Blair et al., *Cell* 63: 417-424 (1990); Goodrich-Blair et al., *Cell* 84: 211-221 (1996), I-PpoI (see, Muscarella et al., *Mol. Cell. Biol.* 10: 3386-3396 (1990), I-DirI (see, Johansen et al., *Cell* 76: 725-734 (1994); Johansen, *Nucleic Acids Res.* 21: 4405 (1993), I-NjaI (see, Elde et al., *Eur. J. Biochem.* 259: 281-288 (1999); De Jonckheere et al., *J. Eukaryot. Microbiol.* 41: 457-463 (1994), I-NanI (see, Elde et al., *S. Eur. J. Biochem.* 259: 281-288 (1999); De Jonckheere et al., *J. Eukaryot. Microbiol.* 41: 457-463 (1994)), I-NitI (see, De Jonckheere et al., *J. Eukaryot. Microbiol.* 41: 457-463 (1994); Elde et al., *Eur. J. Biochem.* 259: 281-288 (1999), I-TevI (see, Chu et al., *Cell* 45: 157-166 (1986), I-TevII (see, Tomaschewski et al., *Nucleic Acids Res.* 15: 3632-3633 (1987), I-TevIII (see, Eddy et al., *Genes Dev.* 5: 1032-1041 (1991), F-TevI (see, Fujisawa et al., *Nucleic Acids Res.* 13: 7473-7481 (1985), F-TevII (see, Kadyrov et al., *Dokl. Biochem.* 339: 145-147 (1994); Kaliman, *Nucleic Acids Res.* 18: 4277 (1990), F-CphI (see, Zeng et al., *Curr. Biol.* 19: 218-222 (2009), PI-MgaI (see, Saves et al., *Nucleic Acids Res.* 29:4310-4318 (2001), I-CsmI (see, Colleaux et al., *Mol. Gen. Genet.* 223:288-296 (1990), I-CeuI (see, Turmel et al., *J. Mol. Biol.* 218: 293-311 (1991) and PI-SceI (see, Hirata et al., *J. Biol. Chem.* 265: 6726-6733 (1990).

In some embodiments of the methods described herein, a naturally occurring variant, and/or engineered derivative of a homing endonuclease is used. Methods for modifying the kinetics, cofactor interactions, expression, optimal conditions, and/or recognition site specificity, and screening for activity are known. See, for example, Epinat, et al., (2003) *Nucleic Acids Res* 31:2952-62; Chevalier, et al., (2002) *Mol Cell* 10:895-905; Gimble, et al., (2003) *Mol Biol* 334:993-1008; Seligman, et al., (2002) *Nucleic Acids Res* 30:3870-9; Sussman, et al., (2004) *J Mol Riot* 342:31-41; Rosen, et al., (2006) *Nucleic Acids Res* 34:4791-800; Chames, et al., (2005) *Nucleic Acids Res* 33:e178; Smith, et al., (2006) *Nucleic Acids Res* 34:e149; Gruen, et al., (2002) *Nucleic Acids Res* 30:e29; Chen and Zhao, (2005) *Nucleic Acids Res*

33:e154; WO2005105989; WO2003078619; WO2006097854; WO2006097853; WO2006097784; and WO2004031346. Useful homing endonucleases also include those described in WO04/067736; WO04/067753; WO06/097784; WO06/097853; WO06/097854; WO07/034262; WO07/049095; WO07/049156; WO07/057781; WO07/060495; WO08/152524; WO09/001159; WO09/095742; WO09/095793; WO10/001189; WO10/015899; and WO10/046786.

Any homing endonuclease can be used as a double-strand break inducing agent including, but not limited to: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-Scel, PI-TfuI, PI-TfuII, PI-Thyl, PI-TliI, or PI-TliII, or any variant or derivative thereof.

In some embodiments, the endonuclease binds a native or endogenous recognition sequence. In other embodiments, the endonuclease is a modified endonuclease that binds a non-native or exogenous recognition sequence and does not bind a native or endogenous recognition sequence.

In some embodiments of the methods provided herein, one or more of the nucleases is a TAL-effector DNA binding domain-nuclease fusion protein (TALEN). TAL effectors of plant pathogenic bacteria in the genus *Xanthomonas* play important roles in disease, or trigger defense, by binding host DNA and activating effector-specific host genes. see, e.g., Gu et al. (2005) *Nature* 435:1122-5; Yang et al., (2006) *Proc. Natl. Acad. Sci. USA* 103:10503-8; Kay et al., (2007) *Science* 318:648-51; Sugio et al., (2007) *Proc. Natl. Acad. Sci. USA* 104:10720-5; Romer et al., (2007) *Science* 318:645-8; Boch et al., (2009) *Science* 326(5959):1509-12; and Moscou and Bogdanove, (2009) 326(5959):1501. A TAL effector comprises a DNA binding domain that interacts with DNA in a sequence-specific manner through one or more tandem repeat domains. The repeated sequence typically comprises 34 amino acids, and the repeats are typically 91-100% homologous with each other. Polymorphism of the repeats is usually located at positions 12 and 13, and there appears to be a one-to-one correspondence between the identity of repeat variable-diresidues at positions 12 and 13 with the identity of the contiguous nucleotides in the TAL-effector's target sequence.

The TAL-effector DNA binding domain may be engineered to bind to a desired target sequence, and fused to a nuclease domain, e.g., from a type II restriction endonuclease, typically a nonspecific cleavage domain from a type II restriction endonuclease such as FokI (see e.g., Kim et al. (1996) *Proc. Natl. Acad. Sci. USA* 93:1156-1160). Other useful endonucleases may include, for example, HhaI, HindIII, Nod, BbvCI, EcoRI, BglI, and AlwI. Thus, in preferred embodiments, the TALEN comprises a TAL effector domain comprising a plurality of TAL effector repeat sequences that, in combination, bind to a specific nucleotide sequence in the target DNA sequence, such that the TALEN cleaves the target DNA within or adjacent to the specific nucleotide sequence. TALENS useful for the methods provided herein include those described in WO10/079430 and U.S. Patent Application Publication No. 2011/0145940.

In some embodiments, the TAL effector domain that binds to a specific nucleotide sequence within the target DNA can comprise 10 or more DNA binding repeats, and preferably 15 or more DNA binding repeats. In some embodiments, each DNA binding repeat comprises a repeat variable-diresidue (RVD) that determines recognition of a base pair in the target DNA sequence, wherein each DNA binding repeat is responsible for recognizing one base pair in the target DNA sequence, and wherein the RVD comprises one or more of: HD for recognizing C; NG for recognizing T; NI for recognizing A; NN for recognizing G or A; NS for recognizing A or C or G or T; N* for recognizing C or T, where * represents a gap in the second position of the RVD; HG for recognizing T; H* for recognizing T, where * represents a gap in the second position of the RVD; IG for recognizing T; NK for recognizing G; HA for recognizing C; ND for recognizing C; HI for recognizing C; HN for recognizing G; NA for recognizing G; SN for recognizing G or A; and YG for recognizing T.

In some embodiments of the methods provided herein, one or more of the nucleases is a site-specific recombinase. A site-specific recombinase, also referred to as a recombinase, is a polypeptide that catalyzes conservative site-specific recombination between its compatible recombination sites, and includes native polypeptides as well as derivatives, variants and/or fragments that retain activity, and native polynucleotides, derivatives, variants, and/or fragments that encode a recombinase that retains activity. For reviews of site-specific recombinases and their recognition sites, see, Sauer (1994) *Curr Op Biotechnol* 5:521-7; and Sadowski, (1993) *FASEB* 7:760-7. In some embodiments, the recombinase is a serine recombinase or a tyrosine recombinase. In some embodiments, the recombinase is from the Integrase or Resolvase families. In some embodiments, the recombinase is an integrase selected from the group consisting of FLP, Cre, lambda integrase, and R. For other members of the Integrase family, see for example, Esposito, et al., (1997) *Nucleic Acids Res* 25:3605-14 and Abremski, et al., (1992) *Protein Eng* 5:87-91. Methods for modifying the kinetics, cofactor interaction and requirements, expression, optimal conditions, and/or recognition site specificity, and screening for activity of recombinases and variants are known, see for example Miller, et al., (1980) *Cell* 20:721-9; Lange-Gustafson and Nash, (1984) *J Biol Chem* 259:12724-32; Christ, et al., (1998) *J Mol Biol* 288:825-36; Lorbach, et al., (2000) *J Mol Biol* 296:1175-81; Vergunst, et al., (2000) *Science* 290:979-82; Dorgai, et al., (1995) *J Mol Biol* 252:178-88; Dorgai, et al., (1998) *J Mol Biol* 277:1059-70; Yagu, et al., (1995) *J Mol Biol* 252:163-7; Sclimente, et al., (2001) *Nucleic Acids Res* 29:5044-51; Santoro and Schultze, (2002) *Proc Natl Acad Sci USA* 99:4185-90; Buchholz and Stewart, (2001) *Nat Biotechnol* 19:1047-52; Voziyanov, et al., (2002) *Nucleic Acids Res* 30:1656-63; Voziyanov, et al., (2003) *J Mol Biol* 326:65-76; Klippel, et al., (1988) *EMBO J* 7:3983-9; Arnold, et al., (1999) *EMBO J* 18:1407-14; WO03/08045; WO99/25840; and WO99/25841. The recognition sites range from about 30 nucleotide minimal sites to a few hundred nucleotides. Any recognition site for a recombinase can be used, including naturally occurring sites, and variants. Variant recognition sites are known, see for example Hoess, et al., (1986) *Nucleic Acids Res* 14:2287-300; Albert, et al., (1995) *Plant J* 7:649-59; Thomson, et al., (2003) *Genesis* 36:162-7; Huang, et al., (1991) *Nucleic Acids Res* 19:443-8; Siebler and Bode, (1997) *Biochemistry* 36:1740-7; Schlake and Bode, (1994) *Biochemistry* 33:12746-51;

Thygarajan, et al., (2001) *Mol Cell Biol* 21:3926-34; Umlauf and Cox, (1988) *EMBO J*7:1845-52; Lee and Saito, (1998) *Gene* 216:55-65; WO01/23545; WO99/25821; WO99/25851; WO01/11058; WO01/07572 and U.S. Pat. No. 5,888,732.

In some embodiments of the methods provided herein, one or more of the nucleases is a transposase. Transposases are polypeptides that mediate transposition of a transposon from one location in the genome to another. Transposases typically induce double strand breaks to excise the transposon, recognize subterminal repeats, and bring together the ends of the excised transposon, in some systems other proteins are also required to bring together the ends during transposition. Examples of transposons and transposases include, but are not limited to, the Ac/Ds, Dt/rdt, Mu-M1/Mn, and Spm(En)/dSpm elements from maize, the Tam elements from snapdragon, the Mu transposon from bacteriophage, bacterial transposons (Tn) and insertion sequences (IS), Ty elements of yeast (retrotransposon), Ta1 elements from *Arabidopsis* (retrotransposon), the P element transposon from *Drosophila* (Gloor, et al., (1991) *Science* 253:1110-1117), the Copia, Mariner and Minos elements from *Drosophila*, the Hermes elements from the housefly, the PiggyBack elements from *Trichplusia ni*, Tc1 elements from *C. elegans*, and IAP elements from mice (retrotransposon).

In some embodiments of the methods provided herein, one or more of the nucleases is a zinc-finger nuclease (ZFN). ZFNs are engineered double-strand break inducing agents comprised of a zinc finger DNA binding domain and a double strand break inducing agent domain. Engineered ZFNs consist of two zinc finger arrays (ZFAs), each of which is fused to a single subunit of a non-specific endonuclease, such as the nuclease domain from the FokI enzyme, which becomes active upon dimerization. Typically, a single ZFA consists of 3 or 4 zinc finger domains, each of which is designed to recognize a specific nucleotide triplet (GGC, GAT, etc.). Thus, ZFNs composed of two "3-finger" ZFAs are capable of recognizing an 18 base pair target site; an 18 base pair recognition sequence is generally unique, even within large genomes such as those of humans and plants. By directing the co-localization and dimerization of two FokI nuclease monomers, ZFNs generate a functional site-specific endonuclease that creates a double-stranded break (DSB) in DNA at the targeted locus.

Useful zinc-finger nucleases include those that are known and those that are engineered to have specificity for one or more target sites (TS) described herein. Zinc finger domains are amenable for designing polypeptides which specifically bind a selected polynucleotide recognition sequence, for example, within the target site of the host cell genome. ZFNs consist of an engineered DNA-binding zinc finger domain linked to a non-specific endonuclease domain, for example nuclease domain from a Type IIs endonuclease such as HO or FokI. Alternatively, engineered zinc finger DNA binding domains can be fused to other double-strand break inducing agents or derivatives thereof that retain DNA nicking/cleaving activity. For example, this type of fusion can be used to direct the double-strand break inducing agent to a different target site, to alter the location of the nick or cleavage site, to direct the inducing agent to a shorter target site, or to direct the inducing agent to a longer target site. In some examples a zinc finger DNA binding domain is fused to a site-specific recombinase, transposase, or a derivative thereof that retains DNA nicking and/or cleaving activity. Additional functionalities can be fused to the zinc-finger binding domain, including transcriptional activator domains, transcription repressor domains, and methylases. In some embodiments, dimerization of nuclease domain is required for cleavage activity.

Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind a 18 nucleotide recognition sequence. Useful designer zinc finger modules include those that recognize various GNN and ANN triplets (Dreier, et al., (2001) *J Biol Chem* 276:29466-78; Dreier, et al., (2000) *J Mol Biol* 303:489-502; Liu, et al., (2002) *J Biol Chem* 277:3850-6), as well as those that recognize various CNN or TNN triplets (Dreier, et al., (2005) *J Biol Chem* 280:35588-97; Jamieson, et al., (2003) *Nature Rev Drug Discov* 2:361-8). See also, Durai, et al., (2005) *Nucleic Acids Res* 33:5978-90; Segal, (2002) *Methods* 26:76-83; Porteus and Carroll, (2005) *Nat Biotechnol* 23:967-73; Pabo, et al., (2001) *Ann Rev Biochem* 70:313-40; Wolfe, et al., (2000) *Ann Rev Biophys Biomol Struct* 29:183-212; Segal and Barbas, (2001) *Curr Opin Biotechnol* 12:632-7; Segal, et al., (2003) *Biochemistry* 42:2137-48; Beerli and Barbas, (2002) *Nat Biotechnol* 20:135-41; Carroll, et al., (2006) *Nature Protocols* 1:1329; Ordiz, et al., (2002) *Proc Natl Acad Sci USA* 99:13290-5; Guan, et al., (2002) *Proc Natl Acad Sci USA* 99:13296-301; WO2002099084; WO00/42219; WO02/42459; WO2003062455; US20030059767; US Patent Application Publication Number 2003/0108880; U.S. Pat. Nos. 6,140,466, 6,511,808 and 6,453,242. Useful zinc-finger nucleases also include those described in WO03/080809; WO05/014791; WO05/084190; WO08/021207; WO09/042186; WO09/054985; and WO10/065123.

6.5 Genomic Target Sites

In the methods provided herein, a nuclease is introduced to the host cell that is capable of causing a double-strand break near or within a genomic target site, which greatly increases the frequency of homologous recombination at or near the cleavage site. In preferred embodiments, the recognition sequence for the nuclease is present in the host cell genome only at the target site, thereby minimizing any off-target genomic binding and cleavage by the nuclease.

In some embodiments, the genomic target site is endogenous to the host cell, such as a native locus. In some embodiments, the native genomic target site is selected according to the type of nuclease to be utilized in the methods of integration provided herein. If the nuclease to be utilized is a zinc finger nuclease, optimal target sites may be selected using a number of publicly available online resources. See, e.g., Reyon et al., *BMC Genomics* 12:83 (2011), which is hereby incorporated by reference in its entirety. For example, Oligomerized Pool Engineering (OPEN) is a highly robust and publicly available protocol for engineering zinc finger arrays with high specificity and in vivo functionality, and has been successfully used to generate ZFNs that function efficiently in plants, zebrafish, and human somatic and pluripotent stem cells. OPEN is a selection-based method in which a pre-constructed randomized pool of candidate ZFAs is screened to identify those with high affinity and specificity for a desired target sequence. ZFNGenome is a GBrowse-based tool for identifying and visualizing potential target sites for OPEN-generated ZFNs. ZFNGenome provides a compendium of potential ZFN target sites in sequenced and annotated genomes of model organisms. ZFNGenome currently includes a total of more than 11.6 million potential ZFN target sites, mapped within the fully sequenced genomes of seven model organisms; *S. cerevisiae, C. reinhardtii, A. thaliana, D. melanogaster, D. rerio, C. elegans*, and *H. sapiens*. Additional model organisms, including three plant species; *Gly-*

*cine max* (soybean), *Oryza sativa* (rice), *Zea mays* (maize), and three animal species *Tribolium castaneum* (red flour beetle), *Mus musculus* (mouse), *Rattus norvegicus* (brown rat) will be added in the near future. ZFNGenome provides information about each potential ZFN target site, including its chromosomal location and position relative to transcription initiation site(s). Users can query ZFNGenome using several different criteria (e.g., gene ID, transcript ID, target site sequence).

If the nuclease to be utilized is a TAL-effector nuclease, in some embodiments, optimal target sites may be selected in accordance with the methods described by Sanjana et al., *Nature Protocols,* 7:171-192 (2012), which is hereby incorporated by reference in its entirety. In brief, TALENs function as dimers, and a pair of TALENs, referred to as the left and right TALENs, target sequences on opposite strands of DNA. TALENs are engineered as a fusion of the TALE DNA-binding domain and a monomeric FokI catalytic domain. To facilitate FokI dimerization, the left and right TALEN target sites are chosen with a spacing of approximately 14-20 bases. Therefore, for a pair of TALENs, each targeting 20-bp sequences, an optimal target site should have the form 5'-$TN^{19}N^{14-20}N^{19}A$-3', where the left TALEN targets 5'-$TN^{19}$-3' and the right TALEN targets the antisense strand of 5'-$N^{19}A$-3' (N=A, G, T or C).

In other embodiments of the methods provided herein, the genomic target site is exogenous to the host cell. For example, one or more genomic target sites can be engineered into the host cell genome using traditional methods, e.g., gene targeting, prior to performing the methods of integration described herein. In some embodiments, multiple copies of the same target sequence are engineered into the host cell genome at different loci, thereby facilitating simultaneous multiple integration events with the use of only a single nuclease that specifically recognizes the target sequence. In other embodiments, a plurality of different target sequences is engineered into the host cell genome at different loci. In some embodiments, the engineered target site comprises a target sequence that is not otherwise represented in the native genome of the host cell. For example, homing endonucleases target large recognition sites (12-40 bp) that are usually embedded in introns or inteins, and as such, their recognition sites are extremely rare, with none or only a few of these sites present in a mammalian-sized genome. Thus, in some embodiments, the exogenous genomic target site is a recognition sequence for a homing endonuclease. In some embodiments, the homing nuclease is selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, or PI-TliII, or any variant or derivative thereof. In particular embodiments, the exogenous genomic target site is the recognition sequence for I-SceI, VDE (PI-SceI), F-CphI, PI-MgaI or PI-MtuII, each of which are provided below.

TABLE 1

Recognition and cleavage sites for select homing endonucleases.

| Nuclease | Recognition sequence |
|---|---|
| I-SceI | TAGGGATAACAGGGTAAT (SEQ ID NO: 52) |
| VDE (PI-SceI) | TATGTCGGGTGCGGAGAAAGAGGTAATGAAA (SEQ ID NO: 53) |
| F-CphI | GATGCACGAGCGCAACGCTCACAA (SEQ ID NO: 54) |
| PI-MgaI | GCGTAGCTGCCCAGTATGAGTCAG (SEQ ID NO: 55) |
| PI-MtuII | ACGTGCACTACGTAGAGGGTCGCACCGCACCGATCTACAA (SEQ ID NO: 56) |

6.6 Delivery

In some embodiments, the one or more nucleases useful for the methods described herein are provided, e.g., delivered into the host cell as a purified protein. In other embodiments, the one or more nucleases are provided via polynucleotide(s) comprising a nucleic acid encoding the nuclease. In other embodiments, the one or more nucleases are introduced into the host cell as purified RNA which can be directly translated in the host cell nucleus.

In certain embodiments, an integration polynucletide, a polynucleotide encoding a nuclease, or a purified nuclease protein as described above, or any combination thereof, may be introduced into a host cell using any conventional technique to introduce exogenous protein and/or nucleic acids into a cell known in the art. Such methods include, but are not limited to, direct uptake of the molecule by a cell from solution, or facilitated uptake through lipofection using, e.g., liposomes or immunoliposomes; particle-mediated transfection; etc. See, e.g., U.S. Pat. No. 5,272,065; Goeddel et al., eds, 1990, *Methods in Enzymology, vol.* 185, Academic Press, Inc., CA; Krieger, 1990, *Gene Transfer and Expression—A Laboratory Manual,* Stockton Press, NY; Sambrook et al., 1989, *Molecular Cloning—A Laboratory Manual*, Cold Spring Harbor Laboratory, NY; and Ausubel et al., eds., Current Edition, *Current Protocols in Molecular Biology*, Greene Publishing Associates and Wiley Interscience, NY. Particular methods for transforming cells are well known in the art. See Hinnen et al., *Proc. Natl. Acad. Sci. USA* 75:1292-3 (1978); Cregg et al., *Mol. Cell. Biol.* 5:3376-3385 (1985). Exemplary techniques include but are not limited to, spheroplasting, electroporation, PEG 1000 mediated transformation, and lithium acetate or lithium chloride mediated transformation.

In some embodiments, biolistics are utilized to introduce an integration polynucletide, a polynucleotide encoding a nuclease, a purified nuclease protein, or any combination thereof into the host cell, in particular, host cells that are otherwise difficult to transform/transfect using conventional techniques, such as plants. Biolistics work by binding the transformation reaction to microscopic gold particles, and then propelling the particles using compressed gas at the target cells.

In some embodiments, the polynucleotide comprising nucleic acid encoding the nuclease is an expression vector that allows for the expression of a nuclease within a host cell. Suitable expression vectors include but are not limited to those known for use in expressing genes in Escherichia coli, yeast, or mammalian cells. Examples of Escherichia coli expression vectors include but are not limited to pSCM525, pDIC73, pSCM351, and pSCM353. Examples of yeast expression vectors include but are not limited to pPEX7 and pPEX408. Other examples of suitable expression vectors include the yeast-*Escherichia coli* pRS series of shuttle vectors comprising CEN.ARS sequences and yeast selectable markers; and 2μ plasmids. In some embodiments, a polynucleotide encoding a nuclease can be modified to substitute codons having a higher frequency of usage in the host cell, as compared to the naturally occurring polynucleotide sequence. For example the polynucleotide encoding the nuclease can be modified to substitute codons having a higher frequency of usage in *S. cerevisiae*, as compared to the naturally occurring polynucleotide sequence.

In some embodiments where the nuclease functions as a heterodimer requiring the separate expression of each monomer, as is the case for zinc finger nucleases and TAL-effector nucleases, each monomer of the heterodimer may be expressed from the same expression plasmid, or from different plasmids. In embodiments where multiple nucleases are introduced to the cell to effect double-strand breaks at different target sites, the nucleases may be encoded on a single plasmid or on separate plasmids.

In certain embodiments, the nuclease expression vector further comprises a selectable marker that allows for selection of host cells comprising the expression vector. Such selection can be helpful to retain the vector in the host cell for a period of time necessary for expression of sufficient amounts of nuclease to occur, for example, for a period of 12, 24, 36, 48, 60, 72, 84, 96, or more than 96 hours, after which the host cells may be grown under conditions under which the expression vector is no longer retained. In certain embodiments, the selectable marker is selected from the group consisting of: URA3, hygromycin B phosphotransferase, aminoglycoside phosphotransferase, zeocin resistance, and phosphinothricin N-acetyltransferase. In some embodiments, the nuclease expression vector vector may comprise a counter-selectable marker that allows for selection of host cells that do not contain the expression vector subsequent to integration of the one or more donor nucleic acid molecules. The nuclease expression vector used may also be a transient vector that has no selection marker, or is one that is not selected for. In particular embodiments, the progeny of a host cell comprising a transient nuclease expression vector loses the vector over time.

In certain embodiments, the expression vector further comprises a transcription termination sequence and a promoter operatively linked to the nucleotide sequence encoding the nuclease. In some embodiments, the promoter is a constitutive promoter. In some embodiments, the promoter is an inducible promoter. Illustrative examples of promoters suitable for use in yeast cells include, but are not limited to the promoter of the TEFL gene of *K. lactis*, the promoter of the PGK1 gene of *Saccharomyces cerevisiae*, the promoter of the TDH3 gene of *Saccharomyces cerevisiae*, repressible promoters, e.g., the promoter of the CTR3 gene of *Saccharomyces cerevisiae*, and inducible promoters, e.g., galactose inducible promoters of *Saccharomyces cerevisiae* (e.g., promoters of the GAL1, GAL7, and GAL10 genes).

In some embodiments, an additional nucleotide sequence comprising a nuclear localization sequence (NLS) is linked to the 5' of the nucleotide sequence encoding the nuclease. The NLS can facilitate nuclear localization of larger nucleases (>25 kD). In some embodiments, the nuclear localization sequence is an SV40 nuclear localization sequence. In some embodiments, the nuclear localization sequence is a yeast nuclear localization sequence.

A nuclease expression vector can be made by any technique apparent to one skilled in the art. In certain embodiments, the vector is made using polymerase chain reaction (PCR) and molecular cloning techniques well known in the art. See, e.g., *PCR Technology: Principles and Applications for DNA Amplification*, ed. H A Erlich, Stockton Press, New York, N.Y. (1989); Sambrook et al., 2001, *Molecular Cloning—A Laboratory Manual*, 3rd edition, Cold Spring Harbor Laboratory, Cold Spring Harbor, N.Y.

6.7 Host Cells

In another aspect, provided herein is a modified host cell generated by any of the methods of genomically integrating one or more exogenous nucleic acids described herein. Suitable host cells include any cell in which integration of a nucleic acid or "donor DNA" of interest into a chromosomal or episomal locus is desired. In some embodiments, the cell is a cell of an organism having the ability to perform homologous recombination. Although several of the illustrative embodiments are demonstrated in yeast (*S. cerevisiae*), it is believed that the methods of genomic modification provided herein can be practiced on all biological organisms having a functional recombination system, even where the recombination system is not as proficient as in yeast. Other cells or cell types that have a functional homologous recombination systems include bacteria such as *Bacillus subtilis* and *E. coli* (which is RecE RecT recombination proficient; Muyrers et al., *EMBO rep.* 1: 239-243, 2000); protozoa (e.g., *Plasmodium, Toxoplasma*); other yeast (e.g., *Schizosaccharomyces pombe*); filamentous fungi (e.g., *Ashbya gossypii*); plants, for instance the moss *Physcomitrella patens* (Schaefer and Zryd, *Plant J.* 11: 1195-1206, 1997); and animal cells, such as mammalian cells and chicken DT40 cells (Dieken et al., *Nat. Genet.* 12:174-182, 1996).

In some embodiments, the host cell is a prokaryotic cell. In some embodiments, the host cell is a eukaryotic cell. In some embodiments, the cell is a fungal cell (for instance, a yeast cell), a bacteria cell, a plant cell, or an animal cell (for instance, a chicken cell). In some embodiments, the host cell is a mammalian cell. In some embodiments, the host cell is a Chinese hamster ovary (CHO) cell, a COS-7 cell, a mouse fibroblast cell, a mouse embryonic carcinoma cell, or a mouse embryonic stem cell. In some embodiments, the host cell is an insect cell. In some embodiments, the host cell is a S2 cell, a Schneider cell, a S12 cell, a 5B1-4 cell, a Tn5 cell, or a Sf9 cell. In some embodiments, the host cell is a unicellular eukaryotic organism cell.

In particular embodiments, the host cell is a yeast cell. Useful yeast host cells include yeast cells that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremas-*

*cus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis*, and *Zygozyma,* among others.

In some embodiments, the yeast host cell is a *Saccharomyces cerevisiae* cell, a *Pichia pastoris* cell, a *Schizosaccharomyces pombe* cell, a *Dekkera bruxellensis* cell, a *Kluyveromyces lactis* cell, a *Arxula adeninivorans* cell, or a *Hansenula polymorphs* (now known as *Pichia angusta*) cell. In a particular embodiment, the yeast host cell is a *Saccharomyces cerevisiae* cell. In some embodiments, the yeast host cell is a *Saccharomyces fragilis* cell or a *Kluyveromyces lactis* (previously called *Saccharomyces lactis*) cell. In some embodiments, the yeast host cell is a cell belonging to the genus *Candida*, such as *Candida lipolytica, Candida guilliermondii, Candida krusei, Candida pseudotropicalis*, or *Candida utilis*. In another particular embodiment, the yeast host cell is a *Kluveromyces marxianus* cell.

In particular embodiments, the yeast host cell is a *Saccharomyces cerevisiae* cell selected from the group consisting of a Baker's yeast cell, a CBS 7959 cell, a CBS 7960 cell, a CBS 7961 cell, a CBS 7962 cell, a CBS 7963 cell, a CBS 7964 cell, a IZ-1904 cell, a TA cell, a BG-1 cell, a CR-1 cell, a SA-1 cell, a M-26 cell, a Y-904 cell, a PE-2 cell, a PE-5 cell, a VR-1 cell, a BR-1 cell, a BR-2 cell, a ME-2 cell, a VR-2 cell, a MA-3 cell, a MA-4 cell, a CAT-1 cell, a CB-1 cell, a NR-1 cell, a BT-1 cell, and a AL-1 cell. In some embodiments, the host cell is a *Saccharomyces cerevisiae* cell selected from the group consisting of a PE-2 cell, a CAT-1 cell, a VR-1 cell, a BG-1 cell, a CR-1 cell, and a SA-1 cell. In a particular embodiment, the *Saccharomyces cerevisiae* host cell is a PE-2 cell. In another particular embodiment, the *Saccharomyces cerevisiae* host cell is a CAT-1 cell. In another particular embodiment, the *Saccharomyces cerevisiae* host cell is a BG-1 cell.

In some embodiments, the yeast host cell is a cell that is suitable for industrial fermentation, e.g., bioethanol fermentation. In particular embodiments, the cell is conditioned to subsist under high solvent concentration, high temperature, expanded substrate utilization, nutrient limitation, osmotic stress due, acidity, sulfite and bacterial contamination, or combinations thereof, which are recognized stress conditions of the industrial fermentation environment.

6.8 Kits

In another aspect, provided herein is a kit useful for performing the methods for genomically integrating one or more exogenous nucleic acids described herein. In some embodiments, the kit comprises:

(a) a plurality of exogenous nucleic acids, wherein each exogenous nucleic acid $(ES)_x$ comprises:

(i) a first homology region $(HR1)_x$ and a second homology region $(HR2)_x$, wherein $(HR1)_x$ and $(HR2)_x$ are capable of initiating host cell mediated homologous recombination of $(ES)_x$ at a selected target site $(TS)_x$ of a host cell genome; and (ii) a nucleic acid of interest $(D)_x$ positioned 3' of $(HR1)_x$ and 5' of $(HR2)_x$;

(b) a plurality of nucleases, wherein each nuclease $(N)_x$ capable of cleaving at $(TS)_x$, whereupon said cleaving results in homologous recombination of $(ES)_x$ at $(TS)_x$;

wherein x is any integer from 1 to n wherein n is at least 2.

In some embodiments, $(D)_x$ is selected from the group consisting of a selectable marker, a promoter, a nucleic acid sequence encoding an epitope tag, a gene of interest, a reporter gene, and a nucleic acid sequence encoding a termination codon. In some embodiments, the kit further comprises a plurality of primer pairs $(P)_x$, wherein each primer pair is capable of identifying integration of $(ES)_x$ at $(TS)_x$ by PCR. In some embodiments, $(ES)_x$ is linear. In some embodiments, $(ES)_x$ is circular.

In a particular embodiment, the kit enables site-specific integration of an exogenous nucleic acid at a unique target site within any of the approximately 6000 genetic loci of the yeast genome. In these embodiments, n=≥6000, wherein each $(TS)_x$ is unique to a single locus of the yeast cell genome.

In some embodiments, the kit further comprises instructions for use that describe methods for integrating one or more exogenous nucleic acids into any genetic locus of a host yeast cell.

7. EXAMPLES

7.1 Example 1

Simultaneous Multiple Integration of a Plurality of Exogenous Nucleic Acids

The methods and compositions described herein are implemented to create a modified yeast cell comprising two exogenous nucleic acids integrated at two loci of the yeast cell genome in a single transformation step, wherein recovery of the modified yeast cell does not require the use of selectable marker(s).

A host strain is provided comprising: (a) a previously introduced recognition site for the F-CphI endonuclease positioned within the NDT80 locus; and (b): a previously introduced recognition site for the I-SceI endonuclease positioned within the HO locus. The host cell is simultaneously transformed with: (1) an expression plasmid encoding F-CphI; (2) an expression plasmid encoding I-SceI; (3) a linear DNA comprising an expression cassette encoding green fluorescent protein (GFP), flanked by two stretches of >500 bp sequence corresponding to the 5' and 3' regions of the NDT80 locus; and (4) a linear DNA comprising an expression cassette encoding lacZ, flanked by two stretches of >500 bp sequence corresponding to the 5' and 3' regions of the HO locus. As an alternative to inclusion of the expression plamids encoding F-CphI and I-SceI, respectively, purified F-CphI and I-SceI protein are included in the transformation reaction. A non-double strand break control is performed by transforming host cells with the linear integration constructs (3) and (4) only, in the absence of F-CphI and I-SceI expression plasmid or purified protein.

Experimental and control transformants are plated on selection-free media, and colonies from each plate are visualized for expression of GFP and lacZ, respectively. Colony PCR is independently performed with a primer pair which anneals upstream and downstream of the junction between the integrated integration construct (3) or (4), respectively, and their respective target sequences, to confirm fidelity and frequency of integration.

7.2 Example 2

Simultaneous Multiple Integration of a Plurality of Exogenous Nucleic Acids

This Example provides results which demonstrate simultaneous integration of three exogenous nucleic acids at three different loci of a *S. cerevisiae* host following the induction of targeted double-stranded breaks in the host cell genome. In brief, an exogenous "target" nucleic acid sequence encoding a truncated, non-functional copy of Emerald Green Fluorescent Protein (emgfpΔ) was integrated into the HO, YGR250c and NDT80 loci, respectively, of host yeast cells. Recombinant cells were transformed with linear "donor" DNA encoding an intact, functional copy of Emerald Green Fluorescent Protein (EmGFP) and either: (1) empty vector; or (2) an expression vector, pZFN.gfp, encoding a zinc-finger nuclease (ZFN.gfp) that specifically recognizes and cleaves a sequence within the emgfpΔ coding sequence. Transformed colonies were screened by colony PCR (cPCR) for the replacement of one, two or three genomically integrated copies of the target emgfpΔ coding sequence with the donor EmGFP coding sequence.

7.2.1. Construction and Integration of Target DNA

To generate exogenous genomic target sites for nuclease-mediated double-strand breaks, target DNAs encoding emgfpΔ were constructed using RYSE-mediated assembly, as described in U.S. Pat. No. 8,110,360, the contents of which are hereby incorporated by reference in their entirety. Nucleotides 450 to 462 of the wild-type EmGFP coding sequence (SEQ ID NO:1) were replaced with the following sequence: 5 '-CGTCTAAATCATG-3' (SEQ ID NO:2), resulting in the introduction of: (1) a premature stop codon at position 152 of EmGFP (emgfpΔ); and (2) the recognition/cleavage sequence for ZFN.gfp.

For the targeted integration of the emgfpΔ coding sequence into each of the HO, YGR250c and NDT80 loci, the emgfpΔ coding sequence was flanked with ~200-500 bp of upstream and downstream homologous sequences for each loci (SEQ ID NOS:3-8). A unique selectable marker was also incorporated into each construct, positioned 5' to the emgfpΔ coding sequence, for selection of colonies having successful integration events. The HO integration construct included KanR, the YGR250c integration construct included URA3, and the NDT80 integration construct included NatR. Each integration construct was transformed sequentially into a naïve CEN.PK2 haploid yeast strain (strain A), and the strain was confirmed to have three integrated copies of the emgfpΔ coding sequence.

7.2.2. Construction of ZFN Yeast Expression Plasmid

Zinc finger nucleases consist of two functional domains: a DNA-binding domain comprised of a chain of zinc finger proteins and a DNA-cleaving domain comprised of the nuclease domain of FokI. The endonuclease domain of FokI functions as an obligate heterodimer in order to cleave DNA, and thus, a pair of ZFNs is required to bind and cut its target sequence. The target sequence of ZFN.gfp (CompoZr® Zinc Finger Nuclease, Sigma-Aldrich, St. Louis, Mo.) is:

```
                                    (SEQ ID NO: 9)
5'-ACAACTACAACAGCCACAACgtctatATCATGGCCGACAAGCA-3',
```

with the recognition sequence indicated in uppercase and the cleavage sequence indicated in lowercase.

A high-copy ZFN.gfp yeast expression plasmid, pZFN.gfp, was constructed as follows. The genes ZFN.gfp.1 and ZFN.gfp.2, each encoding one member of the ZFN.gfp obligate heterodimer, were PCR-amplified from a mammalian expression plasmid and fused to the divergent $P_{GAL10}$promoter and ADH1 and CYC1 terminators, respectively. Individual PCR products of $P_{GAL10}$>ZFN.gfp.1-$T_{ADH1}$ and $P_{GAL1}$>ZFN.gfp.2-$T_{CYC1}$, along with a linearized vector backbone comprising a LEU2 selectable marker, were co-transformed into a naïve yeast strain for in vivo assembly via homologous recombination of overlapping ends. The PCR products recombined at the pGAL1,10 promoter sequence and assembled into the vector backbone via homologous sequences added by the terminal primers. Transformants were selected on minimal media lacking leucine, isolated, and grown in liquid media. The plasmids from multiple clones were extracted from yeast using the Zymoprep Yeast Plasmid Miniprep I kit (Zymo Research). The eluent from the extraction protocol was then transformed into *E. coli* XL-1 blue chemically competent cells. Plasmids were propagated overnight in *E. coli* and miniprepped (Qiagen, Valencia, Calif.). Correct clones were identified by restriction mapping.

7.2.3. Transformation with Donor DNA and Induction of Double-Strand Breaks

A standard lithium acetate/SSDNA/PEG protocol (Gietz and Woods, *Methods Enzymol.* 350:87-96 (2002)) was used to co-transform strain A with linear "donor" DNA encoding EmGFP and either: (1) empty vector; or (2) the pZFN.gfp expression vector. The EmGFP coding sequence differs from the emgfpΔ coding sequence at positions within the recognition/cleavage site for ZFN.gfp, namely positions 450 (C→G), 456 (A→T), 461 (T→C) and 462 (G→C). Thus, ZFN.gfp is expected to recognize and cleave within the emgfpΔ sequence but not within the EmGFP sequence.

One microgram of the appropriate plasmid DNA was co-transformed with 70 ul of linear EmGFP DNA (~300 ng/ul). All transformations were recovered overnight in YP +2% galactose to induce ZFN expression. Various dilutions were plated onto minimal media agar plates lacking leucine to select for colonies transformed with plasmid DNA. Plates were incubated for 3 days at 30° C.

7.2.4. Confirmation of Multiple Simultaneous Integration

Colony PCR was performed to determine the frequency of replacement of the emgfpΔ coding sequence with the EmGFP coding sequence at each target locus. DNA was prepped from 96 colonies from each transformation and probed with primer pairs specific for EmGFP and HO, EmGFP and NDT80, and EmGFP and YGR250c, respectively, such that successful integration of the EmGFP coding sequence at each locus was expected to produce an amplicon of a predicted size, while non-integration was expected to produce no amplicon.

TABLE 2

Primer sequences for cPCR verification of multiple integration of the EmGFP coding sequence

| Primer Name | Description | Sequence | SEQ ID NO |
|---|---|---|---|
| KMH749-Fixed GFP-fwd | Forward primer specific to Em.GFP | CAACTACAACAGCCACAAGGTCT ATATCACC | SEQ ID NO: 10 |
| CR813 | Reverse primer for HO locus | CTCTAACGCTGTTGGTAGATTG | SEQ ID NO: 11 |
| KMH773-NDT80-Ar | Reverse primer for NDT80 locus | ACCATGTGATAATACACTACTAA TGTGACTACTAGTTGA | SEQ ID NO: 12 |
| KMH679-YGR250c 3' rev | Reverse primer for YGR250c locus | TCAGACGCGTTCGGAGGAGAGTG CATTCAC | SEQ ID NO: 13 |

As indicated in FIG. 5, of the 96 colonies transformed with linear EmGFP donor DNA (SEQ ID NO:1) and empty vector control, no amplicons were produced during PCR, indicating that there were no successful integration events, i.e., replacements at any of the three loci comprising the target emgfpΔ coding sequence in the absence of a double-strand break. By contrast, of the 96 colonies transformed with linear EmGFP DNA and pZFN.gfp, 2 colonies had one locus replaced, 4 colonies had two loci replaced, and 23 colonies had all three loci replaced with the EmGFP coding sequence (FIG. 6). Colony PCR results were corroborated by visualizing the fluorescence of transformed colonies on plates (data not shown). None of the colonies transformed with EmGFP DNA and empty vector appeared green, indicating that none of the target emgfpΔ coding sequences were replaced with functional EmGFP coding sequences. By contrast, ~20% of colonies transformed with EmGFP DNA and pZFN.gfp appeared green, roughly correlating with the frequency of integration events observed by cPCR.

These results demonstrate that induction of multiple targeted double-strand breaks in the genome of a host cell can facilitate simultaneous multiple targeted integration of exogenous donor nucleic acids.

7.3 Example 3

Simultaneous Multiple Integration of Terpene Synthase Genes to Facilitate Conversion of a Farnesene Producing Strain to an Amorphadiene Producing Strain This Example provides results which demonstrate simultaneous integration of three sesquiterpene synthase genes at three different engineered loci of a *S. cerevisiae* host engineered for high mevalonate pathway flux. As a result, a parental strain producing farnesene and comprising a plasmid-based copy of the farnesene synthase gene was converted into an amorphadiene producing strain comprising multiple genomically integrated copies of amorphadiene synthase. In brief, URA3, NatR and KanR marker cassettes flanked by F-CphI sites were integrated at the Ga180, HXT3 and Matα locus, respectively, of the host strain. The host was then co-transformed with a plasmid encoding the F-CphI endonuclease as well as three linear "donor" DNA constructs containing distinct codon optimizations of the amorphadiene synthase (ADS) gene expressed from the Gall promoter and terminated by the CYC 1 terminator (ADS cassette), each flanked by homology regions for their respective target locus. Transformed colonies were screened by colony PCR (cPCR) for the replacement of one, two or three genomically integrated target marker loci with the ADS cassettes. A triply-integrated strain was identified and further engineered by integrating a fourth ADS cassette, and the resulting strain was cultured under conditions allowing for loss of the plasmid encoding farnesene synthase, such that its product profile was fully converted from farnesene to amorphadiene.

7.3.1. Construction of a Parental Farnesene Producing Strain

A farnesene-producing yeast strain, Y3639, useful for the multiple simultaneous integration of exogenous donor DNAs encoding amorphadiene synthase, was prepared as follows.

Strains Y93 (MAT A) and Y94 (MAT alpha) were generated by replacing the promoter of the ERG9 gene of yeast strains Y002 and Y003 (CEN.PK2 background MAT A or MAT alpha, respectively; ura3-52; trpl-289; leu2-3,112; his3Δ1; MAL2-8C; SUC2; van Dijken et al. (2000) *Enzyme Microb. Technol.* 26:706-714), respectively, with the promoter of the MET3 gene of *Saccharomyces cerevisiae*. To this end, exponentially growing Y002 and Y003 cells were transformed with integration construct i8 (SEQ ID NO: 14), which comprised the kanamycin resistance marker (KanMX) flanked by the promoter and terminator of the Tef1 gene of *Kluyveromyces lactis*, the ERG9 coding sequence, a truncated segment of the ERG9 promoter (trunc. PERG9), and the MET3 promoter (PMET3), flanked by ERG9 upstream and downstream sequences. Host cell transformants were selected on medium comprising 0.5 μg/mL Geneticin (Invitrogen Corp., Carlsbad, Calif.), and selected clones were confirmed by diagnostic PCR, yielding strains Y93 and Y94.

Strains Y176 (MAT A) and Y177 (MAT alpha) were generated by replacing the coding sequence of the ADE1 gene in strains Y93 and Y94, respectively, with the coding sequence of the LEU2 gene of *Candida glabrata* (CgLEU2). To this end, the 3.5 kb CgLEU2 genomic locus was PCR amplified from *Candida glabrata* genomic DNA (ATCC, Manassas, Va.) using primers 61-67-CPK066-G (SEQ ID NO: 15) and 61-67-CPK067-G (SEQ ID NO: 16), and transforming the PCR product into exponentially growing Y93 and Y94 cells.

Host cell transformants were selected on CSM-L, and selected clones were confirmed by diagnostic PCR, yielding strains Y176 and Y177.

Strain Y188 was generated by introducing into strain Y176 an additional copy of the coding sequences of the ERG13, ERG10, and ERG12 genes of *Saccharomyces cerevisiae,* and a truncated coding sequence of the HMG1 gene of *Saccharomyces cerevisiae*, each under regulatory control of a galactose inducible promoter of the GAL1 or GAL10 gene of *Saccharomyces cerevisiae*. To this end, exponentially growing Y176 cells were transformed with 2 μg of expression plasmids pAM491 and pAM495 digested with PmeI restriction endonuclease (New England Biolabs, Beverly, Mass.). Host cell transformants were selected on CSM lacking uracil and histidine (CSM-U-H), and selected clones were confirmed by diagnostic PCR, yielding strain Y188.

Strain Y189 was generated by introducing into strain Y177 an additional copy of the coding sequences of the ERG20, ERGS, and ERG19 genes of *Saccharomyces cerevisiae,* and a truncated coding sequence of the HMG1 gene of *Saccharomyces cerevisiae*, each under regulatory control of a galactose inducible promoter of the GAL1 or GAL10 gene of *Saccharomyces cerevisiae*. To this end, exponentially growing Y188 cells were transformed with 2 μg of expression plasmids pAM489 and pAM497 digested with PmeI restriction endonuclease. Host cell transformants were selected on CSM lacking tryptophan and histidine (CSM-T-H), and selected clones were confirmed by diagnostic PCR, yielding strain Y189.

Strain Y238 was generated by mating strains Y188 and Y189, and by introducing an additional copy of the coding sequence of the IDI1 gene of *Saccharomyces cerevisiae* and a truncated coding sequence of the HMG1 gene of *Saccharomyces cerevisiae*, each under regulatory control of a galactose inducible promoter of the GAL1 or GAL10 gene of *Saccharomyces cerevisiae*. To this end, approximately $1\times10^7$ cells of strains Y188 and Y189 were mixed on a YPD medium plate for 6 hours at room temperature, diploid cells were selected on CSM-H-U-T, and exponentially growing diploids were transformed with 2 μg of expression plasmid pAM493 digested with PmeI restriction endonuclease. Host cell transformants were selected on CSM lacking adenine (CSM-A), and selected clones were confirmed by diagnostic PCR, yielding strain Y238.

Strains Y210 (MAT A) and Y211 (MAT alpha) were generated by sporulating strain Y238. The diploid cells were sporulated in 2% potassium acetate and 0.02% raffinose liquid medium, and approximlately 200 genetic tetrads were isolated using a Singer Instruments MSM300 series micromanipulator (Singer Instrument Co, LTD. Somerset, UK). Spores were selected on CSM-A-H-U-T, and selected clones were confirmed by diagnostic PCR, yielding strains Y210 (MAT A) and Y211 (MAT alpha).

Strain Y221 was generated by transforming exponentially growing Y211 cells with vector pAM178. Host cell transformants were selected on CSM-L.

Strain Y290 was generated by deleting the coding sequence of the GAL80 gene of strain Y221. To this end, exponentially growing Y221 cells were transformed with integration construct i32 (SEQ ID NO: 17), which comprised the hygromycin B resistance marker (hph) flanked by the promoter and terminator of the Tef1 gene of *Kluyveromyces lactis* flanked by GAL80 upstream and downstream sequences. Host cell transformants were selected on medium comprising hygromycin B, and selected clones were confirmed by diagnostic PCR, yielding strain Y290.

Strain Y318 was generated by removing the pAM178 vector from strain Y290 by serial propagation in leucine-rich media, and testing individual colonies for their inability to grow on CSM-L, yielding strain Y318.

Strain Y409 was generated by introducing a heterologous nucleotide sequence encoding a β-farnesene synthase into strain Y318. To this end, exponentially growing Y318 cells were transformed with expression plasmid pAM404. Host cell transformants were selected on CSM-L, yielding strain Y409.

Strain Y419 was generated by rendering the GAL promoters of strain Y409 constitutively active. To this end, exponentially growing Y409 cells were transformed with integration construct i33 (SEQ ID NO: 18), which comprised the nourseothricin resistance marker of *Streptomyces noursei* (NatR) flanked by the promoter and terminator of the Tef1 gene of *Kluyveromyces lactis*, and the coding sequence of the GAL4 gene of *Saccharomyces cerevisiae* under regulatory control of an “operative constitutive” version of its native promoter (PGAL4oc; Griggs & Johnston (1991) PNAS 88(19):8597-8601) and the GAL4 terminator (TGAL4), flanked by upstream and downstream sequences of the modified ERG9 promoter and coding sequences. Host cell transformants were selected on medium comprising nourseothricin, and selected clones were confirmed by diagnostic PCR, yielding strain Y419.

Strain Y677 was generated by introducing at the modified GAL80 locus of strain Y419 an additional copy of the coding region of the ERG12 gene of *Saccharomyces cerevisiae* under regulatory control of the promoter of the GAL1 gene of *Saccharomyces cerevisiae*. To this end, exponentially growing Y677 cells were transformed with integration construct i37 (SEQ ID NO: 19), which comprised the kanamycin resistance marker of *Streptomyces noursei* (KanR) flanked by the promoter and terminator of the Tef1 gene of *Kluyveromyces lactis*, and the coding and terminator sequences of the ERG12 gene of *Saccharomyces cerevisiae* flanked by the GAL1 promoter (PGAL1) and the ERG12 terminator (TERG12). Host cell transformants were selected on medium comprising kanamycin, and selected clones were confirmed by diagnostic PCR, yielding strain Y677.

Strain Y1551 was generated from strain Y677 by chemical mutagenesis. Mutated strains were screened for increased production of β-farnesene, yielding strain Y1551.

Strain Y1778 was generated from strain Y1551 by chemical mutagenesis. Mutated strains were screened for increased production of β-farnesene, yielding strain Y1778.

Strain Y1816 was generated by replacing the HXT3 coding sequence of strain Y1778 with two copies of an acetoacetyl-CoA thiolase coding sequence, one being derived from *Saccharomyces cerevisiae* and the other from *C. butylicum*, and one copy of the coding sequence of the HMGS gene of *B. juncea*. To this end, exponentially growing Y1778 cells were transformed with integration construct i301 (SEQ ID NO: 20), which comprised the hygromycin B resistance marker (hyg) flanked by the promoter and terminator of the Tef1 gene of *Kluyveromyces lactis*, the coding sequence of the ERG10 gene of *Saccharomyces cerevisiae* flanked by a truncated TDH3 promoter (tPTDH3) and the AHP1 terminator (TAHP1), the coding sequence of the acetoacetyl-CoA thiolase gene of *C. butylicum* (thiolase) flanked by the YPD1 promoter (PYPD1) and CCW12 terminator (TCCW12), and the coding sequence of the HMGS gene of *B. juncea* (HMGS) preceded by the TUB2 promoter (PTUB2), flanked by upstream and downstream sequences of the HXT3 gene of *Saccharomyces cerevisiae*. Host cell transformants were selected on medium comprising hygromycin B, and selected clones were confirmed by diagnostic PCR, yielding strain Y1816.

Strain Y2055 was generated from strain Y1778 by chemical mutagenesis. Mutant strains were screened for increased production of β-farnesene, yielding strain Y2055.

Strain Y2295 was generated from strain Y2055 by chemical mutagenesis. Mutant strains were screened for increased production of β-farnesene, yielding strain Y2295.

Strain Y3111 was generated by switching the mating type of strain Y2295 from MAT A to MAT alpha. To this end, exponentially growing Y2295 cells were transformed with integration construct i476 (SEQ ID NO: 21), which comprised the MAT alpha mating locus and the hygromycin B resistance marker (hygA). Host cell transformants were selected on medium comprising hygromycin B, and selected clones were confirmed by diagnostic PCR, yielding strain Y3111.

Strain Y2168 was generated from strain Y1816 by chemical mutagenesis. Mutant strains were screened for increased production of β-farnesene, yielding strain Y2168.

Strain Y2446 was generated from strain Y2168 by chemical mutagenesis. Mutant strains were screened for increased production of β-farnesene, yielding strain Y2446.

Strain Y3118 was generated by inserting into the native URA3 locus of strain Y2446 the coding sequence, promoter, and terminator of the GAL80 gene of *Saccharomyces cerevisiae*. To this end, exponentially growing Y2446 cells were transformed with integration construct i477 (SEQ ID NO: 22), which comprised the promoter, terminator, and coding sequence of the GAL80 gene of *Saccharomyces cerevisiae* (GAL80) flanked by overlapping URA3 sequences (which enable loop-out excision of the GAL80 gene by homologous recombination and restoration of the original URA3 sequence). Host cell transformants were selected on medium comprising 5-FOA, yielding strain Y3118.

Strain Y3215 was generated by mating strains Y3111 and Y3118. Approximately $1\times10^7$ cells of strains Y3111 and Y3118 were mixed on a YPD medium plate for 6 hours at room temperature to allow for mating, followed by plating on YPD agar plate to isolate single colonies. Diploids were identified by screening by colony PCR for the presence of both the hphA-marked MAT alpha locus and the wild-type MAT A locus.

Strain Y3000 was generated by sporulating strain Y3215 and looping out the GAL80 coding sequence. The diploid cells were sporulated in 2% potassium acetate and 0.02% raffinose liquid medium. Random spores were isolated, plated on YPD agar, grown for 3 days, and then replica-plated to CSM-U to permit growth only of cells lacking GAL80 (i.e., having a functional URA3 gene). Spores were then tested for β-farnesene production, the best producer was identified, and the presence of integration construct i301 was confirmed by diagnostic PCR, yielding strain Y3000.

Strain Y3284 was generated by removing the URA3 marker from strain Y3000. To this end, exponentially growing Y3000 cells were transformed with integration construct i94 (SEQ ID NO: 23), which comprised the hisG coding sequence of *Salmonella*, and the coding sequence of the ERG13 gene and a truncated coding sequence of the HMG1 gene of *Saccharomyces cerevisiae* under control of a galactose inducible promoter of the GAL1 or GAL10 gene of *Saccharomyces cerevisiae*, flanked by upstream and downstream sequences of the URA3 gene of *Saccharomyces cerevisiae*. Host cell transformants were selected on medium comprising 5-FOA, and selected clones were confirmed by diagnostic PCR, yielding strain Y3284.

Strain Y3385 was generated by replacing the NDT80 coding sequence of strain Y3284 with an additional copy of the coding sequence of an acetyl-CoA synthetase gene of *Saccharomyces cerevisiae* and the coding sequence of the PDC gene of *Z. mobilis*. To this end, exponentially growing Y3385 cells were transformed with integration construct i467 (SEQ ID NO: 24), which comprised the URA3 marker, the coding sequence of the ACS2 gene of *Saccharomyces cerevisiae* (ACS2) flanked by the HXT3 promoter (PHXT3) and PGK1 terminator (TPGK1), and the coding sequence of the PDC gene of *Z. mobilis* (zmPDC) flanked by the GAL7 promoter (PGAL7) and the TDH3 terminator (TTDH3), flanked by upstream and downstream NDT80 sequences. Host cell transformants were selected on CSM-U, and selected clones were confirmed by diagnostic PCR, yielding strain Y3385.

Strain Y3547 was generated from strain Y3385 by chemical mutagenesis. Mutated strains were screened for increased production of β-farnesene, yielding strain Y3547.

Strain Y3639 was generated from strain Y3547 by chemical mutagenesis. Mutated strains were screened for increased production of β-farnesene, yielding strain Y3639.

7.3.2. Construction and Integration of Target DNA

Exogenous genomic target sites for FcphI endonuclease-mediated double-strand breaks were integrated into three different loci of strain Y3639. Three target site cassettes were constructed using PCR assembly of overlapping fragments, each comprising the recognition sequence for the FcphI endonuclease and the coding sequence for: (1) URA3 (flanked by homology regions for the modified Ga180 locus) (SEQ ID NO: 25); (2) NatR (flanked by homology regions for the modified HXT3 locus) (SEQ ID NO: 26); and (3) KanR (flanked by homology regions for the modified Matα locus) (SEQ ID NO: 27), respectively. Each target site cassette was serially transformed into Y3639, and the strain was confirmed by colony PCR to have three integrated copies of the F-CphI-flanked marker cassettes at the correct loci ("strain B").

7.3.3. Construction of F-CphI Yeast Expression Plasmid

The F-CphI yeast expression plasmid pAM1799, comprising a HygR selectable marker, has been described previously in U.S. Pat. No. 7,919,605, which is hereby incorporated by reference in its entirety.

7.3.4. Transformation with Donor DNA and Induction of Double-Strand Breaks

The standard lithium acetate/SSDNA/PEG protocol (Gietz and Woods, *Methods Enzymol.* 2002;350:87-96) was modified to include a 30 minute, 30 degree incubation of the cells prior to the 42 degree heat shock. This method was used to co-transform strain B with pAM1799, encoding FcphI endonuclease, and three linear "donor" DNAs, each comprising a codon optimized coding sequence for amorphadiene synthase (ADS) of *Artemisia annua,* flanked by homology regions to the modified Ga180 (SEQ ID NO: 28), HXT3 (SEQ ID NO: 29) and Matα loci (SEQ ID NO: 30), respectively, of strain B.

One microgram of pAM1799 was co-transformed with ~100 ng of each of the ADS donor DNAs. All transformations were recovered overnight in YP +2% galactose to induce F-CphI expression. Various dilutions were plated onto YPD agar plates containing hygromycin to select for colonies transformed with plasmid DNA. Plates were incubated for 3 days at 30° C.

7.3.5. Confirmation of Multiple Simultaneous Integration

Colony PCR (cPCR) was performed to determine the frequency of replacement of the F-CphI-flanked marker cassette coding sequences with the ADS cassette coding sequence. DNA was prepped from 20 colonies probed with primer pairs specific for ADS and the Ga180 locus, ADS and the HXT3 locus, and ADS and the Matα locus, respectively, such that successful integration of the ADS cassette coding sequence at each locus was expected to produce an amplicon of a predicted size, while non-integration was expected to produce no amplicon. PCR reactions to produce amplicons from the 5' and 3' ends of each locus were attempted in multiplex. In some cases, only the 5' or the 3' amplicon was successfully detected, but proper integration of the ADS cassette was confirmed at these loci by sequencing larger PCR fragments.

TABLE 3

Primer sequences for cPCR verification of multiple integration of the ADS cassette coding sequence

| Primer Name | Description | Sequence | SEQ ID NO |
|---|---|---|---|
| CUT24 | Gal80 locus US FOR | GTTTCTTTTGGATTGCGCTTGCC | SEQ ID NO: 31 |
| ART12 | ADS codon v2 5' REV | TACTGACAACCACATGTTAC | SEQ ID NO: 32 |
| ART45 | ADS ORF 5' REV | TACTGCTTCGGTAGTAGTTTCACC CTTCA | SEQ ID NO: 33 |
| ART210 | Gal80 locus DS REV | GGGAAGTCCAATTCAATAGT | SEQ ID NO: 34 |
| HJ207 | HXT3 locus US FOR | CATCTTCTCGAGATAACACCTGG AG | SEQ ID NO: 35 |
| KB349 | CYC1T FOR | ACGCGTGTACGCATGTAAC | SEQ ID NO: 36 |
| HJ602 | HXT3 locus DS REV | CAATTGGGGTTCTGGCAGTC | SEQ ID NO: 37 |
| CUT76 | Matα locus US FOR | GAAGCCTGCTTTCAAAATTAAGA ACAAAGC | SEQ ID NO: 38 |
| HJ632 | Matα locus DS REV | GAATTTACCTGTTCTTAGCTTGTA CCAGAG | SEQ ID NO: 39 |

Of the 20 colonies screened by cPCR, 14 had ADS integrated at the Ga180 locus, 17 had ADS integrated at the HXT3 locus, and four had ADS integrated at the Matα locus. The low rate of integration at the Matα locus can be explained by self-closure at this locus mediated by a direct repeat sequence flanking the F-CphI sites. In total, 6 clones had ADS integrated at a single site, 10 clones had ADS integrated at two sites, and three clones had ADS integrated at all three loci ("strains C"). The triply integrated strains were further confirmed by sequencing longer PCR products encompassing both flanks 1.1.5 Completion of the Integrated ADS Strain and Sesquiterpene Assay The triply integrated ADS strains were further engineered by integrating a final copy of ADS marked with a URA cassette (SEQ ID NO: 40) at the His3 locus using a standard protocol, and a resulting strain was confirmed for this fourth copy ("strain D"). Finally, strain D cells were passaged in non-selective media to lose the Leu+marked high copy farnesene synthase plasmid (pAM404) ("strain E").

Several isolates of strain E were assayed for sesquiterpene production alongside strain D and the original parent strain B. In brief, isolates of strains B, D and E were incubated in separate wells of a 96-well plate containing 360 μL of Bird Seed Medium (BSM) with 2% sucrose per well (preculture). After 3 days of incubation at 33.5° C. with 999 rpm agitation, 14.4 μL of each well was inoculated into a well of a new 96-well plate containing 360 μL of fresh BSM with 4% sucrose (production culture). After another 2 days of incubation at 33.5° C. with 999 rpm agitation, samples were taken and analyzed for sesquiterpene production by gas chromatography (GC) analysis. Samples were extracted with methanol-heptane (1:1 v/v), and the mixtures were centrifuged to remove cellular material. An aliquot of the methanol-heptane extract was diluted into heptane, and then injected onto a methyl silicone stationary phase using a pulsed split injection. Farnesene and amorphadiene were separated by boiling point using GC with flame ionization detection (FID). Trans-β-caryophyllene was used as a retention time marker to monitor successful injection and elution during the specified GC oven profile.

As shown in FIG. 7, total sesquiterpene production remained nearly identical (3-3.5 g/L) for all strains, but the product profile was successfully converted from Farnesene (strain B) to mixed product (strain D) to amorphadiene (strain E).

These results demonstrate that induction of multiple targeted double-strand breaks in the genome of a host cell can facilitate simultaneous multiple integrations of a functional gene cassette, in this case facilitating conversion of a farnesene-producing strain into an amorphadiene-producing strain in a single transformation.

7.4 Example 4

Simultaneous Replacement of Multiple Integrated Copies of Farnesene Synthase with Amorphadiene Synthase This Example provides results which demonstrate the simultaneous replacement of four genomically integrated terpene synthase genes, facilitated by designer nuclease-induced double-strand breaks within the synthase coding regions. In brief, an existing farnesene production strain, derived from strain Y3639 (described in Example 3) but comprising four integrated rather than extrachromasomal copies of the farnesene synthase (FS) gene, was co-transformed with a plasmid encoding a designer TAL-effector nuclease (TALEN) and four linear donor DNAs encoding new terpene synthase genes. The designer TALEN is capable of binding to and cleaving a sequence unique to the integrated farnesene synthase genes. Transformed colonies were screened by colony PCR (cPCR) and strains with one, two or three or four genomically integrated target marker loci were identified.

7.4.1. Construction and Integration of Target DNA

Four donor cassettes, each comprising a terpene synthase coding sequence flanked by homology regions (~500 bp) to its respective target loci, were assembled by overlap PCR. Three of the donor DNAs comprised ADS coding sequences and no selectable marker (SEQ ID NOs: 41-43), while the final donor DNA was a cassette comprising a novel codon optimization of the farnesene synthase (FS) fused to a URA3 marker cassette (SEQ ID NO: 44). None of the donor DNAs contained the target site recognized by the FS-specific TALEN (5'-TAGTGGAGGAATTAAAAGAGGAAGTTAA-GAAGGAATTGATAACTATCAA-3' (SEQ ID NO:45)).

For the replacement of the four integrated FS cassettes in the strain (Strain F), the hyg+marked TALEN plasmid was co-transformed into the host strain along with ~500 ng of each linear donor DNA using the protocol described in Example 3. Various dilutions were plated onto CSM-URA+Hyg plates and incubated at 30 degrees for 3 day.

7.4.2. Confirmation of Multiple Simultaneous Integration

After selection for the TALEN plasmid and integration of the URA3 marked codon-FS cassette on CSM-URA +Hyg plates, colony PCR was performed to determine the frequency of replacement of the integrated FS cassettes with the unmarked ADS cassettes at three loci. DNA was prepped from 20 colonies and probed with primer pairs specific for integration of the ADS cassette at the NDT80, DIT1 and ERG10 loci, such that successful integration of the ADS cassette coding sequence at each locus was expected to produce an amplicon of a predicted size, while non-integration was expected to produce no amplicon.

TABLE 4

Primer sequences for cPCR verification of replacement of multiple farnesene synthase cassettes with amorphadiene synthase cassettes.

| Primer Name | Description | Sequence | SEQ ID NO |
|---|---|---|---|
| HJ272 | NDT80 5' FOR | ATAACAATATTATAAAAAGCGCTTAA | SEQ ID NO: 46 |
| ART45 | ADS ORF 5' REV | TACTGCTTCGGTAGTAGTTTCACCCTTCA | SEQ ID NO: 47 |
| HJ643 | DIT1 5' FOR | AAAATCCTTATATTATTGGCCC | SEQ ID NO: 48 |
| HJ799 | ERG10 5' FOR | GTAGCCTAAAACAAGCGCC | SEQ ID NO: 49 |

Three out of 48 clones examined had integrated a single ADS cassette in addition to the URA3-marked FS, one clone had integrated two ADS cassettes, and one clone had integrated all three ADS cassettes. Multiple integration results were further confirmed by sequencing longer PCR products encompassing both flanks These results demonstrate that expression of a site-specific designer nuclease in a host cell comprising a biosynthetic pathway can facilitate the simultaneous replacement of multiple integrated copies of a pathway gene with new pathway genes in a single transformation step.

7.5 Example 5

Simultaneous Multiple Integration of Markerless DNA Constructs into Two Loci Cut with Distinct Designer Nucleases This Example provides results which demonstrate the simultaneous integration of two markerless DNA constructs at two native target sites, each site being cut with a distinct designer nuclease. In brief, an ADE host strain was co-transformed with: (1) a linear DNA fragment comprising a GFP cassette (flanked by upstream and downstream regions homologous to the SFC1 locus); (2) a linear DNA fragment comprising an ADE2 cassette (flanked with upstream and downstream regions homologous to the YJR030c locus); and (3) plasmid(s) encoding designer nucleases that target sequences in the native SFC1 and YJR030c open reading frames, respectively. After selection for the plasmid(s), transformed colonies were screened visually for GFP fluorescence and for white color, indicating complementation of the ADE phenotype. Colony PCR (cPCR) was also performed to confirm replacement of both loci. Interestingly, a significant improvement in the rate of integration at both target loci was observed when the designer endonucleases were used in combination compared to the rate of integration when only a single designer nuclease was used.

7.5.1. Construction of Donor DNA Cassettes

Two donor DNAs were generated using PCR assembly of overlapping fragments: (1) a linear DNA fragment comprising a GFP cassette flanked by ~500 bp of upstream and downstream regions homologous to the SFC1 locus (SEQ ID NO: 58); and (2) a linear DNA fragment comprising an ADE2 cassette flanked by ~500 bp of upstream and downstream regions homologous to the YJR030c locus (SEQ ID NO: 59).

7.5.2. Construction of Heterodimeric ZFN Expression Plasmids

A plasmid encoding the YJR030c-specific zinc finger nuclease (ZFN) was constructed in two ways. In the first version, the two ORFs of a heterodimeric ZFN under expression of a divergent Gal1-10 promoter and terminated by the Adhl and CYC1 terminators were cloned into a Kan marked CEN-ARS vector by a three part gap repair in yeast (pCUT006). A second version was also constructed wherein both ORFs of the heterodimeric ZFN were expressed from the Gal10 promoter as a single ORF with the monomers separated by a DNA sequence encoding a cleavable peptide linker. This second plasmid was constructed by a three-part ligation using linkers produced by type IIS restriction enzyme digest of PCR fragments into a Kan marked CEN-ARS vector backbone (pCUT016). A plasmid encoding the SFC1-specific ZFN was also constructed as a single ORF using the same linker strategy, marker and backbone (pCUT015). The marker was then changed to URA by means of a gap repair reaction in yeast (pCUT058). To construct a single plasmid for expression of both the YJR030c and SFC1-specific nucleases, the single ORFs from pCUT16 and pCUT15 were subcloned into a new CEN-ARS Kan+vector backbone, and expressed from the Gal1-10 divergent promoter with Cyc1 and Adh1 terminators (pCUT032).

7.5.1. Transformation with Donor DNA and Induction of Double-Strand Breaks

One microgram of each designer nuclease plasmid DNA, or the plasmid containing both designer endonucleases on a single plasmid, was co-transformed with ~1 microgram of each of the donor DNAs. All transformations were recovered overnight in YP +2% galactose to induce nuclease expression. Various dilutions were plated onto URA dropout+Kan agar plates (for the dual plasmids) or YPD+Kan to select for colonies transformed with plasmid DNA. Plates were incubated for 3-4 days at 30° C.

7.5.2. Confirmation of Multiple Simultaneous Integration

Marker-less integration at the SFC1 locus was scored by observation of GFP fluorescence under UV light using appropriate filters. Marker-less integration of ADE2 was scored by observation of a white colony color, indicating complementation of the ADE2 deletion phenotype (pink colonies) in the host strain. In a typical experiment, 50-150 colonies were assayed. The visual scoring strategy was confirmed in a subset of colonies by colony PCR using primers 5' of the integration construct and an internal reverse primer. Integration at each locus was expected to produce an amplicon of a predicted size, while non-integration was expected to produce no amplicon. The cPCR results confirmed the accuracy of the visual scoring method.

TABLE 4

Primer sequences for successful cPCR verification of multiple integration of the ADS cassette coding sequence

| Primer Name | Description | Sequence | SEQ ID NO |
|---|---|---|---|
| CUT351 | SFC1 5' cPCR | GCGAATGAGCCATGAATTATTAA CCGC | SEQ ID NO: 63 |
| CUT350 | YJR030c 5' cPCR | AGATGAAACGAATTACTAGCATT TTATCCGTTC | SEQ ID NO: 64 |
| CUT371 | ADE2 cassette REV | TAACTACCATTACTCAGTGTACTT GATTGTTTTGTCCGATTTTCTTG | SEQ ID NO: 65 |
| HJ788 | GFP cassette REV | GCCGGGTGACAGAGAAATATTG | SEQ ID NO: 66 |

As indicated in FIG. 8, in cells co-transformed with linear donor DNAs for the SFC1 and YJR030c loci, and the YJR030c endonuclease plasmid (pCUT006) and SFC1 endonuclease plasmid (pCUT058), 80% of colonies selected on URA dropout+Kan agar plates were GFP positive. Of these colonies, 91% were positive for ADE2 integration. In total, 72.8% of colonies had integrated the donor DNA at both loci.

In cells co-transformed with linear donor DNA for the SFC 1 locus and the designer nuclease plasmid targeting SFC1 (pCUT015), 50% of the cells were positive for GFP. When cells were co-transformed with linear donor DNA for the YJR030c locus and the designer nuclease plasmid targeting the YJR030c locus (pCUT016), only 5% of the cells were positive for ADE2 integration. When the host cells were co-transformed with linear DNAs for the SFC1 and YJR030c loci, and the SFC1/YJR030c designer nuclease plasmid (pCUT032), 76% of the cells were GFP positive, and 63% were ADE2 positive. This result is notable in that it demonstrates an unexpectedly significant improvement in integration efficiency when multiple sites are targeted by designer endonucleases.

These results demonstrate that induction of multiple targeted double-strand breaks at native loci in the genome of a host cell can facilitate simultaneous, multiple, marker-less integrations of functional gene cassettes.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A method for simultaneously integrating a plurality of (n) exogenous nucleic acids into a plurality of (n) target sites of a host cell genome, wherein n is at least two, the method comprising:

(a) simultaneously contacting a host cell with:

(i) said plurality of exogenous nucleic acids, wherein: x is an integer that varies from 1 to n, and for each integer x, each exogenous nucleic acid $(ES)_x$ comprises a first homology region $(HR1)_x$ and a second homology region $(HR2)_x$, wherein $(HR1)_x$ and $(HR2)_x$ are capable of initiating host cell mediated homologous recombination of $(ES)_x$ at a target site $(TS)_x$ selected from said plurality of (n) target sites of said host cell genome; and (ii) for each said target site $(TS)_x$, a nuclease $(N)_x$ capable of cleaving at $(TS)_x$ whereupon said cleaving results in homologous recombination of $(ES)_x$ at $(TS)_x$; and (b) recovering a host cell wherein each exogenous nucleic acid $(ES)_x$ has integrated at its selected target site $(TS)_x$, wherein said recovering occurs at a frequency of about one every 10, 9, 8, 7, 6, 5, 4, 3, or 2 contacted host cells, or clonal populations thereof, screened.

2. The method of claim 1, wherein $(HR1)_x$ is homologous to a 5' region of $(TS)_x$ and $(HR2)_x$ is homologous to a 3' region of $(TS)_x$.

3. The method of claim 2, wherein $(N)_x$ is capable of cleaving at a region positioned between said 5' and 3' regions of $(TS)_x$.

4. The method of claim 1, wherein a single nuclease is capable of cleaving each $(TS)_x$.

5. The method of claim 1, wherein n=3, 4, 5, 6, 7, 8, 9 or 10.

6. The method of claim 1, wherein said recovering does not require integration of a selectable marker.

7. The method of claim 1, wherein said recovering occurs at a higher frequency as compared to not contacting the host cell with a nuclease capable of cleaving at said target site.

8. The method of claim 1, wherein said recovering comprises identifying said integrations by at least one method selected from the group consisting of PCR, Southern blot, restriction mapping, and DNA sequencing.

9. The method of claim 1, wherein $(N)_x$ is capable of cleaving an endogenous genomic sequence within $(TS)_x$.

10. The method of claim 1, wherein $(N)_x$ is capable of cleaving an exogenous sequence within $(TS)_x$.

11. The method of claim 10, wherein the exogenous sequence is a recognition sequence for a homing endonuclease.

12. The method of claim 11, wherein the homing endonuclease is F-cphI.

13. The method of claim 1, wherein $(ES)_x$ further comprises a nucleic acid of interest $(D)_x$ positioned 3' of $(HR1)_x$ and 5' of $(HR2)_x$.

14. The method of claim 13, wherein $(D)_x$ is selected from the group consisting of a selectable marker, a promoter, a nucleic acid sequence encoding an epitope tag, a gene of interest, a reporter gene, and a nucleic acid sequence encoding a termination codon.

15. The method of claim 1, wherein $(ES)_x$ is linear.

16. The method of claim 1, wherein the host cell comprises one or more heterologous nucleotide sequences encoding one or more enzymes of a biosynthetic pathway.

17. The method of claim 16, wherein the one or more heterologous nucleotide sequences encoding one or more enzymes of a biosynthetic pathway are genomically integrated.

18. The method of claim 1, wherein each said exogenous nucleic acid $(ES)_x$ comprises a nucleic acid of interest $(D)_x$ positioned 3' of $(HR1)_x$ and 5' of $(HR2)_x$, encoding an enzyme of a biosynthetic pathway.

19. The method of claim 18, wherein $(D)_x$ is a member of a library $(L)_x$ comprising a plurality of nucleic acid molecules that encode variants of an enzyme of a biosynthetic pathway.

20. The method of claim 1, wherein the host cell comprises one or more heterologous nucleotide sequences encoding one or more enzymes of a mevalonate (MEV) pathway for making isopentenyl pyrophosphate.

21. The method of claim 20, wherein the one or more enzymes of the mevalonate pathway are selected from acetyl-CoA thiolase, HMG-CoA synthase, HMG-CoA reductase, mevalonate kinase, phosphomevalonate kinase and mevalonate pyrophosphate decarboxylase.

22. The method of claim 20, wherein the host cell comprises a plurality of heterologous nucleic acids encoding each the enzymes of a MEV pathway.

23. The method of claim 20, wherein each said exogenous nucleic acid $(ES)_x$ comprises a nucleic acid of interest $(D)_x$ positioned 3' of $(HR1)_x$ and 5' of $(HR2)_x$, encoding a terpene synthase.

24. The method of claim 23, wherein the terpene synthase is selected from the group consisting of a monoterpene synthase, a diterpene synthase, a sesquiterpene synthase, a sesterterpene synthase, a triterpene synthase, a tetraterpene synthase, and a polyterpene synthase.

25. The method of claim 1, wherein $(N)_x$ is provided as an expression vector comprising a nucleic acid sequence encoding $(N)_x$.

26. The method of claim 1, wherein $(N)_x$ is transformed into the host cell as a purified protein.

27. The method of claim 1, wherein $(N)_x$ is selected from the group consisting of an endonuclease, a zinc finger nuclease, a TAL-effector DNA binding domain-nuclease fusion protein (TALEN), a transposase, and a site-specific recombinase.

28. The method of claim 27, wherein the zinc finger nuclease is a fusion protein comprising the cleavage domain of a TypeIIS restriction endonuclease fused to an engineered zinc finger binding domain.

29. The method of claim 28, wherein the TypeIIS restriction endonuclease is selected from the group consisting of HO endonuclease and Fok I endonuclease.

30. The method of claim 28, wherein the zinc finger binding domain comprises 3, 5 or 6 zinc fingers.

31. The method of claim 27, wherein the endonuclease is a homing endonuclease selected from the group consisting of: an LAGLIDADG homing endonuclease, an HNH homing endonuclease, a His-Cys box homing endonuclease, a GIY-YIG homing endonuclease, and a cyanobacterial homing endonuclease.

32. The method of claim 27, wherein the endonuclease is selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, i-UarAP, i-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-Thyl, PI-TliI, and PI-TliII.

33. The method of claim 27, wherein the endonuclease is modified to specifically bind an endogenous genomic sequence, wherein the modified endonuclease no longer binds to its wild type endonuclease recognition sequence.

34. The method of claim 33, wherein the modified endonuclease is derived from a homing endonuclease selected from the group consisting of: an LAGLIDADG homing endonuclease, an HNH homing endonuclease, a His-Cys box homing endonuclease, a GIY-YIG homing endonuclease, and a cyanobacterial homing endonuclease.

35. The method of claim 33, wherein the modified endonuclease is derived from an endonuclease selected from the group consisting of:

H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, i-UarAP, i-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-Scel, PI-TfuI, PI-TfuII, PI-Thyl, PI-TliI, and PI-THII.

36. The method of claim 1, wherein the host cell is selected from the group consisting of a fungal cell, a bacterial cell, a plant cell, and an animal cell.

37. The method of claim 1, wherein the host cell is a yeast cell.

38. The method of claim 37, wherein the yeast cell is a *Saccharomyces cerevisiae* cell.

39. The method of claim 38, wherein the *Saccharomyces cerevisiae* cell is of the Baker's yeast, Mauri, Santa Fe, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1 or AL-1 strain.

40. A method for integrating a plurality of exogenous nucleic acids into a host cell genome, the method comprising:

(a) contacting a host cell with:

(i) a plurality of exogenous nucleic acids, wherein:

for each integer x, each exogenous nucleic acid $(ES)_x$ comprises a first homology region $(HR1)_x$ and a second homology region $(HR2)_x$, wherein $(HR1)_x$ and $(HR2)_x$ are capable of initiating host cell mediated homologous recombination of $(ES)_x$ at a target site $(TS)_x$ selected from a plurality of target sites of said host cell genome; and (ii) for each said target site $(TS)_x$, a nuclease $(N)_x$ capable of cleaving at $(TS)_x$, whereupon said cleaving results in homologous recombination of $(ES)_x$ at $(TS)_x$; and (b) recovering a host cell wherein each exogenous nucleic acid $(ES)_x$ has integrated at its selected target site $(TS)_x$, wherein said recovering occurs at a frequency of about one every 10, 9, 8, 7, 6, 5, 4, 3, or 2 contacted host cells, or clonal populations thereof, screened.

41. The method of claim 40, wherein $(HR1)_x$ is homologous to a 5' region of $(TS)_x$, and $(HR2)_x$ is homologous to a 3' region of $(TS)_x$.

42. The method of claim 41, wherein $(N)_x$ is capable of cleaving at a region positioned between said 5' and 3' regions of $(TS)_x$.

43. The method of claim 40, wherein a single nuclease is capable of cleaving each $(TS)_x$.

44. The method of claim 40, wherein n=3, 4, 5, 6, 7, 8, 9 or 10.

45. The method of claim 40, wherein said recovering does not require integration of a selectable marker.

46. The method of claim 40, wherein said recovering occurs at a higher frequency as compared to not contacting the host cell with a nuclease capable of cleaving at said target site.

47. The method of claim 40, wherein said recovering comprises identifying said integrations by at least one method selected from the group consisting of PCR, Southern blot, restriction mapping, and DNA sequencing.

48. The method of claim 40, wherein $(N)_x$ is capable of cleaving an endogenous genomic sequence within $(TS)_x$.

49. The method of claim 40, wherein $(N)_x$ is capable of cleaving an exogenous sequence within $(TS)_x$.

50. The method of claim 49, wherein the exogenous sequence is a recognition sequence for a homing endonuclease.

51. The method of claim 50, wherein the homing endonuclease is F-cphI.

52. The method of claim 40, wherein $(ES)_x$ further comprises a nucleic acid of interest $(D)_x$ positioned 3' of $(HR1)_x$ and 5' of $(HR2)_x$.

53. The method of claim 52, wherein $(D)_x$ is selected from the group consisting of a selectable marker, a promoter, a nucleic acid sequence encoding an epitope tag, a gene of interest, a reporter gene, and a nucleic acid sequence encoding a termination codon.

54. The method of claim 40, wherein $(ES)_x$ is linear.

55. The method of claim 40, wherein the host cell comprises one or more heterologous nucleotide sequences encoding one or more enzymes of a biosynthetic pathway.

56. The method of claim 55, wherein the one or more heterologous nucleotide sequences encoding one or more enzymes of a biosynthetic pathway are genomically integrated.

57. The method of claim 40, wherein each said exogenous nucleic acid $(ES)_x$ comprises a nucleic acid of interest $(D)_x$ positioned 3' of $(HR1)_x$ and 5' of $(HR2)_x$, encoding an enzyme of a biosynthetic pathway.

58. The method of claim 57, wherein $(D)_x$ is a member of a library $(L)_x$ comprising a plurality of nucleic acid molecules that encode variants of an enzyme of a biosynthetic pathway.

59. The method of claim 40, wherein the host cell comprises one or more heterologous nucleotide sequences encoding one or more enzymes of a mevalonate (MEV) pathway for making isopentenyl pyrophosphate.

60. The method of claim 59, wherein the one or more enzymes of the mevalonate pathway are selected from acetyl-CoA thiolase, HMG-CoA synthase, HMG-CoA reductase, mevalonate kinase, phosphomevalonate kinase and mevalonate pyrophosphate decarboxylase.

61. The method of claim 59, wherein the host cell comprises a plurality of heterologous nucleic acids encoding each the enzymes of a MEV pathway.

62. The method of claim 59, wherein each said exogenous nucleic acid $(ES)_x$ comprises a nucleic acid of interest $(D)_x$ positioned 3' of $(HR1)_x$ and 5' of $(HR2)_x$, encoding a terpene synthase.

63. The method of claim 62, wherein the terpene synthase is selected from the group consisting of a monoterpene synthase, a diterpene synthase, a sesquiterpene synthase, a sesterterpene synthase, a triterpene synthase, a tetraterpene synthase, and a polyterpene synthase.

64. The method of claim 40, wherein $(N)_x$ is provided as an expression vector comprising a nucleic acid sequence encoding $(N)_x$.

65. The method of claim 40, wherein $(N)_x$ is transformed into the host cell as a purified protein.

66. The method of claim 40, wherein $(N)_x$ is selected from the group consisting of an endonuclease, a zinc finger nuclease, a TAL-effector DNA binding domain-nuclease fusion protein (TALEN), a transposase, and a site-specific recombinase.

67. The method of claim 66, wherein the zinc finger nuclease is a fusion protein comprising the cleavage domain of a TypeIIS restriction endonuclease fused to an engineered zinc finger binding domain.

68. The method of claim 67, wherein the TypeIIS restriction endonuclease is selected from the group consisting of HO endonuclease and Fok I endonuclease.

69. The method of claim 67, wherein the zinc finger binding domain comprises 3, 5 or 6 zinc fingers.

70. The method of claim 66, wherein the endonuclease is a homing endonuclease selected from the group consisting of: an LAGLIDADG homing endonuclease, an HNH homing endonuclease, a His-Cys box homing endonuclease, a GIY-YIG homing endonuclease, and a cyanobacterial homing endonuclease.

71. The method of claim 66, wherein the endonuclease is selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, i-UarAP, i-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-Scel, PI-TfuI, PI-TfuII, PI-Thyl, PI-TliI, and PI-TliII.

72. The method of claim 66, wherein the endonuclease is modified to specifically bind an endogenous genomic sequence, wherein the modified endonuclease no longer binds to its wild type endonuclease recognition sequence.

73. The method of claim 72, wherein the modified endonuclease is derived from a homing endonuclease selected from the group consisting of: an LAGLIDADG homing endonuclease, an HNH homing endonuclease, a His-Cys box homing endonuclease, a GIY-YIG homing endonuclease, and a cyanobacterial homing endonuclease.

74. The method of claim 72, wherein the modified endonuclease is derived from an endonuclease selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, i-UarAP, i-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-Scel, PI-TfuI, PI-TfuII, PI-Thyl, PI-TliI, and PI-TliII.

75. The method of claim 40, wherein the host cell is selected from the group consisting of a fungal cell, a bacterial cell, a plant cell, and an animal cell.

76. The method of claim 40, wherein the host cell is a yeast cell.

77. The method of claim 76, wherein the yeast cell is a *Saccharomyces cerevisiae* cell.

78. The method of claim 77, wherein the *Saccharomyces cerevisiae* cell is of the Baker's yeast, Mauri, Santa Fe, IZ-1904, TA, BG-1 , CR-1, SA-1, M-26, Y-904, PE-2, PE-5, VR-1, BR-1, BR-2, ME-2, VR-2, MA-3, MA-4, CAT-1, CB-1, NR-1, BT-1 and AL-1 strain.

* * * * *

UNITED STATES PATENT AND TRADEMARK OFFICE

CERTIFICATE OF CORRECTION

PATENT NO. : 8,685,737 B2
APPLICATION NO. : 13/459034
DATED : April 1, 2014
INVENTOR(S) : Zach Serber et al.

It is certified that error appears in the above-identified patent and that said Letters Patent is hereby corrected as shown below:

In the Claims

Column 192, line 59, “I-Ani1” should be changed to --I-AniI--.

Column 193, lines 3 to 4, “PI-Thy1” should be changed to --PI-ThyI--; line 34, “PI-Sce1” should be changed to --PI-SceI--; and line 35, “PI-Thy1” should be changed to --PI-ThyI-- and “PI-THIII” should be changed to --PI-TlilI--.

Column 195, line 40, “I-Cmoe1” should be changed to --I-CmoeI--.

Column 196, line 4, “PI-Sce1” should be changed to --PI-SceI--; lines 4 to 5, “PI-Thy1” should be changed to --PI-ThyI--; line 22, “I-Ani1” should be changed to --I-AniI-- and “I-Cmoe1” should be changed to --I-CmoeI--; and lines 33 to 34, “PI-Thy1” should be changed to --PI-ThyI--.

Signed and Sealed this
Twenty-fourth Day of June, 2014

Michelle K. Lee
*Deputy Director of the United States Patent and Trademark Office*

SEQUENCE LISTING

<160> NUMBER OF SEQ ID NOS: 66

<210> SEQ ID NO 1
<211> LENGTH: 741
<212> TYPE: DNA
<213> ORGANISM: Artificial Sequence
<220> FEATURE:
<223> OTHER INFORMATION: Synthetic: Wild-type Em.GFP coding sequence

<400> SEQUENCE: 1
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccttgaccta cggcgtgcag tgcttcgccc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaag gtctatatca ccgccgacaa gcagaagaac 480
ggcatcaagg tgaacttcaa gacccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtaa 720
ctcgagaagc ttgatccggc t 741

<210> SEQ ID NO 2
<211> LENGTH: 13
<212> TYPE: DNA
<213> ORGANISM: Artificial Sequence
<220> FEATURE:
<223> OTHER INFORMATION: Synthetic: EmGFP linker encoding premature stop codon

<400> SEQUENCE: 2
cgtctaaatc atg 13

<210> SEQ ID NO 3
<211> LENGTH: 500
<212> TYPE: DNA
<213> ORGANISM: Artificial Sequence
<220> FEATURE:
<223> OTHER INFORMATION: Synthetic: HO upstream integration sequence

<400> SEQUENCE: 3
cgcaagtcct gtttctatgc ctttctctta gtaattcacg aaataaacct atggtttacg 60
aaatgatcca cgaaaatcat gttattattt acatcaacat atcgcgaaaa ttcatgtcat 120
gtccacatta acatcattgc agagcaacaa ttcattttca tagagaaatt tgctactatc 180
acccactagt actaccattg gtacctacta ctttgaattg tactaccgct gggcgttatt 240
aggtgtgaaa ccacgaaaag ttcaccataa cttcgaataa agtcgcggaa aaaagtaaac 300
agctattgct actcaaatga ggtttgcaga agcttgttga agcatgatga agcgttctaa 360
acgcactatt catcattaaa tatttaaagc tcataaaatt gtattcaatt cctattctaa 420
atggctttta tttctattac aactattagc tctaaatcca tatcctcata agcagcaatc 480
aattctatct atactttaaa 500

<210> SEQ ID NO 4
<211> LENGTH: 200
<212> TYPE: DNA
<213> ORGANISM: Artificial Sequence
<220> FEATURE:
<223> OTHER INFORMATION: Synthetic: HO downstream integration sequence

<400> SEQUENCE: 4
aatgtgtata ttagtttaaa aagttgtatg taataaaagt aaaatttaat attttggatg 60
aaaaaaacca tttttagact ttttcttaac tagaatgctg gagtagaaat acgccatctc 120
aagatacaaa aagcgttacc ggcactgatt tgtttcaacc agtatataga ttattattgg 180
gtcttgatca actttcctca 200

<210> SEQ ID NO 5
<211> LENGTH: 490
<212> TYPE: DNA
<213> ORGANISM: Artificial Sequence
<220> FEATURE:
<223> OTHER INFORMATION: Synthetic: YGR250c upstream integration sequence

<400> SEQUENCE: 5
gtacgatgtt tctcccgctg atccgattac tagccgaaga cgtaaaattg gcgcttgatt 60
caatttatgc ccttcccggg aatagttgac caaagggcaa aaaaattcag tcggagattc 120
cctattgggc ggaatttagt agatctcttt ccgtgcataa cgcctgcccg ttagtcgtta 180
tttcacgtta acattttctt ggccactgcg ctatataaat aaatacatat atatatgtca 240
agcacaataa agaaacttcc cttaaatatt gaataagtaa ataatagttg aaaagtgcct 300
tttgttcgaa ggattagagt gttcttaatt ttagttcgtt caacggtctc aaaaaaagtg 360
tgaacaagta aagcatagca cacatcccaa attacaaggc accctgatta aaaatccaaa 420
aataaaccat aagttttatt ttactaaaaa cattatacgt gaaagacaaa ccgcatcaga 480
agtttcgagg 490

<210> SEQ ID NO 6
<211> LENGTH: 185
<212> TYPE: DNA
<213> ORGANISM: Artificial Sequence
<220> FEATURE:
<223> OTHER INFORMATION: Synthetic: YGR250c downstream integration sequence

<400> SEQUENCE: 6
attgcatcag gtccataaaa tgtttttgtc tgcttttttt tcttcatgta ttagttggtt 60
tttattttta tattttcatt tatcttattc atacttttta ctcctttttt cttcattctt 120
tacgatcttg gacattcaac tagcctatgg taacttttct tattactttg cccctccttg 180
aggtg 185

<210> SEQ ID NO 7
<211> LENGTH: 504
<212> TYPE: DNA
<213> ORGANISM: Artificial Sequence
<220> FEATURE:
<223> OTHER INFORMATION: Synthetic: NDT80 upstream integration sequence

<400> SEQUENCE: 7
catcaagcgc tccaagctga cataaatcgc actttgtatc tacttttttt tattcgaaaa 60
caaggcacaa caatgaatct atcgccctgt gagattttca atctcaagtt tgtgtaatag 120

-continued atagcgttat attatagaac tataaaggtc cttgaatata catagtgttt cattcctatt 180
actgtatatg tgactttaca ttgttacttc cgcggctatt tgacgttttc tgcttcaggt 240
gcggcttgga gggcaaagtg tcagaaaatc ggccaggccg tatgacacaa aagagtagaa 300
aacgagatct caaatatctc gaggcctgtc ctctatacaa ccgcccagct ctctgacaaa 360
gctccagaac ggttgtcttt tgtttcgaaa agccaaggtc ccttataatt gccctccatt 420
ttgtgtcacc tatttaagca aaaaattgaa agtttactaa cctttcatta aagagaaata 480
acaatattat aaaaagcgct taaa 504

<210> SEQ ID NO 8
<211> LENGTH: 202
<212> TYPE: DNA
<213> ORGANISM: Artificial Sequence
<220> FEATURE:
<223> OTHER INFORMATION: Synthetic: NDT80 downstream integration sequence

<400> SEQUENCE: 8
ataaactaat gattttaaat cgttaaaaaa atatgcgaat tctgtggatc gaacacagga 60
cctccagata acttgaccga agttttttct tcagtctggc gctctcccaa ctgagctaaa 120
tccgcttact atttgttatc agttcccttc atatctacat agaataggtt aagtatttta 180
ttagttgcca gaagaactac tg 202

<210> SEQ ID NO 9
<211> LENGTH: 43
<212> TYPE: DNA
<213> ORGANISM: Artificial Sequence
<220> FEATURE:
<223> OTHER INFORMATION: Synthetic: Recognition sequence for ZFN.gfp

<400> SEQUENCE: 9
acaactacaa cagccacaac gtctatatca tggccgacaa gca 43

<210> SEQ ID NO 10
<211> LENGTH: 31
<212> TYPE: DNA
<213> ORGANISM: Artificial Sequence
<220> FEATURE:
<223> OTHER INFORMATION: Synthetic: Forward primer specific to Em.GFP

<400> SEQUENCE: 10
caactacaac agccacaagg tctatatcac c 31

<210> SEQ ID NO 11
<211> LENGTH: 22
<212> TYPE: DNA
<213> ORGANISM: Artificial Sequence
<220> FEATURE:
<223> OTHER INFORMATION: Synthetic: Reverse primer for HO locus

<400> SEQUENCE: 11
ctctaacgct gttggtagat tg 22

<210> SEQ ID NO 12
<211> LENGTH: 39
<212> TYPE: DNA
<213> ORGANISM: Artificial Sequence
<220> FEATURE:
<223> OTHER INFORMATION: Synthetic: Reverse primer for NDT80 locus

<400> SEQUENCE: 12
accatgtgat aatacactac taatgtgact actagttga 39

<210> SEQ ID NO 13
<211> LENGTH: 30
<212> TYPE: DNA
<213> ORGANISM: Artificial Sequence
<220> FEATURE:
<223> OTHER INFORMATION: Synthetic: Reverse primer for YGR250c locus

<400> SEQUENCE: 13
tcagacgcgt tcggaggaga gtgcattcac 30

<210> SEQ ID NO 14
<211> LENGTH: 5251
<212> TYPE: DNA
<213> ORGANISM: Artificial Sequence
<220> FEATURE:
<223> OTHER INFORMATION: Synthetic: Integration construct i8

<400> SEQUENCE: 14
ttgcctatgc tttgtttgct ttgaacactt gtttccgctc tccttttact tattggctac 60
taaaactacg tgtaaaagat cgcccagcgc aaaaaggtcc ggcggtttca aataatctcg 120
aactattcct ataatatgca aaatagtagg taggaacaag tcgactctag gcagataagg 180
aagatgtccg gtaaatggag actagtgctg accgggatag gcaatccaga gcctcagtac 240
gctggtaccc gtcacaatgt agggctatat atgctggagc tgctacgaaa gcggcttggt 300
ctgcagggga gaacttattc ccctgtgcct aatacgggcg gcaaagtgca ttatatagaa 360
gacgaacatt gtacgatact aagatcggat ggccagtaca tgaatctaag tggagaacag 420
gtgtgcaagg tctgggcccg gtacgccaag taccaagccc gacacgtagt tattcatgac 480
gagttaagtg tggcgtgtgg aaaagtgcag ctcagagccc ccagcaccag tattagaggt 540
cataatgggc tgcgaagcct gctaaaatgc agtggaggcc gtgtaccctt tgccaaattg 600
gctattggaa tcggcagaga acctgggtcc cgttctagag accctgcgag cgtgtcccgg 660
tgggttctgg gagctctaac tccgcaggaa ctacaaacct tgcttacaca gagtgaacct 720
gctgcctggc gtgctctgac tcagtacatt tcatagtgga tggcggcgtt agtatcgaat 780
cgacagcagt atagcgacca gcattcacat acgattgacg catgatatta ctttctgcgc 840
acttaacttc gcatctgggc agatgatgtc gaggcgaaaa aaaatataaa tcacgctaac 900
atttgattaa aatagaacaa ctacaatata aaaaaactat acaaatgaca agttcttgaa 960
aacaagaatc tttttattgt cagtactgat tagaaaaact catcgagcat caaatgaaac 1020
tgcaatttat tcatatcagg attatcaata ccatattttt gaaaaagccg tttctgtaat 1080
gaaggagaaa actcaccgag gcagttccat aggatggcaa gatcctggta tcggtctgcg 1140
attccgactc gtccaacatc aatacaacct attaatttcc cctcgtcaaa aataaggtta 1200
tcaagtgaga aatcaccatg agtgacgact gaatccggtg agaatggcaa aagcttatgc 1260
atttctttcc agacttgttc aacaggccag ccattacgct cgtcatcaaa atcactcgca 1320
tcaaccaaac cgttattcat tcgtgattgc gcctgagcga gacgaaatac gcgatcgctg 1380
ttaaaaggac aattacaaac aggaatcgaa tgcaaccggc gcaggaacac tgccagcgca 1440
tcaacaatat tttcacctga atcaggatat tcttctaata cctggaatgc tgttttgccg 1500
gggatcgcag tggtgagtaa ccatgcatca tcaggagtac ggataaaatg cttgatggtc 1560
ggaagaggca taaattccgt cagccagttt agtctgacca tctcatctgt aacatcattg 1620
gcaacgctac ctttgccatg tttcagaaac aactctggcg catcgggctt cccatacaat 1680

-continued

```
cgatagattg tcgcacctga ttgcccgaca ttatcgcgag cccatttata cccatataaa   1740
tcagcatcca tgttggaatt taatcgcggc ctcgaaacgt gagtcttttc cttacccatg   1800
gttgtttatg ttcggatgtg atgtgagaac tgtatcctag caagatttta aaaggaagta   1860
tatgaaagaa gaacctcagt ggcaaatcct aacctttat atttctctac aggggcgcgg   1920
cgtggggaca attcaacgcg tctgtgaggg gagcgtttcc ctgctcgcag gtctgcagcg   1980
aggagccgta atttttgctt cgcgccgtgc ggccatcaaa atgtatggat gcaaatgatt   2040
atacatgggg atgtatgggc taaatgtacg ggcgacagtc acatcatgcc cctgagctgc   2100
gcacgtcaag actgtcaagg agggtattct gggcctccat gtcgctggcc gggtgacccg   2160
gcggggacga ggcaagctaa acagatctga tcttgaaact gagtaagatg ctcagaatac   2220
ccgtcaagat aagagtataa tgtagagtaa tataccaagt attcagcata ttctcctctt   2280
cttttgtata aatcacggaa gggatgattt ataagaaaaa tgaatactat tacacttcat   2340
ttaccaccct ctgatctaga ttttccaacg atatgtacgt agtggtataa ggtgaggggg   2400
tccacagata taacatcgtt taatttagta ctaacagaga cttttgtcac aactacatat   2460
aagtgtacaa atatagtaca gatatgacac acttgtagcg ccaacgcgca tcctacggat   2520
tgctgacaga aaaaaaggtc acgtgaccag aaaagtcacg tgtaattttg taactcaccg   2580
cattctagcg gtccctgtcg tgcacactgc actcaacacc ataaacctta gcaacctcca   2640
aaggaaatca ccgtataaca aagccacagt tttacaactt agtctcttat gaagttactt   2700
accaatgaga aatagaggct ctttctcgag aaatatgaat atggatatat atatatatat   2760
atatatatat atatatatat gtaaacttgg ttcttttta gcttgtgatc tctagcttgg   2820
gtctctctct gtcgtaacag ttgtgatatc ggaagaagag aaaagacgaa gagcagaagc   2880
ggaaaacgta tacacgtcac atatcacaca cacacaatgg gaaagctatt acaattggca   2940
ttgcatccgg tcgagatgaa ggcagctttg aagctgaagt tttgcagaac accgctattc   3000
tccatctatg atcagtccac gtctccatat ctcttgcact gtttcgaact gttgaacttg   3060
acctccagat cgtttgctgc tgtgatcaga gagctgcatc cagaattgag aaactgtgtt   3120
actctctttt atttgatttt aagggctttg gataccatcg aagacgatat gtccatcgaa   3180
cacgatttga aaattgactt gttgcgtcac ttccacgaga aattgttgtt aactaaatgg   3240
agtttcgacg gaaatgcccc cgatgtgaag gacagagccg ttttgacaga tttcgaatcg   3300
attcttattg aattccacaa attgaaacca gaatatcaag aagtcatcaa ggagatcacc   3360
gagaaaatgg gtaatggtat ggccgactac atcttagatg aaaattacaa cttgaatggg   3420
ttgcaaaccg tccacgacta cgacgtgtac tgtcactacg tagctggttt ggtcggtgat   3480
ggtttgaccc gtttgattgt cattgccaag tttgccaacg aatctttgta ttctaatgag   3540
caattgtatg aaagcatggg tcttttccta caaaaaacca acatcatcag agattacaat   3600
gaagatttgg tcgatggtag atccttctgg cccaaggaaa tctggtcaca atacgctcct   3660
cagttgaagg acttcatgaa acctgaaaac gaacaactgg ggttggactg tataaaccac   3720
ctcgtcttaa acgcattgag tcatgttatc gatgtgttga cttatttggc cggtatccac   3780
gagcaatcca ctttccaatt ttgtgccatt ccccaagtta tggccattgc aaccttggct   3840
ttggtattca acaaccgtga agtgctacat ggcaatgtaa agattcgtaa gggtactacc   3900
tgctatttaa ttttgaaatc aaggactttg cgtggctgtg tcgagatttt tgactattac   3960
ttacgtgata tcaaatctaa attggctgtg caagatccaa atttcttaaa attgaacatt   4020
caaatctcca agatcgaaca gtttatggaa gaaatgtacc aggataaatt acctcctaac   4080
```

gtgaagccaa atgaaactcc aattttcttg aaagttaaag aaagatccag atacgatgat 4140
gaattggttc caacccaaca agaagaagag tacaagttca atatggtttt atctatcatc 4200
ttgtccgttc ttcttgggtt ttattatata tacactttac acagagcgtg aagtctgcgc 4260
caaataacat aaacaaacaa ctccgaacaa taactaagta cttacataat aggtagaggc 4320
ctatccttaa agataacctt atatttcatt acatcaacta attcgacctt attatctttc 4380
gaattgaaat gcattatacc catcggtacg tctagctttg tcaccttccc cagtaaacgc 4440
tgtttcttgc cgacaaacaa tgtggccctc tctccgtcaa tctgtaacga cccaaatcgt 4500
attaaagttt cgccgtcctg ttcactgaac cttccctcat ttggagaatc tctcctcgcc 4560
agcgacgcaa agtccttagg caactctagt tcaccttgaa tctccagcat catcatccca 4620
agcggtgtta tcaccgtggt ctgcttttct cttgactgtg tcaacttctg ccattgacta 4680
gcatctatat ctacactagg cattcttttc agctgtttat tgggctgaat gatagtgata 4740
attctttttt ctatcactcc tttggctata ttagtggtta gcttactaaa aaagattaaa 4800
ggaaaaatga aattcaagat gctaacgttg acatgtatat tttaagaaaa caaaaatcat 4860
acaaagagga gatcggatat aaaagaataa cataaatatg tttagtgcat taggtaaatg 4920
ggtccgaggc tctcgcaatg ataaggactt tgtgacgaag tataccgcag atttatcaca 4980
aataacttca cagatccatc aattagatgt cgcgttaaag aaaagccaat ccatcttgag 5040
tcaatggcaa tcaaatctga ccttttatgg tattgcgtta acggtattgg ccctgagcta 5100
cacatattgg gagtaccatg gttatcgacc ataccttgtg gtgactgcgc tactatgcat 5160
aggctcgcta atcttgttca aatgggcatt aaccaaactc tatgcatttt ataacaacaa 5220
taggttacgc aagttggcaa aactccgtgc a 5251

<210> SEQ ID NO 15
<211> LENGTH: 70
<212> TYPE: DNA
<213> ORGANISM: Artificial Sequence
<220> FEATURE:
<223> OTHER INFORMATION: Synthetic: Primer 61-67-CPK066-G

<400> SEQUENCE: 15
ggtaagacgg ttgggtttta tcttttgcag ttggtactat taagaacaat cacaggaaac 60
agctatgacc 70

<210> SEQ ID NO 16
<211> LENGTH: 70
<212> TYPE: DNA
<213> ORGANISM: Artificial Sequence
<220> FEATURE:
<223> OTHER INFORMATION: Synthetic: Primer 61-67-CPK067-G

<400> SEQUENCE: 16
ttgcgttttg tactttggtt cgctcaattt tgcaggtaga taatcgaaaa gttgtaaaac 60
gacggccagt 70

<210> SEQ ID NO 17
<211> LENGTH: 4162
<212> TYPE: DNA
<213> ORGANISM: Artificial Sequence
<220> FEATURE:
<223> OTHER INFORMATION: Synthetic: Integration construct i32

<400> SEQUENCE: 17
gcctgtctac aggataaaga cgggtcggat acctgcacaa gcaatttggc acctgcatac 60

-continued

```
cccatttccc cagtagataa cttcaacaca cacatcaatg tccctcacca gtttatttcc    120
aaaagagacg ctttttacta cctgactaga ttttcatttt gtttcttttg gattgcgctt    180
gcctttgtag gtgtgtcgtt tatcctttac gttttgactt ggtgctcgaa gatgctttca    240
gagatggtgc ttatcctcat gtcttttggg tttgtcttca atacggcagc cgttgtcttg    300
caaacggccg cctctgccat ggcaaagaat gctttccatg acgatcatcg tagtgcccaa    360
ttgggtgcct ctatgatggg tatggcttgg gcaagtgtct ttttatgtat cgtggaattt    420
atcctgctgg tcttctggtc tgttagggca aggttggcct ctacttactc catcgacaat    480
tcaagataca gaacctcctc cagatggaat cccttccata gagagaagga gcaagcaact    540
gacccaatat tgactgccac tggacctgaa gacatgcaac aaagtgcaag catagtgggg    600
ccttcttcca atgctaatcc ggtcactgcc actgctgcta cggaaaacca acctaaaggt    660
attaacttct tcactataag aaaatcacac gagcgcccgg acgatgtctc tgtttaaatg    720
gcgcaagttt tccgctttgt aatatatatt tatacccctt tcttctctcc cctgcaatat    780
aatagtttaa ttctaatatt aataatatcc tatattttct tcatttaccg gcgcactctc    840
gcccgaacga cctcaaaatg tctgctacat tcataataac caaaagctca taactttttt    900
ttttgaacct gaatatatat acatcacata tcactgctgg tccttgccga ccagcgtata    960
caatctcgat agttggtttc ccgttctttc cactcccgtc cacaggaaac agctatgacc   1020
atgattacgc caagctattt aggtgacact atagaatact caagctatgc atcaagcttg   1080
gtaccgagct cggatccact agtaacggcc gccagtgtgc tggaattcgc cctgtcgaca   1140
ctagtaatac acatcatcgt cctacaagtt catcaaagtg ttggacagac aactatacca   1200
gcatggatct cttgtatcgg ttcttttctc ccgctctctc gcaataacaa tgaacactgg   1260
gtcaatcata gcctacacag gtgaacagag tagcgtttat acagggttta tacggtgatt   1320
cctacggcaa aaatttttca tttctaaaaa aaaaaagaaa aatttttctt tccaacgcta   1380
gaaggaaaag aaaaatctaa ttaaattgat ttggtgattt tctgagagtt cccttttca    1440
tatatcgaat tttgaatata aaaggagatc gaaaaaattt ttctattcaa tctgtttttct  1500
ggttttattt gatagttttt ttgtgtatta ttattatgga ttagtactgg tttatatggg   1560
tttttctgta taacttcttt ttattttagt ttgtttaatc ttattttgag ttacattata   1620
gttccctaac tgcaagagaa gtaacattaa aaatgaaaaa gcctgaactc accgcgacgt   1680
ctgtcgagaa gtttctgatc gaaaagttcg acagcgtctc cgacctgatg cagctctcgg   1740
agggcgaaga atctcgtgct ttcagcttcg atgtaggagg gcgtggatat gtcctgcggg   1800
taaatagctg cgccgatggt ttctacaaag atcgttatgt ttatcggcac tttgcatcgg   1860
ccgcgctccc gattccggaa gtgcttgaca ttggggaatt cagcgagagc ctgacctatt   1920
gcatctcccg ccgtgcacag ggtgtcacgt tgcaagacct gcctgaaacc gaactgcccg   1980
ctgttctgca gccggtcgcg gaggccatgg atgcgatcgc tgcggccgat cttagccaga   2040
cgagcgggtt cggcccattc ggaccgcaag gaatcggtca atacactaca tggcgtgatt   2100
tcatatgcgc gattgctgat ccccatgtgt atcactggca aactgtgatg gacgacaccg   2160
tcagtgcgtc cgtcgcgcag gctctcgatg agctgatgct ttgggccgag gactgccccg   2220
aagtccggca cctcgtgcac gcggatttcg gctccaacaa tgtcctgacg gacaatggcc   2280
gcataacagc ggtcattgac tggagcgagg cgatgttcgg ggattcccaa tacgaggtcg   2340
ccaacatctt cttctggagg ccgtggttgg cttgtatgga gcagcagacg cgctacttcg   2400
agcggaggca tccggagctt gcaggatcgc cgcggctccg ggcgtatatg ctccgcattg   2460
```

```
gtcttgacca actctatcag agcttggttg acggcaattt cgatgatgca gcttgggcgc   2520

agggtcgatg cgacgcaatc gtccgatccg gagccgggac tgtcgggcgt acacaaatcg   2580

cccgcagaag cgcggccgtc tggaccgatg gctgtgtaga agtactcgcc gatagtggaa   2640

accgacgccc cagcactcgt ccgagggcaa aggaataggt ttaacttgat actactagat   2700

tttttctctt catttataaa atttttggtt ataattgaag ctttagaagt atgaaaaaat   2760

cctttttttt cattctttgc aaccaaaata agaagcttct tttattcatt gaaatgatga   2820

atataaacct aacaaaagaa aaagactcga atatcaaaca ttaaaaaaaa ataaaagagg   2880

ttatctgttt tcccatttag ttggagtttg cattttctaa tagatagaac tctcaattaa   2940

tgtggattta gtttctctgt tcgttttttt ttgttttgtt ctcactgtat ttacatttct   3000

atttagtatt tagttattca tataatctta acttctcgag gagctctaag ggcgaattct   3060

gcagatatcc atcacactgg cggccgctcg agcatgcatc tagagggccc aattcgccct   3120

atagtgagtc gtattacaat tcactggccg tcgttttaca acaagcatct tgccctgtgc   3180

ttggcccccca gtgcagcgaa cgttataaaa acgaatactg agtatatatc tatgtaaaac   3240

aaccatatca tttcttgttc tgaactttgt ttacctaact agttttaaat ttcccttttt   3300

cgtgcatgcg ggtgttctta tttattagca tactacattt gaaatatcaa atttccttag   3360

tagaaaagtg agagaaggtg cactgacaca aaaaataaaa tgctacgtat aactgtcaaa   3420

actttgcagc agcgggcatc cttccatcat agcttcaaac atattagcgt tcctgatctt   3480

catacccgtg ctcaaaatga tcaaacaaac tgttattgcc aagaaataaa cgcaaggctg   3540

ccttcaaaaa ctgatccatt agatcctcat atcaagcttc ctcatagaac gcccaattac   3600

aataagcatg ttttgctgtt atcaccgggt gataggtttg ctcaaccatg gaaggtagca   3660

tggaatcata atttggatac taatacaaat cggccatata atgccattag taaattgcgc   3720

tcccatttag gtggttctcc aggaatacta ataaatgcgg tgcatttgca aaatgaattt   3780

attccaaggc caaaacaaca cgatgaatgg ctttattttt ttgttattcc tgacatgaag   3840

ctttatgtaa ttaaggaaac ggacatcgag gaatttgcat ctttttttaga tgaaggagct   3900

attcaagcac caaagctatc cttccaggat tatttaagcg gtaaggccaa ggcttcccaa   3960

caggttcatg aagtgcatca tagaaagctt acaaggtttc agggtgaaac ttttctaaga   4020

gattggaact tagtctgtgg gcattataag agagatgcta agtgtggaga aatgggaccc   4080

gacataattg cagcatttca agatgaaaag ctttttcctg agaataatct agccttaatt   4140

tctcatattg gggtcatat tt                                             4162
```

```
<210> SEQ ID NO 18
<211> LENGTH: 7879
<212> TYPE: DNA
<213> ORGANISM: Artificial Sequence
<220> FEATURE:
<223> OTHER INFORMATION: Synthetic: Integration construct i33
<220> FEATURE:
<221> NAME/KEY: misc_feature
<222> LOCATION: (270)..(270)
<223> OTHER INFORMATION: n is a, c, g, or t

<400> SEQUENCE: 18

atgaattggc cagtttttc caattatgga acgcctgttc ctgatccacg gcctgcactt     60

gcgaccacaa ttccacacct gaggcgcctg cctcttttcc agcatgtggc aactgtcccc    120

acgacagggc atcccagaat cctctggtaa atcttaaatg aaactgacgc gtggcagtag    180

attccaacaa tggtgggatg gcccgtggga aagtcgtgta gtgctcatac gcatcatatg    240
```

-continued

```
acatggatga tacggccggg tcaaacggtn cgattgcagt tggaatgcaa atgagagtag    300
cagatcattg ttgggcagcg gcttcaacac cagtgcttcg tcgtacggat accataaact    360
gtcatttata ccaatctgcg acaccgtgtc ttctgcgaac acacccagca gtagagtgcc    420
cagcatgaaa taggccagtg tgaggatcat cgtcgtcttg cctatgcttt gtttgctttg    480
aacacttgtt tccgctctcc ttttacttat tggctactaa aactacgtgt aaaagatcgc    540
ccagcgcaaa aaggtccggc ggtttcaaat aatctcgaac tattcctata atatgcaaaa    600
tagtaggtag gaacaagtca actctaggca gataacgaag atgtccggta aatggagact    660
agtgctgact gggataggca atccagagcc tcagtacgct ggcacccgtc acaatgtagg    720
gctatatatg ctggagctgc tacgaaagcg gcttggtctg caggggagaa cttattcccc    780
tgtgcctaat acgggcggca aagtgcatta tatagaagac gaacattgta cgatactaag    840
atcggatggc cagtacatga atctaagtgg agaacaggtg tgcaaggtct gggcccggta    900
cgccaagtac caagcccgac acgttgttat tcatgacgag ttaagtgtgg cgtgtggaaa    960
agtgcagctc agagccccca gcaccagtat tagaggtcat aatgggctgc gaagcctgct   1020
aaaatgcagt ggaggccgtg taccctttgc caaattggct attggaatcg gcagagaacc   1080
tgggtcccgt tctagagacc ctgcgagcgt gtcccggtgg gttctgggag ctctaactcc   1140
gcaggaacta caaaccttgc ttacacagag tgaacctgct gcctggcgtg ctctgactca   1200
gtacatttca taggacagca ttcgcccagt attttttta ttctacaaac cttctataat   1260
ttcaaagtat ttacataatt ctgtatcagt ttaatcacca taatatcgtt ttctttgttt   1320
agtgcaatta attttccta ttgttacttc gggccttttt ctgttttatg agctattttt   1380
tccgtcatcc ttccggatcc agattttcag cttcatctcc agattgtgtc tacgtaatgc   1440
acgccatcat tttaagagag gacagagaag caagcctcct gaaagatgaa gctactgtct   1500
tctatcgaac aagcatgcga tatttgccga cttaaaaagc tcaagtgctc caaagaaaaa   1560
ccgaagtgcg ccaagtgtct gaagaacaac tgggagtgtc gctactctcc caaaaccaaa   1620
aggtctccgc tgactagggc acatctgaca gaagtggaat caaggctaga aagactggaa   1680
cagctatttc tactgatttt tcctcgagaa gaccttgaca tgattttgaa aatggattct   1740
ttacaggata taaaagcatt gttaacagga ttatttgtac aagataatgt gaataaagat   1800
gccgtcacag atagattggc ttcagtggag actgatatgc ctctaacatt gagacagcat   1860
agaataagtg cgacatcatc atcggaagag agtagtaaca aaggtcaaag acagttgact   1920
gtatcgattg actcggcagc tcatcatgat aactccacaa ttccgttgga ttttatgccc   1980
agggatgctc ttcatggatt tgattggtct gaagaggatg acatgtcgga tggcttgccc   2040
ttcctgaaaa cggaccccaa caataatggg ttctttggcg acggttctct cttatgtatt   2100
cttcgatcta ttggctttaa accggaaaat tacacgaact ctaacgttaa caggctcccg   2160
accatgatta cggatagata cacgttggct tctagatcca caacatcccg tttacttcaa   2220
agttatctca ataattttca cccctactgc cctatcgtgc actcaccgac gctaatgatg   2280
ttgtataata accagattga aatcgcgtcg aaggatcaat ggcaaatcct tttaactgc    2340
atattagcca ttggagcctg gtgtatagag gggaatcta ctgatataga tgttttttac    2400
tatcaaaatg ctaaatctca tttgacgagc aaggtcttcg agtcaggttc cataattttg   2460
gtgacagccc tacatcttct gtcgcgatat acacagtgga ggcagaaaac aaatactagc   2520
tataattttc acagcttttc cataagaatg gccatatcat tgggcttgaa tagggacctc   2580
ccctcgtcct tcagtgatag cagcattctg gaacaaagac gccgaatttg gtggtctgtc   2640
```

-continued tactcttggg agatccaatt gtccctgctt tatggtcgat ccatccagct ttctcagaat 2700
acaatctcct tcccttcttc tgtcgacgat gtgcagcgta ccacaacagg tcccaccata 2760
tatcatggca tcattgaaac agcaaggctc ttacaagttt tcacaaaaat ctatgaacta 2820
gacaaaacag taactgcaga aaaaagtcct atatgtgcaa aaaaatgctt gatgatttgt 2880
aatgagattg aggaggtttc gagacaggca ccaaagtttt tacaaatgga tatttccacc 2940
accgctctaa ccaatttgtt gaaggaacac ccttggctat cctttacaag attcgaactg 3000
aagtggaaac agttgtctct tatcatttat gtattaagag attttttcac taattttacc 3060
cagaaaaagt cacaactaga acaggatcaa aatgatcatc aaagttatga agttaaacga 3120
tgctccatca tgttaagcga tgcagcacaa agaactgtta tgtctgtaag tagctatatg 3180
gacaatcata atgtcacccc atattttgcc tggaattgtt cttattactt gttcaatgca 3240
gtcctagtac ccataaagac tctactctca aactcaaaat cgaatgctga gaataacgag 3300
accgcacaat tattacaaca aattaacact gttctgatgc tattaaaaaa actggccact 3360
tttaaaatcc agacttgtga aaaatacatt caagtactgg aagaggtatg tgcgccgttt 3420
ctgttatcac agtgtgcaat cccattaccg catatcagtt ataacaatag taatggtagc 3480
gccattaaaa atattgtcgg ttctgcaact atcgcccaat accctactct tccggaggaa 3540
aatgtcaaca atatcagtgt taaatatgtt tctcctggct cagtagggcc ttcacctgtg 3600
ccattgaaat caggagcaag tttcagtgat ctagtcaagc tgttatctaa ccgtccaccc 3660
tctcgtaact ctccagtgac aataccaaga agcacacctt cgcatcgctc agtcacgcct 3720
tttctagggc aacagcaaca gctgcaatca ttagtgccac tgaccccgtc tgctttgttt 3780
ggtggcgcca attttaatca aagtgggaat attgctgata gctcattgtc cttcactttc 3840
actaacagta gcaacggtcc gaacctcata acaactcaaa caaattctca agcgctttca 3900
caaccaattg cctcctctaa cgttcatgat aacttcatga ataatgaaat cacggctagt 3960
aaaattgatg atggtaataa ttcaaaacca ctgtcacctg gttggacgga ccaaactgcg 4020
tataacgcgt ttggaatcac tacagggatg tttaatacca ctacaatgga tgatgtatat 4080
aactatctat tcgatgatga agatacccca ccaaacccaa aaaaagagta aaatgaatcg 4140
tagatactga aaaaccccgc aagttcactt caactgtgca tcgtgcacca tctcaatttc 4200
tttcatttat acatcgtttt gccttctttt atgtaactat actcctctaa gtttcaatct 4260
tggccatgta acctctgatc tatagaattt tttaaatgac tagaattaat gcccatcttt 4320
tttttggacc taaattcttc atgaaaatat attacgaggg cttattcaga agcttcgctc 4380
agtcgacact agtaatacac atcatcgtcc tacaagttca tcaaagtgtt ggacagacaa 4440
ctataccagc atggatctct tgtatcggtt cttttctccc gctctctcgc aataacaatg 4500
aacactgggt caatcatagc ctacacaggt gaacagagta gcgtttatac agggtttata 4560
cggtgattcc tacggcaaaa atttttcatt tctaaaaaaa aaaagaaaaa tttttctttc 4620
caacgctaga aggaaaagaa aaatctaatt aaattgattt ggtgattttc tgagagttcc 4680
ctttttcata tatcgaattt tgaatataaa aggagatcga aaaaattttt ctattcaatc 4740
tgttttctgg ttttatttga tagttttttt gtgtattatt attatggatt agtactggtt 4800
tatatgggtt tttctgtata acttcttttt attttagttt gtttaatctt attttgagtt 4860
acattatagt tccctaactg caagagaagt aacattaaaa atgaccactc ttgacgacac 4920
ggcttaccgg taccgcacca gtgtcccggg ggacgccgag gccatcgagg cactggatgg 4980
gtccttcacc accgacaccg tcttccgcgt caccgccacc ggggacggct tcaccctgcg 5040

-continued

```
ggaggtgccg gtggacccgc ccctgaccaa ggtgttcccc gacgacgaat cggacgacga   5100
atcggacgcc ggggaggacg gcgacccgga ctcccggacg ttcgtcgcgt acggggacga   5160
cggcgacctg gcgggcttcg tggtcgtctc gtactccggc tggaaccgcc ggctgaccgt   5220
cgaggacatc gaggtcgccc cggagcaccg ggggcacggg gtcgggcgcg cgttgatggg   5280
gctcgcgacg gagttcgccc gcgagcgggg cgccgggcac ctctggctgg aggtcaccaa   5340
cgtcaacgca ccggcgatcc acgcgtaccg gcggatgggg ttcaccctct gcggcctgga   5400
caccgccctg tacgacggca ccgcctcgga cggcgagcag gcgctctaca tgagcatgcc   5460
ctgcccctga gtttaacttg atactactag atttttctc ttcatttata aaatttttgg   5520
ttataattga agctttagaa gtatgaaaaa atcctttttt ttcattcttt gcaaccaaaa   5580
taagaagctt cttttattca ttgaaatgat gaatataaac ctaacaaaag aaaaagactc   5640
gaatatcaaa cattaaaaaa aaataaaaga ggttatctgt tttcccattt agttggagtt   5700
tgcattttct aatagataga actctcaatt aatgtggatt tagtttctct gttcgttttt   5760
ttttgttttg ttctcactgt atttacattt ctatttagta tttagttatt catataatct   5820
taacttctcg aggagctcga tcttgaaact gagtaagatg ctcagaatac ccgtcaagat   5880
aagagtataa tgtagagtaa tataccaagt attcagcata ttctcctctt cttttgtata   5940
aatcacggaa gggatgattt ataagaaaaa tgaatactat tacacttcat ttaccaccct   6000
ctgatctaga ttttccaacg atatgtacgt agtggtataa ggtgaggggg tccacagata   6060
taacatcgtt taatttagta ctaacagaga cttttgtcac aactacatat aagtgtacaa   6120
atatagtaca gatatgacac acttgtagcg ccaacgcgca tcctacggat tgctgacaga   6180
aaaaaaggtc acgtgaccag aaaagtcacg tgtaattttg taactcaccg cattctagcg   6240
gtccctgtcg tgcacactgc actcaacacc ataaacctta gcaacctcca aaggaaatca   6300
ccgtataaca aagccacagt tttacaactt agtctcttat gaagtgtctc tctctgtcgt   6360
aacagttgtg atatcggaag aagagaaaag acgaagagca gaagcggaaa acgtatacac   6420
gtcacatatc acacacacac aatgggaaag ctattacaat tggcattgca tccggtcgag   6480
atgaaggcag ctttgaagct gaagttttgc agaacaccgc tattctccat ctatgatcag   6540
tccacgtctc catatctctt gcactgtttc gaactgttga acttgacctc cagatcgttt   6600
gctgctgtga tcagagagct gcatccagaa ttgagaaact gtgttactct cttttatttg   6660
attttaaggg ctttggatac catcgaagac gatatgtcca tcgaacacga tttgaaaatt   6720
gacttgttgc gtcacttcca cgagaaattg ttgttaacta aatggagttt cgacggaaat   6780
gcccccgatg tgaaggacag agccgttttg acagatttcg aatcgattct tattgaattc   6840
cacaaattga aaccagaata tcaagaagtc atcaaggaga tcaccgagaa aatgggtaat   6900
ggtatggccg actacatctt ggatgaaaat tacaacttga atgggttgca aaccgtccac   6960
gactacgacg tgtactgtca ctacgtagct ggtttggtcg gtgatggttt gacccgtttg   7020
attgtcattg ccaagtttgc caacgaatct ttgtattcta atgagcaatt gtatgaaagc   7080
atgggtcttt tcctacaaaa aaccaacatc atcagagact acaatgaaga tttggtcgat   7140
ggtagatcct tctggcccaa ggaaatctgg tcacaatacg ctcctcagtt gaaggacttc   7200
atgaaacctg aaaacgaaca actggggttg gactgtataa accacctcgt cttaaacgca   7260
ttgagtcatg ttatcgatgt gttgacttat ttggccagta tccacgagca atccactttc   7320
caattttgtg ccattcccca agttatggcc attgcaacct tggctttggt attcaacaac   7380
cgtgaagtgc tacatggcaa tgtaaagatt cgtaagggta ctacctgcta tttaattttg   7440
```

aaatcaagga ctttgcgtgg ctgtgtcgag atttttgact attacttacg tgatatcaaa 7500
tctaaattgg ctgtgcaaga tccaaatttc ttaaaattga acattcaaat ctccaagatc 7560
gaacaattca tggaagaaat gtaccaggat aaattacctc ctaacgtgaa gccaaatgaa 7620
actccaattt tcttgaaagt taaagaaaga tccagatacg atgatgaatt ggtcccaacc 7680
caacaagaag aagagtacaa gttcaatatg gttttatcta tcatcttgtc cgttcttctt 7740
gggttttatt atatatacac tttacacaga gcgtgaagtc tgcgccaaat aacataaaca 7800
aacaactccg aacaataact aagtacttac ataataggta gaggcctatc cttaaagata 7860
accttatatt tcattacat 7879

<210> SEQ ID NO 19
<211> LENGTH: 5714
<212> TYPE: DNA
<213> ORGANISM: Artificial Sequence
<220> FEATURE:
<223> OTHER INFORMATION: Synthetic: Integration construct i37

<400> SEQUENCE: 19
gcctgtctac aggataaaga cgggtcggat acctgcacaa gcaatttggc acctgcatac 60
cccatttccc cagtagataa cttcaacaca cacatcaatg tccctcacca gtttatttcc 120
aaaagagacg ctttttacta cctgactaga ttttcatttt gtttcttttg gattgcgctt 180
gcctttgtag gtgtgtcgtt tatcctttac gttttgactt ggtgctcgaa gatgctttca 240
gagatggtgc ttatcctcat gtcttttggg tttgtcttca atacggcagc cgttgtcttg 300
caaacggccg cctctgccat ggcaaagaat gctttccatg acgatcatcg tagtgcccaa 360
ttgggtgcct ctatgatggg tttaaacgta tggcttgggc aagtgtcttt ttatgtatcg 420
tggaatttat cctgctggtc ttctggtctg ttagggcaag gttggcctct acttactcca 480
tcgacaattc aagatacaga acctcctcca gatggaatcc cttccataga gagaaggagc 540
aagcaactga cccaatattg actgccactg gacctgaaga catgcaacaa agtgcaagca 600
tagtggggcc ttcttccaat gctaatccgg tcactgccac tgctgctacg gaaaaccaac 660
ctaaaggtat taacttcttc actataagaa aatcacacga gcgcccggac gatgtctctg 720
tttaaatggc gcaagttttc cgctttgtaa tatatattta taccccttc ttctctcccc 780 tgcaatataa tagtttaatt ctaatattaa taatatccta tattttcttc atttaccggc 840
gcactctcgc ccgaacgacc tcaaaatgtc tgctacattc ataataacca aaagctcata 900
actttttttt ttgaacctga atatatatac atcacatatc actgctggtc ctgagaagtt 960
aagattatat gaataactaa atactaaata gaaatgtaaa tacagtgaga acaaaacaaa 1020
aaaaaacgaa cagagaaact aaatccacat taattgagag ttctatctat tagaaaatgc 1080
aaactccaac taaatgggaa aacagataac ctcttttatt ttttttaat gtttgatatt 1140 cgagtctttt tcttttgtta ggtttatatt catcatttca atgaataaaa gaagcttctt 1200
attttggttg caaagaatga aaaaaaagga tttttcata cttctaaagc ttcaattata 1260
accaaaaatt ttataaatga agagaaaaaa tctagtagta tcaagttaaa cttagaaaaa 1320
ctcatcgagc atcaaatgaa actgcaattt attcatatca ggattatcaa taccatattt 1380
ttgaaaaagc cgtttctgta atgaaggaga aaactcaccg aggcagttcc ataggatggc 1440
aagatcctgg tatcggtctg cgattccgac tcgtccaaca tcaatacaac ctattaattt 1500
cccctcgtca aaaataaggt tatcaagtga gaaatcacca tgagtgacga ctgaatccgg 1560
tgagaatggc aaaagcttat gcatttcttt ccagacttgt tcaacaggcc agccattacg 1620

-continued

```
ctcgtcatca aaatcactcg catcaaccaa accgttattc attcgtgatt gcgcctgagc   1680
gagacgaaat acgcgatcgc tgttaaaagg acaattacaa acaggaatcg aatgcaaccg   1740
gcgcaggaac actgccagcg catcaacaat attttcacct gaatcaggat attcttctaa   1800
tacctggaat gctgttttgc cggggatcgc agtggtgagt aaccatgcat catcaggagt   1860
acggataaaa tgcttgatgg tcggaagagg cataaattcc gtcagccagt ttagtctgac   1920
catctcatct gtaacatcat tggcaacgct acctttgcca tgtttcagaa acaactctgg   1980
cgcatcgggc ttcccataca atcgatagat tgtcgcacct gattgcccga cattatcgcg   2040
agcccattta tacccatata aatcagcatc catgttggaa tttaatcgcg gcctcgaaac   2100
gtgagtcttt tccttaccca tttttaatgt tacttctctt gcagttaggg aactataatg   2160
taactcaaaa taagattaaa caaactaaaa taaaaagaag ttatacagaa aaacccatat   2220
aaaccagtac taatccataa taataataca caaaaaaact atcaaataaa accagaaaac   2280
agattgaata gaaaaatttt ttcgatctcc ttttatattc aaaattcgat atatgaaaaa   2340
gggaactctc agaaaatcac caaatcaatt taattagatt tttcttttcc ttctagcgtt   2400
ggaaagaaaa atttttcttt tttttttag aaatgaaaaa tttttgccgt aggaatcacc   2460
gtataaaccc tgtataaacg ctactctgtt cacctgtgta ggctatgatt gacccagtgt   2520
tcattgttat tgcgagagag cgggagaaaa gaaccgatac aagagatcca tgctggtata   2580
gttgtctgtc caacactttg atgaacttgt aggacgatga tgtgtattac tagtgtcgac   2640
accatataca tatccatatc taatcttact tatatgttgt ggaaatgtaa agagccccat   2700
tatcttagcc taaaaaaacc ttctctttgg aactttcagt aatacgctta actgctcatt   2760
gctatattga agtacggatt agaagccgcc gagcgggcga cagccctccg acggaagact   2820
ctcctccgtg cgtcctggtc ttcaccggtc gcgttcctga aacgcagatg tgcctcgcgc   2880
cgcactgctc cgaacaataa agattctaca atactagctt ttatggttat gaagaggaaa   2940
aattggcagt aacctggccc cacaaacctt caaatcaacg aatcaaatta acaaccatag   3000
gataataatg cgattagttt tttagcctta tttctggggt aattaatcag cgaagcgatg   3060
atttttgatc tattaacaga tatataaatg caaaagctgc ataaccactt taactaatac   3120
tttcaacatt ttcggtttgt attacttctt attcaaatgt cataaaagta tcaacaaaaa   3180
attgttaata tacctctata ctttaacgtc aaggagaaaa aactataatg tcattaccgt   3240
tcttaacttc tgcaccggga aaggttatta tttttggtga acactctgct gtgtacaaca   3300
agcctgccgt cgctgctagt gtgtctgcgt tgagaaccta cctgctaata agcgagtcat   3360
ctgcaccaga tactattgaa ttggacttcc cggacattag ctttaatcat aagtggtcca   3420
tcaatgattt caatgccatc accgaggatc aagtaaactc ccaaaaattg gccaaggctc   3480
aacaagccac cgatggcttg tctcaggaac tcgttagtct tttggatccg ttgttagctc   3540
aactatccga atccttccac taccatgcag cgttttgttt cctgtatatg tttgtttgcc   3600
tatgcccccca tgccaagaat attaagtttt ctttaaagtc tactttaccc atcggtgctg   3660
ggttgggctc aagcgcctct atttctgtat cactggcctt agctatggcc tacttggggg   3720
ggttaatagg atctaatgac ttggaaaagc tgtcagaaaa cgataagcat atagtgaatc   3780
aatgggcctt cataggtgaa aagtgtattc acggtacccc ttcaggaata gataacgctg   3840
tggccactta tggtaatgcc ctgctatttg aaaaagactc acataatgga acaataaaca   3900
caaacaattt taagttctta gatgatttcc cagccattcc aatgatccta acctatacta   3960
gaattccaag gtctacaaaa gatcttgttg ctcgcgttcg tgtgttggtc accgagaaat   4020
```

-continued ttcctgaagt tatgaagcca attctagatg ccatgggtga atgtgcccta caaggcttag 4080
agatcatgac taagttaagt aaatgtaaag gcaccgatga cgaggctgta gaaactaata 4140
atgaactgta tgaacaacta ttggaattga taagaataaa tcatggactg cttgtctcaa 4200
tcggtgtttc tcatcctgga ttagaactta ttaaaaatct gagcgatgat ttgagaattg 4260
gctccacaaa acttaccggt gctggtggcg gcggttgctc tttgactttg ttacgaagag 4320
acattactca agagcaaatt gacagtttca aaaagaaatt gcaagatgat tttagttacg 4380
agacatttga aacagacttg ggtgggactg gctgctgttt gttaagcgca aaaaatttga 4440
ataaagatct taaaatcaaa tccctagtat tccaattatt tgaaaataaa actaccacaa 4500
agcaacaaat tgacgatcta ttattgccag gaaacacgaa tttaccatgg acttcataag 4560
ctaatttgcg ataggcatta tttattagtt gtttttaatc ttaactgtgt atgaagtttt 4620
atgtaataaa gatagaaaga gaaacaaaaa aaaatttttc gtagtatcaa ttcagctttc 4680
gaagacagaa tgaaatttaa gcagaccatc atcttgccct gtgcttggcc cccagtgcag 4740
cgaacgttat aaaaacgaat actgagtata tatctatgta aaacaaccat atcatttctt 4800
gttctgaact ttgtttacct aactagtttt aaatttccct tttcgtgca tgcgggtgtt 4860 cttatttatt agcatactac atttgaaata tcaaatttcc ttagtagaaa agtgagagaa 4920
ggtgcactga cacaaaaaat aaaatgctac gtataactgt caaaactttg cagcagcggg 4980
catccttcca tcatagcttc aaacatatta gcgttcctga tcttcatacc cgtgctcaaa 5040
atgatcaaac aaactgttat tgccaagaaa taaacgcaag gctgccttca aaaactgatc 5100
cattagatcc tcatatcaag cttcctcata gaacgcccaa ttacaataag catgttttgc 5160
tgttatcacc gggtgatagg tttgctcaac catggaaggt agcatggaat cataatttgg 5220
atactaatac aaatcggcca tataatgcca ttagtaaatt gcgctcccat ttaggtggtt 5280
ctccaggcaa atttgaatac taataaatgc ggtgcatttg caaaatgaat ttattccaag 5340
gccaaaacaa cacgatgaat ggctttattt ttttgttatt cctgacatga agctttatgt 5400
aattaaggaa acggacatcg aggaatttgc atctttttta gatgaaggag ctattcaagc 5460
accaaagcta tccttccagg attatttaag cggtaaggcc aaggcttccc aacaggttca 5520
tgaagtgcat catagaaagc ttacaaggtt tcagggtgaa acttttctaa gagattggaa 5580
cttagtctgt gggcattata agagagatgc taagtgtgga gaaatgggac ccgacataat 5640
tgcagcattt caagatgaaa agctttttcc tgagaataat ctagccttaa tttctcatat 5700
tgggggtcat attt 5714

<210> SEQ ID NO 20
<211> LENGTH: 7688
<212> TYPE: DNA
<213> ORGANISM: Artificial Sequence
<220> FEATURE:
<223> OTHER INFORMATION: Synthetic: Integration construct i301

<400> SEQUENCE: 20
gacggcacgg ccacgcgttt aaaccgccga gctattcgcg gaacattcta gctcgtttgc 60
atcttcttgc atttggtagg ttttcaatag ttcggtaata ttaacggata cctactatta 120
tcccctagta ggctcttttc acggagaaat tcgggagtgt ttttttccg tgcgcatttt 180 cttagctata ttcttccagc ttcgcctgct gcccggtcat cgttcctgtc acgtagtttt 240
tccggattcg tccggctcat ataataccgc aataaacacg gaatatctcg ttccgcggat 300
tcggttaaac tctcggtcgc ggattatcac agagaaagct tcgtggagaa tttttccaga 360

```
ttttccgctt tccccgatgt tggtatttcc ggaggtcatt atactgaccg ccattataat    420
gactgtacaa cgaccttctg gagaaagaaa caactcaata acgatgtggg acattggggg    480
cccactcaaa aaatctgggg actatatccc cagagaattt ctccagaaga gaagaaaagt    540
caaagttttt tttcgcttgg gggttgcata taaagctcac acgcggccag ggggagccat    600
gaaaaagcct gaactcaccg cgacgtctgt cgagaagttt ctgatcgaaa agttcgacag    660
cgtctccgac ctgatgcagc tctcggaggg cgaagaatct cgtgctttca gcttcgatgt    720
aggagggcgt ggatatgtcc tgcgggtaaa tagctgcgcc gatggtttct acaaagatcg    780
ttatgtttat cggcactttg catcggccgc gctcccgatt ccggaagtgc ttgacattgg    840
ggaattcagc gagagcctga cctattgcat ctcccgccgt gcacagggtg tcacgttgca    900
agacctgcct gaaaccgaac tgcccgctgt tctgcagccg gtcgcggagg ccatggatgc    960
gatcgctgcg gccgatctta gccagacgag cgggttcggc ccattcggac cgcaaggaat   1020
cggtcaatac actacatggc gtgatttcat atgcgcgatt gctgatcccc atgtgtatca   1080
ctggcaaact gtgatggacg acaccgtcag tgcgtccgtc gcgcaggctc tcgatgagct   1140
gatgctttgg gccgaggact gccccgaagt ccggcacctc gtgcacgcgg atttcggctc   1200
caacaatgtc ctgacggaca atggccgcat aacagcggtc attgactgga gcgaggcgat   1260
gttcggggat tcccaatacg aggtcgccaa catcttcttc tggaggccgt ggttggcttg   1320
tatggagcag cagacgcgct acttcgagcg gaggcatccg gagcttgcag gatcgccgcg   1380
gctccgggcg tatatgctcc gcattggtct tgaccaactc tatcagagct tggttgacgg   1440
caatttcgat gatgcagctt gggcgcaggg tcgatgcgac gcaatcgtcc gatccggagc   1500
cgggactgtc gggcgtacac aaatcgcccg cagaagcgcg gccgtctgga ccgatggctg   1560
tgtagaagta ctcgccgata gtggaaaccg acgccccagc actcgtccga gggcaaagga   1620
atagcgctcg tccaacgccg gcggacctcg ctcgtccaac gccggcggac ctcttttaat   1680
tctgctgtaa cccgtacatg cccaaaatag ggggcgggtt acacagaata tataacatcg   1740
taggtgtctg ggtgaacagt ttattcctgg catccactaa atataatgga gcccgctttt   1800
taagctggca tccagaaaaa aaaagaatcc cagcaccaaa atattgtttt cttcaccaac   1860
catcagttca taggtccatt ctcttagcgc aactacagag aacaggggca caaacaggca   1920
aaaaacgggc acaacctcaa tggagtgatg caacctgcct ggagtaaatg atgacacaag   1980
gcaattgacc cacgcatgta tctatctcat tttcttacac cttctattac cttctgctct   2040
ctctgatttg gaaaaagctg aaaaaaaagg ttgaaaccag ttccctgaaa ttattcccct   2100
acttgactaa taagtatata aagacggtag gtattgattg taattctgta aatctatttc   2160
ttaaacttct taaattctac ttttatagtt agtctttttt ttagttttaa aacaccaaga   2220
acttagtttc gatccccgcg tgcttggccg gccgtatccc cgcgtgcttg gccggccgta   2280
tgtctcagaa cgtttacatt gtatcgactg ccagaacccc aattggttca ttccagggtt   2340
ctctatcctc caagacagca gtggaattgg gtgctgttgc tttaaaaggc gccttggcta   2400
aggttccaga attggatgca tccaaggatt ttgacgaaat tatttttggt aacgttcttt   2460
ctgccaattt gggccaagct ccggccagac aagttgcttt ggctgccggt ttgagtaatc   2520
atatcgttgc aagcacagtt aacaaggtct gtgcatccgc tatgaaggca atcattttgg   2580
gtgctcaatc catcaaatgt ggtaatgctg atgttgtcgt agctggtggt tgtgaatcta   2640
tgactaacgc accatactac atgccagcag cccgtgcggg tgccaaattt ggccaaactg   2700
ttcttgttga tggtgtcgaa agagatgggt tgaacgatgc gtacgatggt ctagccatgg   2760
```

-continued

```
gtgtacacgc agaaaagtgt gcccgtgatt gggatattac tagagaacaa caagacaatt   2820
ttgccatcga atcctaccaa aaatctcaaa aatctcaaaa ggaaggtaaa ttcgacaatg   2880
aaattgtacc tgttaccatt aagggattta gaggtaagcc tgatactcaa gtcacgaagg   2940
acgaggaacc tgctagatta cacgttgaaa aattgagatc tgcaaggact gttttccaaa   3000
aagaaaacgg tactgttact gccgctaacg cttctccaat caacgatggt gctgcagccg   3060
tcatcttggt ttccgaaaaa gttttgaagg aaaagaattt gaagcctttg gctattatca   3120
aaggttgggg tgaggccgct catcaaccag ctgattttac atgggctcca tctcttgcag   3180
ttccaaaggc tttgaaacat gctggcatcg aagacatcaa ttctgttgat tactttgaat   3240
tcaatgaagc cttttcggtt gtcggtttgg tgaacactaa gattttgaag ctagacccat   3300
ctaaggttaa tgtatatggt ggtgctgttg ctctaggtca cccattgggt tgttctggtg   3360
ctagagtggt tgttacactg ctatccatct tacagcaaga aggaggtaag atcggtgttg   3420
ccgccatttg taatggtggt ggtggtgctt cctctattgt cattgaaaag atatgattac   3480
gttctgcgat ttctcatga tctttttcat aaaatacata aatatataaa tggctttatg   3540
tataacaggc ataatttaaa gttttatttg cgattcatcg tttttcaggt actcaaacgc   3600
tgaggtgtgc cttttgactt acttttccgc cttggcaagc tggccgggtg atacttgcac   3660
aagttccact aattactgac atttgtggta ttaactcgtt tgactgctct acaattgtag   3720
gatgttaatc aatgtcttgg ctgcctaacc tgcaggccgc gagcgccgat atgctatgta   3780
atagacaata aaaccatgtt tatataaaaa aaattcaaaa tagaaaacga ttctgtacaa   3840
ggagtatttt ttttttgttc tagtgtgttt atattatcct tggctaagag gcactgcgta   3900
tacttcaagg taccctgtg ttttgaaaaa aaacaacagt aaaataggaa ctccgcgagg   3960
ttcaggaacc tgaaacaaaa tcaataaaaa cattatatgc gtttcgaaca aaattaaaga   4020
aaaagaataa atatagatta aaaaaaaaaa gaagaaatta aaagaatttc tactaaatcc   4080
caattgttat atatttgtta aatgccaaaa aagtttataa aaaatttaga atgtataaat   4140
aataataaac taagtaacgc gatcgccgac gccgccgata tctccctcgc cagcggccgc   4200
cttatggcta agaatgttgg aattttggcc atggacatct acttcccacc aacttgtgtt   4260
cagcaggagg ctttagaagc acatgacgga gcctcaaagg gtaagtacac aatcggatta   4320
ggacaggatt gcttagcatt ctgcactgaa ttggaggacg tcatctcaat gtctttcaac   4380
gccgtcacct cattgttaga gaagtacaaa atcgacccaa accagatcgg aaggttggaa   4440
gtcggttctg aaaccgtcat cgacaagtct aaatcaatca agactttcgt tatgcagttg   4500
ttcgaaaagt gcggtaatac tgacgtcgag ggtgtagact ctactaacgc ttgttatggt   4560
ggtaccgcag ctttattgaa ctgcgtaaac tgggttgagt caaactcatg ggatggtagg   4620
tacggattag tcatttgcac cgattctgcc gtctacgccg agggtccagc aaggccaacc   4680
ggtggagctg cagctattgc tatgttaatc ggaccagatg cccctatagt cttcgagtct   4740
aagttgaggg gttcacacat ccctaacgtc tacgacttct acaagccaaa cttggcctca   4800
gagtatccag ttgtcgacgg aaagttatct cagacatgct acttgatggc cttagattca   4860
tgttacaagc acttatgcaa caagttcgaa aagttggagg gaaaggagtt ctcaattaac   4920
gacgccgact acttcgtttt tcactctcca tacaacaaat tggtccagaa gtcattcgcc   4980
aggttattgt acaacgattt tttgagaaac gcatcatcta tcgatgaggc cgccaaggag   5040
aaattcaccc catattcttc tttgtcattg gacgagtctt accagtctag ggacttggag   5100
aaggtatcac agcaattggc taaaaccttc tatgacgcca aagttcagcc aaccaccttg   5160
```

-continued

```
gtccctaaac aggtcggaaa tatgtatact gcatctttgt atgccgcctt tgcctctttg   5220
atccacaaca agcacaacga tttagtcgga aaaagggttg tcatgttttc ttacggtgcc   5280
ggatctactg ccactatgtt ctcattgagg ttatgcgaaa accagtcacc attttcattg   5340
tctaacatcg cctcagtcat ggacgtaggt gtctcacctg agaagttcgt agaaaccatg   5400
aagttgatgg agcacagata cggtgccaaa gaattcgtca cttcaaaaga gggaatcttg   5460
gatttgttgg ccccaggaac ctactatttg aaggaggtcg actctttgta cagaaggttc   5520
tatggaaaga agggagacga cggatctgtc gcaaacggtc agtaaatcgg cggcgtcggc   5580
gatcgcgtta aggcggccgc tggcgaggga gatatttcaa cctgggccta acagtaaaga   5640
tatcctcctc aaaactggtg cacttaatcg ctgaatttgt tctggcttct cttctttttc   5700
tttattcccc ccatgggcca aaaaaaatag tactatcagg aatttggcgc cgggtcacga   5760
tatacgtgta cagtgaccta ggcgacgcca caaggaaaaa ggaaaaaaac agaaaaaaca   5820
acaaaaacta aaacaaacac gaaaacttta atagatctaa gtgaagtagt ggtgaggcaa   5880
ttggagtgac atagcagcta ctacaactac aaaaaaggcg cgccacggtc gtgcggatat   5940
gaaagaggtc gttatagctt ctgccgtcag gaccgccatc ggatcttacg gtaagtcatt   6000
aaaggacgtc cctgccgttg atttaggagc caccgcaatt aaagaggccg ttaaaaaggc   6060
aggtataaag ccagaggacg tcaacgaggt catcttggga aatgtcttac aagccggatt   6120
aggtcaaaac ccagcaagac aagcatcatt caaagccggt ttacctgtcg agatacctgc   6180
aatgaccatc aacaaggttt gcggttcagg attaaggacc gtttctttag cagcacagat   6240
cattaaggct ggagatgcag acgttatcat tgctggtggt atggaaaaca tgtcaagagc   6300
cccatacttg gctaataacg ccaggtgggg atataggatg ggaaacgcca agtttgtcga   6360
cgaaatgatt actgacggat tgtgggacgc cttcaatgac tatcacatgg gtataaccgc   6420
agaaaacatt gccgagaggt ggaatatctc aagagaagaa caggatgagt ttgcattggc   6480
ctcacagaaa aaagcagagg aggcaataaa gtcaggtcag tttaaggatg aaatcgtccc   6540
agtcgtcatc aagggaagaa agggtgagac agttgtcgac accgacgaac accctagatt   6600
tggttcaacc atcgagggat tagcaaagtt gaagccagcc ttcaagaaag acggaaccgt   6660
aaccgccggt aatgcatctg gattgaacga ttgcgcagca gttttggtca taatgtcagc   6720
cgagaaagct aaggagttgg gtgtcaagcc attggcaaaa attgtttcat acggatcagc   6780
cggtgtcgac cctgccatca tgggttacgg accttttttac gccaccaagg ctgcaatcga   6840
aaaggccggt tggaccgtag atgaattgga tttgatcgag tcaaacgagg cctttgccgc   6900
ccaatcattg gctgtcgcca aggacttgaa gttcgacatg aacaaggtca acgtcaacgg   6960
tggtgccatc gcattgggtc accctatcgg agcctctggt gccaggatct tggttacctt   7020
ggtccacgcc atgcagaaga gggacgcaaa gaagggtttg gccaccttgt gcatcggtgg   7080
aggtcaggga acagctatct tgttagagaa atgcagcccc tcagcccccc tagcgtcgaa   7140
taaaagacat tggtacatga tatcaaacag aattttaaca tttcttgatc cagtttgtaa   7200
acaaaacaaa caatttttct accatttaac ttcataccat cggcgagagc cgaacaggaa   7260
aaaaaagaag tctccggtta tcgtaagcag tatcaaataa taagaatgta tgtgtgtgca   7320
atttgttata cccacgaaga agtgcgcagt agagttagaa aaccaactga gtaatcttta   7380
ctcccgacaa tcgtccaata atcctcttgt tgctaggaac gtgatgatgg atttcgtttg   7440
aaatccggac ggaaaactca aaagaagtcc aaccaccaac cattttcgag cctcaagaat   7500
ctctaagcag gtttctttac taaggggatg gcctttctgt cctggacatt ttttccttcc   7560
```

-continued

```
tttttttcatt tccttgaaag gaacagattt tttttgactt ttgccacaca gctgcactat   7620

ctcaacccct tttacatttt aagttttcgg gttgaatggc cggtgtttaa accccagcgc   7680

ctggcggg                                                           7688
```

<210> SEQ ID NO 21
<211> LENGTH: 5025
<212> TYPE: DNA
<213> ORGANISM: Artificial Sequence
<220> FEATURE:
<223> OTHER INFORMATION: Synthetic: Integration construct i476

<400> SEQUENCE: 21

```
caggatccga cggcacggcc acgcgtttaa accgcctggg ataggatagt agcaactctt     60

ggaggagagc attgtcagtt gtccagtctc tgaagttaag tagtaagttt gcggagtcaa    120

agggggatgg cttttgccat ttgtgagagt tgtgcggcag catcttattc aaatagagct    180

gtattctgaa gacctcttgt agaacatcat ccatactaaa aagtaaatcg tcctgtccca    240

ttacgagctg tattagtgct gtgaccctct gtatatttac gttgccatga agaaggtaat    300

gggcgatatt ttgatacaat tcctgagttg catgttggat tgagtttacg aagggtcgcc    360

agacggccag aaacctccag gcggagttaa caactagtaa tacggcatcc atgtttgcat    420

cagcgccgag cctataccag tcactgagta gacgttttct tgctcttttt atgtcctgac    480

ttcttttgac gagggggcat tctctagaga cacaggcagt tgcttccagc aactgccgta    540

cggccgttct catgctgtcg aggatttttt ttgggacgat attgtcatta tagggcagtg    600

tgtgacttat gaattgttgt agaaggacgt ctgtgatgtt ggagatatgt attttgttaa    660

ctcttcttga gacgatttgg ccctggatag cgaagcgtgc ggttacaaat aggtcgtctt    720

gttcaagaag gtaggcgagg acattatcta tcagtacaaa catcttagta gtgtctgagg    780

agagggttga ttgtttatgt atttttgcga aatatatata tatatattct acacagatat    840

atacatattt gtttttcggg ctcattcttt cttctttgcc agaggctcac cgctcaagag    900

gtccgctaat tctggagcga ttgttattgt tttttctttt cttcttctat tcgaaaccca    960

gtttttgatt tgaatgcgag ataaactggt attcttcatt agattctcta ggcccttggt   1020

atctagatat gggttctcga tgttctttgc aaaccaactt tctagtattc ggacattttc   1080

ttttgtaaac cggtgtcctc tgtaaggttt agtacttttg tttatcatat cttgagttac   1140

cacattaaat accaacccat ccgccgattt atttttctgt gtaagttgat aattacttct   1200

atcgttttct atgctgcgca tttctttgag taatacagta atggtagtag tgagttgaga   1260

tgttgtttgc aacaacttct tctcctcatc actaatctta cggtttttgt tggccctaga   1320

taagaatcct aatatatccc ttaattcaac ttcttcttct gttgttacac tctctggtaa   1380

cttaggtaaa ttacagcaaa tagaaaagag ctttttattt atgtctagta tgctggattt   1440

aaactcatct gtgatttgtg gatttaaaag gtctttaatg ggtattttat tcattttttc   1500

ttgcttatct tcctttttt cttgcccact tctaagctga tttcaatctc tcctttatat   1560

atatttttaa gttccaacat tttatgtttc aaaacattaa tgatgtctgg gttttgtttg   1620

ggatgcaatt tattgcttcc caatgtagaa aagtacatca tatgaaacaa cttaaactct   1680

taactacttc ttttaacctt cactttttat gaaatgtatc aaccatatat aataacttaa   1740

tagacgacat tcacaatatg tttacttcga agcctgcttt caaaattaag aacaaagcat   1800

ccaaatcata cagaaacaca gcggtttcaa aaaagctgaa agaaaaacgt ctagctgagc   1860

atgtgaggcc aagctgcttc aatattattc gaccactcaa gaaagatatc cagattcctg   1920
```

-continued

```
ttccttcctc tcgattttta aataaaatcc aaattcacag gatagcgtct ggaagtcaaa   1980
atactcagtt tcgacagttc aataagacat ctataaaatc ttcaaagaaa tatttaaact   2040
catttatggc ttttagagca tattactcac agtttggctc cggtgtaaaa caaaatgtct   2100
tgtcttctct gctcgctgaa gaatggcacg cggacaaaat gcagcacgga atatgggact   2160
acttcgcgca acagtataat tttataaacc ctggttttgg ttttgtagag tggttgacga   2220
ataattatgc tgaagtacgt ggtgacggat attgggaaga tgtgtttgta catttggcct   2280
tatagagtgt ggtcgtggcg gaggttgttt atctttcgag tactgaatgt tgtcagtata   2340
gctatcctat ttgaaactcc ccatcgtctt gctcttgttc ccaatgtttg tttatacact   2400
catatggcta tacccttatc tacttgcctc ttttgtttat gtctatgtat ttgtataaaa   2460
tatgatatta ctcagactca agcaaacaat caatgctcac acgcggccag ggggagcctc   2520
gacactagta atacacatca tcgtcctaca agttcatcaa agtgttggac agacaactat   2580
accagcatgg atctcttgta tcggttcttt tctcccgctc tctcgcaata acaatgaaca   2640
ctgggtcaat catagcctac acaggtgaac agagtagcgt ttatacaggg tttatacggt   2700
gattcctacg gcaaaaattt ttcatttcta aaaaaaaaaa gaaaaatttt tctttccaac   2760
gctagaagga aaagaaaaat ctaattaaat tgatttggtg attttctgag agttcccttt   2820
ttcatatatc gaattttgaa tataaaagga gatcgaaaaa atttttctat tcaatctgtt   2880
ttctggtttt atttgatagt ttttttgtgt attattatta tggattagta ctggtttata   2940
tgggtttttc tgtataactt ctttttattt tagtttgttt aatcttattt tgagttacat   3000
tatagttccc taactgcaag agaagtaaca ttaaaaatga aaaagcctga actcaccgcg   3060
acgtctgtcg agaagtttct gatcgaaaag ttcgacagcg tctccgacct gatgcagctc   3120
tcggagggcg aagaatctcg tgctttcagc ttcgatgtag gagggcgtgg atatgtcctg   3180
cgggtaaata gctgcgccga tggtttctac aaagatcgtt atgtttatcg gcactttgca   3240
tcggccgcgc tcccgattcc ggaagtgctt gacattgggg aattcagcga gagcctgacc   3300
tattgcatct cccgccgtgc acagggtgtc acgttgcaag acctgcctga aaccgaactg   3360
cccgctgttc tgcagccggt cgcggaggcc atggatgcga tcgctgcggc cgatcttagc   3420
cagacgagcg ggttcggccc attcggaccg caaggaatcg gtcaatacac tacatggcgt   3480
gatttcatat gcgcgattgc tgatccccat gtgtatcact ggcaaactgt gatggacgac   3540
accgtcagtg cgtccgtcgc gcaggctctc gatgagctga tgctttgggc cgaggactgc   3600
cccgaagtcc ggcacctcgt gcacgcggat ttcggctcca acaatgtcct gacggacaat   3660
ggccgcataa cagcggtcat tgactggagc gaggcgatgt tcggggattc ccaatacgag   3720
gtcgccaaca tcttcttctg gaggccgtgg ttggcttgta tggagcagca gacgcgctac   3780
ttcgagcgga ggcatccgga gcttgcagga tcgccgcggc tccgggcgta tatgctccgc   3840
attggtcttg accaactcta tcagagcttg gttgacggca atttcgatga tgcagcttgg   3900
gcgcagggtc gatgcgacgc aatcgtccga tccggagccg ggactgtcgg gcgtacacaa   3960
atcgcccgca gaagcgcggc cgtctggacc gatggctgtg tagaagtact cgccgatagt   4020
ggaaaccgac gccccagcac tcgtccgagg gcaaaggaat aggtttaact tgatactact   4080
agatttttc tcttcattta taaaattttt ggttataatt gaagctttag aagtatgaaa    4140
aaatcctttt ttttcattct ttgcaaccaa aataagaagc ttcttttatt cattgaaatg   4200
atgaatataa acctaacaaa agaaaaagac tcgaatatca aacattaaaa aaaaataaaa   4260
gaggttatct gttttcccat ttagttggag tttgcatttt ctaatagata gaactctcaa   4320
```

```
ttaatgtgga tttagtttct ctgttcgttt ttttttgttt tgttctcact gtatttacat   4380

ttctatttag tatttagtta ttcatataat cttaacttct cgaggagctc cgctcgtcca   4440

acgccggcgg acctcggagg ttgtttatct ttcgagtact gaatgttgtc agtatagcta   4500

tcctatttga aactccccat cgtcttgctc ttgttcccaa tgtttgttta tacactcata   4560

tggctatacc cttatctact tgcctctttt gtttatgtct atgtatttgt ataaaatatg   4620

atattactca gactcaagca aacaatcaat tcttagcatc attctttgtt cttatcttaa   4680

ccataaacga tcttgatgtg acttttgtaa tttgaacgaa ttggctatac gggacggatg   4740

acaaatgcac cattactcta ggttgttgtt ggatcttaac aaaccgtaaa ggtaaactgc   4800

ccatgcggtt cacatgactt ttgactttcc tttgtttgct agttaccttc ggcttcacaa   4860

tttgtttttc cacttttcta acaggtttat cacctttcaa acttatcttt atcttattcg   4920

ccttcttggg tgcctccaca gtagaggtta cttccttttt aatatgtact tttaggatac   4980

tttcacgctt tataacacgg tgtttaaacc ccagcgcctg gcggg                   5025
```

<210> SEQ ID NO 22
<211> LENGTH: 3665
<212> TYPE: DNA
<213> ORGANISM: Artificial Sequence
<220> FEATURE:
<223> OTHER INFORMATION: Synthetic: Integration construct i477

<400> SEQUENCE: 22

```
agctcgagga cggcacggcc acgcgtttaa accgccaagc ttttcaattc atcttttttt     60

tttttgttct ttttttgat tccggtttct ttgaaatttt tttgattcgg taatctccga    120

gcagaaggaa gaacgaagga aggagcacag acttagattg gtatatatac gcatatgtgg    180

tgttgaagaa acatgaaatt gcccagtatt cttaacccaa ctgcacagaa caaaaacctg    240

caggaaacga agataaatca tgtcgaaagc tacatataag gaacgtgctg ctactcatcc    300

tagtcctgtt gctgccaagc tatttaatat catgcacgaa aagcaaacaa acttgtgtgc    360

ttcattggat gttcgtacca ccaaggaatt actggagtta gttgaagcat taggtcccaa    420

aatttgttta ctaaaaacac atgtggatat cttgactgat tttccatgg agggcacagt    480

taagccgcta aaggcattat ccgccaagta caatttttta ctcttcgaag acagaaaatt    540

tgctgacatt ggtaatacag tcaaattgca gtactctgcg ggtgtataca gaatagcaga    600

atgggcagac attacgaatg cacacggtgt ggtgggccca ggtattgtta gcggtttgaa    660

gcaggcggca gaagaagtaa caaaggaacc tagaggcctt ttgatgttag cagaattgtc    720

atgcaagggc tccctatcta ctggagaata tactaagggt actgttgaca ttgcgaagag    780

tgacaaagat tttgttatcg gctttattgc tcaaagagac atgggtggaa gagatgaagg    840

ttacgattgg ttgattatga cacccggtgt gggtttagat gacaagggag acgcattggg    900

tcaacagtat agaaccgtgg atgatgtggt ctctacagga tctgacatta ttattgttgg    960

aagcgctcgt ccaacgccgg cggacctatg gcgcaagttt tccgctttgt aatatatatt   1020

tataccccttt tcttctctcc cctgcaatat aatagtttaa ttctaatatt aataatatcc   1080

tatattttct tcatttaccg gcgcactctc gcccgaacga cctcaaaatg tctgctacat   1140

tcataataac caaaagctca taactttttt ttttgaacct gaatatatat acatcacata   1200

tcactgctgg tccttgccga ccagcgtata caatctcgat agttggtttc ccgttctttc   1260

cactcccgtc atggactaca acaagagatc ttcggtctca accgtgccta atgcagctcc   1320

cataagagtc ggattcgtcg gtctcaacgc agccaaagga tgggcaatca agacacatta   1380
```

-continued

```
ccccgccata ctgcaactat cgtcacaatt tcaaatcact gccttataca gtccaaaaat   1440
tgagacttct attgccacca tccagcgtct aaaattgagt aatgccactg cttttcccac   1500
tttagagtca tttgcatcat cttccactat agatatgata gtgatagcta tccaagtggc   1560
cagtcattat gacgttgtta tgcctctctt ggaattctcc aaaaataatc cgaacctcaa   1620
gtatcttttc gtagaatggg cccttgcatg ttcactagat caagccgaat ccatttataa   1680
ggctgctgct gaacgtgggg ttcaaaccat catctcttta caaggtcgta aatcaccata   1740
tattttgaga gcaaaagaat taatatctca aggctatatc ggcgacatta attctatcga   1800
gattgctgga aatggcggtt ggtacggcta cgaaaggcct gttaaatcac caaaatacat   1860
ctatgaaatc gggaacggtg tagatctggt aaccacaaca tttggtcaca caatcgatat   1920
tttacaatac atgacaagtt cgtacttttc caggataaat gcaatggttt tcaataatat   1980
tccagagcaa gagctgatag atgagcgtgg taaccgattg ggccagcgag tcccaaagac   2040
agtaccggat catcttttat tccaaggcac attgttaaat ggcaatgttc cagtgtcatg   2100
cagtttcaaa ggtggcaaac ctaccaaaaa atttaccaaa aatttggtca ttgatattca   2160
cggtaccaag ggagatttga aacttgaagg cgatgccgga ttcgcagaaa tttcaaatct   2220
ggtcctttac tacagtggaa ctagagcaaa cgacttcccg ctagctaatg gacaacaagc   2280
tcctttagac ccggggtatg atgcaggtaa agaaatcatg gaagtatatc atttacgaaa   2340
ttataatgcc attgtcggta atattcatcg actgtatcaa tctatctctg acttccactt   2400
caatacaaag aaaattcctg aattaccctc acaatttgta atgcaaggtt tcgatttcga   2460
aggctttccc accttgatgg atgctctgat attacacagg ttaatcgaga gcgtttataa   2520
aagtaacatg atgggctcca cattaaacgt tagcaatatc tcgcattata gtttataaaa   2580
gcatcttgcc ctgtgcttgg cccccagtgc agcgaacgtt ataaaaacga atactgagta   2640
tatatctatg taaaacaacc atatcatttc ttgttctgaa ctttgtttac ctaactagtt   2700
ttaaatttcc ctttttcgtg catgcgggtg ttcttattta ttagcatact acatttgaaa   2760
tatcaaattt ccttagtaga aaagtgagag aaggtgcact gacacaaaaa ataaaatccc   2820
cgcgtgcttg gccggccgtc ttcattggat gttcgtacca ccaaggaatt actggagtta   2880
gttgaagcat taggtcccaa aatttgttta ctaaaaacac atgtggatat cttgactgat   2940
ttttccatgg agggcacagt taagccgcta aaggcattat ccgccaagta caatttttta   3000
ctcttcgaag acagaaaatt tgctgacatt ggtaatacag tcaaattgca gtactctgcg   3060
ggtgtataca gaatagcaga atgggcagac attacgaatg cacacggtgt ggtgggccca   3120
ggtattgtta gcggtttgaa gcaggcggca gaagaagtaa caaaggaacc tagaggcctt   3180
ttgatgttag cagaattgtc atgcaagggc tccctatcta ctggagaata tactaagggt   3240
actgttgaca ttgcgaagag tgacaaagat tttgttatcg gctttattgc tcaaagagac   3300
atgggtggaa gagatgaagg ttacgattgg ttgattatga cacccggtgt gggtttagat   3360
gacaagggag acgcattggg tcaacagtat agaaccgtgg atgatgtggt ctctacagga   3420
tctgacatta ttattgttgg aagaggacta tttgcaaagg gaagggatgc taaggtagag   3480
ggtgaacgtt acagaaaagc aggctgggaa gcatatttga gaagatgcgg ccagcaaaac   3540
taaaaaactg tattataagt aaatgcatgt atactaaact cacaaattag agcttcaatt   3600
taattatatc agttattacc cgggaatctc ggtgtttaaa ccccagcgcc tggcgggtct   3660
agatc                                                              3665
```

<210> SEQ ID NO 23

<211> LENGTH: 10623
<212> TYPE: DNA
<213> ORGANISM: Artificial Sequence
<220> FEATURE:
<223> OTHER INFORMATION: Synthetic: Integration construct i94

<400> SEQUENCE: 23
atgagtgata gggaattcgt cacggtagat cccgtcacta tcataatcaa agaatgcatt 60
aatttatcga cagcgatgcg gaaatactct aaatttacct ctcaatctgg agtggccgct 120
ttgctggggg gaggaagtga aatatttagc aatcaagatg actacttggc tcacacattc 180
aacaatttga ataccaacaa gcacaatgat ccatttttat ctggattcat tcagttaaga 240
cttatgttga ataaactgaa aaatctagat aatatagatt cactaaccat attgcagcca 300
tttttattaa ttgtgagtac aagttccatt tctggttaca tcacttccct ggccctggac 360
tctttgcaga aattctttac cttgaatatc atcaatgaat catcgcaaaa ctatattggt 420
gcacacaggg cgacggtaaa tgctctaaca cattgtaggt ttgaaggatc tcaacaactt 480
tctgatgatt cagttctttt gaaagtcgtg tttttactgc gttcaatcgt cgactcacct 540
tacggagatt tattatcaaa ctctatcata tatgacgtat tgcaaacgat tctttcattg 600
gcttgtaata acagaaggag cgaagtcctt aggaatgctg cacaatcaac aatgatagcc 660
gttaccgtaa agattttctc aaaactaaag actattgagc ctgttaatgt gaatcaaata 720
tacatcaatg atgaaagtta cacaaatgat gtattgaagg ccgatacaat tggcacaaat 780
gtagaatcca aagaagaagg aagtcaagaa gatcccatcg gcatgaaagt gaataatgag 840
gaagctatta gcgaggacga tggcattgaa gaagagcata ttcattcaga gaagagcaca 900
aatggcgccg aacaactaga tattgtgcaa aaaacaacaa gatcaaattc caggatccaa 960
gcgtatgctg atgataacta tggattgccc gtggttaggc aatatttaaa cttattacta 1020
tcattgattg cgccagaaaa tgaattaaaa cattcatact ccactagaat atttggccta 1080
gagttaattc aaacggcatt agaaatttca ggtgatcgat tgcagctata cccacggctt 1140
tttacactga tatcagatcc tattttcaaa agcattttgt ttatcataca gaacactaca 1200
aaattatcac tacttcaagc tacattgcag ctatttacta ctctagttgt tatattgggc 1260
aacaacttac aattacagat cgagctcact ctaacaagaa tattttctat tcttttagat 1320
gatggtaccg caaataactc gagttctgaa aataagaaca agccatcaat aataaaggaa 1380
cttctaattg agcaaatatc catcttatgg actaggtcgc catctttttt tacttctact 1440
tttatcaatt tcgattgtaa tctcgatagg gcagacgttt ccataaactt tttgaaggct 1500
ttgactaaat tggccttacc agaatccgcc ttaactacca cagaaagtgt accacccatt 1560
tgccttgagg gattggtctc cctagtcgat gatatgttcg atcacatgaa ggacattgac 1620
agagaagaat ttggcaggca aaagaatgaa atggaaatct taaaaaagag ggaccgtaaa 1680
acagagttta ttgaatgtac caatgcattc aatgaaaagc ccaaaaaggg tattccgatg 1740
ttaatagaaa aaggtttcat tgcttccgac tccgataaag atattgcgga gtttcttttc 1800
aataataaca accgtatgaa taaaaaaaca atcggtttgc tactttgcca tccggacaaa 1860
gtaagcttgt tgaatgaata tattcgtttg tttgattttt cagggttaag ggtcgatgaa 1920
gctattagaa ttttgttgac gaaatttagg ttgcctggtg aatcgcaaca aattgaaaga 1980
atcatcgaag ccttctcgtc tgcgtattgt gaaaatcaag attacgatcc atccaaaatc 2040
agtgacaacg cggaggatga catttctact gttcaaccag acgctgattc tgttttcatt 2100
ttaagttatt caattattat gttgaacact gacctacata accctcaagt gaaggaacac 2160

-continued

```
atgtcatttg aagattactc tggtaactta aagggatgct gtaatcacaa agacttccca   2220
ttctggtatt tggatagaat ttactgttca atcagagata aagaaattgt tatgcctgaa   2280
gagcaccacg gcaacgaaaa gtggtttgaa gatgcttgga ataacttgat atcttcaact   2340
actgttataa ctgaaataaa aaaagacaca caatctgtca tggataaatt aacacccttg   2400
gagcttttga actttgatag agcaattttt aaacaagttg gcccaagtat tgtcagtact   2460
ttattcaaca tttacgtagt tgcatctgat gaccatatat ctaccagaat gataacaagt   2520
ttggacaaat gttcctatat ttccgcattt tttgacttca aagatctctt taatgatata   2580
ctaaactcca ttgctaaggg cactactttg attaattcaa gccatgacga tgaactttca   2640
actttagctt ttgaatatgg cccaatgcca ctggtgcaaa ttaaattcga agacactaac   2700
actgagatcc cggttagtac agatgctgtt agatttggta gatcatttaa gggtcaacta   2760
aatacagttg tttttttccg gattattcgc aggaacaaag atcctaaaat tttctccaag   2820
gaattatggt taaacattgt taatattata ctaacattgt acgaagactt gattttgtct   2880
cctgatattt tccctgattt acaaaaaaga ctgaaattaa gcaacttgcc taagccatct   2940
cctgaaattt ctattaacaa gagcaaagaa agcaaaggtc tcttatcaac atttgcttct   3000
tatttaaaag gtgatgaaga acccacagaa gaggaaatca aatcctcaaa aaaagcgatg   3060
gagtgcataa agtcgagtaa tattgccgcc tctgtctttg gaaatgaatc aaatataaca   3120
gcggatttaa taaaaacttt actagactcc gccaaaactg agaaaaacgc agataattcc   3180
aggtattttg aagcagaact tttatttatc atcgaattga ctattgcatt atttctattt   3240
tgcaaagagg agaaaagaatt aggaaagttc atacttcaaa aagttttcca actttctcac   3300
acgaaaggcc tcacgaaaag gactgttcgt agaatgctaa catacaaaat tttgttaatt   3360
tcgttatgtg cggatcagac ggagtacttg tccaaattaa taaacgatga gctgttaaaa   3420
aagggggata tttttaccca aaaatttttt gcaactaatc aaggtaagga atttttgaag   3480
agactatttt cattgaccga atcagagttt tatagaggat tttttactagg aaatgagaat   3540
ttttggaaat ttttaagaaa agttacagca atgaaagagc agagcgagag catttttgaa   3600
tatttaaatg aatcgatcaa gacagacagc aatattttga caaatgagaa cttcatgtgg   3660
gtcctaggac tattagatga aatttcatca atgggtgccg ttggaaatca ctgggaaata   3720
gaatacaaga aattgacaga aagtggtcat aaaaattgata aggagaatcc atacaagaaa   3780
tcgatcgaat tatcattgaa atccattcaa ctaacatcac acttgctgga agataataac   3840
gatctgcgta aaaacgagat attcgctatt attcaagctt tggcacatca atgcatcaat   3900
ccgtgtaagc agataagtga atttgcagtg gtaacgctag agcagacgct catcaataaa   3960
atcgaaattc caactaatga gatggaatcg gtagaagaat taattgaggg cggattacta   4020
ccgttgctaa attcgagtga aacacaggaa gaccagaaaa tcctcatttc atccatatta   4080
acaataattt caaatgttta tttgcattat ttgaaactag ggaagacaag caacgaaacg   4140
tttttgaaaa ttttgagtat tttcaataaa tttgtagagg actcagatat tgaaaaaaag   4200
ctacagcaat taatacttga taagaagagt attgagaagg gcaacggttc atcatctcat   4260
ggatctgcac atgaacaaac accagagtca aacgacgttg aaattgaggc tactgcgcca   4320
attgatgaca atacagacga tgataacaaa ccgaagttat ctgatgtaga aaaggattaa   4380
agatgctaag agatagtgat gatatttcat aaataatgta attctatata tgttaattac   4440
ctttttttgcg aggcatattt atggtgaagg ataagttttg accatcaaag aaggttaatg   4500
tggctgtggt ttcagggtcc atacccggga gttatgacaa ttacaacaac agaattcttt   4560
```

-continued

```
ctatatatgc acgaacttgt aatatggaag aaattatgac gtacaaacta taaagtaaat   4620
attttacgta acacatggtg ctgttgtgct tctttttcaa gagaatacca atgacgtatg   4680
actaagttta ggatttaatg caggtgacgg acccatcttt caaacgattt atatcagtgg   4740
cgtccaaatt gttaggtttt gttggttcag caggtttcct gttgtgggtc atatgacttt   4800
gaaccaaatg gccggctgct agggcagcac ataaggataa ttcacctgcc aagacggcac   4860
aggcaactat tcttgctaat tgacgtgcgt tggtaccagg agcggtagca tgtgggcctc   4920
ttacacctaa taagtccaac atggcacctt gtggttctag aacagtacca ccaccgatgg   4980
tacctacttc gatggatggc atggatacgg aaattctcaa atcaccgtcc acttctttca   5040
tcaatgttat acagttggaa ctttcgacat tttgtgcagg atcttgtcct aatgccaaga   5100
aaacagctgt cactaaatta gctgcatgtg cgttaaatcc accaacagac ccagccattg   5160
cagatccaac caaattctta gcaatgttca actcaaccaa tgcggaaaca tcacttttta   5220
acacttttct gacaacatca ccaggaatag tagcttctgc gacgacactc ttaccacgac   5280
cttcgatcca gttgatggca gctggttttt tgtcggtaca gtagttacca gaaacggaga   5340
caacctccat atcttcccag ccatactctt ctaccatttg ctttaatgag tattcgacac   5400
ccttagaaat catattcata cccattgcgt caccagtagt tgttctaaat ctcatgaaga   5460
gtaaatctcc tgctagacaa gtttgaatat gttgcagacg tgcaaatctt gatgtagagt   5520
taaaagcttt tttaattgcg ttttgtccct cttctgagtc taaccatatc ttacaggcac   5580
cagatctttt caaagttggg aaacggacta ctgggcctct tgtcatacca tccttagtta   5640
aaacagttgt tgcaccaccg ccagcattga ttgccttaca gccacgcatg gcagaagcta   5700
ccaaacaacc ctctgtagtt gccattggta tatgataaga tgtaccatcg ataaccaagg   5760
ggcctataac accaacgggc aaaggcatgt aacctataac attttcacaa caagcgccaa   5820
atacgcggtc gtagtcataa tttttatatg gtaaacgatc agatgctaat acaggagctt   5880
ctgccaaaat tgaaagagcc ttcctacgta ccgcaaccgc tctcgtagta tcacctaatt   5940
ttttctccaa agcgtacaaa ggtaacttac cgtgaataac caaggcagcg acctctttgt   6000
tcttcaattg ttttgtattt ccactactta ataatgcttc taattcttct aaaggacgta   6060
ttttcttatc caagctttca atatcgcggg aatcatcttc ctcactagat gatgaaggtc   6120
ctgatgagct cgattgcgca gatgataaac ttttgacttt cgatccagaa atgactgttt   6180
tattggttaa aactggtgta gaagcctttt gtacaggagc agtaaaagac ttcttggtga   6240
cttcagtctt caccaattgg tctgcagcca ttatagtttt ttctccttga cgttaaagta   6300
tagaggtata ttaacaattt tttgttgata cttttatgac atttgaataa gaagtaatac   6360
aaaccgaaaa tgttgaaagt attagttaaa gtggttatgc agcttttgca tttatatatc   6420
tgttaataga tcaaaaatca tcgcttcgct gattaattac cccagaaata aggctaaaaa   6480
actaatcgca ttattatcct atggttgtta atttgattcg ttgatttgaa ggtttgtggg   6540
gccaggttac tgccaatttt tcctcttcat aaccataaaa gctagtattg tagaatcttt   6600
attgttcgga gcagtgcggc gcgaggcaca tctgcgtttc aggaacgcga ccggtgaaga   6660
ccaggacgca cggaggagag tcttccgtcg gagggctgtc gcccgctcgg cggcttctaa   6720
tccgtacttc aatatagcaa tgagcagtta agcgtattac tgaaagttcc aaagagaagg   6780
ttttttttagg ctaagataat ggggctcttt acatttccac aacatataag taagattaga   6840
tatggatatg tatatggtgg tattgccatg taatatgatt attaaacttc tttgcgtcca   6900
tccaaaaaaa aagtaagaat ttttgaaaat tcaatataaa tgaaactctc aactaaactt   6960
```

-continued

```
tgttggtgtg gtattaaagg aagacttagg ccgcaaaagc aacaacaatt acacaataca   7020
aacttgcaaa tgactgaact aaaaaaacaa aagaccgctg aacaaaaaac cagacctcaa   7080
aatgtcggta ttaaaggtat ccaaatttac atcccaactc aatgtgtcaa ccaatctgag   7140
ctagagaaat ttgatggcgt ttctcaaggt aaatacacaa ttggtctggg ccaaaccaac   7200
atgtcttttg tcaatgacag agaagatatc tactcgatgt ccctaactgt tttgtctaag   7260
ttgatcaaga gttacaacat cgacaccaac aaaattggta gattagaagt cggtactgaa   7320
actctgattg acaagtccaa gtctgtcaag tctgtcttga tgcaattgtt tggtgaaaac   7380
actgacgtcg aaggtattga cacgcttaat gcctgttacg gtggtaccaa cgcgttgttc   7440
aactctttga actggattga atctaacgca tgggatggta gagacgccat tgtagtttgc   7500
ggtgatattg ccatctacga taagggtgcc gcaagaccaa ccggtggtgc cggtactgtt   7560
gctatgtgga tcggtcctga tgctccaatt gtatttgact ctgtaagagc ttcttacatg   7620
gaacacgcct acgattttta caagccagat ttcaccagcg aatatcctta cgtcgatggt   7680
catttttcat taacttgtta cgtcaaggct cttgatcaag tttacaagag ttattccaag   7740
aaggctattt ctaaagggtt ggttagcgat cccgctggtt cggatgcttt gaacgttttg   7800
aaatatttcg actacaacgt tttccatgtt ccaacctgta aattggtcac aaaatcatac   7860
ggtagattac tatataacga tttcagagcc aatcctcaat tgttcccaga agttgacgcc   7920
gaattagcta ctcgcgatta tgacgaatct ttaaccgata agaacattga aaaaactttt   7980
gttaatgttg ctaagccatt ccacaaagag agagttgccc aatctttgat tgttccaaca   8040
aacacaggta acatgtacac cgcatctgtt tatgccgcct ttgcatctct attaaactat   8100
gttggatctg acgacttaca aggcaagcgt gttggtttat tttcttacgg ttccggttta   8160
gctgcatctc tatattcttg caaaattgtt ggtgacgtcc aacatattat caaggaatta   8220
gatattacta acaaattagc caagagaatc accgaaactc caaaggatta cgaagctgcc   8280
atcgaattga gagaaaatgc ccatttgaag aagaacttca aacctcaagg ttccattgag   8340
catttgcaaa gtggtgttta ctacttgacc aacatcgatg acaaatttag aagatcttac   8400
gatgttaaaa aataatcttc ccccatcgat tgcatcttgc tgaaccccct tcataaatgc   8460
tttatttttt tggcagcctg cttttttttag ctctcattta atagagtagt tttttaatct   8520
atatactagg aaaactcttt atttaataac aatgatatat atatattcca gtggtgcatg   8580
aacgcatgag aaagcccccg gaagatcatc ttccgggggc tttttttttg gcgcgcgata   8640
cagaccggtt cagacaggat aaagaggaac gcagaatgtt agacaacacc cgcttacgca   8700
tagctattca gaaatcaggc cgtttaagcg atgattcacg agaattgctg gcccgctgcg   8760
gcataaaaat taatttacac actcagcgcc tgattgcgat ggcggaaaac atgccgattg   8820
atatcctgcg cgtgcgtgat gatgacattc cgggtctggt aatggatggc gtggtcgatc   8880
tcggtattat cggcgaaaac gtgctggaag aagagctact caaccgccgc gcacagggcg   8940
aagatccacg ctatttaacc ctgcgccgtc ttgacttcgg cggctgccgt ttatcgctgg   9000
caacaccggt tgacgaagcc tgggacggcc cggccgcgct ggacggtaaa cgtatcgcta   9060
cctcatatcc gcacctcctc aaacgctacc tcgaccagaa aggcgtctct tttaaatcgt   9120
gtctgttaaa tggttctgtc gaagtcgcgc cgcgcgcggg gctggccgac gctatctgcg   9180
atttggtctc taccggcgcg acgcttgaag ctaacggcct gcgtgaagtc gaagttatct   9240
accgctctaa agcctgtctg attcagcgcg acggtgagat ggcacagagc aagcaagagc   9300
tgatcgataa attgctgacc cgtattcagg gcgtgattca ggcgcgcgaa tcgaaataca   9360
```

-continued

```
tcatgatgca cgcgccaagt gaacgcctgg aagaggttat cgccctgctg ccaggcgccg   9420

aaaggccgac aattctgccg ctggcaggcg agcaacagcg cgtggcgatg cacatggtca   9480

gcagcgaaac gttgttctgg gaaaccatgg agaaactgaa agcgcttggc gccagctcga   9540

ttctggtact gccgatcgag aagatgatgg agtgatctga cgcctgatgg cgctgcgctt   9600

atcaggccta cgtaatgcgt tgaaaaactg tattataagt aaatgcatgt atactaaact   9660

cacaaattag agcttcaatt taattatatc agttattacc cgggaatctc ggtcgtaatg   9720

atttctataa tgacgaaaaa aaaaaaattg gaaagaaaaa gcttcatggc ctttataaaa   9780

aggaactatc caatacctcg ccagaaccaa gtaacagtat tttacggggc acaaatcaag   9840

aacaataaga caggactgta aagatggacg cattgaactc caaagaacaa caagagttcc   9900

aaaaagtagt ggaacaaaag caaatgaagg atttcatgcg tttgtactct aatctggtag   9960

aaagatgttt cacagactgt gtcaatgact tcacaacatc aaagctaacc aataaggaac  10020

aaacatgcat catgaagtgc tcagaaaagt tcttgaagca tagcgaacgt gtagggcagc  10080

gtttccaaga acaaaacgct gccttgggac aaggcttggg ccgataaggt gtactggcgt  10140

atatatatct aattatgtat ctctggtgta gcccattttt agcatgtaaa tataaagaga  10200

aaccatatct aatctaacca aatccaaaca aaattcaata gttactatcg ctttttttctt  10260

tctgtatcgc aaataagtga aaattaaaaa agaaagatta aattggaagt tggatatggg  10320

ctggaacagc agcagtaatc ggtatcgggt tcgccactaa tgacgtccta cgattgcact  10380

caacagacct tgacgctcac gccgtagcgg gcgacaagtc aaacggaaca accgttgccg  10440

ttcccatcgg agtccgacct aggccgaact ccgtgaattt ctgataacaa cggtcggtaa  10500

agactggttc cccagtatat ttcttctctc aggagcaggg gccaatgcca aaagcgacat  10560

taacccggag gacaaggctc cactgtgttc caccgaattt cccacctgat aatatctgat  10620

aac                                                                 10623
```

<210> SEQ ID NO 24
<211> LENGTH: 8479
<212> TYPE: DNA
<213> ORGANISM: Artificial Sequence
<220> FEATURE:
<223> OTHER INFORMATION: Synthetic: Integration construct i467

<400> SEQUENCE: 24

```
gacggcacgg ccacgcgttt aaaccgccct ccaagctgac ataaatcgca ctttgtatct     60

actttttttt attcgaaaac aaggcacaac aatgaatcta tcgccctgtg agattttcaa    120

tctcaagttt gtgtaataga tagcgttata ttatagaact ataaaggtcc ttgaatatac    180

atagtgtttc attcctatta ctgtatatgt gactttacat tgttacttcc gcggctattt    240

gacgttttct gcttcaggtg cggcttggag ggcaaagtgt cagaaaatcg gccaggccgt    300

atgacacaaa agagtagaaa acgagatctc aaatatctcg aggcctgtcc tctatacaac    360

cgcccagctc tctgacaaag ctccagaacg gttgtctttt gtttcgaaaa gccaaggtcc    420

cttataattg ccctccattt tgtgtcacct atttaagcaa aaaattgaaa gtttactaac    480

ctttcattaa agagaaataa caatattata aaaagcgctt aaagctcaca cgcggccagg    540

gggagccgtt catcatctca tggatctgca catgaacaaa caccagagtc aaacgacgtt    600

gaaattgagg ctactgcgcc aattgatgac aatacagacg atgataacaa accgaagtta    660

tctgatgtag aaaaggatta aagatgctaa gagatagtga tgatatttca taaataatgt    720

aattctatat atgttaatta cctttttttgc gaggcatatt tatggtgaag gataagtttt    780
```

-continued

```
gaccatcaaa gaaggttaat gtggctgtgg tttcagggtc cataaagctt ttcaattcat    840
cttttttttt tttgttcttt tttttgattc cggtttcttt gaaatttttt tgattcggta    900
atctccgagc agaaggaaga acgaaggaag gagcacagac ttagattggt atatatacgc    960
atatgtggtg ttgaagaaac atgaaattgc ccagtattct taacccaact gcacagaaca   1020
aaaacctgca ggaaacgaag ataaatcatg tcgaaagcta catataagga acgtgctgct   1080
actcatccta gtcctgttgc tgccaagcta tttaatatca tgcacgaaaa gcaaacaaac   1140
ttgtgtgctt cattggatgt tcgtaccacc aaggaattac tggagttagt tgaagcatta   1200
ggtcccaaaa tttgtttact aaaaacacat gtggatatct tgactgattt ttccatggag   1260
ggcacagtta agccgctaaa ggcattatcc gccaagtaca atttttttact cttcgaagac   1320
agaaaatttg ctgacattgg taatacagtc aaattgcagt actctgcggg tgtatacaga   1380
atagcagaat gggcagacat tacgaatgca cacggtgtgg tgggcccagg tattgttagc   1440
ggtttgaagc aggcggcaga agaagtaaca aaggaaccta gaggcctttt gatgttagca   1500
gaattgtcat gcaagggctc cctatctact ggagaatata ctaagggtac tgttgacatt   1560
gcgaagagtg acaaagattt tgttatcggc tttattgctc aaagagacat gggtggaaga   1620
gatgaaggtt acgattggtt gattatgaca cccggtgtgg gtttagatga caagggagac   1680
gcattgggtc aacagtatag aaccgtggat gatgtggtct ctacaggatc tgacattatt   1740
attgttggaa gaggactatt tgcaaaggga agggatgcta aggtagaggg tgaacgttac   1800
agaaaagcag gctgggaagc atatttgaga agatgcggcc agcaaaacta aaaaactgta   1860
ttataagtaa atgcatgtat actaaactca caaattagag cttcaattta attatatcag   1920
ttattacccg ggaatctcgg tcgtaatgat ttctataatg acgaaaaaaa aaaaattgga   1980
aagaaaaagc ttcatggcct ttataaaaag gaactatcca atacctcgcc agaaccaagt   2040
aacagtattt tacggggcac aaatcaagaa caataagaca ggactgtaaa gatggacgca   2100
tcgctcgtcc aacgccggcg gacctgtttt caatagttcg gtaatattaa cggataccta   2160
ctattatccc ctagtaggct cttttcacgg agaaattcgg gagtgttttt tttccgtgcg   2220
cattttctta gctatattct tccagcttcg cctgctgccc ggtcatcgtt cctgtcacgt   2280
agtttttccg gattcgtccg gctcatataa taccgcaata aacacggaat atctcgttcc   2340
gcggattcgg ttaaactctc ggtcgcggat tatcacagag aaagcttcgt ggagaatttt   2400
tccagatttt ccgctttccc cgatgttggt atttccggag gtcattatac tgaccgccat   2460
tataatgact gtacaacgac cttctggaga aagaaacaac tcaataacga tgtgggacat   2520
tgggggccca ctcaaaaaat ctggggacta tatccccaga gaatttctcc agaagagaag   2580
aaaagtcaaa gtttttttc gcttgggggt tgcatataaa tacaggcgct gttttatctt   2640
cagcatgaat attccataat tttacttaat agcttttcat aaataataga atcacaaaca   2700
aaatttacat ctgagttaaa caatcatgac aatcaaggaa cataaagtag tttatgaagc   2760
tcacaacgta aaggctctta aggctcctca acatttttac aacagccaac ccggcaaggg   2820
ttacgttact gatatgcaac attatcaaga aatgtatcaa caatctatca atgagccaga   2880
aaaattcttt gataagatgg ctaaggaata cttgcattgg gatgctccat acaccaaagt   2940
tcaatctggt tcattgaaca atggtgatgt tgcatggttt ttgaacggta aattgaatgc   3000
atcatacaat tgtgttgaca gacatgcctt tgctaatccc gacaagccag ctttgatcta   3060
tgaagctgat gacgaatccg acaacaaaat catcacattt ggtgaattac tcagaaaagt   3120
ttcccaaatc gctggtgtct taaaaagctg gggcgttaag aaaggtgaca cagtggctat   3180
```

```
ctatttgcca atgattccag aagcggtcat tgctatgttg gctgtggctc gtattggtgc   3240
tattcactct gttgtctttg ctgggttctc cgctggttcg ttgaaagatc gtgtcgttga   3300
cgctaattct aaagtggtca tcacttgtga tgaaggtaaa agaggtggta agaccatcaa   3360
cactaaaaaa attgttgacg aaggtttgaa cggagtcgat ttggtttccc gtatcttggt   3420
tttccaaaga actggtactg aaggtattcc aatgaaggcc ggtagagatt actggtggca   3480
tgaggaggcc gctaagcaga gaacttacct acctcctgtt tcatgtgacg ctgaagatcc   3540
tctattttta ttatacactt ccggttccac tggttctcca aagggtgtcg ttcacactac   3600
aggtggttat ttattaggtg ccgctttaac aactagatac gtttttgata ttcacccaga   3660
agatgttctc ttcactgccg gtgacgtcgg ctggatcacg ggtcacacct atgctctata   3720
tggtccatta accttgggta ccgcctcaat aattttcgaa tccactcctg cctacccaga   3780
ttatggtaga tattggagaa ttatccaacg tcacaaggct acccatttct atgtggctcc   3840
aactgcttta agattaatca aacgtgtagg tgaagccgaa attgccaaat atgacacttc   3900
ctcattacgt gtcttgggtt ccgtcggtga accaatctct ccagacttat gggaatggta   3960
tcatgaaaaa gtgggtaaca aaaactgtgt catttgtgac actatgtggc aaacagagtc   4020
tggttctcat ttaattgctc ctttggcagg tgctgtccca acaaaacctg gttctgctac   4080
cgtgccattc tttggtatta acgcttgtat cattgaccct gttacaggtg tggaattaga   4140
aggtaatgat gtcgaaggtg tccttgccgt taaatcacca tggccatcaa tggctagatc   4200
tgtttggaac caccacgacc gttacatgga tacttacttg aaaccttatc ctggtcacta   4260
tttcacaggt gatggtgctg gtagagatca tgatggttac tactggatca ggggtagagt   4320
tgacgacgtt gtaaatgttt ccggtcatag attatccaca tcagaaattg aagcatctat   4380
ctcaaatcac gaaaacgtct cggaagctgc tgttgtcggt attccagatg aattgaccgg   4440
tcaaaccgtc gttgcatatg tttccctaaa agatggttat ctacaaaaca acgctactga   4500
aggtgatgca gaacacatca caccagataa tttacgtaga gaattgatct tacaagttag   4560
gggtgagatt ggtcctttcg cctcaccaaa aaccattatt ctagttagag atctaccaag   4620
aacaaggtca ggaaagatta tgagaagagt tctaagaaag gttgcttcta acgaagccga   4680
acagctaggt gacctaacta ctttggccaa cccagaagtt gtacctgcca tcatttctgc   4740
tgtagagaac caatttttct ctcaaaaaaa gaaataaatt gaattgaatt gaaatcgata   4800
gatcaatttt tttcttttct ctttccccat cctttacgct aaaataatag tttattttat   4860
tttttgaata ttttttattt atatacgtat atatagacta ttatttatct tttaatgatt   4920
attaagattt ttattaaaaa aaaattcgct cctcttttaa tgcctttatg cagttttttt   4980
ttcccattcg atatttctat gttcgggttc agcgtatttt aagtttaata actcgaaaat   5040
tctgcgttcg ttaaagcttt cgagaaggat attatttcga aataaaccgt gttgtgtaag   5100
cttgaagcct ttttgcgctg ccaatattct tatccatcta ttgtactctt tagatccagt   5160
atagtgtatt cttcctgctc caagctcatc ccatccccgc gtgcttggcc ggccgttttg   5220
ccagcttact atccttcttg aaaatatgca ctctatatct tttagttctt aattgcaaca   5280
catagatttg ctgtataacg aattttatgc tattttttaa atttggagtt cagtgataaa   5340
agtgtcacag cgaatttcct cacatgtagg gaccgaattg tttacaagtt ctctgtacca   5400
ccatggagac atcaaaaatt gaaaatctat ggaaagatat ggacggtagc aacaagaata   5460
tagcacgagc cgcggagttc atttcgttac ttttgatatc actcacaact attgcgaagc   5520
gcttcagtga aaaaatcata aggaaaagtt gtaaatatta ttggtagtat tcgtttggta   5580
```

-continued

```
aagtagaggg ggtaattttt cccctttatt ttgttcatac attcttaaat tgctttgcct   5640
ctccttttgg aaagctatac ttcggagcac tgttgagcga aggctcatta gatatatttt   5700
ctgtcatttt ccttaaccca aaaataaggg aaagggtcca aaaagcgctc ggacaactgt   5760
tgaccgtgat ccgaaggact ggctatacag tgttcacaaa atagccaagc tgaaaataat   5820
gtgtagctat gttcagttag tttggctagc aaagatataa aagcaggtcg gaaatattta   5880
tgggcattat tatgcagagc atcaacatga taaaaaaaaa cagttgaata ttccctcaaa   5940
aatgtcttac accgtcggaa cctacttggc cgagaggttg gtccagatcg gattgaagca   6000
ccacttcgcc gtcgccggtg actacaactt ggtcttgttg gacaacttgt tgttgaacaa   6060
gaacatggag caggtctatt gctgcaacga gttgaactgc ggtttctcag cagaaggtta   6120
tgcaagagcc aagggagcag ccgctgccgt cgtcacctac tcagtcggtg cattatcagc   6180
attcgatgca attggaggtg cttacgctga gaacttgcca gtcatcttga tctctggagc   6240
acctaacaac aacgaccatg ctgctggtca cgtattgcac cacgccttgg gtaaaacaga   6300
ctaccactac cagttggaaa tggcaaaaaa tattaccgca gccgcagagg ccatctacac   6360
cccagaggaa gcacctgcca aaattgacca cgtcataaag accgctttga gagagaagaa   6420
gcctgtttac ttggagatcg cctgcaacat cgcttctatg ccatgcgccg cacctggtcc   6480
agcctctgct ttgttcaacg acgaggcctc tgacgaagct tcattgaacg ccgcagtcga   6540
agagacatta aagttcatcg ccaacaggga caaagttgcc gtcttagtcg gttcaaagtt   6600
gagggccgct ggtgccgaag aggcagctgt caagttcgct gacgccttgg gaggagccgt   6660
cgccaccatg gccgcagcaa aatctttctt tcctgaggag aacccacatt acatcggaac   6720
ctcatggggt gaagtatcat atcctggagt agaaaaaacc atgaaagagg ccgatgccgt   6780
aatagcattg gctcctgtct tcaacgacta ctcaaccaca ggatggactg atataccaga   6840
tccaaagaaa ttagtcttgg ctgagcctag gtctgtcgtc gtaaacggta tcaggttccc   6900
ttctgttcat ttgaaggact acttaacaag attggcccaa aaggtatcta aaaagactgg   6960
tgccttggac ttcttcaagt cattaaacgc aggagaattg aaaaaagcag caccagccga   7020
tccatcagcc ccattagtta acgctgaaat cgctagacaa gtagaggctt tgttgactcc   7080
aaacactacc gtcatagctg agacaggtga ctcttggttc aacgcacaga gaatgaaatt   7140
gccaaatggt gccagggtcg agtatgaaat gcagtgggga catataggtt ggtcagtccc   7200
agccgccttt ggatacgcag taggtgcccc tgagaggagg aacatattga tggttggtga   7260
tggttcattc caattaacag cccaggaggt agcccaaatg gtcaggttga agttgcctgt   7320
catcatcttc ttgatcaaca attacggata caccatcgag gtcatgatcc acgacggacc   7380
ttacaacaac atcaaaaact gggactacgc cggtttgatg gaggttttca acggtaacgg   7440
tggttatgac tcaggagccg gtaagggatt aaaggctaag accggtggtg aattggctga   7500
agcaattaag gtcgcattgg ccaacaccga tggacctaca ttgattgaat gcttcatcgg   7560
aagggaggac tgcaccgagg aattggttaa atggggtaaa agggtagccg ctgctaattc   7620
aagaaaacca gttaataaat tattataata agtgaattta ctttaaatct tgcatttaaa   7680
taaattttct ttttatagct ttatgactta gtttcaattt atatactatt ttaatgacat   7740
tttcgattca ttgattgaaa gctttgtgtt ttttcttgat gcgctattgc attgttcttg   7800
tctttttcgc cacatgtaat atctgtagta gatacctgat acattgtgga tgctgagtga   7860
aattttagtt aataatggag gcgctcttaa taattttggg gatattggct taacctgcag   7920
gccgcgagcg ccgatataaa ctaatgattt taaatcgtta aaaaaatatg cgaattctgt   7980
```

```
ggatcgaaca caggacctcc agataacttg accgaagttt tttcttcagt ctggcgctct   8040

cccaactgag ctaaatccgc ttactatttg ttatcagttc ccttcatatc tacatagaat   8100

aggttaagta ttttattagt tgccagaaga actactgata gttgggaata tttggtgaat   8160

aatgaagatt gggtgaataa tttgataatt ttgagattca attgttaatc aatgttacaa   8220

tattatgtat acagagtata ctagaagttc tcttcggaga tcttgaagtt cacaaaaggg   8280

aatcgatatt tctacataat attatcatta cttcttcccc atcttatatt tgtcattcat   8340

tattgattat gatcaatgca ataatgattg gtagttgcca aacatttaat acgatcctct   8400

gtaatatttc tatgaataat tatcacagca acgttcaatt atcttcaatt ccggtgttta   8460

aaccccagcg cctggcggg                                                8479
```

<210> SEQ ID NO 25
<211> LENGTH: 5628
<212> TYPE: DNA
<213> ORGANISM: Artificial Sequence
<220> FEATURE:
<223> OTHER INFORMATION: Synthetic: URA3 FcphI target site cassette

<400> SEQUENCE: 25

```
gcctgtctac aggataaaga cgggtcggat acctgcacaa gcaatttggc acctgcatac     60

cccatttccc cagtagataa cttcaacaca cacatcaatg tccctcacca gtttatttcc    120

aaaagagacg ctttttacta cctgactaga ttttcatttt gtttcttttg gattgcgctt    180

gcctttgtag gtgtgtcgtt tatcctttac gttttgactt ggtgctcgaa gatgctttca    240

gagatggtgc ttatcctcat gtcttttggg tttgtcttca atacggcagc cgttgtcttg    300

caaacggccg cctctgccat ggcaaagaat gctttccatg acgatcatcg tagtgcccaa    360

ttgggtgcct ctatgatggg tttaaacgta tggcttgggc aagtgtcttt ttatgtatcg    420

tggaatttat cctgctggtc ttctggtctg ttagggcaag gttggcctct acttactcca    480

tcgacaattc aagatacaga acctcctcca gatggaatcc cttccataga gagaaggagc    540

aagcaactga cccaatattg actgccactg gacctgaaga catgcaacaa agtgcaagca    600

tagtggggcc ttcttccaat gctaatccgg tcactgccac tgctgctacg gaaaaccaac    660

ctaaaggtat taacttcttc actataagaa aatcacacga gcgcccggac gatgtctctg    720

tttaaatggc gcaagtttc cgctttgtaa tatatattta tacccctttc ttctctcccc    780

tgcaatataa tagtttaatt ctaatattaa taatatccta tattttcttc atttaccggc    840

gcactctcgc ccgaacgacc tcaaaatgtc tgctacattc ataataacca aaagctcata    900

actttttttt ttgaacctga atatatatac atcacatatc actgctggtc ctttgtgagc    960

gttgcgctcg tgcatcatgc gtccatcttt acagtcctgt cttattgttc ttgatttgtg   1020

ccccgtaaaa tactgttact tggttctggc gaggtattgg atagttcctt tttataaagg   1080

ccatgaagct ttttctttcc aatttttttt ttttcgtcat tatagaaatc attacgaccg   1140

agattcccgg gtaataactg atataattaa attgaagctc taatttgtga gtttagtata   1200

catgcattta cttataatac agttttttag ttttgctggc cgcatcttct caaatatgct   1260

tcccagcctg cttttctgta acgttcaccc tctaccttag catcccttcc ctttgcaaat   1320

agtcctcttc caacaataat aatgtcagat cctgtagaga ccacatcatc cacggttcta   1380

tactgttgac ccaatgcgtc tcccttgtca tctaaaccca caccgggtgt cataatcaac   1440

caatcgtaac cttcatctct tccacccatg tctctttgag caataaagcc gataacaaaa   1500

tctttgtcac tcttcgcaat gtcaacagta ccccttagtat attctccagt agatagggag   1560
```

-continued

```
cccttgcatg acaattctgc taacatcaaa aggcctctag gttcctttgt tacttcttct   1620
gccgcctgct tcaaaccgct aacaatacct gggcccacca caccgtgtgc attcgtaatg   1680
tctgcccatt ctgctattct gtatacaccc gcagagtact gcaatttgac tgtattacca   1740
atgtcagcaa attttctgtc ttcgaagagt aaaaaattgt acttggcgga taatgccttt   1800
agcggcttaa ctgtgccctc catggaaaaa tcagtcaaga tatccacatg tgtttttagt   1860
aaacaaattt tgggacctaa tgcttcaact aactccagta attccttggt ggtacgaaca   1920
tccaatgaag cacacaagtt tgtttgcttt tcgtgcatga tattaaatag cttggcagca   1980
acaggactag gatgagtagc agcacgttcc ttatatgtag ctttcgacat gatttatctt   2040
cgtttcctgc aggtttttgt tctgtgcagt tgggttaaga atactgggca atttcatgtt   2100
tcttcaacac cacatatgcg tatatatacc aatctaagtc tgtgctcctt ccttcgttct   2160
tccttctgct cggagattac cgaatcaaaa aaatttcaaa gaaaccggaa tcaaaaaaaa   2220
gaacaaaaaa aaaaaagatg aattgaaaag ctttatggac cctgaaacca cagccacatt   2280
aaccttcttt gatggtcaaa acttatcctt caccataaat atgcctcgca aaaaaggtaa   2340
ttaacatata tagaattaca ttatttatga aatatcatca ctatctctta gcatctttaa   2400
tccttttcta catcagataa cttcggtttg ttatcatcgt ctgtattgtc atcaattggc   2460
gcagtagcct caatttcaac gtcgtttgac tctggtgttt gttcatgtgc agatccatga   2520
gatgatgaac ttgtgagcgt tgcgctcgtg catcaccata tacatatcca tatctaatct   2580
tacttatatg ttgtggaaat gtaaagagcc ccattatctt agcctaaaaa aaccttctct   2640
ttggaacttt cagtaatacg cttaactgct cattgctata ttgaagtacg gattagaagc   2700
cgccgagcgg gcgacagccc tccgacggaa gactctcctc cgtgcgtcct ggtcttcacc   2760
ggtcgcgttc ctgaaacgca gatgtgcctc gcgccgcact gctccgaaca ataaagattc   2820
tacaatacta gcttttatgg ttatgaagag gaaaaattgg cagtaacctg gccccacaaa   2880
ccttcaaatc aacgaatcaa attaacaacc ataggataat aatgcgatta gtttttttagc  2940
cttatttctg gggtaattaa tcagcgaagc gatgattttt gatctattaa cagatatata   3000
aatgcaaaag ctgcataacc actttaacta atactttcaa cattttcggt ttgtattact   3060
tcttattcaa atgtcataaa agtatcaaca aaaaattgtt aatatacctc tatactttaa   3120
cgtcaaggag aaaaaactat aatgtcatta ccgttcttaa cttctgcacc gggaaaggtt   3180
attattttttg gtgaacactc tgctgtgtac aacaagcctg ccgtcgctgc tagtgtgtct  3240
gcgttgagaa cctacctgct aataagcgag tcatctgcac cagatactat tgaattggac   3300
ttcccggaca ttagctttaa tcataagtgg tccatcaatg atttcaatgc catcaccgag   3360
gatcaagtaa actcccaaaa attggccaag gctcaacaag ccaccgatgg cttgtctcag   3420
gaactcgtta gtcttttgga tccgttgtta gctcaactat ccgaatcctt ccactaccat   3480
gcagcgtttt gtttcctgta tatgtttgtt tgcctatgcc cccatgccaa gaatattaag   3540
ttttctttaa agtctacttt acccatcggt gctgggttgg gctcaagcgc ctctatttct   3600
gtatcactgg ccttagctat ggcctacttg ggggggttaa taggatctaa tgacttggaa   3660
aagctgtcag aaaacgataa gcatatagtg aatcaatggg ccttcatagg tgaaaagtgt   3720
attcacggta ccccttcagg aatagataac gctgtggcca cttatggtaa tgccctgcta   3780
tttgaaaaag actcacataa tggaacaata aacacaaaca attttaagtt cttagatgat   3840
ttcccagcca ttccaatgat cctaacctat actagaattc caaggtctac aaaagatctt   3900
gttgctcgcg ttcgtgtgtt ggtcaccgag aaatttcctg aagttatgaa gccaattcta   3960
```

```
gatgccatgg gtgaatgtgc cctacaaggc ttagagatca tgactaagtt aagtaaatgt   4020

aaaggcaccg atgacgaggc tgtagaaact aataatgaac tgtatgaaca actattggaa   4080

ttgataagaa taaatcatgg actgcttgtc tcaatcggtg tttctcatcc tggattagaa   4140

cttattaaaa atctgagcga tgatttgaga attggctcca caaaacttac cggtgctggt   4200

ggcggcggtt gctctttgac tttgttacga agagacatta ctcaagagca aattgacagt   4260

ttcaaaaaga aattgcaaga tgattttagt tacgagacat ttgaaacaga cttgggtggg   4320

actggctgct gtttgttaag cgcaaaaaat ttgaataaag atcttaaaat caaatcccta   4380

gtattccaat tatttgaaaa taaaactacc acaaagcaac aaattgacga tctattattg   4440

ccaggaaaca cgaatttacc atggacttca taagctaatt tgcgataggc attatttatt   4500

agttgttttt aatcttaact gtgtatgaag ttttatgtaa taaagataga aagagaaaca   4560

aaaaaaaatt tttcgtagta tcaattcagc tttcgaagac agaatgaaat ttaagcagac   4620

catcatcttg ccctgtgctt ggcccccagt gcagcgaacg ttataaaaac gaatactgag   4680

tatatatcta tgtaaaacaa ccatatcatt tcttgttctg aactttgttt acctaactag   4740

ttttaaattt cccttttcg tgcatgcggg tgttcttatt tattagcata ctacatttga   4800

aatatcaaat ttccttagta gaaaagtgag agaaggtgca ctgacacaaa aaataaaatg   4860

ctacgtataa ctgtcaaaac tttgcagcag cgggcatcct tccatcatag cttcaaacat   4920

attagcgttc ctgatcttca tacccgtgct caaaatgatc aaacaaactg ttattgccaa   4980

gaaataaacg caaggctgcc ttcaaaaact gatccattag atcctcatat caagcttcct   5040

catagaacgc ccaattacaa taagcatgtt ttgctgttat caccgggtga taggtttgct   5100

caaccatgga aggtagcatg gaatcataat ttggatacta atacaaatcg gccatataat   5160

gccattagta aattgcgctc ccatttaggt ggttctccag gcaaatttga atactaataa   5220

atgcggtgca tttgcaaaat gaatttattc caaggccaaa acaacacgat gaatggcttt   5280

atttttttgt tattcctgac atgaagcttt atgtaattaa ggaaacggac atcgaggaat   5340

ttgcatcttt tttagatgaa ggagctattc aagcaccaaa gctatccttc caggattatt   5400

taagcggtaa ggccaaggct tcccaacagg ttcatgaagt gcatcataga aagcttacaa   5460

ggtttcaggg tgaaactttt ctaagagatt ggaacttagt ctgtgggcat tataagagag   5520

atgctaagtg tggagaaatg ggacccgaca taattgcagc atttcaagat gaaaagcttt   5580

ttcctgagaa taatctagcc ttaatttctc atattggggg tcatattt                5628
```

<210> SEQ ID NO 26
<211> LENGTH: 10019
<212> TYPE: DNA
<213> ORGANISM: Artificial Sequence
<220> FEATURE:
<223> OTHER INFORMATION: Synthetic: HXT3 FcphI target site cassette

<400> SEQUENCE: 26

```
accggtatat caaatggcgg tgtagtttga aaagtacact gtatgtccat taataaaatt     60

acgccgaaga acactgacta gctataaatt ctcttccggc gtccaatttc aacctaaggc    120

aagtattgtt aatcaataat gcgtgttggt aaatatgaag cccgatgttg attaagaaga    180

attattcgta taagaattaa gcaagcaaaa ttaaggaaaa ttttttcttt cctattcgtc    240

atcgcagaca gccttcatct tctcgagata acacctggag gaggagcaat gaaatgaaag    300

gaaaaaaaaa tactttcttt ttcttgaaaa aagaaaaaaa ttgtaagatg agctattcgc    360

ggaacattct agctcgtttg catcttcttg catttggtag gttttcaata gttcggtaat    420
```

-continued

```
attaacggat acctactatt atcccctagt aggctctttt cacggagaaa ttcgggagtg    480
ttttttttcc gtgcgcattt tcttagctat attcttccag cttcgcctgc tgcccggtca    540
tcgttcctgt cacgtagttt ttccggattc gtccggctca tataataccg caataaacac    600
ggaatatctc gttccgcgga ttcggttaaa ctctcggtcg cggattatca cagagaaagc    660
ttcgtggaga atttttccag attttccgct ttccccgatg ttggtatttc cggaggtcat    720
tatactgacc gccattataa tgactgtaca acgaccttct ggagaaagaa acaactcaat    780
aacgatgtgg gacattgggg gcccactcaa aaaatctggg gactatatcc ccagagaatt    840
tctccagaag agaagaaaag tcaaagtttt ttttcgcttg ggggttgcat ataaattgtg    900
agcgttgcgc tcgtgcatcg tcgacactag taatacacat catcgtccta caagttcatc    960
aaagtgttgg acagacaact ataccagcat ggatctcttg tatcggttct tttctcccgc   1020
tctctcgcaa taacaatgaa cactgggtca atcatagcct acacaggtga acagagtagc   1080
gtttatacag ggtttatacg gtgattccta cggcaaaaat ttttcatttc taaaaaaaaa   1140
aagaaaaatt tttctttcca acgctagaag gaaaagaaaa atctaattaa attgatttgg   1200
tgattttctg agagttccct ttttcatata tcgaattttg aatataaaag gagatcgaaa   1260
aaatttttct attcaatctg ttttctggtt ttatttgata gttttttttgt gtattattat   1320
tatggattag tactggttta tatgggtttt tctgtataac ttctttttat tttagtttgt   1380
ttaatcttat tttgagttac attatagttc cctaactgca agagaagtaa cattaaaaat   1440
gaccactctt gacgacacgg cttaccggta ccgcaccagt gtcccggggg acgccgaggc   1500
catcgaggca ctggatgggt ccttcaccac cgacaccgtc ttccgcgtca ccgccaccgg   1560
ggacggcttc accctgcggg aggtgccggt ggacccgccc ctgaccaagg tgttccccga   1620
cgacgaatcg gacgacgaat cggacgccgg ggaggacggc gacccggact cccggacgtt   1680
cgtcgcgtac ggggacgacg gcgacctggc gggcttcgtg gtcgtctcgt actccggctg   1740
gaaccgccgg ctgaccgtcg aggacatcga ggtcgccccg gagcaccggg ggcacggggt   1800
cgggcgcgcg ttgatggggc tcgcgacgga gttcgcccgc gagcggggcg ccgggcacct   1860
ctggctggag gtcaccaacg tcaacgcacc ggcgatccac gcgtaccggc ggatggggtt   1920
caccctctgc ggcctggaca ccgccctgta cgacggcacc gcctcggacg gcgagcaggc   1980
gctctacatg agcatgccct gcccctgagt ttaacttgat actactagat tttttctctt   2040
catttataaa atttttggtt ataattgaag ctttagaagt atgaaaaaat cctttttttt   2100
cattctttgc aaccaaaata agaagcttct tttattcatt gaaatgatga atataaacct   2160
aacaaaagaa aaagactcga atatcaaaca ttaaaaaaaa ataaaagagg ttatctgttt   2220
tcccatttag ttggagtttg cattttctaa tagatagaac tctcaattaa tgtggattta   2280
gtttctctgt tcgttttttt ttgttttgtt ctcactgtat ttacatttct atttagtatt   2340
tagttattca tataatctta acttctcgag gagctcgatg cgtccatctt tacagtcctg   2400
tcttattgtt cttgatttgt gccccgtaaa atactgttac ttggttctgg cgaggtattg   2460
gatagttcct ttttataaag gccatgaagc tttttctttc caattttttt tttttcgtca   2520
ttatagaaat cattacgacc gagattcccg ggtaataact gatataatta aattgaagct   2580
ctaatttgtg agtttagtat acatgcattt acttataata cagtttttta gttttgctgg   2640
ccgcatcttc tcaaatatgc ttcccagcct gcttttctgt aacgttcacc ctctacctta   2700
gcatcccttc cctttgcaaa tagtcctctt ccaacaataa taatgtcaga tcctgtagag   2760
accacatcat ccacggttct atactgttga cccaatgcgt ctcccttgtc atctaaaccc   2820
```

-continued

```
acaccgggtg tcataatcaa ccaatcgtaa ccttcatctc ttccacccat gtctctttga   2880
gcaataaagc cgataacaaa atctttgtca ctcttcgcaa tgtcaacagt acccttagta   2940
tattctccag tagataggga gcccttgcat gacaattctg ctaacatcaa aaggcctcta   3000
ggttcctttg ttacttcttc tgccgcctgc ttcaaaccgc taacaatacc tgggcccacc   3060
acaccgtgtg cattcgtaat gtctgcccat tctgctattc tgtatacacc cgcagagtac   3120
tgcaatttga ctgtattacc aatgtcagca aattttctgt cttcgaagag taaaaaattg   3180
tacttggcgg ataatgcctt tagcggctta actgtgccct ccatggaaaa atcagtcaag   3240
atatccacat gtgtttttag taaacaaatt ttgggaccta atgcttcaac taactccagt   3300
aattccttgg tggtacgaac atccaatgaa gcacacaagt ttgtttgctt ttcgtgcatg   3360
atattaaata gcttggcagc aacaggacta ggatgagtag cagcacgttc cttatatgta   3420
gctttcgaca tgatttatct tcgtttcctg caggtttttg ttctgtgcag ttgggttaag   3480
aatactgggc aatttcatgt ttcttcaaca ccacatatgc gtatatatac caatctaagt   3540
ctgtgctcct tccttcgttc ttccttctgc tcggagatta ccgaatcaaa aaaatttcaa   3600
agaaaccgga atcaaaaaaa agaacaaaaa aaaaaaagat gaattgaaaa gctttatgga   3660
ccctgaaacc acagccacat taaccttctt tgatggtcaa aacttatcct tcaccataaa   3720
tatgcctcgc aaaaaaggta attaacatat atagaattac attatttatg aaatatcatc   3780
actatctctt agcatcttta atccttttct acatcagata acttcggttt gttatcatcg   3840
tctgtattgt catcaattgg cgcagtagcc tcaatttcaa cgtcgtttga ctctggtgtt   3900
tgttcatgtg cagatccatg agatgatgaa cttgtgagcg ttgcgctcgt gcatccgctc   3960
gtccaacgcc ggcggacctc gctcgtccaa cgccggcgga cctcttttaa ttctgctgta   4020
acccgtacat gcccaaaata gggggcgggt tacacagaat atataacatc gtaggtgtct   4080
gggtgaacag tttattcctg gcatccacta aatataatgg agcccgcttt ttaagctggc   4140
atccagaaaa aaaaagaatc ccagcaccaa aatattgttt tcttcaccaa ccatcagttc   4200
ataggtccat tctcttagcg caactacaga gaacaggggc acaaacaggc aaaaaacggg   4260
cacaacctca atggagtgat gcaacctgcc tggagtaaat gatgacacaa ggcaattgac   4320
ccacgcatgt atctatctca ttttcttaca ccttctatta ccttctgctc tctctgattt   4380
ggaaaaagct gaaaaaaaag gttgaaacca gttccctgaa attattcccc tacttgacta   4440
ataagtatat aaagacggta ggtattgatt gtaattctgt aaatctattt cttaaacttc   4500
ttaaattcta cttttatagt tagtcttttt tttagtttta aaacaccaag aacttagttt   4560
cgatccccgc gtgcttggcc ggccgtatcc ccgcgtgctt ggccggccgt atgtctcaga   4620
acgtttacat tgtatcgact gccagaaccc caattggttc attccagggt tctctatcct   4680
ccaagacagc agtggaattg ggtgctgttg ctttaaaagg cgccttggct aaggttccag   4740
aattggatgc atccaaggat tttgacgaaa ttatttttgg taacgttctt tctgccaatt   4800
tgggccaagc tccggccaga caagttgctt tggctgccgg tttgagtaat catatcgttg   4860
caagcacagt taacaaggtc tgtgcatccg ctatgaaggc aatcattttg ggtgctcaat   4920
ccatcaaatg tggtaatgct gatgttgtcg tagctggtgg ttgtgaatct atgactaacg   4980
caccatacta catgccagca gcccgtgcgg gtgccaaatt tggccaaact gttcttgttg   5040
atggtgtcga aagagatggg ttgaacgatg cgtacgatgg tctagccatg ggtgtacacg   5100
cagaaaagtg tgcccgtgat tgggatatta ctagagaaca acaagacaat tttgccatcg   5160
aatcctacca aaaatctcaa aaatctcaaa aggaaggtaa attcgacaat gaaattgtac   5220
```

-continued

```
ctgttaccat taagggattt agaggtaagc ctgatactca agtcacgaag gacgaggaac   5280
ctgctagatt acacgttgaa aaattgagat ctgcaaggac tgttttccaa aaagaaaacg   5340
gtactgttac tgccgctaac gcttctccaa tcaacgatgg tgctgcagcc gtcatcttgg   5400
tttccgaaaa agttttgaag gaaaagaatt tgaagccttt ggctattatc aaaggttggg   5460
gtgaggccgc tcatcaacca gctgatttta catgggctcc atctcttgca gttccaaagg   5520
ctttgaaaca tgctggcatc gaagacatca attctgttga ttactttgaa ttcaatgaag   5580
ccttttcggt tgtcggtttg gtgaacacta agattttgaa gctagaccca tctaaggtta   5640
atgtatatgg tggtgctgtt gctctaggtc acccattggg ttgttctggt gctagagtgg   5700
ttgttacact gctatccatc ttacagcaag aaggaggtaa gatcggtgtt gccgccattt   5760
gtaatggtgg tggtggtgct tcctctattg tcattgaaaa gatatgatta cgttctgcga   5820
ttttctcatg atctttttca taaaatacat aaatatataa atggctttat gtataacagg   5880
cataatttaa agttttattt gcgattcatc gtttttcagg tactcaaacg ctgaggtgtg   5940
ccttttgact tacttttccg ccttggcaag ctggccgggt gatacttgca caagttccac   6000
taattactga catttgtggt attaactcgt ttgactgctc tacaattgta ggatgttaat   6060
caatgtcttg gctgcctaac ctgcaggccg cgagcgccga tatgctatgt aatagacaat   6120
aaaaccatgt ttatataaaa aaaattcaaa atagaaaacg attctgtaca aggagtattt   6180
tttttttgtt ctagtgtgtt tatattatcc ttggctaaga ggcactgcgt atacttcaag   6240
gtacccctgt gttttgaaaa aaaacaacag taaaatagga actccgcgag gttcaggaac   6300
ctgaaacaaa atcaataaaa acattatatg cgtttcgaac aaaattaaag aaaaagaata   6360
aatatagatt aaaaaaaaaa agaagaaatt aaaagaattt ctactaaatc ccaattgtta   6420
tatatttgtt aaatgccaaa aaagtttata aaaaatttag aatgtataaa taataataaa   6480
ctaagtaacg cgatcgccga cgccgccgat atctccctcg ccagcggccg ccttatggct   6540
aagaatgttg gaattttggc catggacatc tacttcccac caacttgtgt tcagcaggag   6600
gctttagaag cacatgacgg agcctcaaag ggtaagtaca caatcggatt aggacaggat   6660
tgcttagcat tctgcactga attggaggac gtcatctcaa tgtctttcaa cgccgtcacc   6720
tcattgttag agaagtacaa aatcgaccca aaccagatcg gaaggttgga agtcggttct   6780
gaaaccgtca tcgacaagtc taaatcaatc aagactttcg ttatgcagtt gttcgaaaag   6840
tgcggtaata ctgacgtcga gggtgtagac tctactaacg cttgttatgg tggtaccgca   6900
gctttattga actgcgtaaa ctgggttgag tcaaactcat gggatggtag gtacggatta   6960
gtcatttgca ccgattctgc cgtctacgcc gagggtccag caaggccaac cggtggagct   7020
gcagctattg ctatgttaat cggaccagat gcccctatag tcttcgagtc taagttgagg   7080
ggttcacaca tccctaacgt ctacgacttc tacaagccaa acttggcctc agagtatcca   7140
gttgtcgacg gaaagttatc tcagacatgc tacttgatgg ccttagattc atgttacaag   7200
cacttatgca acaagttcga aaagttggag ggaaaggagt tctcaattaa cgacgccgac   7260
tacttcgttt ttcactctcc atacaacaaa ttggtccaga agtcattcgc caggttattg   7320
tacaacgatt ttttgagaaa cgcatcatct atcgatgagg ccgccaagga gaaattcacc   7380
ccatattctt ctttgtcatt ggacgagtct taccagtcta gggacttgga gaaggtatca   7440
cagcaattgg ctaaaacctt ctatgacgcc aaagttcagc caaccacctt ggtccctaaa   7500
caggtcggaa atatgtatac tgcatctttg tatgccgcct ttgcctcttt gatccacaac   7560
aagcacaacg atttagtcgg aaaaagggtt gtcatgtttt cttacggtgc cggatctact   7620
```

-continued

```
gccactatgt tctcattgag gttatgcgaa aaccagtcac cattttcatt gtctaacatc   7680
gcctcagtca tggacgtagg tgtctcacct gagaagttcg tagaaaccat gaagttgatg   7740
gagcacagat acggtgccaa agaattcgtc acttcaaaag agggaatctt ggatttgttg   7800
gccccaggaa cctactattt gaaggaggtc gactctttgt acagaaggtt ctatggaaag   7860
aagggagacg acggatctgt cgcaaacggt cagtaaatcg gcggcgtcgg cgatcgcgtt   7920
aaggcggccg ctggcgaggg agatatttca acctgggcct aacagtaaag atatcctcct   7980
caaaactggt gcacttaatc gctgaatttg ttctggcttc tcttcttttt ctttattccc   8040
cccatgggcc aaaaaaaata gtactatcag gaatttggcg ccgggtcacg atatacgtgt   8100
acagtgacct aggcgacgcc acaaggaaaa aggaaaaaaa cagaaaaaac aacaaaaact   8160
aaaacaaaca cgaaaacttt aatagatcta agtgaagtag tggtgaggca attggagtga   8220
catagcagct actacaacta caaaaaaggc gcgccacggt cgtgcggata tgaaagaggt   8280
cgttatagct tctgccgtca ggaccgccat cggatcttac ggtaagtcat taaaggacgt   8340
ccctgccgtt gatttaggag ccaccgcaat taaagaggcc gttaaaaagg caggtataaa   8400
gccagaggac gtcaacgagg tcatcttggg aaatgtctta caagccggat taggtcaaaa   8460
cccagcaaga caagcatcat tcaaagccgg tttacctgtc gagatacctg caatgaccat   8520
caacaaggtt tgcggttcag gattaaggac cgtttcttta gcagcacaga tcattaaggc   8580
tggagatgca gacgttatca ttgctggtgg tatggaaaac atgtcaagag ccccatactt   8640
ggctaataac gccaggtggg gatataggat gggaaacgcc aagtttgtcg acgaaatgat   8700
tactgacgga ttgtgggacg ccttcaatga ctatcacatg ggtataaccg cagaaaacat   8760
tgccgagagg tggaatatct caagagaaga acaggatgag tttgcattgg cctcacagaa   8820
aaaagcagag gaggcaataa agtcaggtca gtttaaggat gaaatcgtcc cagtcgtcat   8880
caagggaaga aagggtgaga cagttgtcga caccgacgaa caccctagat ttggttcaac   8940
catcgaggga ttagcaaagt tgaagccagc cttcaagaaa gacggaaccg taaccgccgg   9000
taatgcatct ggattgaacg attgcgcagc agttttggtc ataatgtcag ccgagaaagc   9060
taaggagttg ggtgtcaagc cattggcaaa aattgtttca tacggatcag ccggtgtcga   9120
ccctgccatc atgggttacg gaccttttta cgccaccaag gctgcaatcg aaaaggccgg   9180
ttggaccgta gatgaattgg atttgatcga gtcaaacgag gcctttgccg cccaatcatt   9240
ggctgtcgcc aaggacttga agttcgacat gaacaaggtc aacgtcaacg gtggtgccat   9300
cgcattgggt caccctatcg gagcctctgg tgccaggatc ttggttacct tggtccacgc   9360
catgcagaag agggacgcaa agaagggttt ggccaccttg tgcatcggtg gaggtcaggg   9420
aacagctatc ttgttagaga aatgcagccc ctcagccccc ctagcgtcga ataaaagaca   9480
ttggtacatg atatcaaaca gaattttaac atttcttgat ccagtttgta aacaaaacaa   9540
acaatttttc taccatttaa cttcatacca tcggcgagag ccgaacagga aaaaaaagaa   9600
gtctccggtt atcgtaagca gtatcaaata ataagaatgt atgtgtgtgc aatttgttat   9660
acccacgaag aagtgcgcag tagagttaga aaaccaactg agtaatcttt actcccgaca   9720
atcgtccaat aatcctcttg ttgctaggaa cgtgatgatg gatttcgttt gaaatccgga   9780
cggaaaactc aaaagaagtc caaccaccaa ccattttcga gcctcaagaa tctctaagca   9840
ggtttcttta ctaaggggat ggcctttctg tcctggacat tttttccttc ctttttttcat   9900
ttccttgaaa ggaacagatt ttttttgact tttgccacac agctgcacta tctcaacccc   9960
ttttacattt taagttttcg ggttgaatgg ccggtgttta aaccccagcg cctggcggg   10019
```

<210> SEQ ID NO 27
<211> LENGTH: 5027
<212> TYPE: DNA
<213> ORGANISM: Artificial Sequence
<220> FEATURE:
<223> OTHER INFORMATION: Synthetic: Mat alpha FcphI target site cassette

<400> SEQUENCE: 27
tgatgtctgg gttttgtttg ggatgcaatt tattgcttcc caatgtagaa aagtacatca 60
tatgaaacaa cttaaactct taactacttc ttttaacctt cactttttat gaaatgtatc 120
aaccatatat aataacttaa tagacgacat tcacaatatg tttacttcga agcctgcttt 180
caaaattaag aacaaagcat ccaaatcata cagaaacaca gcggtttcaa aaaagctgaa 240
agaaaaacgt ctagctgagc atgtgaggcc aagctgcttc aatattattc gaccactcaa 300
gaaagatatc cagattcctg ttccttcctc tcgattttta aataaaatcc aaattcacag 360
gatagcgtct ggaagtcaaa atactcagtt tcgacagttc aataagacat ctataaaatc 420
ttcaaagaaa tatttaaact catttatggc ttttagagca tattactcac agtttggctc 480
cggtgtaaaa caaaatgtct tgtcttctct gctcgctgaa gaatggcacg cggacaaaat 540
gcagcacgga atatgggact acttcgcgca acagtataat tttataaacc ctggttttgg 600
ttttgtagag tggttgacga ataattatgc tgaagtacgt ggtgacggat attgggaaga 660
tgtgtttgta catttggcct tatagagtgt ggtcgtggcg gaggttgttt atctttcgag 720
tactgaatgt tgtcagtata gctatcctat ttgaaactcc ccatcgtctt gctcttgttc 780
ccaatgtttg tttatacact catatggcta tacccttatc tacttgcctc ttttgtttat 840
gtctatgtat ttgtataaaa tatgatatta ctcagactca agcaaacaat caatttgtga 900
gcgttgcgct cgtgcatcga gaagttaaga ttatatgaat aactaaatac taaatagaaa 960
tgtaaataca gtgagaacaa aacaaaaaaa aacgaacaga gaaactaaat ccacattaat 1020
tgagagttct atctattaga aaatgcaaac tccaactaaa tgggaaaaca gataacctct 1080
tttatttttt tttaatgttt gatattcgag tctttttctt ttgttaggtt tatattcatc 1140
atttcaatga ataaaagaag cttcttattt tggttgcaaa gaatgaaaaa aaaggatttt 1200
ttcatacttc taaagcttca attataacca aaaattttat aaatgaagag aaaaaatcta 1260
gtagtatcaa gttaaactta gaaaaactca tcgagcatca aatgaaactg caatttattc 1320
atatcaggat tatcaatacc atatttttga aaaagccgtt tctgtaatga aggagaaaac 1380
tcaccgaggc agttccatag gatggcaaga tcctggtatc ggtctgcgat tccgactcgt 1440
ccaacatcaa tacaacctat taatttcccc tcgtcaaaaa taaggttatc aagtgagaaa 1500
tcaccatgag tgacgactga atccggtgag aatggcaaaa gcttatgcat ttctttccag 1560
acttgttcaa caggccagcc attacgctcg tcatcaaaat cactcgcatc aaccaaaccg 1620
ttattcattc gtgattgcgc ctgagcgaga cgaaatacgc gatcgctgtt aaaaggacaa 1680
ttacaaacag gaatcgaatg caaccggcgc aggaacactg ccagcgcatc aacaatattt 1740
tcacctgaat caggatattc ttctaatacc tggaatgctg ttttgccggg gatcgcagtg 1800
gtgagtaacc atgcatcatc aggagtacgg ataaaatgct tgatggtcgg aagaggcata 1860
aattccgtca gccagtttag tctgaccatc tcatctgtaa catcattggc aacgctacct 1920
ttgccatgtt tcagaaacaa ctctggcgca tcgggcttcc catacaatcg atagattgtc 1980
gcacctgatt gcccgacatt atcgcgagcc catttatacc catataaatc agcatccatg 2040
ttggaattta atcgcggcct cgaaacgtga gtcttttcct tacccatttt taatgttact 2100

-continued

```
tctcttgcag ttagggaact ataatgtaac tcaaaataag attaaacaaa ctaaaataaa   2160
aagaagttat acagaaaaac ccatataaac cagtactaat ccataataat aatacacaaa   2220
aaaactatca aataaaacca gaaaacagat tgaatagaaa aatttttcg atctcctttt   2280
atattcaaaa ttcgatatat gaaaaaggga actctcagaa aatcaccaaa tcaatttaat   2340
tagattttc ttttccttct agcgttggaa agaaaaattt ttcttttttt ttttagaaat   2400
gaaaaatttt tgccgtagga atcaccgtat aaaccctgta taaacgctac tctgttcacc   2460
tgtgtaggct atgattgacc cagtgttcat tgttattgcg agagagcggg agaaaagaac   2520
cgatacaaga gatccatgct ggtatagttg tctgtccaac actttgatga acttgtagga   2580
cgatgatgtg tattactagt gtcgacatgc gtccatcttt acagtcctgt cttattgttc   2640
ttgatttgtg ccccgtaaaa tactgttact tggttctggc gaggtattgg atagttcctt   2700
tttataaagg ccatgaagct ttttctttcc aatttttttt ttttcgtcat tatagaaatc   2760
attacgaccg agattcccgg gtaataactg atataattaa attgaagctc taatttgtga   2820
gtttagtata catgcattta cttataatac agttttttag ttttgctggc cgcatcttct   2880
caaatatgct tcccagcctg cttttctgta acgttcaccc tctaccttag catcccttcc   2940
ctttgcaaat agtcctcttc caacaataat aatgtcagat cctgtagaga ccacatcatc   3000
cacggttcta tactgttgac ccaatgcgtc tcccttgtca tctaaaccca caccgggtgt   3060
cataatcaac caatcgtaac cttcatctct tccacccatg tctctttgag caataaagcc   3120
gataacaaaa tctttgtcac tcttcgcaat gtcaacagta cccttagtat attctccagt   3180
agatagggag cccttgcatg acaattctgc taacatcaaa aggcctctag gttcctttgt   3240
tacttcttct gccgcctgct tcaaaccgct aacaatacct gggcccacca caccgtgtgc   3300
attcgtaatg tctgcccatt ctgctattct gtatacaccc gcagagtact gcaatttgac   3360
tgtattacca atgtcagcaa attttctgtc ttcgaagagt aaaaaattgt acttggcgga   3420
taatgccttt agcggcttaa ctgtgccctc catggaaaaa tcagtcaaga tatccacatg   3480
tgtttttagt aaacaaattt tgggacctaa tgcttcaact aactccagta attccttggt   3540
ggtacgaaca tccaatgaag cacacaagtt tgtttgcttt tcgtgcatga tattaaatag   3600
cttggcagca acaggactag gatgagtagc agcacgttcc ttatatgtag ctttcgacat   3660
gatttatctt cgtttcctgc aggtttttgt tctgtgcagt tgggttaaga atactgggca   3720
atttcatgtt tcttcaacac cacatatgcg tatatatacc aatctaagtc tgtgctcctt   3780
ccttcgttct tccttctgct cggagattac cgaatcaaaa aaatttcaaa gaaaccggaa   3840
tcaaaaaaaa gaacaaaaaa aaaaaagatg aattgaaaag ctttatggac cctgaaacca   3900
cagccacatt aaccttcttt gatggtcaaa acttatcctt caccataaat atgcctcgca   3960
aaaaaggtaa ttaacatata tagaattaca ttatttatga aatatcatca ctatctctta   4020
gcatctttaa tccttttcta catcagataa cttcggtttg ttatcatcgt ctgtattgtc   4080
atcaattggc gcagtagcct caatttcaac gtcgtttgac tctggtgttt gttcatgtgc   4140
agatccatga gatgatgaac ttgtgagcgt tgcgctcgtg catccggagg ttgtttatct   4200
ttcgagtact gaatgttgtc agtatagcta tcctatttga aactccccat cgtcttgctc   4260
ttgttcccaa tgtttgttta tacactcata tggctatacc cttatctact tgcctctttt   4320
gtttatgtct atgtatttgt ataaaatatg atattactca gactcaagca aacaatcaat   4380
tcttagcatc attctttgtt cttatcttaa ccataaacga tcttgatgtg acttttgtaa   4440
tttgaacgaa ttggctatac gggacggatg acaaatgcac cattactcta ggttgttgtt   4500
```

```
ggatcttaac aaaccgtaaa ggtaaactgc ccatgcggtt cacatgactt ttgactttcc   4560

tttgtttgct agttaccttc ggcttcacaa tttgtttttc cacttttcta acaggtttat   4620

cacctttcaa acttatcttt atcttattcg ccttcttggg tgcctccaca gtagaggtta   4680

cttccttttt aatatgtact tttaggatac tttcacgctt tataacaata tcaagtttac   4740

cttcttcatt actattcatc ttcgccacaa gtcttctctc ccttggtgtt tccaatctaa   4800

ctacaaaact gttgattagg gtgtacatca ccctaacaag atcatgtatt tgcttcctct   4860

ggtacaagct aagaacaggt aaattcaaaa catcccagag taatatcttc aaagggctat   4920

acctttaaa catatctcgg catatttgta ttaacccact aatattttga cggccaatct   4980

tttctatttt tattttcata tcatcgacgt aatgaccact taaaaac               5027


<210> SEQ ID NO 28
<211> LENGTH: 6126
<212> TYPE: DNA
<213> ORGANISM: Artificial Sequence
<220> FEATURE:
<223> OTHER INFORMATION: Synthetic: ADS_GAL80 donor cassette

<400> SEQUENCE: 28

gcctgtctac aggataaaga cgggtcggat acctgcacaa gcaatttggc acctgcatac     60

cccatttccc cagtagataa cttcaacaca cacatcaatg tccctcacca gtttatttcc    120

aaaagagacg ctttttacta cctgactaga ttttcatttt gtttcttttg gattgcgctt    180

gcctttgtag gtgtgtcgtt tatcctttac gttttgactt ggtgctcgaa gatgctttca    240

gagatggtgc ttatcctcat gtcttttggg tttgtcttca atacggcagc cgttgtcttg    300

caaacggccg cctctgccat ggcaaagaat gctttccatg acgatcatcg tagtgcccaa    360

ttgggtgcct ctatgatggg tttaaacgta tggcttgggc aagtgtcttt ttatgtatcg    420

tggaatttat cctgctggtc ttctggtctg ttagggcaag gttggcctct acttactcca    480

tcgacaattc aagatacaga acctcctcca gatggaatcc cttccataga gagaaggagc    540

aagcaactga cccaatattg actgccactg gacctgaaga catgcaacaa agtgcaagca    600

tagtggggcc ttcttccaat gctaatccgg tcactgccac tgctgctacg gaaaaccaac    660

ctaaaggtat taacttcttc actataagaa aatcacacga gcgcccggac gatgtctctg    720

tttaaatggc gcaagttttc cgctttgtaa tatatattta taccccttc ttctctcccc    780

tgcaatataa tagtttaatt ctaatattaa taatatccta tattttcttc atttaccggc    840

gcactctcgc ccgaacgacc tcaaaatgtc tgctacattc ataataacca aaagctcata    900

acttttttt ttgaacctga atatatatac atcacatatc actgctggtc ctcttcgagc    960

gtcccaaaac cttctcaagc aaggttttca gtataatgtt acatgcgtac acgcgtctgt   1020

acagaaaaaa aagaaaaatt tgaaatataa ataacgttct taatactaac ataactataa   1080

aaaaataaat agggacctag acttcaggtt gtctaactcc ttccttttcg gttagagcgg   1140

atcttagcta gcttaaatag acatgggata aactaataaa gacttaatta aatgcttgta   1200

ctcatctccc atacgagtga agttatcttt acccgcgtac tgcacttcca ggaattgaca   1260

aagatagata actgccatca gtaatggtct gggtatgttt ttagtggtca agtattctct   1320

gtttatgtcc ttccaaacgt cttcgacttc cttgtatatg agggtttgtg cgtattcctc   1380

atttacatta tattccttca tataagattc tagagaagat gatgagtgct ttctctcctg   1440

ttctgccttg tgcgtcatca agtcgtttag acgacgaccc aaaataccag aataccggaa   1500

tagtggtggc gctgacacgg cccattcaac tgattcttta gtgaaaatat ctgacatccc   1560
```

-continued

```
caggtaacat gtggttgtca gtaggttcgc tccaccagtt ataataacaa ctggatcgtg   1620
ttcttcagtg gtcggtatgt gcccttcgtt tgcccacttt gcttcgacca tgagattccg   1680
tacaaattcc ttaacaaact cttttccgca attaaataaa tctgttctcc cttcttttgc   1740
aagaaattcc tccatttctg tatacgtatc catgaataat ttatagatag gcttcatgta   1800
ttctggcagc gtatcaaggc aggtaatcga ccaacgttct acagcttcag tgaaaatttt   1860
taattcttca tatgttccat aagcatcgta agtatcatca atcagggtta taacggctac   1920
cactttggtg aagaaaactc gtgctcttga atattgtggt tcataaccag aacctaaacc   1980
ccagaaataa cactctacaa tgcggtcgcg caaacaaggt gcgttctttt ttatatcaaa   2040
tgctttccac catttacaga cgtggctaag ctcctccttg tgcaaagatt gcagcaggtt   2100
gaattctaat tttgctaatt ttaaaagcgt cttattatga gagtcttgtt gttggtagaa   2160
aggaatatac tgagcagctt ctatgcgggg aagacgcttc cataaaggtt gttttaatgc   2220
tctttgtatt tcggtaaaca aagccggatt agtggagaat gcatccttag tcattataga   2280
taatcgactt ctagtaaacc caagcgcgtc ttccaaaata atttcgcctg gaacccgcat   2340
ggaagtcgcc tcatataact ctaataaccc ttccacatca ttagccaatg attgtttaaa   2400
agcaccgttt ttatctttgt aattattgaa aacatcacag gtcacgtagt agccttgctt   2460
cctcatcaag cgaaaccata gtgaactgcg atctccattc cagttgtctc cgtatgtctc   2520
gtaaatacat tgaagagcat ggtcaatttc cctttcaaaa tggtatggaa ttcctagtct   2580
ctgtatttca tctattaatt ttaacaaatt agcatgcttc ataggaatgt ctaaggcttc   2640
cttcaggagc tgtcttactt ctttcttcag atcgtttaca atttgttcga ccccttgttc   2700
tacttgtttc tcataaatga gaaactgatc accccaaata gagggaggga aattggctat   2760
aggtctaatc ggtttctcct cggttagtgc catggatcct tcagttacag taaatgtttt   2820
agttgcatcg tcataggtcc attcaccatc aacaccatta tcattagcat attgcttaaa   2880
gacctttttcg gctgttgctg catctactgc ttcggtagta gtttcaccct tcaaagtttt   2940
accattcaaa attaatttat attgacccat ttatattgaa ttttcaaaaa ttcttacttt   3000
ttttttggat ggacgcaaag aagtttaata atcatattac atggcattac caccatatac   3060
atatccatat ctaatcttac ttatatgttg tggaaatgta aagagcccca ttatcttagc   3120
ctaaaaaaac cttctctttg gaactttcag taatacgctt aactgctcat tgctatattg   3180
aagtacggat tagaagccgc cgagcgggcg acagccctcc gacggaagac tctcctccgt   3240
gcgtcctcgt cttcaccggt cgcgttcctg aaacgcagat gtgcctcgcg ccgcactgct   3300
ccgaacaata aagattctac aatactagct tttatggtta tgaagaggaa aaattggcag   3360
taacctggcc ccacaaacct tcaaattaac gaatcaaatt aacaaccata ggatgataat   3420
gcgattagtt ttttagcctt atttctgggg taattaatca gcgaagcgat gatttttgat   3480
ctattaacag atatataaat ggaaaagctg cataaccact ttaactaata ctttcaacat   3540
tttcagtttg tattacttct tattcaaatg tcataaaagt atcaacaaaa aattgttaat   3600
atacctctat actttaacgt caaggagaaa aaactataat gtcattaccg ttcttaactt   3660
ctgcaccggg aaaggttatt atttttggtg aacactctgc tgtgtacaac aagcctgccg   3720
tcgctgctag tgtgtctgcg ttgagaacct acctgctaat aagcgagtca tctgcaccag   3780
atactattga attggacttc ccggacatta gctttaatca taagtggtcc atcaatgatt   3840
tcaatgccat caccgaggat caagtaaact cccaaaaatt ggccaaggct caacaagcca   3900
ccgatggctt gtctcaggaa ctcgttagtc ttttggatcc gttgttagct caactatccg   3960
```

-continued

```
aatccttcca ctaccatgca gcgttttgtt tcctgtatat gtttgtttgc ctatgccccc   4020
atgccaagaa tattaagttt tctttaaagt ctactttacc catcggtgct gggttgggct   4080
caagcgcctc tatttctgta tcactggcct tagctatggc ctacttgggg gggttaatag   4140
gatctaatga cttggaaaag ctgtcagaaa acgataagca tatagtgaat caatgggcct   4200
tcataggtga aaagtgtatt cacggtaccc cttcaggaat agataacgct gtggccactt   4260
atggtaatgc cctgctattt gaaaaagact cacataatgg aacaataaac acaaacaatt   4320
ttaagttctt agatgatttc ccagccattc caatgatcct aacctatact agaattccaa   4380
ggtctacaaa agatcttgtt gctcgcgttc gtgtgttggt caccgagaaa tttcctgaag   4440
ttatgaagcc aattctagat gccatgggtg aatgtgccct acaaggctta gagatcatga   4500
ctaagttaag taaatgtaaa ggcaccgatg acgaggctgt agaaactaat aatgaactgt   4560
atgaacaact attggaattg ataagaataa atcatggact gcttgtctca atcggtgttt   4620
ctcatcctgg attagaactt attaaaaatc tgagcgatga tttgagaatt ggctccacaa   4680
aacttaccgg tgctggtggc ggcggttgct ctttgacttt gttacgaaga gacattactc   4740
aagagcaaat tgacagtttc aaaaagaaat tgcaagatga ttttagttac gagacatttg   4800
aaacagactt gggtgggact ggctgctgtt tgttaagcgc aaaaaatttg aataaagatc   4860
ttaaaatcaa atccctagta ttccaattat ttgaaaataa aactaccaca aagcaacaaa   4920
ttgacgatct attattgcca ggaaacacga atttaccatg gacttcataa gctaatttgc   4980
gataggcatt atttattagt tgtttttaat cttaactgtg tatgaagttt tatgtaataa   5040
agatagaaag agaaacaaaa aaaaattttt cgtagtatca attcagcttt cgaagacaga   5100
atgaaattta agcagaccat tcatcttgcc ctgtgcttgg cccccagtgc agcgaacgtt   5160
ataaaaacga atactgagta tatatctatg taaaacaacc atatcatttc ttgttctgaa   5220
ctttgtttac ctaactagtt ttaaatttcc ctttttcgtg catgcgggtg ttcttattta   5280
ttagcatact acatttgaaa tatcaaattt ccttagtaga aaagtgagag aaggtgcact   5340
gacacaaaaa ataaaatgct acgtataact gtcaaaactt tgcagcagcg ggcatccttc   5400
catcatagct tcaaacatat tagcgttcct gatcttcata cccgtgctca aaatgatcaa   5460
acaaactgtt attgccaaga aataaacgca aggctgcctt caaaaactga tccattagat   5520
cctcatatca agcttcctca tagaacgccc aattacaata agcatgtttt gctgttatca   5580
ccgggtgata ggtttgctca accatggaag gtagcatgga atcataattt ggatactaat   5640
acaaatcggc catataatgc cattagtaaa ttgcgctccc atttaggtgg ttctccaggc   5700
aaatttgaat actaataaat gcggtgcatt tgcaaaatga atttattcca aggccaaaac   5760
aacacgatga atggctttat ttttttgtta ttcctgacat gaagctttat gtaattaagg   5820
aaacggacat cgaggaattt gcatcttttt tagatgaagg agctattcaa gcaccaaagc   5880
tatccttcca ggattattta agcggtaagg ccaaggcttc ccaacaggtt catgaagtgc   5940
atcatagaaa gcttacaagg tttcagggtg aaacttttct aagagattgg aacttagtct   6000
gtgggcatta taagagagat gctaagtgtg gagaaatggg acccgacata attgcagcat   6060
ttcaagatga aaagcttttt cctgagaata atctagcctt aatttctcat attgggggtc   6120
atattt                                                              6126
```

<210> SEQ ID NO 29
<211> LENGTH: 9550
<212> TYPE: DNA
<213> ORGANISM: Artificial Sequence
<220> FEATURE:

<223> OTHER INFORMATION: Synthetic: ADS_HXT3 donor cassette

<400> SEQUENCE: 29
accggtatat caaatggcgg tgtagtttga aaagtacact gtatgtccat taataaaatt 60
acgccgaaga acactgacta gctataaatt ctcttccggc gtccaatttc aacctaaggc 120
aagtattgtt aatcaataat gcgtgttggt aaatatgaag cccgatgttg attaagaaga 180
attattcgta taagaattaa gcaagcaaaa ttaaggaaaa ttttttcttt cctattcgtc 240
atcgcagaca gccttcatct tctcgagata acacctggag gaggagcaat gaaatgaaag 300
gaaaaaaaaa tactttcttt ttcttgaaaa aagaaaaaaa ttgtaagatg agctattcgc 360
ggaacattct agctcgtttg catcttcttg catttggtag gttttcaata gttcggtaat 420
attaacggat acctactatt atcccctagt aggctctttt cacggagaaa ttcgggagtg 480 tttttttcc gtgcgcattt tcttagctat attcttccag cttcgcctgc tgcccggtca 540
tcgttcctgt cacgtagttt ttccggattc gtccggctca tataataccg caataaacac 600
ggaatatctc gttccgcgga ttcggttaaa ctctcggtcg cggattatca cagagaaagc 660
ttcgtggaga atttttccag attttccgct ttccccgatg ttggtatttc cggaggtcat 720
tatactgacc gccattataa tgactgtaca acgaccttct ggagaaagaa acaactcaat 780
aacgatgtgg gacattgggg gcccactcaa aaaatctggg gactatatcc ccagagaatt 840
tctccagaag agaagaaaag tcaaagtttt ttttcgcttg gggggttgcat ataaacttcg 900 agcgtcccaa aaccttctca agcaaggttt tcagtataat gttacatgcg tacacgcgtc 960
tgtacagaaa aaaaagaaaa atttgaaata taaataacgt tcttaatact aacataacta 1020
taaaaaaata aatagggacc tagacttcag gttgtctaac tccttccttt tcggttagag 1080
cggatcttag atagacatag ggtagaccaa caaagactta attaagtgct tatattcgtc 1140
acccattctg gtgaaattgt ctttaccagc gtattgaact tctaagaatt gacataaata 1200
gataacagcc attaacaatg gacgtggaat atttttggtg gtcaagtatt ctctgttaat 1260
atctttccaa acgtcttcaa cttccttgta aatcaaagtt tgagcgtatt cttcgttaac 1320
gttgtattcc ttcatgtaag attctaagga agaggaggag tgctttcttt cttgctcagc 1380
cttgtgagtc atcaaatcgt ttaatcttct acccaaaata ccagagtatc tgaacaaagg 1440
tggagcggaa acggcccatt caacagattc cttggtgaaa atatcagaca tacctaagta 1500
acaagtagta gtcaacaagt tagcaccacc agtaatgata acgactggat cgtgttcttc 1560
agtagttgga atatgacctt cgttagccca tttagcttca accatcaagt tacgaacgaa 1620
ttccttaacg aattccttac cacaattgaa caagtcggta cgaccttcct tagccaagaa 1680
ttcttccatt tcggtgtaag tgtccatgaa caacttataa attggcttca tgtattctgg 1740
taaagtatct aaacaggtaa tggaccatct ttcgacagct tcagtgaaaa tcttcaattc 1800
ttcgtaggta ccgtaagcgt cgtaagtgtc gtcaatcaag gtaataacag caaccacctt 1860
agtaaagaaa actctagctc tagagtattg tggttcgtaa ccggaaccca aaccccagaa 1920
gtaacattcg acaattctat ctctcaaaca tggagcgttc ttcttaatat cgaaggcttt 1980
ccaccactta caaacgtgag acaattcttc cttgtgcaag gattgcaaca agttaaattc 2040
caatttagcc aatttcaaca aggttttgtt gtgagagtct tgttgttggt agaatgggat 2100
gtattgagca gcttcgattc ttggcaaacg cttccacaat ggttgtttca aagctctttg 2160
gatttcagtg aacaaagctg ggttagtaga gaaggcatct ttagtcatga tggacaatct 2220
agatctagta aaacccaaag cgtcttccaa gatgatttca ccaggaactc tcatggaggt 2280

-continued

```
ggcttcatac aattctaaca aaccttcaac atcgttggcc aaagattgct taaaagcacc   2340
attcttatct ttgtagttgt tgaaaacgtc acaagtaacg tagtaacctt gctttctcat   2400
taatctgaac cataaggaag atctgtcacc gttccagtta tcaccgtaag tttcgtaaat   2460
acattgcaaa gcgtgatcaa tttctctttc gaaatggtat ggaataccta atctttggat   2520
ttcgtcgatt aatttcaata agttagcgtg cttcattggg atgtccaaag cttccttcaa   2580
caattgtcta acttccttct tcaaatcgtt aacgatttgt tcaacacctt gctcaacttg   2640
cttttcgtag atcaagaatt ggtcacccca gatagaaggt ggaaaattag caattggtct   2700
gattggtttt tcttcagtca aagccatgga tccttcagtt acagtaaatg ttttagttgc   2760
atcgtcatag gtccattcac catcaacacc attatcatta gcatattgct taaagacctt   2820
ttcggctgtt gctgcatcta ctgcttcggt agtagtttca cccttcaaag ttttaccatt   2880
caaaattaat ttatattgac ccatttatat tgaattttca aaaattctta cttttttttt   2940
ggatggacgc aaagaagttt aataatcata ttacatggca ttaccaccat atacatatcc   3000
atatctaatc ttacttatat gttgtggaaa tgtaaagagc cccattatct tagcctaaaa   3060
aaaccttctc tttggaactt tcagtaatac gcttaactgc tcattgctat attgaagtac   3120
ggattagaag ccgccgagcg ggcgacagcc ctccgacgga agactctcct ccgtgcgtcc   3180
tcgtcttcac cggtcgcgtt cctgaaacgc agatgtgcct cgcgccgcac tgctccgaac   3240
aataaagatt ctacaatact agcttttatg gttatgaaga ggaaaaattg gcagtaacct   3300
ggccccacaa accttcaaat taacgaatca aattaacaac cataggatga taatgcgatt   3360
agtttttag ccttatttct ggggtaatta atcagcgaag cgatgatttt tgatctatta    3420
acagatatat aaatggaaaa gctgcataac cactttaact aatactttca acattttcag   3480
tttgtattac ttcttattca aatgtcataa aagtatcaac aaaaaattgt taatatttta   3540
attctgctgt aacccgtaca tgcccaaaat aggggggcggg ttacacagaa tatataacat   3600
cgtaggtgtc tgggtgaaca gtttattcct ggcatccact aaatataatg gagcccgctt   3660
tttaagctgg catccagaaa aaaaaagaat cccagcacca aaatattgtt ttcttcacca   3720
accatcagtt cataggtcca ttctcttagc gcaactacag agaacagggg cacaaacagg   3780
caaaaaacgg gcacaacctc aatggagtga tgcaacctgc ctggagtaaa tgatgacaca   3840
aggcaattga cccacgcatg tatctatctc attttcttac accttctatt accttctgct   3900
ctctctgatt tggaaaaagc tgaaaaaaaa ggttgaaacc agttccctga aattattccc   3960
ctacttgact aataagtata taaagacggt aggtattgat tgtaattctg taaatctatt   4020
tcttaaactt cttaaattct acttttatag ttagtctttt ttttagtttt aaaacaccaa   4080
gaacttagtt tcgatccccg cgtgcttggc cggccgtatc cccgcgtgct tggccggccg   4140
tatgtctcag aacgtttaca ttgtatcgac tgccagaacc ccaattggtt cattccaggg   4200
ttctctatcc tccaagacag cagtggaatt gggtgctgtt gctttaaaag gcgccttggc   4260
taaggttcca gaattggatg catccaagga ttttgacgaa attatttttg gtaacgttct   4320
ttctgccaat ttgggccaag ctccggccag acaagttgct ttggctgccg gtttgagtaa   4380
tcatatcgtt gcaagcacag ttaacaaggt ctgtgcatcc gctatgaagg caatcatttt   4440
gggtgctcaa tccatcaaat gtggtaatgc tgatgttgtc gtagctggtg gttgtgaatc   4500
tatgactaac gcaccatact acatgccagc agcccgtgcg ggtgccaaat ttggccaaac   4560
tgttcttgtt gatggtgtcg aaagagatgg gttgaacgat gcgtacgatg gtctagccat   4620
gggtgtacac gcagaaaagt gtgcccgtga ttgggatatt actagagaac aacaagacaa   4680
```

-continued

```
ttttgccatc gaatcctacc aaaaatctca aaaatctcaa aaggaaggta aattcgacaa   4740
tgaaattgta cctgttacca ttaagggatt tagaggtaag cctgatactc aagtcacgaa   4800
ggacgaggaa cctgctagat tacacgttga aaaattgaga tctgcaagga ctgttttcca   4860
aaaagaaaac ggtactgtta ctgccgctaa cgcttctcca atcaacgatg gtgctgcagc   4920
cgtcatcttg gtttccgaaa aagttttgaa ggaaaagaat ttgaagcctt tggctattat   4980
caaaggttgg ggtgaggccg ctcatcaacc agctgatttt acatgggctc catctcttgc   5040
agttccaaag gctttgaaac atgctggcat cgaagacatc aattctgttg attactttga   5100
attcaatgaa gccttttcgg ttgtcggttt ggtgaacact aagattttga agctagaccc   5160
atctaaggtt aatgtatatg gtggtgctgt tgctctaggt cacccattgg gttgttctgg   5220
tgctagagtg gttgttacac tgctatccat cttacagcaa gaaggaggta agatcggtgt   5280
tgccgccatt tgtaatggtg gtggtggtgc ttcctctatt gtcattgaaa agatatgatt   5340
acgttctgcg attttctcat gatcttttc ataaaataca taaatatata aatggcttta   5400
tgtataacag gcataattta aagttttatt tgcgattcat cgtttttcag gtactcaaac   5460
gctgaggtgt gccttttgac ttacttttcc gccttggcaa gctggccggg tgatacttgc   5520
acaagttcca ctaattactg acatttgtgg tattaactcg tttgactgct ctacaattgt   5580
aggatgttaa tcaatgtctt ggctgcctaa cctgcaggcc gcgagcgccg atatgctatg   5640
taatagacaa taaaaccatg tttatataaa aaaaattcaa aatagaaaac gattctgtac   5700
aaggagtatt tttttttgt tctagtgtgt ttatattatc cttggctaag aggcactgcg   5760
tatacttcaa ggtacccctg tgttttgaaa aaaaacaaca gtaaaatagg aactccgcga   5820
ggttcaggaa cctgaaacaa aatcaataaa aacattatat gcgtttcgaa caaaattaaa   5880
gaaaaagaat aaatatagat taaaaaaaaa aagaagaaat taaaagaatt tctactaaat   5940
cccaattgtt atatatttgt taaatgccaa aaaagtttat aaaaaattta gaatgtataa   6000
ataataataa actaagtaac gcgatcgccg acgccgccga tatctccctc gccagcggcc   6060
gccttatggc taagaatgtt ggaattttgg ccatggacat ctacttccca ccaacttgtg   6120
ttcagcagga ggctttagaa gcacatgacg gagcctcaaa gggtaagtac acaatcggat   6180
taggacagga ttgcttagca ttctgcactg aattggagga cgtcatctca atgtctttca   6240
acgccgtcac ctcattgtta gagaagtaca aaatcgaccc aaaccagatc ggaaggttgg   6300
aagtcggttc tgaaaccgtc atcgacaagt ctaaatcaat caagactttc gttatgcagt   6360
tgttcgaaaa gtgcggtaat actgacgtcg agggtgtaga ctctactaac gcttgttatg   6420
gtggtaccgc agctttattg aactgcgtaa actgggttga gtcaaactca tgggatggta   6480
ggtacggatt agtcatttgc accgattctg ccgtctacgc cgagggtcca gcaaggccaa   6540
ccggtggagc tgcagctatt gctatgttaa tcggaccaga tgcccctata gtcttcgagt   6600
ctaagttgag ggttcacac atccctaacg tctacgactt ctacaagcca aacttggcct   6660
cagagtatcc agttgtcgac ggaaagttat ctcagacatg ctacttgatg gccttagatt   6720
catgttacaa gcacttatgc aacaagttcg aaaagttgga gggaaaggag ttctcaatta   6780
acgacgccga ctacttcgtt tttcactctc catacaacaa attggtccag aagtcattcg   6840
ccaggttatt gtacaacgat tttttgagaa acgcatcatc tatcgatgag gccgccaagg   6900
agaaattcac cccatattct tctttgtcat tggacgagtc ttaccagtct agggacttgg   6960
agaaggtatc acagcaattg gctaaaacct tctatgacgc caaagttcag ccaaccacct   7020
tggtccctaa acaggtcgga aatatgtata ctgcatcttt gtatgccgcc tttgcctctt   7080
```

-continued

```
tgatccacaa caagcacaac gatttagtcg gaaaaagggt tgtcatgttt tcttacggtg   7140
ccggatctac tgccactatg ttctcattga ggttatgcga aaaccagtca ccattttcat   7200
tgtctaacat cgcctcagtc atggacgtag gtgtctcacc tgagaagttc gtagaaacca   7260
tgaagttgat ggagcacaga tacggtgcca aagaattcgt cacttcaaaa gagggaatct   7320
tggatttgtt ggccccagga acctactatt tgaaggaggt cgactctttg tacagaaggt   7380
tctatggaaa gaagggagac gacggatctg tcgcaaacgg tcagtaaatc ggcggcgtcg   7440
gcgatcgcgt taaggcggcc gctggcgagg gagatatttc aacctgggcc taacagtaaa   7500
gatatcctcc tcaaaactgg tgcacttaat cgctgaattt gttctggctt ctcttctttt   7560
tctttattcc ccccatgggc caaaaaaaat agtactatca ggaatttggc gccgggtcac   7620
gatatacgtg tacagtgacc taggcgacgc cacaaggaaa aaggaaaaaa acagaaaaaa   7680
caacaaaaac taaaacaaac acgaaaactt taatagatct aagtgaagta gtggtgaggc   7740
aattggagtg acatagcagc tactacaact acaaaaaagg cgcgccacgg tcgtgcggat   7800
atgaaagagg tcgttatagc ttctgccgtc aggaccgcca tcggatctta cggtaagtca   7860
ttaaaggacg tccctgccgt tgatttagga gccaccgcaa ttaaagaggc cgttaaaaag   7920
gcaggtataa agccagagga cgtcaacgag gtcatcttgg gaaatgtctt acaagccgga   7980
ttaggtcaaa acccagcaag acaagcatca ttcaaagccg gtttacctgt cgagatacct   8040
gcaatgacca tcaacaaggt ttgcggttca ggattaagga ccgtttcttt agcagcacag   8100
atcattaagg ctggagatgc agacgttatc attgctggtg gtatggaaaa catgtcaaga   8160
gccccatact tggctaataa cgccaggtgg ggatatagga tgggaaacgc caagtttgtc   8220
gacgaaatga ttactgacgg attgtgggac gccttcaatg actatcacat gggtataacc   8280
gcagaaaaca ttgccgagag gtggaatatc tcaagagaag aacaggatga gtttgcattg   8340
gcctcacaga aaaaagcaga ggaggcaata aagtcaggtc agtttaagga tgaaatcgtc   8400
ccagtcgtca tcaagggaag aaagggtgag acagttgtcg acaccgacga acaccctaga   8460
tttggttcaa ccatcgaggg attagcaaag ttgaagccag ccttcaagaa agacggaacc   8520
gtaaccgccg gtaatgcatc tggattgaac gattgcgcag cagttttggt cataatgtca   8580
gccgagaaag ctaaggagtt gggtgtcaag ccattggcaa aaattgtttc atacggatca   8640
gccggtgtcg accctgccat catgggttac ggaccttttt acgccaccaa ggctgcaatc   8700
gaaaaggccg gttggaccgt agatgaattg gatttgatcg agtcaaacga ggcctttgcc   8760
gcccaatcat tggctgtcgc caaggacttg aagttcgaca tgaacaaggt caacgtcaac   8820
ggtggtgcca tcgcattggg tcaccctatc ggagcctctg gtgccaggat cttggttacc   8880
ttggtccacg ccatgcagaa gagggacgca aagaagggtt tggccacctt gtgcatcggt   8940
ggaggtcagg gaacagctat cttgttagag aaatgcagcc cctcagcccc cctagcgtcg   9000
aataaaagac attggtacat gatatcaaac agaattttaa catttcttga tccagtttgt   9060
aaacaaaaca aacaattttt ctaccattta acttcatacc atcggcgaga gccgaacagg   9120
aaaaaaaaga agtctccggt tatcgtaagc agtatcaaat aataagaatg tatgtgtgtg   9180
caatttgtta tacccacgaa gaagtgcgca gtagagttag aaaaccaact gagtaatctt   9240
tactcccgac aatcgtccaa taatcctctt gttgctagga acgtgatgat ggatttcgtt   9300
tgaaatccgg acggaaaact caaaagaagt ccaaccacca accattttcg agcctcaaga   9360
atctctaagc aggtttcttt actaagggga tggcctttct gtcctggaca ttttttcctt   9420
cctttttca tttccttgaa aggaacagat ttttttgac ttttgccaca cagctgcact   9480
```

-continued atctcaaccc cttttacatt ttaagttttc gggttgaatg gccggtgttt aaaccccagc 9540
gcctggcggg 9550

<210> SEQ ID NO 30
<211> LENGTH: 4429
<212> TYPE: DNA
<213> ORGANISM: Artificial Sequence
<220> FEATURE:
<223> OTHER INFORMATION: Synthetic: ADS_Mat alpha donor cassette

<400> SEQUENCE: 30
tgatgtctgg gttttgtttg ggatgcaatt tattgcttcc caatgtagaa aagtacatca 60
tatgaaacaa cttaaactct taactacttc ttttaacctt cactttttat gaaatgtatc 120
aaccatatat aataacttaa tagacgacat tcacaatatg tttacttcga agcctgcttt 180
caaaattaag aacaaagcat ccaaatcata cagaaacaca gcggtttcaa aaaagctgaa 240
agaaaaacgt ctagctgagc atgtgaggcc aagctgcttc aatattattc gaccactcaa 300
gaaagatatc cagattcctg ttccttcctc tcgattttta aataaaatcc aaattcacag 360
gatagcgtct ggaagtcaaa atactcagtt tcgacagttc aataagacat ctataaaatc 420
ttcaaagaaa tatttaaact catttatggc ttttagagca tattactcac agtttggctc 480
cggtgtaaaa caaaatgtct tgtcttctct gctcgctgaa gaatggcacg cggacaaaat 540
gcagcacgga atatgggact acttcgcgca acagtataat tttataaacc ctggttttgg 600
ttttgtagag tggttgacga ataattatgc tgaagtacgt ggtgacggat attgggaaga 660
tgtgtttgta catttggcct tatagagtgt ggtcgtggcg gaggttgttt atctttcgag 720
tactgaatgt tgtcagtata gctatcctat ttgaaactcc ccatcgtctt gctcttgttc 780
ccaatgtttg tttatacact catatggcta tacccttatc tacttgcctc ttttgtttat 840
gtctatgtat ttgtataaaa tatgatatta ctcagactca agcaaacaat caattttcaa 900
aaattcttac tttttttttg gatggacgca aagaagttta ataatcatat tacatggcat 960
taccaccata tacatatcca tatacatatc catatctaat cttacttata tgttgtggaa 1020
atgtaaagag ccccattatc ttagcctaaa aaaaccttct ctttggaact ttcagtaata 1080
cgcttaactg ctcattgcta tattgaagta cggattagaa gccgccgagc gggtgacagc 1140
cctccgaagg aagactctcc tccgtgcgtc ctcgtcttca ccggtcgcgt tcctgaaacg 1200
cagatgtgcc tcgcgccgca ctgctccgaa caataaagat tctacaatac tagcttttat 1260
ggttatgaag aggaaaaatt ggcagtaacc tggccccaca aaccttcaaa tgaacgaatc 1320
aaattaacaa ccataggatg ataatgcgat tagtttttta gccttatttc tggggtaatt 1380
aatcagcgaa gcgatgattt ttgatctatt aacagatata taaatgcaaa aactgcataa 1440
ccactttaac taatactttc aacattttcg gtttgtatta cttcttattc aaatgtaata 1500
aaagtatcaa caaaaaattg ttaatatacc tctatacttt aacgtcaagg agaaaaaacc 1560
ccggatccat gggtcaatat aaattaattt tgaatggtaa aactttgaag ggtgaaacta 1620
ctaccgaagc agtagatgca gcaacagccg aaaaggtctt taagcaatat gctaatgata 1680
atggtgttga tggtgaatgg acctatgacg atgcaactaa aacatttact gtaactgaag 1740
gatccatggc cttaacagaa gagaagccaa tcagacccat agccaacttc cctccatcaa 1800
tatggggtga tcaatttctt atatacgaaa agcaagttga acaaggtgtc gaacaaatcg 1860
tcaacgatct aaagaaggag gtcaggcagt tattaaaaga agctctggac ataccgatga 1920
aacatgctaa tctactaaaa ttaattgatg agattcaaag attgggcatc ccttatcact 1980

-continued

```
tcgagagaga gattgatcat gcattgcaat gtatatacga gacgtacggt gataactgga   2040
acggagatag gagtagtcta tggttcaggt tgatgagaaa gcaaggctac tatgtgacat   2100
gcgatgtctt taataactat aaggacaaaa atggtgcatt taagcaatct ctagccaacg   2160
atgttgaagg tttattagaa ttatatgaag ccacaagcat gagagtccca ggagagatca   2220
tattggaaga tgctctaggg ttcacacgtt ctagattgtc aataatgacc aaggacgcat   2280
tcagtactaa ccctgcgtta ttcactgaaa tccaaagggc actaaagcaa cctctttgga   2340
aaagattgcc tcgtattgaa gcagcacaat atatacccttt ctatcagcag caggactctc   2400
acaacaaaac tctacttaaa ttagcaaagt tagaattcaa tttgttgcaa agtttacata   2460
aggaagaatt atctcacgta tgcaaatggt ggaaagcttt cgatattaag aagaacgccc   2520
catgcctgag agacagaata gttgagtgtt atttctgggg tctgggttcc ggttatgaac   2580
cacaatattc tagggccaga gtctttttta ccaaagttgt cgcggtcata actttaatcg   2640
acgatactta tgatgcttat ggtacctacg aggagttaaa gatattcacc gaagctgtgg   2700
aaaggtggtc tataacttgc ttggacaccc taccagaata tatgaaacca atttacaaat   2760
tgtttatgga tacttatact gaaatggagg aattcctggc aaaagaaggt agaactgatt   2820
tgtttaattg cggtaaggaa tttgtgaagg aattcgtaag aaacttaatg gtcgaggcaa   2880
aatgggccaa cgaaggacac attccaacaa ccgaagagca tgatcctgtc gtgataatca   2940
ccggtggcgc taacctacta accactacct gctacctagg tatgtctgat atcttcacaa   3000
aagagagtgt tgaatgggca gttagtgctc cgcctttgtt caggtatagc ggtatacttg   3060
gcaggcgttt aaatgatctt atgacccata aagccgaaca agaaagaaaa cactcaagct   3120
cctctcttga atcctatatg aaggaataca atgttaacga ggaatatgcg caaactttaa   3180
tatacaagga ggtggaagat gtgtggaaag atatcaacag agaatatctt actacaaaga   3240
acataccccg tccacttttg atggcagtga tttacttgtg tcagttctta gaggtacaat   3300
acgctggtaa ggataacttt acaagaatgg gcgacgaata caaacatttg atcaagtcat   3360
tattagttta tcccatgtcc atctaagcta gctaagatcc gctctaaccg aaaaggaagg   3420
agttagacaa cctgaagtct aggtccctat ttattttttt atagttatgt tagtattaag   3480
aacgttattt atatttcaaa tttttctttt ttttctgtac agacgcgtgt acgcatgtaa   3540
cattatactg aaaaccttgc ttgagaaggt tttgggacgc tcgaagcgga ggttgtttat   3600
ctttcgagta ctgaatgttg tcagtatagc tatcctattt gaaactcccc atcgtcttgc   3660
tcttgttccc aatgtttgtt tatacactca tatggctata cccttatcta cttgcctctt   3720
ttgtttatgt ctatgtattt gtataaaata tgatattact cagactcaag caaacaatca   3780
attcttagca tcattctttg ttcttatctt aaccataaac gatcttgatg tgacttttgt   3840
aatttgaacg aattggctat acgggacgga tgacaaatgc accattactc taggttgttg   3900
ttggatctta acaaaccgta aaggtaaact gcccatgcgg ttcacatgac ttttgacttt   3960
cctttgtttg ctagttacct tcggcttcac aatttgtttt tccacttttc taacaggttt   4020
atcacctttc aaacttatct ttatcttatt cgccttcttg ggtgcctcca cagtagaggt   4080
tacttccttt ttaatatgta cttttaggat actttcacgc tttataacaa tatcaagttt   4140
accttcttca ttactattca tcttcgccac aagtcttctc tcccttggtg tttccaatct   4200
aactacaaaa ctgttgatta gggtgtacat caccctaaca agatcatgta tttgcttcct   4260
ctggtacaag ctaagaacag gtaaattcaa aacatcccag agtaatatct tcaaagggct   4320
ataccettta aacatatctc ggcatatttg tattaaccca ctaatatttt gacggccaat   4380
```

-continued ctttctatt tttattttca tatcatcgac gtaatgacca cttaaaaac 4429

<210> SEQ ID NO 31
<211> LENGTH: 23
<212> TYPE: DNA
<213> ORGANISM: Artificial Sequence
<220> FEATURE:
<223> OTHER INFORMATION: Synthetic: Primer CUT24

<400> SEQUENCE: 31
gtttcttttg gattgcgctt gcc 23

<210> SEQ ID NO 32
<211> LENGTH: 20
<212> TYPE: DNA
<213> ORGANISM: Artificial Sequence
<220> FEATURE:
<223> OTHER INFORMATION: Synthetic: Primer ART12

<400> SEQUENCE: 32
tactgacaac cacatgttac 20

<210> SEQ ID NO 33
<211> LENGTH: 29
<212> TYPE: DNA
<213> ORGANISM: Artificial Sequence
<220> FEATURE:
<223> OTHER INFORMATION: Synthetic: Primer ART45

<400> SEQUENCE: 33
tactgcttcg gtagtagttt cacccttca 29

<210> SEQ ID NO 34
<211> LENGTH: 20
<212> TYPE: DNA
<213> ORGANISM: Artificial Sequence
<220> FEATURE:
<223> OTHER INFORMATION: Synthetic: Primer ART210

<400> SEQUENCE: 34
gggaagtcca attcaatagt 20

<210> SEQ ID NO 35
<211> LENGTH: 25
<212> TYPE: DNA
<213> ORGANISM: Artificial Sequence
<220> FEATURE:
<223> OTHER INFORMATION: Synthetic: Primer HJ207

<400> SEQUENCE: 35
catcttctcg agataacacc tggag 25

<210> SEQ ID NO 36
<211> LENGTH: 19
<212> TYPE: DNA
<213> ORGANISM: Artificial Sequence
<220> FEATURE:
<223> OTHER INFORMATION: Synthetic: Primer KB349

<400> SEQUENCE: 36
acgcgtgtac gcatgtaac 19

<210> SEQ ID NO 37
<211> LENGTH: 20
<212> TYPE: DNA
<213> ORGANISM: Artificial Sequence
<220> FEATURE:

<223> OTHER INFORMATION: Synthetic: Primer HJ602

<400> SEQUENCE: 37
caattggggt tctggcagtc 20

<210> SEQ ID NO 38
<211> LENGTH: 30
<212> TYPE: DNA
<213> ORGANISM: Artificial Sequence
<220> FEATURE:
<223> OTHER INFORMATION: Synthetic: Primer CUT76

<400> SEQUENCE: 38
gaagcctgct ttcaaaatta agaacaaagc 30

<210> SEQ ID NO 39
<211> LENGTH: 30
<212> TYPE: DNA
<213> ORGANISM: Artificial Sequence
<220> FEATURE:
<223> OTHER INFORMATION: Synthetic: Primer HJ362

<400> SEQUENCE: 39
gaatttacct gttcttagct tgtaccagag 30

<210> SEQ ID NO 40
<211> LENGTH: 6523
<212> TYPE: DNA
<213> ORGANISM: Artificial Sequence
<220> FEATURE:
<223> OTHER INFORMATION: Synthetic: ADS_HIS3 donor cassette

<400> SEQUENCE: 40
attgtgaggg tcagttattt catccagata taacccgaga ggaaacttct tagcgtctgt 60
tttcgtacca taaggcagtt catgaggtat attttcgtta ttgaagccca gctcgtgaat 120
gcttaatgct gctgaactgg tgtccatgtc gcctaggtac gcaatctcca caggctgcaa 180
aggttttgtc tcaagagcaa tgttattgtg caccccgtaa ttggtcaaca agtttaatct 240
gtgcttgtcc accagctctg tcgtaacctt cagttcatcg actatctgaa gaaatttact 300
aggaatagtg ccatggtaca gcaaccgaga atggcaattt ctactcgggt tcagcaacgc 360
tgcataaacg ctgttggtgc cgtagacata ttcgaagata ggattatcat tcataagttt 420
cagagcaatg tccttattct ggaacttgga tttatggctc ttttggttta atttcgcctg 480
attcttgatc tcctttagct tctcgacgtg ggcctttttc ttgccatatg gatccgctgc 540
acggtcctgt tccctagcat gtacgtgagc gtatttcctt ttaaaccacg acgctttgtc 600
ttcattcaac gtttcccatt gttttttttct actattgctt tgctgtggga aaaacttatc 660
gaaagatgac gactttttct taattctcgt tttaagagct tggtgagcgc taggagtcac 720
tgccaggtat cgtttgaaca cggcattagt cagggaagtc ataacacagt cctttcccgc 780
aattttcttt ttctattact cttggcctcc tctagtacac tctatatttt tttatgcctc 840
ggtaatgatt ttcatttttt ttttttccac ctagcggatg actctttttt tttcttagcg 900
attggcatta tcacataatg aattatacat tatataaagt aatgtgattt cttcgaagaa 960
tatactaaaa aaatcgttat tgtcttgaag gtgaaatttc tactcttatt aatggtgaac 1020
gttaagctga tgctatgatg gaagctgatt ggtcttaact tgcttgtcat cttgctaatg 1080
gtcattggct cgtgttatta cttaagttat ttgtactcgt tttgaacgta atgctaatga 1140
tcatcttatg gaataatagt gagtggtttc agggtccata aagcttttca attcatcttt 1200

-continued

```
ttttttttg ttctttttt tgattccggt ttctttgaaa tttttttgat tcggtaatct   1260
ccgagcagaa ggaagaacga aggaaggagc acagacttag attggtatat atacgcatat   1320
gtggtgttga agaaacatga aattgcccag tattcttaac ccaactgcac agaacaaaaa   1380
cctgcaggaa acgaagataa atcatgtcga aagctacata taaggaacgt gctgctactc   1440
atcctagtcc tgttgctgcc aagctattta atatcatgca cgaaaagcaa acaaacttgt   1500
gtgcttcatt ggatgttcgt accaccaagg aattactgga gttagttgaa gcattaggtc   1560
ccaaaatttg tttactaaaa acacatgtgg atatcttgac tgatttttcc atggagggca   1620
cagttaagcc gctaaaggca ttatccgcca agtacaattt tttactcttc gaagacagaa   1680
aatttgctga cattggtaat acagtcaaat tgcagtactc tgcgggtgta tacagaatag   1740
cagaatgggc agacattacg aatgcacacg gtgtggtggg cccaggtatt gttagcggtt   1800
tgaagcaggc ggcggaagaa gtaacaaagg aacctagagg ccttttgatg ttagcagaat   1860
tgtcatgcaa gggctcccta gctactggag aatatactaa gggtactgtt gacattgcga   1920
agagtgacaa agattttgtt atcggcttta ttgctcaaag agacatgggt ggaagagatg   1980
aaggttacga ttggttgatt atgacacccg gtgtgggttt agatgacaag ggagacgcat   2040
tgggtcaaca gtatagaacc gtggatgatg tggtctctac aggatctgac attattattg   2100
ttggaagagg actatttgca aagggaaggg atgctaaggt agagggtgaa cgttacagaa   2160
aagcaggctg ggaagcatat ttgagaagat gcggccagca aaactaaaaa actgtattat   2220
aagtaaatgc atgtatacta aactcacaaa ttagagcttc aatttaatta tatcagttat   2280
taccacgaaa atcgttattg tcttgaaggt gaaatttcta ctcttattaa tggtgaacgt   2340
taagctgatg ctatgatgga agctgattgg tcttaacttg cttgtcatct tgctaatggt   2400
catatggctc gtgttattac ttaagttatt tgtactcgtt ttgaacgtaa tgctaatgat   2460
catcttatgc ttcgagcgtc ccaaaacctt ctcaagcaag gttttcagta taatgttaca   2520
tgcgtacacg cgtctgtaca gaaaaaaaag aaaaatttga aatataaata acgttcttaa   2580
tactaacata actataaaaa aataaatagg gacctagact tcaggttgtc taactccttc   2640
cttttcggtt agagcggatc ttagctagct tagctagctt agatagacat agggtagacc   2700
aacaaagact taattaagtg cttatattcg tcacccattc tggtgaaatt gtctttacca   2760
gcgtattgaa cttctaagaa ttgacataaa tagataacag ccattaacaa tggacgtgga   2820
atatttttgg tggtcaagta ttctctgtta atatctttcc aaacgtcttc aacttccttg   2880
taaatcaaag tttgagcgta ttcttcgtta acgttgtatt ccttcatgta agattctaag   2940
gaagaggagg agtgctttct ttcttgctca gccttgtgag tcatcaaatc gtttaatctt   3000
ctacccaaaa taccagagta tctgaacaaa ggtggagcgg aaacggccca ttcaacagat   3060
tccttggtga aaatatcaga catacctaag taacaagtag tagtcaacaa gttagcacca   3120
ccagtaatga taacgactgg atcgtgttct tcagtagttg gaatatgacc ttcgttagcc   3180
catttagctt caaccatcaa gttacgaacg aattccttaa cgaattcctt accacaattg   3240
aacaagtcgg tacgaccttc cttagccaag aattcttcca tttcggtgta agtgtccatg   3300
aacaacttat aaattggctt catgtattct ggtaaagtat ctaaacaggt aatggaccat   3360
ctttcgacag cttcagtgaa aatcttcaat tcttcgtagg taccgtaagc gtcgtaagtg   3420
tcgtcaatca aggtaataac agcaacagcc ttagtaaaga aaactctagc tctagagtat   3480
tgtggttcgt aaccggaacc caaaccccag aagtaacatt cgacaattct atctctcaaa   3540
catggagcgt tcttcttaat atcgaaggct ttccaccact tacaaacgtg agacaattct   3600
```

-continued

```
tccttgtgca aggattgcaa caagttaaat tccaatttag ccaatttcaa caaggttttg   3660
ttgtgagagt cttgttgttg gtagaatggg atgtattgag cagcttcgat tcttggcaaa   3720
cgcttccaca atggttgttt caaagctctt tggatttcag tgaacaaagc tgggttagta   3780
gagaaggcat ctttagtcat gatggacaat ctagatctag taaaacccaa agcgtcttcc   3840
aagatgattt caccaggaac tctcatggag gtggcttcat acaattctaa caaaccttca   3900
acatcgttgg ccaaagattg cttaaaagca ccattcttat ctttgtagtt gttgaaaacg   3960
tcacaagtaa cgtagtaacc ttgctttctc attaatctga accataagga agatctgtca   4020
ccgttccagt tatcaccgta agtttcgtaa atacattgca aagcgtgatc aatttctctt   4080
tcgaaatggt atggaatacc taatctttgg atttcgtcga ttaatttcaa taagttagcg   4140
tgcttcattg ggatgtccaa agcttccttc aacaattgtc taacttcctt cttcaaatcg   4200
ttaacgattt gttcaacacc ttgctcaact tgcttttcgt agatcaagaa ttggtcaccc   4260
cagatagaag gtggaaaatt agcaattggt ctgattggtt tttcttcagt caaagccatg   4320
gatccttcag ttacagtaaa tgttttagtt gcatcgtcat aggtccattc accatcaaca   4380
ccattatcat tagcatattg cttaaagacc ttttcggctg ttgctgcatc tactgcttcg   4440
gtagtagttt cacccttcaa agttttacca ttcaaaatta atttatattg acccattata   4500
gtttttctc cttgacgtta aagtatagag gtatattaac aattttttgt tgatactttt   4560
attacatttg aataagaagt aatacaaacc gaaaatgttg aaagtattag ttaaagtggt   4620
tatgcagttt ttgcatttat atatctgtta atagatcaaa aatcatcgct tcgctgatta   4680
attaccccag aaataaggct aaaaaactaa tcgcattatc atcctatggt tgttaatttg   4740
attcgttcat ttgaaggttt gtggggccag gttactgcca atttttcctc ttcataacca   4800
taaaagctag tattgtagaa tctttattgt tcggagcagt gcggcgcgag gcacatctgc   4860
gtttcaggaa cgcgaccggt gaagacgagg acgcacggag gagagtcttc cttcggaggg   4920
ctgtcacccg ctcggcggct tctaatccgt acttcaatat agcaatgagc agttaagcgt   4980
attactgaaa gttccaaaga gaaggttttt ttaggctaag ataatggggc tctttacatt   5040
tccacaacat ataagtaaga ttagatatgg atatgtatat ggatatgtat atggtggtaa   5100
tgccatgtaa tatgattatt aaacttcttt gcgtccatcc aaaaaaaaag taagaatttt   5160
tgaaaattca atataaatgt ctcagaacgt ttacattgta tcgactgcca gaaccccaat   5220
tggttcattc cagggttctc tatcctccaa gacagcagtg gaattgggtg ctgttgcttt   5280
aaaaggcgcc ttggctaagg ttccagaatt ggatgcatcc aaggattttg acgaaattat   5340
ttttggtaac gttctttctg ccaatttggg ccaagctccg gccagacaag ttgctttggc   5400
tgccggtttg agtaatcata tcgttgcaag cacagttaac aaggtctgtg catccgctat   5460
gaaggcaatc attttgggtg ctcaatccat caaatgtggt aatgctgatg ttgtcgtagc   5520
tggtggttgt gaatctatga ctaacgcacc atactacatg ccagcagccc gtgcgggtgc   5580
caaatttggc caaactgttc ttgttgatgg tgtcgaaaga gatgggttga acgatgcgta   5640
cgatggtcta gccatgggtg tacacgcaga aaagtgtgcc cgtgattggg atattactag   5700
agaacaacaa gacaattttg ccatcgaatc ctaccaaaaa tctcaaaaat ctcaaaagga   5760
aggtaaattc gacaatgaaa ttgtacctgt taccattaag ggatttagag gtaagcctga   5820
tactcaagtc acgaaggacg aggaacctgc tagattacac gttgaaaaat tgagatctgc   5880
aaggactgtt ttccaaaaag aaaacggtac tgttactgcc gctaacgctt ctccaatcaa   5940
cgatggtgct gcagccgtca tcttggtttc cgaaaaagtt ttgaaggaaa agaatttgaa   6000
```

gcctttggct attatcaaag gttggggtga ggccgctcat caaccagctg attttacatg 6060
ggctccatct cttgcagttc caaaggcttt gaaacatgct ggcatcgaag acatcaattc 6120
tgttgattac tttgaattca atgaagcctt ttcggttgtc ggtttggtga acactaagat 6180
tttgaagcta gacccatcta aggttaatgt atatggtggt gctgttgctc taggtcaccc 6240
attgggttgt tctggtgcta gagtggttgt tacactgcta tccatcttac agcaagaagg 6300
aggtaagatc ggtgttgccg ccatttgtaa tggtggtggt ggtgcttcct ctattgtcat 6360
tgaaaagata tgattacgtt ctgcgatttt ctcatgatct tttcataaa atacataaat 6420 atataaatgg ctttatgtat aacaggcata atttaaagtt ttatttgcga ttcatcgttt 6480
ttcaggtact caaacgctga ggtgtgcctt ttgacttact ttt 6523

<210> SEQ ID NO 41
<211> LENGTH: 10379
<212> TYPE: DNA
<213> ORGANISM: Artificial Sequence
<220> FEATURE:
<223> OTHER INFORMATION: Synthetic: ADS_FS.1 donor cassette

<400> SEQUENCE: 41
atattgtttt ttccctagct gttttcggtt tggttatgaa cgcattgtct gcgaaaagaa 60
acgtggataa gtattataga aacagcactt cttcggccaa caatatcacg caaattgagc 120
aagatagtgc tataaaaggt cttttgccct tttttgccta ttatgcaagc attgctttac 180
tagtgtggat gcaaccaagc tttattacac tctctttcat cctttccgtt ggtttcacgg 240
gagcatttac cgtcggaaga ataatcgttt gccatttaac taagcagagc tttcccatgt 300
tcaatgcacc catgttaatt cctttgtgcc agatagtatt gtacaaaata tgtctatccc 360
tttggggaat tgagtctaat aaaatcgtct ttgccctatc ttggcttggg ttcggtctct 420
cactaggtgt tcacattatg tttatgaatg acattatcca tgaatttact gagtacctgg 480
acgtttatgc tttatccatc aagcgctcca agctgacata aatcgcactt tgtatctact 540 ttttttttatt cgaaaacaag gcacaacaat gaatctatcg ccctgtgaga ttttcaatct 600
caagtttgtg taatagatag cgttatatta tagaactata aaggtccttg aatatacata 660
gtgtttcatt cctattactg tatatgtgac tttacattgt tacttccgcg gctatttgac 720
gttttctgct tcaggtgcgg cttggagggc aaagtgtcag aaaatcggcc aggccgtatg 780
acacaaaaga gtagaaaacg agatctcaaa tatctcgagg cctgtcctct atacaaccgc 840
ccagctctct gacaaagctc cagaacggtt gtcttttgtt tcgaaaagcc aaggtccctt 900
ataattgccc tccattttgt gtcacctatt taagcaaaaa attgaaagtt tactaacctt 960
tcattaaaga gaaataacaa tattataaaa agcgcttaaa tatacctgag aaagcaacct 1020
gacctacagg aaagagttac tcaagaataa gaattttcgt tttaaaacct aagagtcact 1080
ttaaaatttg tatacactta ttttttttat aacttattta ataataaaaa tcataaatca 1140
taagaaattc gcttatttag aagtgtcaac aacgtatcta ccaacgattt gaccctttc 1200 catcttttcg taaatttctg gcaaggtaga caagccgaca accttgattg gagacttgac 1260
caaacctctg gcgaagaatt gttaattaag agctcagatc ttatcgtcgt catccttgta 1320
atccatcgat actagtgcgg ccgcccttta gtgagggttg aattcgaatt ttcaaaaatt 1380
cttacttttt ttttggatgg acgcaaagaa gtttaataat catattacat ggcattacca 1440
ccatatacat atccatatac atatccatat ctaatcttac ttatatgttg tggaaatgta 1500
aagagcccca ttatcttagc ctaaaaaaac cttctctttg gaactttcag taatacgctt 1560

-continued

```
aactgctcat tgcgccgccg agcgggtgac agccctccga aggaagactc tcctccgtgc   1620
gtcctcgtct tcaccggtcg cgttcctgaa acgcagatgt gcctcgcgcc gcactgctcc   1680
gaacaataaa gattctacaa tactagcttt tatggttatg aagaggaaaa attggcagta   1740
acctggcccc acaaaccttc aaatgaacga atcaaattaa caaccatagg atgataatgc   1800
gattagtttt ttagccttat ttctggggta attaatcagc gaagcgatga tttttgatct   1860
attaacagat atataaatgc aaaaactgca taaccacttt aactaatact ttcaacattt   1920
tcggtttgta ttacttctta ttcaaatgta ataaaagtat caacaaaaaa ttgttaatat   1980
acctctatac tttaacgtca aggagaaaaa actataatgg gtcaatataa attaattttg   2040
aatggtaaaa ctttgaaggg tgaaactact accgaagcag tagatgcagc aacagccgaa   2100
aaggtcttta agcaatatgc taatgataat ggtgttgatg gtgaatggac ctatgacgat   2160
gcaactaaaa catttactgt aactgaagga tccatggctt tgactgaaga aaaaccaatc   2220
agaccaattg ctaattttcc accttctatc tggggtgacc aattcttgat ctacgaaaag   2280
caagttgagc aaggtgttga acaaatcgtt aacgatttga agaaggaagt tagacaattg   2340
ttgaaggaag ctttggacat cccaatgaag cacgctaact tattgaaatt aatcgacgaa   2400
atccaaagat taggtattcc ataccatttc gaaagagaaa ttgatcacgc tttgcaatgt   2460
atttacgaaa cttacggtga taactggaac ggtgacagat cttccttatg gttcagatta   2520
atgagaaagc aaggttacta cgttacttgt gacgttttca acaactacaa agataagaat   2580
ggtgctttta agcaatcttt ggccaacgat gttgaaggtt tgttagaatt gtatgaagcc   2640
acctccatga gagttcctgg tgaaatcatc ttggaagacg ctttgggttt tactagatct   2700
agattgtcca tcatgactaa agatgccttc tctactaacc cagctttgtt cactgaaatc   2760
caaagagctt tgaaacaacc attgtggaag cgtttgccaa gaatcgaagc tgctcaatac   2820
atcccattct accaacaaca agactctcac aacaaaacct tgttgaaatt ggctaaattg   2880
gaatttaact tgttgcaatc cttgcacaag gaagaattgt ctcacgtttg taagtggtgg   2940
aaagccttcg atattaagaa gaacgctcca tgtttgagag atagaattgt cgaatgttac   3000
ttctggggtt tgggttccgg ttacgaacca caatactcta gagctagagt tttctttact   3060
aaggtggttg ctgttattac cttgattgac gacacttacg acgcttacgg tacctacgaa   3120
gaattgaaga ttttcactga agctgtcgaa agatggtcca ttacctgttt agatacttta   3180
ccagaataca tgaagccaat ttataagttg ttcatggaca cttacaccga aatggaagaa   3240
ttcttggcta aggaaggtcg taccgacttg ttcaattgtg gtaaggaatt cgttaaggaa   3300
ttcgttcgta acttgatggt tgaagctaaa tgggctaacg aaggtcatat tccaactact   3360
gaagaacacg atccagtcgt tatcattact ggtggtgcta acttgttgac tactacttgt   3420
tacttaggta tgtctgatat tttcaccaag gaatctgttg aatgggccgt ttccgctcca   3480
cctttgttca gatactctgg tattttgggt agaagattaa acgatttgat gactcacaag   3540
gctgagcaag aaagaaagca ctcctcctct tccttagaat cttacatgaa ggaatacaac   3600
gttaacgaag aatacgctca aactttgatt tacaaggaag ttgaagacgt ttggaaagat   3660
attaacagag aatacttgac caccaaaaat attccacgtc cattgttaat ggctgttatc   3720
tatttatgtc aattcttaga agttcaatac gctggtaaag acaatttcac cagaatgggt   3780
gacgaatata agcacttaat taagtctttg ttggtctacc ctatgtctat ctaagatccg   3840
ctctaaccga aaaggaagga gttagacaac ctgaagtcta ggtccctatt tattttttta   3900
tagttatgtt agtattaaga acgttattta tatttcaaat ttttcttttt tttctgtaca   3960
```

-continued

```
gacgcgtgta cgcatgtaac attatactga aaaccttgct tgagaaggtt ttgggacgct   4020
cgaaggtttt caatagttcg gtaatattaa cggataccta ctattatccc ctagtaggct   4080
cttttcacgg agaaattcgg gagtgttttt tttccgtgcg cattttctta gctatattct   4140
tccagcttcg cctgctgccc ggtcatcgtt cctgtcacgt agtttttccg gattcgtccg   4200
gctcatataa taccgcaata aacacggaat atctcgttcc gcggattcgg ttaaactctc   4260
ggtcgcggat tatcacagag aaagcttcgt ggagaatttt tccagatttt ccgctttccc   4320
cgatgttggt atttccggag gtcattatac tgaccgccat tataatgact gtacaacgac   4380
cttctggaga aagaaacaac tcaataacga tgtgggacat tgggggccca ctcaaaaaat   4440
ctggggacta tatccccaga gaatttctcc agaagagaag aaaagtcaaa gtttttttc    4500
gcttggggt tgcatataaa tacaggcgct gttttatctt cagcatgaat attccataat    4560
tttacttaat agcttttcat aaataataga atcacaaaca aaatttacat ctgagttaaa   4620
caatcatgac aatcaaggaa cataaagtag tttatgaagc tcacaacgta aaggctctta   4680
aggctcctca acatttttac aacagccaac ccggcaaggg ttacgttact gatatgcaac   4740
attatcaaga aatgtatcaa caatctatca atgagccaga aaaattcttt gataagatgg   4800
ctaaggaata cttgcattgg gatgctccat acaccaaagt tcaatctggt tcattgaaca   4860
atggtgatgt tgcatggttt ttgaacggta aattgaatgc atcatacaat tgtgttgaca   4920
gacatgcctt tgctaatccc gacaagccag ctttgatcta tgaagctgat gacgaatccg   4980
acaacaaaat catcacattt ggtgaattac tcagaaaagt ttcccaaatc gctggtgtct   5040
taaaaagctg gggcgttaag aaaggtgaca cagtggctat ctatttgcca atgattccag   5100
aagcggtcat tgctatgttg gctgtggctc gtattggtgc tattcactct gttgtctttg   5160
ctgggttctc cgctggttcg ttgaaagatc gtgtcgttga cgctaattct aaagtggtca   5220
tcacttgtga tgaaggtaaa agaggtggta agaccatcaa cactaaaaaa attgttgacg   5280
aaggtttgaa cggagtcgat ttggtttccc gtatcttggt tttccaaaga actggtactg   5340
aaggtattcc aatgaaggcc ggtagagatt actggtggca tgaggaggcc gctaagcaga   5400
gaacttacct acctcctgtt tcatgtgacg ctgaagatcc tctattttta ttatacactt   5460
ccggttccac tggttctcca aagggtgtcg ttcacactac aggtggttat ttattaggtg   5520
ccgctttaac aactagatac gtttttgata ttcacccaga agatgttctc ttcactgccg   5580
gtgacgtcgg ctggatcacg ggtcacacct atgctctata tggtccatta accttgggta   5640
ccgcctcaat aattttcgaa tccactcctg cctacccaga ttatggtaga tattggagaa   5700
ttatccaacg tcacaaggct acccatttct atgtggctcc aactgcttta agattaatca   5760
aacgtgtagg tgaagccgaa attgccaaat atgacacttc ctcattacgt gtcttgggtt   5820
ccgtcggtga accaatctct ccagacttat gggaatggta tcatgaaaaa gtgggtaaca   5880
aaaactgtgt catttgtgac actatgtggc aaacagagtc tggttctcat ttaattgctc   5940
ctttggcagg tgctgtccca acaaaacctg gttctgctac cgtgccattc tttggtatta   6000
acgcttgtat cattgaccct gttacaggtg tggaattaga aggtaatgat gtcgaaggtg   6060
tccttgccgt taaatcacca tggccatcaa tggctagatc tgtttggaac caccacgacc   6120
gttacatgga tacttacttg aaaccttatc ctggtcacta tttcacaggt gatggtgctg   6180
gtagagatca tgatggttac tactggatca ggggtagagt tgacgacgtt gtaaatgttt   6240
ccggtcatag attatccaca tcagaaattg aagcatctat ctcaaatcac gaaaacgtct   6300
cggaagctgc tgttgtcggt attccagatg aattgaccgg tcaaaccgtc gttgcatatg   6360
```

-continued

```
tttccctaaa agatggttat ctacaaaaca acgctactga aggtgatgca gaacacatca   6420
caccagataa tttacgtaga gaattgatct tacaagttag ggtgagatt ggtcctttcg   6480
cctcaccaaa aaccattatt ctagttagag atctaccaag aacaaggtca ggaaagatta   6540
tgagaagagt tctaagaaag gttgcttcta acgaagccga acagctaggt gacctaacta   6600
ctttggccaa cccagaagtt gtacctgcca tcatttctgc tgtagagaac caattttct   6660
ctcaaaaaaa gaaataaatt gaattgaatt gaaatcgata gatcaatttt tttcttttct   6720
ctttccccat cctttacgct aaaataatag tttattttat tttttgaata tttttattt   6780
atatacgtat atatagacta ttatttatct tttaatgatt attaagattt ttattaaaaa   6840
aaaattcgct cctcttttaa tgcctttatg cagtttttttt ttcccattcg atatttctat   6900
gttcgggttc agcgtatttt aagtttaata actcgaaaat tctgcgttcg ttaaagcttt   6960
cgagaaggat attatttcga aataaaccgt gttgtgtaag cttgaagcct ttttgcgctg   7020
ccaatattct tatccatcta ttgtactctt tagatccagt atagtgtatt cttcctgctc   7080
caagctcatc ccatccccgc gtgcttggcc ggccgttttg ccagcttact atccttcttg   7140
aaaatatgca ctctatatct tttagttctt aattgcaaca catagatttg ctgtataacg   7200
aattttatgc tattttttaa atttggagtt cagtgataaa agtgtcacag cgaatttcct   7260
cacatgtagg gaccgaattg tttacaagtt ctctgtacca ccatggagac atcaaaaatt   7320
gaaaatctat ggaaagatat ggacggtagc aacaagaata tagcacgagc cgcggagttc   7380
atttcgttac ttttgatatc actcacaact attgcgaagc gcttcagtga aaaaatcata   7440
aggaaaagtt gtaaatatta ttggtagtat tcgtttggta aagtagaggg ggtaattttt   7500
cccctttatt ttgttcatac attcttaaat tgctttgcct ctccttttgg aaagctatac   7560
ttcggagcac tgttgagcga aggctcatta gatatatttt ctgtcatttt ccttaaccca   7620
aaaataaggg aaagggtcca aaaagcgctc ggacaactgt tgaccgtgat ccgaaggact   7680
ggctatacag tgttcacaaa atagccaagc tgaaaataat gtgtagctat gttcagttag   7740
tttggctagc aaagatataa aagcaggtcg gaaatattta tgggcattat tatgcagagc   7800
atcaacatga taaaaaaaaa cagttgaata ttccctcaaa aatgtcttac accgtcggaa   7860
cctacttggc cgagaggttg gtccagatcg gattgaagca ccacttcgcc gtcgccggtg   7920
actacaactt ggtcttgttg gacaacttgt tgttgaacaa gaacatggag caggtctatt   7980
gctgcaacga gttgaactgc ggtttctcag cagaaggtta tgcaagagcc aagggagcag   8040
ccgctgccgt cgtcacctac tcagtcggtg cattatcagc attcgatgca attggaggtg   8100
cttacgctga gaacttgcca gtcatcttga tctctggagc acctaacaac aacgaccatg   8160
ctgctggtca cgtattgcac cacgccttgg gtaaaacaga ctaccactac cagttggaaa   8220
tggcaaaaaa tattaccgca gccgcagagg ccatctacac cccagaggaa gcacctgcca   8280
aaattgacca cgtcataaag accgctttga gagagaagaa gcctgtttac ttggagatcg   8340
cctgcaacat cgcttctatg ccatgcgccg cacctggtcc agcctctgct ttgttcaacg   8400
acgaggcctc tgacgaagct tcattgaacg ccgcagtcga agagacatta aagttcatcg   8460
ccaacaggga caaagttgcc gtcttagtcg gttcaaagtt gagggccgct ggtgccgaag   8520
aggcagctgt caagttcgct gacgccttgg gaggagccgt cgccaccatg gccgcagcaa   8580
aatctttctt tcctgaggag aacccacatt acatcggaac ctcatggggt gaagtatcat   8640
atcctggagt agaaaaaacc atgaaagagg ccgatgccgt aatagcattg gctcctgtct   8700
tcaacgacta ctcaaccaca ggatggactg atataccaga tccaaagaaa ttagtcttgg   8760
```

ctgagcctag gtctgtcgtc gtaaacggta tcaggttccc ttctgttcat ttgaaggact 8820
acttaacaag attggcccaa aaggtatcta aaaagactgg tgccttggac ttcttcaagt 8880
cattaaacgc aggagaattg aaaaaagcag caccagccga tccatcagcc ccattagtta 8940
acgctgaaat cgctagacaa gtagaggctt tgttgactcc aaacactacc gtcatagctg 9000
agacaggtga ctcttggttc aacgcacaga gaatgaaatt gccaaatggt gccagggtcg 9060
agtatgaaat gcagtgggga catataggtt ggtcagtccc agccgccttt ggatacgcag 9120
taggtgcccc tgagaggagg aacatattga tggttggtga tggttcattc caattaacag 9180
cccaggaggt agcccaaatg gtcaggttga agttgcctgt catcatcttc ttgatcaaca 9240
attacggata caccatcgag gtcatgatcc acgacggacc ttacaacaac atcaaaaact 9300
gggactacgc cggtttgatg gaggttttca acggtaacgg tggttatgac tcaggagccg 9360
gtaagggatt aaaggctaag accggtggtg aattggctga agcaattaag gtcgcattgg 9420
ccaacaccga tggacctaca ttgattgaat gcttcatcgg aagggaggac tgcaccgagg 9480
aattggttaa atggggtaaa agggtagccg ctgctaattc aagaaaacca gttaataaat 9540
tattataata agtgaattta ctttaaatct tgcatttaaa taaattttct ttttatagct 9600
ttatgactta gtttcaattt atatactatt ttaatgacat tttcgattca ttgattgaaa 9660
gctttgtgtt ttttcttgat gcgctattgc attgttcttg tctttttcgc cacatgtaat 9720
atctgtagta gatacctgat acattgtgga tgctgagtga aattttagtt aataatggag 9780
gcgctcttaa taattttggg gatattggct taacctgcag gccgcgagcg ccgatataaa 9840
ctaatgattt taaatcgtta aaaaaatatg cgaattctgt ggatcgaaca caggacctcc 9900
agataacttg accgaagttt tttcttcagt ctggcgctct cccaactgag ctaaatccgc 9960
ttactatttg ttatcagttc ccttcatatc tacatagaat aggttaagta ttttattagt 10020
tgccagaaga actactgata gttgggaata tttggtgaat aatgaagatt gggtgaataa 10080
tttgataatt ttgagattca attgttaatc aatgttacaa tattatgtat acagagtata 10140
ctagaagttc tcttcggaga tcttgaagtt cacaaaaggg aatcgatatt tctacataat 10200
attatcatta cttcttcccc atcttatatt tgtcattcat tattgattat gatcaatgca 10260
ataatgattg gtagttgcca aacatttaat acgatcctct gtaatatttc tatgaataat 10320
tatcacagca acgttcaatt atcttcaatt ccggtgttta aaccccagcg cctggcggg 10379

<210> SEQ ID NO 42
<211> LENGTH: 4140
<212> TYPE: DNA
<213> ORGANISM: Artificial Sequence
<220> FEATURE:
<223> OTHER INFORMATION: Synthetic: ADS_FS.2 donor cassette

<400> SEQUENCE: 42
tcctcttgtg gtccgtggct tgtaattttc gggaaagata gaaatcactg cattcatcga 60
aagaagtgaa aataaattgt atcggggaag taatgagggg tggaatacgt aattgcttct 120
caatttgata atacaagtta cagtcttttt attgagagtc cctggaagga aaattattga 180
tgtttacctt tttttgcgac gcgcgtctgg ccataaataa aagggttctc ttgccaagaa 240
aaaataaaaa ggcgccttaa gggaccttct atgacaaata tggtgaggta tgcaacctca 300
atgaagagca atgagaaaat ttaaggggta agtaagcatc ggaatttgtt gtttcctaac 360
aatttgtcta atttactcaa taatatcagg agaattgatc gaaaaaagca aaccaggaac 420
ccctcacaaa taagggaaca taaagtaatt gctcgtcttt acatacatgg cactcaatcc 480

-continued

```
cagacgtcgc gtgctaaaaa tccttatatt attggcccct caggagttta tttgaatttt    540
gattgcattg ctttcagtgg acagtatatc ataaaatttg caagggcata gtgcctgccc    600
tacgatgttg taaaacaatt tctgaaaata ggttcagaat caaaaatgat gtataaatat    660
tgaaataaat tttcacataa attgtgctcc tccgcaaagt cttgactaaa taaacaattt    720
gttaatatcc tttcaaaaat tcttactttt tttttggatg gacgcaaaga agtttaataa    780
tcatattaca tggcattacc accatataca tatccatata catatccata tctaatctta    840
cttatatgtt gtggaaatgt aaagagcccc attatcttag cctaaaaaaa ccttctcttt    900
ggaactttca gtaatacgct taactgctca ttgctatatt gaagtacgga ttagaagccg    960
ccgagcgggt gacagccctc cgaaggaaga ctctcctccg tgcgtcctcg tcttcaccgg   1020
tcgcgttcct gaaacgcaga tgtgcctcgc gccgcactgc tccgaacaat aaagattcta   1080
caatactagc ttttatggtt atgaagagga aaaattggca gtaacctggc cccacaaacc   1140
ttcaaatgaa cgaatcaaat taacaaccat aggatgataa tgcgattagt tttttagcct   1200
tatttctggg gtaattaatc agcgaagcga tgatttttga tctattaaca gatatataaa   1260
tgcaaaaact gcataaccac tttaactaat actttcaaca ttttcggttt gtattacttc   1320
ttattcaaat gtaataaaag tatcaacaaa aaattgttaa tatacctcta tactttaacg   1380
tcaaggagaa aaaaccccgg atccatgggt caatataaat taattttgaa tggtaaaact   1440
ttgaagggtg aaactactac cgaagcagta gatgcagcaa cagccgaaaa ggtctttaag   1500
caatatgcta atgataatgg tgttgatggt gaatggacct atgacgatgc aactaaaaca   1560
tttactgtaa ctgaaggatc catggctttg actgaagaaa aaccaatcag accaattgct   1620
aattttccac cttctatctg gggtgaccaa ttcttgatct acgaaaagca agttgagcaa   1680
ggtgttgaac aaatcgttaa cgatttgaag aaggaagtta gacaattgtt gaaggaagct   1740
ttggacatcc caatgaagca cgctaactta ttgaaattaa tcgacgaaat ccaaagatta   1800
ggtattccat accatttcga aagagaaatt gatcacgctt tgcaatgtat ttacgaaact   1860
tacggtgata actggaacgg tgacagatct tccttatggt tcagattaat gagaaagcaa   1920
ggttactacg ttacttgtga cgttttcaac aactacaaag ataagaatgg tgcttttaag   1980
caatctttgg ccaacgatgt tgaaggtttg ttagaattgt atgaagccac ctccatgaga   2040
gttcctggtg aaatcatctt ggaagacgct ttgggtttta ctagatctag attgtccatc   2100
atgactaaag atgccttctc tactaaccca gctttgttca ctgaaatcca aagagctttg   2160
aaacaaccat tgtggaagcg tttgccaaga atcgaagctg ctcaatacat cccattctac   2220
caacaacaag actctcacaa caaaaccttg ttgaaattgg ctaaattgga atttaacttg   2280
ttgcaatcct tgcacaagga agaattgtct cacgtttgta agtggtggaa agccttcgat   2340
attaagaaga acgctccatg tttgagagat agaattgtcg aatgttactt ctggggtttg   2400
ggttccggtt acgaaccaca atactctaga gctagagttt tctttactaa ggtggttgct   2460
gttattacct tgattgacga cacttacgac gcttacggta cctacgaaga attgaagatt   2520
ttcactgaag ctgtcgaaag atggtccatt acctgtttag atactttacc agaatacatg   2580
aagccaattt ataagttgtt catggacact tacaccgaaa tggaagaatt cttggctaag   2640
gaaggtcgta ccgacttgtt caattgtggt aaggaattcg ttaaggaatt cgttcgtaac   2700
ttgatggttg aagctaaatg ggctaacgaa ggtcatattc caactactga agaacacgat   2760
ccagtcgtta tcattactgg tggtgctaac ttgttgacta ctacttgtta cttaggtatg   2820
tctgatattt tcaccaagga atctgttgaa tgggccgttt ccgctccacc tttgttcaga   2880
```

tactctggta ttttgggtag aagattaaac gatttgatga ctcacaaggc tgagcaagaa 2940
agaaagcact cctcctcttc cttagaatct tacatgaagg aatacaacgt taacgaagaa 3000
tacgctcaaa ctttgattta caaggaagtt gaagacgttt ggaaagatat taacagagaa 3060
tacttgacca ccaaaaatat tccacgtcca ttgttaatgg ctgttatcta tttatgtcaa 3120
ttcttagaag ttcaatacgc tggtaaagac aatttcacca gaatgggtga cgaatataag 3180
cacttaatta agtctttgtt ggtctaccct atgtctatct aagatccgct ctaaccgaaa 3240
aggaaggagt cagacaacct gaagtctagg tccctattta ttttttata gttatgttag 3300 tattaagaac gttatttata tttcaaattt ttcttttttt tctgtacaga cgcgtgtacg 3360
catgtaacat tatactgaaa accttgcttg agaaggtttt gggacgctcg aagctacctt 3420
tttgttcttt tacttaaaca ttagttagtt cgttttcttt ttctcatttt tttatgtttc 3480
ccccccaaag ttctgatttt ataatatttt atttcacaca attccattta acagaggggg 3540
aatagattct ttagcttaga aaattagtga tcaatatata tttgcctttc ttttcatctt 3600
ttcagtgata ttaatggttt cgagacactg caatggccct agttgtctaa gaggatagat 3660
gttactgtca aagatgatat tttgaatttc aattgacgta attaatgata ctattaataa 3720
tacagagcgt atatgaagta ttgcaaataa catgcacagt tcttttggga tgagaatgat 3780
aatgaaaggc gaaggcgggc gttcagaaaa gcgttgcgga gtaacaagtg attaaatagc 3840
acccaaataa tcttctttga tactaccgat tgcgtgaata gaactcactt gactgataca 3900
accttcaatt ttaactctaa ttctactttt tatggtgatg acatcctcgg aactttggta 3960
tgatggtggg tttgaacccg cattaaaggt taaatcttga ggcatcagat gctttgtcac 4020
aaatactttc attggaccta cttgcacttc gaacccgtgc tgagaacatg aaacgactgt 4080
gccgtccact acttcccctt taaatggttt gaaaactaca gctctatatt tcacgttgaa 4140

<210> SEQ ID NO 43
<211> LENGTH: 4475
<212> TYPE: DNA
<213> ORGANISM: Artificial Sequence
<220> FEATURE:
<223> OTHER INFORMATION: Synthetic: ADS_FS.3 donor cassette

<400> SEQUENCE: 43
attgaagcac ctgtggagta tttaaaaact gcggttacat ggcctacaga tgaaatatgt 60
gctcaactaa tgacacaatt cccaccagga acgccgacca gtgtcctgct gcagactatt 120
tcagatgagc tagagaaaag ttctgacaac ctgttcacgt tatctgattt aaagagcaaa 180
ctgaaagtta ttggcttatt cgagcacatg gaagatatcc catttttcga caagctgaaa 240
ctaagcaatg cgcccgtgaa ggacatgcct atggtcacaa aggcgttcac caaattttgc 300
gaaacaatag caaaaaggca tacaagaggc ctactgtcat accgattacc ttttaaccta 360
ctggactaca attgcatacc gaatgagagt tattcattag aggtttatga gtcattgtac 420
aacatcatta ctctatactt ctggctcagc aacaggtacc caaactactt cattgacatg 480
gaatctgcta aagatttgaa gtatttctgt gagatgatta ttttcgagaa acttgatcga 540
ttaaagaaga atccttacgc acataagccc tttggttcta caagaggtca cctctcatct 600
tcgagaagaa gattgcgtac ataatctacg atatatcctg taaatagaaa cagctacact 660
gcttgaaagc cttaacatga tacatttctg gtatgatgcc attgttgtgc cctgccgggt 720
ttatcgtttc ctaacaggca cgtcacttat aacgaggtgc ctgtcgttta ccgcccaagc 780 cggtttttc gctggagagt acggtactac tagcccacca cacgttcgtg gccaggttga 840

-continued

```
taggccaccg ttgagcaaag ggcagtaaaa tatataaaag aggaacaagc gcttccatta    900
agagcactgc taagcctact cgttttctag ttctctgaaa aaaggtagcc taaaacaagc    960
gccatatcat atatatttat acagattaga cgtactcaaa attcttactt ttttttgga    1020
tggacgcaaa gaagtttaat aatcatatta catggcatta ccaccatata catatccata   1080
tacatatcca tatctaatct tacttatatg ttgtggaaat gtaaagagcc ccattatctt   1140
agcctaaaaa aaccttctct ttggaacttt cagtaatacg cttaactgct cattgcgccg   1200
ccgagcgggt gacagccctc cgaaggaaga ctctcctccg tgcgtcctcg tcttcaccgg   1260
tcgcgttcct gaaacgcaga tgtgcctcgc gccgcactgc tccgaacaat aaagattcta   1320
caatactagc ttttatggtt atgaagagga aaaattggca gtaacctggc cccacaaacc   1380
ttcaaatgaa cgaatcaaat taacaaccat aggatgataa tgcgattagt tttttagcct   1440
tatttctggg gtaattaatc agcgaagcga tgatttttga tctattaaca gatatataaa   1500
tgcaaaaact gcataaccac tttaactaat actttcaaca ttttcggttt gtattacttc   1560
ttattcaaat gtaataaaag tatcaacaaa aaattgttaa tatacctcta tactttaacg   1620
tcaaggagaa aaaactataa tggtcaata taaattaatt ttgaatggta aaactttgaa    1680
gggtgaaact actaccgaag cagtagatgc agcaacagcc gaaaaggtct ttaagcaata   1740
tgctaatgat aatggtgttg atggtgaatg gacctatgac gatgcaacta aaacatttac   1800
tgtaactgaa ggatccatgg ctttgactga agaaaaacca atcagaccaa ttgctaattt   1860
tccaccttct atctggggtg accaattctt gatctacgaa aagcaagttg agcaaggtgt   1920
tgaacaaatc gttaacgatt tgaagaagga agttagacaa ttgttgaagg aagctttgga   1980
catcccaatg aagcacgcta acttattgaa attaatcgac gaaatccaaa gattaggtat   2040
tccataccat ttcgaaagag aaattgatca cgctttgcaa tgtatttacg aaacttacgg   2100
tgataactgg aacggtgaca gatcttcctt atggttcaga ttaatgagaa agcaaggtta   2160
ctacgttact tgtgacgttt tcaacaacta caaagataag aatggtgctt ttaagcaatc   2220
tttggccaac gatgttgaag gtttgttaga attgtatgaa gccacctcca tgagagttcc   2280
tggtgaaatc atcttggaag acgctttggg ttttactaga tctagattgt ccatcatgac   2340
taaagatgcc ttctctacta acccagcttt gttcactgaa atccaaagag ctttgaaaca   2400
accattgtgg aagcgtttgc caagaatcga agctgctcaa tacatcccat tctaccaaca   2460
acaagactct cacaacaaaa ccttgttgaa attggctaaa ttggaattta acttgttgca   2520
atccttgcac aaggaagaat tgtctcacgt ttgtaagtgg tggaaagcct tcgatattaa   2580
gaagaacgct ccatgtttga gagatagaat tgtcgaatgt tacttctggg gtttgggttc   2640
cggttacgaa ccacaatact ctagagctag agtttcttt actaaggtgg ttgctgttat    2700
taccttgatt gacgacactt acgacgctta cggtacctac gaagaattga agattttcac   2760
tgaagctgtc gaaagatggt ccattacctg tttagatact ttaccagaat acatgaagcc   2820
aatttataag ttgttcatgg acacttacac cgaaatggaa gaattcttgg ctaaggaagg   2880
tcgtaccgac ttgttcaatt gtggtaagga attcgttaag gaattcgttc gtaacttgat   2940
ggttgaagct aaatgggcta acgaaggtca tattccaact actgaagaac acgatccagt   3000
cgttatcatt actggtggtg ctaacttgtt gactactact tgttacttag gtatgtctga   3060
tattttcacc aaggaatctg ttgaatgggc cgtttccgct ccacctttgt tcagatactc   3120
tggtattttg ggtagaagat taaacgattt gatgactcac aaggctgagc aagaaagaaa   3180
gcactcctcc tcttccttag aatcttacat gaaggaatac aacgttaacg aagaatacgc   3240
```

tcaaactttg atttacaagg aagttgaaga cgtttggaaa gatattaaca gagaatactt 3300
gaccaccaaa aatattccac gtccattgtt aatggctgtt atctatttat gtcaattctt 3360
agaagttcaa tacgctggta aagacaattt caccagaatg ggtgacgaat ataagcactt 3420
aattaagtct ttgttggtct accctatgtc tatctaagat ccgctctaac cgaaaaggaa 3480
ggagttagac aacctgaagt ctaggtccct atttattttt ttatagttat gttagtatta 3540
agaacgttat ttatatttca aatttttctt ttttttctgt acagacgcgt gtacgcatgt 3600
aacattatac tgaaaacctt gcttgagaag gttttgggac gctcgaagga tacttgcaca 3660
agttccacta attactgaca tttgtggtat taactcgttt gactgctcta caattgtagg 3720
atgttaatca atgtcttggc tgccttcatt ctcttcaggc tctattaatt ttaaccgtta 3780
taagttcctt ttctcccttg gaagcaaaca tcaactgcct taaaatctgg tggcgaggaa 3840
agaggaaatg gcatgtacta atgatggtcc taataaatat cccgaaattg tgagtgttaa 3900
gcacctgttc caacattcgg gatccaagca tgaatttagt gctggtaaac gattttcaaa 3960
atccattggt aaaatattca aacgaaactc tgctttgaaa acttctagaa ctgaaacggc 4020
aaatcataaa atggaattga aaaaaagaga gggtgttacc ttattgccac ctgtcccaga 4080
atcattatta cataaactca attcttggtt ggaaactttt tcttccacca agaacatgaa 4140
aatcgaagaa aacaaaattg ttattaatga aaaagagatt cgggattcag tctcttacta 4200
ccctgataag aatggaggaa gtgctgtatt ttgttacttg cccgaccttg tgctatatta 4260
taagccgcct ataaaagtca caggcaagca atgtccaata aagagaagtc cttgggaatc 4320
gatggaaatc caatatcaaa agtttatgta ccccttagaa aggttggaaa gacagtttga 4380
ggaagttcca tttaggccct ggtattttgc aatgcgatta aaggaacttt acagatgctg 4440
tgaaaggtct tttactaacg cggcaaatag aggaa 4475

<210> SEQ ID NO 44
<211> LENGTH: 8247
<212> TYPE: DNA
<213> ORGANISM: Artificial Sequence
<220> FEATURE:
<223> OTHER INFORMATION: Synthetic: 9XFS_URA3_FS.4 donor cassette

<400> SEQUENCE: 44
attgctattg agtaagttcg atccgtttgg cgtcttttgg ggtgtaacgc caaacttatt 60
acttttccta tttgaggttg gtattgattg ttgtcaaaga atgaaaatat acacaaacgc 120
cacaatatac gtaccaggtt cacgaaaact gatcgtatgg ttcataccct gacttggcaa 180
acctaatgtg accgtcgctg attagcggat cacgaaaagt gatctcgata caattagagg 240
atccacgaaa atgatgtgaa tgaatacatg aaagattcat gagatctgac aacatggtag 300
acgtgtgtgt ctcatggaaa ttgatgcagt tgaagacatg tgcgtcacga aaaaagaaat 360
caatcctaca cagggcttaa gggcaaatgt attcatgtgt gtcacgaaaa gtgatgtaac 420
taaatacacg attaccatgg aaattaacgt accttttttg tgcgtgtatt gaaatattat 480
gacatattac agaaagggtt cgcaagtcct gtttctatgc ctttctctta gtaattcacg 540
aaataaacct atggtttacg aaatgatcca cgaaaatcat gttattattt acatcaacat 600
atcgcgaaaa ttcatgtcat gtccacatta acatcattgc agagcaacaa ttcattttca 660
tagagaaatt tgctactatc acccactagt actaccattg gtacctacta ctttgaattg 720
tactaccgct gggcgttatt aggtgtgaaa ccacgaaaag ttcaccataa cttcgaataa 780
agtcgcggaa aaaagtaaac agctattgct actcaaatga ggtttgcaga agcttgttga 840

-continued

```
agcatgatga agcgttctaa acgcactatt catcattaaa tatttaaagc tcataaaatt    900
gtattcaatt cctattctaa atggctttta tttctattac aactattagc tctaaatcca    960
tatcctcata agcagcaatc aattctatct atactttaaa agtaaaattc ttgagggaac   1020
tttcaccatt atgggaaatg gttcaagaag gtattgactt aaactccatc aaatggtcag   1080
gtcattgagt gtttttttatt tgttgtattt tttttttttt agagaaaatc ctccaatatc   1140
aaattaggaa tcgtagtttc atgattttct gttacaccta actttttgtg tggtgccctc   1200
ctccttgtca atattaatgt taaagtgcaa ttctttttcc ttatcacgtt gagccattag   1260
tatcaatttg cttacctgta ttcctttact atcctccttt ttctccttct tgataaatgt   1320
atgtagattg cgtatatagt ttcgtctacc ctatgaacat attccatttt gtaatttcgt   1380
gtcgtttcta ttatgaattt catttataaa gtttatgtac aaatatcata aaaaaagaga   1440
atctttttaa gcaaggattt tcttaacttc ttcggcgaca gcatcaccga cttcggtggt   1500
actgttggaa ccacctaaat caccagttct gatacctgca tccaaaacct ttttaactgc   1560
atcttcaatg gccttacctt cttcaggcaa gttcaatgac aatttcaaca tcattgcagc   1620
agacaagata gtggcgatag ggtcaacctt attctttggc aaatctggag cagaaccgtg   1680
gcatggttcg tacaaaccaa atgcggtgtt cttgtctggc aaagaggcca aggacgcaga   1740
tggcaacaaa cccaaggaac ctgggataac ggaggcttca tcggagatga tatcaccaaa   1800
catgttgctg gtgattataa taccatttag gtgggttggg ttcttaacta ggatcatggc   1860
ggcagaatca atcaattgat gttgaacctt caatgtaggg aattcgttct tgatggtttc   1920
ctccacagtt tttctccata atcttgaaga ggccaaaaca ttagctttat ccaaggacca   1980
aataggcaat ggtggctcat gttgtagggc catgaaagcg gccattcttg tgattctttg   2040
cacttctgga acggtgtatt gttcactatc ccaagcgaca ccatcaccat cgtcttcctt   2100
tctcttacca aagtaaatac ctcccactaa ttctctgaca acaacgaagt cagtaccttt   2160
agcaaattgt ggcttgattg gagataagtc taaaagagag tcggatgcaa agttacatgg   2220
tcttaagttg gcgtacaatt gaagttcttt acggattttt agtaaacctt gttcaggtct   2280
aacactaccg gtaccccatt taggaccacc cacagcacct aacaaaacgg catcaacctt   2340
cttggaggct tccagcgcct catctggaag tgggacacct gtagcatcga tagcagcacc   2400
accaattaaa tgattttcga aatcgaactt gacattggaa cgaacatcag aaatagcttt   2460
aagaacctta atggcttcgg ctgtgatttc ttgaccaacg tggtcacctg gcaaaacgac   2520
gatcttctta ggggcagaca taggggcaga cattagaatg gtatatcctt gaaatatata   2580
tatatattgc tgaaatgtaa aaggtaagaa aagttagaaa gtaagacgat tgctaaccac   2640
ctattggaaa aaacaatagg tccttaaata atattgtcaa cttcaagtat tgtgatgcaa   2700
gcatttagtc atgaacgctt ctctattcta tatgaaaagc cggttccggc ctctcacctt   2760
tccttttttct cccaattttt cagttgaaaa aggtatatgc gtcaggcgac ctctgaaatt   2820
aacaaaaaat ttccagtcat cgaatttgat tctgtgcgat agcgcccctg tgtgttctcg   2880
ttatgttgag gaaaaaaata atggttgcta agagattcga actcttgcat cttacgatac   2940
ctgagtattc ccacagttaa ctgcggtcaa gatatttctt gaatcaggcg ccttagaccg   3000
ctcggccaaa caaccaatta cttgttgaga aatagagtat aattatccta taaatataac   3060
gtttttgaac acacatgaac aaggaagtac aggacaattg attttgaaga gaatgtggat   3120
tttgatgtaa ttgttgggat tccatttttta ataaggcaat aatattaggt atgtggatat   3180
actagaagtt ctcctcgacc gtaataatca tattacatgg cattaccacc atatacatat   3240
```

-continued

```
ccatatacat atccatatct aatcttactt atatgttgtg gaaatgtaaa gagccccatt   3300
atcttagcct aaaaaaacct tctctttgga actttcagta atacgcttaa ctgctcattg   3360
cgccgccgag cgggtgacag ccctccgaag gaagactctc ctccgtgcgt cctcgtcttc   3420
accggtcgcg ttcctgaaac gcagatgtgc ctcgcgccgc actgctccga acaataaaga   3480
ttctacaata ctagctttta tggttatgaa gaggaaaaat tggcagtaac ctggccccac   3540
aaaccttcaa atgaacgaat caaattaaca accataggat gataatgcga ttagtttttt   3600
agccttattt ctggggtaat taatcagcga agcgatgatt tttgatctat taacagatat   3660
ataaatgcaa aaactgcata accactttaa ctaatacttt caacattttc ggtttgtatt   3720
acttcttatt caaatgtaat aaaagtatca acaaaaaatt gttaatatac ctctatactt   3780
taacgtcaag gagaaaaaac tataatgtcc actttgccta tttcctctgt ttcttcctct   3840
ccatctactt ccccaattgt tgtcgatgat aaggattcta ccaagccaga cgttattaga   3900
cataccgcta acttcaacgc ttccatttgg ggtgatcaat tttgacttta cgatgaacca   3960
gaggacttgg ttatgaagaa gcaattagtc gaagagttaa aggaggaagt taagaaggaa   4020
ttgattacta ttaagggttc taacgaacct atgcaacatg ttaagttgat cgaattaatc   4080
aatgctgttc aacgtttagg tattgcttac cattttgaag aagaaatcga agaagcttta   4140
caacatatcc atgtcactta cggtgaacaa tgggtcgata aggaaaattt acaatctatc   4200
tccttgtggt ttcgtttgtt gcgtcaacaa ggtttcaatg tctcctctgg tgttttcaag   4260
gactttatgg acgaaaaagg taaatttaag gaatctttgt gtaacgacgc tcaaggtatc   4320
ttggccttgt acgaagctgc tttcatgaga gtcgaagatg aaaccatctt ggacaacgct   4380
ttggaattct ctaaggttca cttggacatt attgccaagg atccatcttg tgactcttcc   4440
ttaagaaccc aaatccacca agccttgaag caaccattga gaagaagatt ggccagaatc   4500
gaagctttac actatatgcc aatttaccaa caagaaactt ctcacgacga ggtttttgttg   4560
aagttggcta agttagattt ctctgttttg caatccatgc ataagaaaga attgtctcac   4620
atctgcaagt ggtggaaaga tttagacttg caaaacaaat tgccattcgt tcgtgataga   4680
gttgtcgaag gttacttctg gattttgtct atttactatg aaccacaaca tgccagaacc   4740
agaatgttct tgatgaagtc ttgtatgtgg ttggtcgttt tggatgatac cttcgacaac   4800
tacggtacct acgaagaatt ggaaattttc actcaagccg ttgagaagtg gtccatttct   4860
tgtttggaca tgttgccaga atacatgaag ttgatctacc aagaattggt taacttgcac   4920
gttgaaatgg aagaatcttt agaaaaggaa ggtaaggctt atcaaatcca ctacgttaag   4980
gaaatggcta aggaattggt cagaaactac ttggttgaag ccagatggtt gaaagaaggt   5040
tacatgccta ctttggaaga gtacatgtct gtttccatgg ttaccggtac ctacggtttg   5100
atcactgcta gatcttacgt tggtagaggt gacattgtta acgaggacac ttttaaatgg   5160
gtttcttcct acccacctat tgttgaagct tcttgtgtta tcattagatt gatggatgat   5220
attgtctctc ataaagaaga acaagaaaga ggtcatgttg cctcctccat cgaatgttat   5280
tctaaggaat ccggtgcttc tgaagaagaa gcctgtgaat acatctctag aaaagtcgaa   5340
gacgcctgga aggttattaa cagagaatct ttgagaccaa ccgccgttcc attccctttg   5400
ttaatgccag ctatcaactt ggctagaatg tgtgaagttt tatactctgt taacgatggt   5460
ttcactcacg ccgaaggtga catgaaatct tacatgaagt ccttctttgt ccatccaatg   5520
gtcgtttgag cgaatttctt atgatttatg atttttatta ttaaataagt tataaaaaaa   5580
ataagtgtat acaaatttta aagtgactct taggttttaa aacgaaaatt cttattcttg   5640
```

-continued agtaactctt tcctgtaggt caggttgctt tctcaggtat agcatgaggt cgctcatgcg 5700
tccatcttta cagtcctgtc ttattgttct tgatttgtgc cccgtaaaat actgttactt 5760
ggttctggcg aggtattgga tagttccttt ttataaaggc catgaagctt tttctttcca 5820
attttttttt tttcgtcatt atagaaatca ttacgaccga gattcccggg taataactga 5880
tataattaaa ttgaagctct aatttgtgag tttagtatac atgcatttac ttataataca 5940 gtttttagt tttgctggcc gcatcttctc aaatatgctt cccagcctgc ttttctgtaa 6000
cgttcaccct ctaccttagc atcccttccc tttgcaaata gtcctcttcc aacaataata 6060
atgtcagatc ctgtagagac cacatcatcc acggttctat actgttgacc caatgcgtct 6120
cccttgtcat ctaaacccac accgggtgtc ataatcaacc aatcgtaacc ttcatctctt 6180
ccacccatgt ctctttgagc aataaagccg ataacaaaat ctttgtcact cttcgcaatg 6240
tcaacagtac ccttagtata ttctccagta gatagggagc ccttgcatga caattctgct 6300
aacatcaaaa ggcctctagg ttcctttgtt acttcttctg ccgcctgctt caaaccgcta 6360
acaatacctg ggcccaccac accgtgtgca ttcgtaatgt ctgcccattc tgctattctg 6420
tatacacccg cagagtactg caatttgact gtattaccaa tgtcagcaaa ttttctgtct 6480
tcgaagagta aaaaattgta cttggcggat aatgccttta gcggcttaac tgtgccctcc 6540
atggaaaaat cagtcaagat atccacatgt gtttttagta aacaaatttt gggacctaat 6600
gcttcaacta actccagtaa ttccttggtg gtacgaacat ccaatgaagc acacaagttt 6660
gtttgctttt cgtgcatgat attaaatagc ttggcagcaa caggactagg atgagtagca 6720
gcacgttcct tatatgtagc tttcgacatg atttatcttc gtttcctgca ggtttttgtt 6780
ctgtgcagtt gggttaagaa tactgggcaa tttcatgttt cttcaacacc acatatgcgt 6840
atatatacca atctaagtct gtgctccttc cttcgttctt ccttctgctc ggagattacc 6900
gaatcaaaaa aatttcaaag aaaccggaat caaaaaaaag aacaaaaaaa aaaaagatga 6960
attgaaaagc tttatggacc ctgaaaccac agccacatta accttctttg atggtcaaaa 7020
cttatccttc accataaata tgcctcgcaa aaaaggtaat taacatatat agaattacat 7080
tatttatgaa atatcatcac tatctcttag catctttaat ccttttctac atcagataac 7140
ttcggtttgt tatcatcgtc tgtattgtca tcaattggcg cagtagcctc aatttcaacg 7200
tcgtttgact ctggtgtttg ttcatgtgca gatccatgag atgatgaaat gtgtatatta 7260
gtttaaaaag ttgtatgtaa taaaagtaaa atttaatatt ttggatgaaa aaaaccattt 7320
ttagactttt tcttaactag aatgctggag tagaaatacg ccatctcaag atacaaaaag 7380
cgttaccggc actgatttgt ttcaaccagt atatagatta ttattgggtc ttgatcaact 7440
ttcctcagac atatcagtaa cagttatcaa gctaaatatt tacgcgaaag aaaaacaaat 7500
attttaattg tgatacttgt gaattttatt ttattaagga tacaaagtta agagaaaaca 7560
aaatttatat acaatataag taatattcat atatatgtga tgaatgcagt cttaacgaga 7620
agacatggcc ttggtgacaa ctctcttcaa accaacttca gcctttctca attcatcagc 7680
agatgggtct tcgatttgca aagcagccaa agcatcggac aaagcagctt caatcttgga 7740
cttggaacct ctcttcaatt tagaagacaa gactgggtca gtgacagttt gttcgatgga 7800
ggcaacgtag gattccaatc tttgtctagc ttcgtgcttc ttggcaaaag cttcatcggc 7860
agccttgaac tcttcagctt ggttaaccat cttttcaatt tcttcagaag acaatctacc 7920
aacagcgtta gagatagtga tgttagaaga cttaccggta gacttttcga cggcagtaac 7980
cttcaagata ccgttagcat caacttcgaa gatagcttcc aagactggtt caccagctgg 8040

```
catcattggg atgttcttca agtcgaattc acccaacaaa gtgttttctt tacagttaac    8100

acgttcacct tggtagactg ggaattgaac ggtggtttgg ttgtcagcac atgtagtaaa    8160

ggttcttctc ttgatggttg gaacagtagt gtttcttgga acaacgatac cgaacatgtc    8220

accttgcata ccaacaccta gagataa                                        8247

<210> SEQ ID NO 45
<211> LENGTH: 49
<212> TYPE: DNA
<213> ORGANISM: Artificial Sequence
<220> FEATURE:
<223> OTHER INFORMATION: Synthetic: Recognition sequence for FS-specific
      TALEN

<400> SEQUENCE: 45

tagtggagga attaaaagag gaagttaaga aggaattgat aactatcaa                49

<210> SEQ ID NO 46
<211> LENGTH: 26
<212> TYPE: DNA
<213> ORGANISM: Artificial Sequence
<220> FEATURE:
<223> OTHER INFORMATION: Synthetic: Primer HJ272

<400> SEQUENCE: 46

ataacaatat tataaaaagc gcttaa                                         26

<210> SEQ ID NO 47
<211> LENGTH: 29
<212> TYPE: DNA
<213> ORGANISM: Artificial Sequence
<220> FEATURE:
<223> OTHER INFORMATION: Synthetic: Primer ART45

<400> SEQUENCE: 47

tactgcttcg gtagtagttt cacccttca                                      29

<210> SEQ ID NO 48
<211> LENGTH: 22
<212> TYPE: DNA
<213> ORGANISM: Artificial Sequence
<220> FEATURE:
<223> OTHER INFORMATION: Synthetic: Primer HJ643

<400> SEQUENCE: 48

aaaatcctta tattattggc cc                                             22

<210> SEQ ID NO 49
<211> LENGTH: 19
<212> TYPE: DNA
<213> ORGANISM: Artificial Sequence
<220> FEATURE:
<223> OTHER INFORMATION: Synthetic: Primer HJ799

<400> SEQUENCE: 49

gtagcctaaa acaagcgcc                                                 19

<210> SEQ ID NO 50
<211> LENGTH: 9
<212> TYPE: PRT
<213> ORGANISM: Artificial Sequence
<220> FEATURE:
<223> OTHER INFORMATION: Synthetic: Homing endonuclease family conserved
      motif

<400> SEQUENCE: 50
```

```
Leu Ala Gly Leu Ile Asp Ala Asp Gly
1               5


<210> SEQ ID NO 51
<211> LENGTH: 6
<212> TYPE: PRT
<213> ORGANISM: Artificial Sequence
<220> FEATURE:
<223> OTHER INFORMATION: Synthetic: Homing endonuclease family conserved
      motif

<400> SEQUENCE: 51

Gly Ile Tyr Tyr Ile Gly
1               5


<210> SEQ ID NO 52
<211> LENGTH: 18
<212> TYPE: DNA
<213> ORGANISM: Artificial Sequence
<220> FEATURE:
<223> OTHER INFORMATION: Synthetic: Recognition sequence for I-SceI

<400> SEQUENCE: 52

tagggataac agggtaat                                                    18


<210> SEQ ID NO 53
<211> LENGTH: 31
<212> TYPE: DNA
<213> ORGANISM: Artificial Sequence
<220> FEATURE:
<223> OTHER INFORMATION: Synthetic: Recognition sequence for VDE
      (PI-SceI)

<400> SEQUENCE: 53

tatgtcgggt gcggagaaag aggtaatgaa a                                     31


<210> SEQ ID NO 54
<211> LENGTH: 24
<212> TYPE: DNA
<213> ORGANISM: Artificial Sequence
<220> FEATURE:
<223> OTHER INFORMATION: Synthetic: Recognition sequence for F-CphI

<400> SEQUENCE: 54

gatgcacgag cgcaacgctc acaa                                             24


<210> SEQ ID NO 55
<211> LENGTH: 24
<212> TYPE: DNA
<213> ORGANISM: Artificial Sequence
<220> FEATURE:
<223> OTHER INFORMATION: Synthetic: Recognition sequence for PI-MgaI

<400> SEQUENCE: 55

gcgtagctgc ccagtatgag tcag                                             24


<210> SEQ ID NO 56
<211> LENGTH: 40
<212> TYPE: DNA
<213> ORGANISM: Artificial Sequence
<220> FEATURE:
<223> OTHER INFORMATION: Synthetic: Recognition sequence for PI-MtuII

<400> SEQUENCE: 56

acgtgcacta cgtagagggt cgcaccgcac cgatctacaa                            40


<210> SEQ ID NO 57
```

<211> LENGTH: 4300
<212> TYPE: DNA
<213> ORGANISM: Artificial Sequence
<220> FEATURE:
<223> OTHER INFORMATION: Synthetic: ADE2_SFC1 donor cassette

<400> SEQUENCE: 57
ccggtggtgc ttatactgtt tctactgcag ctgccgctac tgttagatct accatcagaa 60
gattaagaga aatggttgaa gcttaaactt ctttcattca ttttctcttg gctttcacta 120
ggtatatcta ttccataacg actatgtttt gtatttgtta atttacataa aaccatatca 180
gtacatcaac gaactgtaaa aaagaaactt tagcataatt attgcggata tttaaactca 240
cttgcaggta agagcaaaag gcgattgatt tccagtccgc ctcttgtcac gtgatttagt 300
aagaaatttt gacagcaccc tcggtttaat ggaaaagagg ggcgtttttc gatgaacccg 360
aggggagact agagaatcat ctcggttgaa tggagcatta ttttttagt agcgcccgcc 420 cggagaaatg gacgttggcg aatgagccat gaattattaa ccgcccatgt ctaccagata 480
gacggcacgg ccacgcgttt aaaccgcccc acatcgtatg acagtaccag cctagtcccg 540
gtaaaccgca aacggacctt aattgtgacg aagggcccaa atttgatggg tcggtgttaa 600
tgattagtcc tcattgtcat aataaagtgt gatgatggag gcaatgatga tatacggtag 660
tactactgct cgaggtgcta tcttttaacc aatcctttga gattcttgtc gccacggagt 720
tactaccttt tacaaaccgt aatgtcacat tttgcatata tcttatgtat aaatatatag 780
ttcacttact acttgttctc gttttgttaa ctttcttgtt gtagttcttc ttgttcttgg 840
cgtttccccc tttgttttct atctgcttca taagtaaagt gcaaagcatt ttggaagata 900
ttatcaattg agtcattgaa agaaacttgg catcttccct attactaaaa ctaagaatac 960
ttgattcaag aaagaagttt atattagttt tagccgtaag ataacataac aaagaagaag 1020
aaagaaaatt cttgaataat acataacttt tcttaaaaga atcaaagaca gataaaattt 1080
aagagatatt aaatattagt gagaagccga gaattttgta acaccaacat aacactgaca 1140
tctttaacaa cttttaatta tgatacattt cttacgtcat gattgattat tacagctatg 1200
ctgacaaatg actcttgttg catggctacg aaccgggtaa tactaagtga ttgactcttg 1260
ctgacctttt attaagaact aaatggacaa tattatggag catttcatgt ataaattggt 1320
gcgtaaaatc gttggatctc tcttctaagt acatcctact ataacaatca agaaaaacaa 1380
gaaaatcgga caaaacaatc aagtatggat tctagaacag ttggtatatt aggaggggga 1440
caattgggac gtatgattgt tgaggcagca aacaggctca acattaagac ggtaatacta 1500
gatgctgaaa attctcctgc caaacaaata agcaactcca atgaccacgt taatggctcc 1560
ttttccaatc ctcttgatat cgaaaaacta gctgaaaaat gtgatgtgct aacgattgag 1620
attgagcatg ttgatgttcc tacactaaag aatcttcaag taaaacatcc caaattaaaa 1680
atttaccctt ctccagaaac aatcagattg atacaagaca aatatattca aaaagagcat 1740
ttaatcaaaa atggtatagc agttacccaa agtgttcctg tggaacaagc cagtgagacg 1800
tccctattga atgttggaag agatttgggt tttccattcg tcttgaagtc gaggactttg 1860
gcatacgatg gaagaggtaa cttcgttgta aagaataagg aaatgattcc ggaagctttg 1920
gaagtactga aggatcgtcc tttgtacgcc gaaaaatggg caccatttac taaagaatta 1980
gcagtcatga ttgtgaggtc tgttaacggt ttagtgtttt cttacccaat tgtagagact 2040
atccacaagg acaatatttg tgacttatgt tatgcgcctg ctagagttcc ggactccgtt 2100
caacttaagg cgaagttgtt ggcagaaaat gcaatcaaat cttttcccgg ttgtggtata 2160

-continued

```
tttggtgtgg aaatgttcta tttagaaaca ggggaattgc ttattaacga aattgcccca   2220
aggcctcaca actctggaca ttataccatt gatgcttgcg tcacttctca atttgaagct   2280
catttgagat caatattgga tttgccaatg ccaaagaatt tcacatcttt ctccaccatt   2340
acaacgaacg ccattatgct aaatgttctt ggagacaaac atacaaaaga taaagagcta   2400
gaaacttgcg aaagagcatt ggcgactcca ggttcctcag tgtacttata tggaaaagag   2460
tctagaccta acagaaaagt aggtcacata aatattattg cctccagtat ggcggaatgt   2520
gaacaaaggc tgaactacat tacaggtaga actgatattc caatcaaaat ctctgtcgct   2580
caaaagttgg acttggaagc aatggtcaaa ccattggttg gaatcatcat gggatcagac   2640
tctgacttgc cggtaatgtc tgccgcatgt gcggttttaa aagattttgg cgttccattt   2700
gaagtgacaa tagtctctgc tcatagaact ccacatagga tgtcagcata tgctatttcc   2760
gcaagcaagc gtggaattaa aacaattatc gctggagctg gtggggctgc tcacttgcca   2820
ggtatggtgg ctgcaatgac accacttcct gtcatcggtg tgcccgtaaa aggttcttgt   2880
ctagatggag tagattcttt acattcaatt gtgcaaatgc ctagaggtgt tccagtagct   2940
accgtcgcta ttaataatag tacgaacgct gcgctgttgg ctgtcagact gcttggcgct   3000
tatgattcaa gttatacaac gaaaatggaa cagtttttat taaagcaaga agaagaagtt   3060
cttgtcaaag cacaaaagtt agaaactgtc ggttacgaag cttatctaga aaacaagtaa   3120
tatataagtt tattgatata cttgtacagc aaataattat aaaatgatat acctattttt   3180
taggctttgt tatgattaca tcaaatgtgg acttcataca tagaaatcaa cgcttacagg   3240
tgtccttttt taagaatttc atacataaga tcatgatgaa caatgggact acaaaatgaa   3300
ataaagaaaa aatagaaata gaatagaaga tcaattatta atcgccctat tcttccttat   3360
tacctacaca aaataaagca gcaacataag aaacaaaaac aaaatgaaaa caaaccaaat   3420
aaatctatgt aagcatactc atttcaattt gatattcatt acttgacttt tttgtcctta   3480
tttgaggctc cataagcgcg ccattttccc ctactccctt ttttcgtaaa tagtaataat   3540
gtgctgaaaa gaacaatgaa gtagttatca tacatattcc gtcgtgtcga tatgagggga   3600
ggtgtctctt tctttcatcc cttgtcgcaa cctccaatat ataagagcat aagcaactga   3660
tcttacttta gtaattaact tagcatacct ggcccgaagg aagaaaaaaa attcacctca   3720
acaacatggt tcctaagttt tacaaacttt caaacggctt caaaatccca agcattgctt   3780
tgggaaccta ccggtgttta aaccccagcg cctggcgggg atattccaag atcgcaaaca   3840
gccgaaattg tgtatgaagg tgtcaagtgc ggctaccgtc atttcgatac tgctgttctt   3900
tatggtaatg agaaggaagt tggcgatggt atcattaaat ggttgaacga agatccaggg   3960
aaccataaac gtgaggaaat cttctacact actaaattat ggaattcgca aaacggatat   4020
aaaagagcta aagctgccat tcagcaatgt ttgaatgaag tctcgggctt gcaatacatc   4080
gatcttcttt tgattcattc gccactggaa ggttctaaat taaggttgga aacttggcgc   4140
gccatgcaag aagcggttga tgaaggattg gttaagtcta taggggtttc caactatggg   4200
aaaaagcaca ttgatgaact tttgaactgg ccagaactga agcacaagcc agtggtcaac   4260
caaatcgaga tatcaccttg gattatgaga caagaattag                        4300
```

<210> SEQ ID NO 58
<211> LENGTH: 3586
<212> TYPE: DNA
<213> ORGANISM: Artificial Sequence
<220> FEATURE:
<223> OTHER INFORMATION: Synthetic: GFP_SFC1 donor cassette

<400> SEQUENCE: 58

```
ccggtggtgc ttatactgtt tctactgcag ctgccgctac tgttagatct accatcagaa     60
gattaagaga aatggttgaa gcttaaactt ctttcattca ttttctcttg gctttcacta    120
ggtatatcta ttccataacg actatgtttt gtatttgtta atttacataa aaccatatca    180
gtacatcaac gaactgtaaa aaagaaactt tagcataatt attgcggata tttaaactca    240
cttgcaggta agagcaaaag gcgattgatt tccagtccgc ctcttgtcac gtgatttagt    300
aagaaatttt gacagcaccc tcggtttaat ggaaaagagg ggcgtttttc gatgaacccg    360
aggggagact agagaatcat ctcggttgaa tggagcatta tttttttagt agcgcccgcc    420
cggagaaatg gacgttggcg aatgagccat gaattattaa ccgcccatgt ctaccagata    480
gacggcacgg ccacgcgttt aaaccgcccc acatcgtatg acagtaccag cctagtcccg    540
gtaaaccgca aacggacctt aattgtgacg aagggcccaa atttgatggg tcggtgttaa    600
tgattagtcc tcattgtcat aataaagtgt gatgatggag gcaatgatga tatacggtag    660
tactactgct cgaggtgcta tcttttaacc aatcctttga gattcttgtc gccacggagt    720
tactaccttt tacaaaccgt aatgtcacat tttgcatata tcttatgtat aaatatatag    780
ttcacttact acttgttctc gttttgttaa ctttcttgtt gtagttcttc ttgttcttgg    840
cgtttccccc tttgttttct atctgcttca taagtaaagt gcaaagcatt ttggaagata    900
ttatcaattg agtcattgaa agaaacttgg catcttccct attactaaaa ctaagaatac    960
ttgattcaag aaagaagttt atattagttt tagccgtaag ataacataac aaagaagaag   1020
aaagaaaaac acaattacag taacaataac aagaggacag atactaccaa aatgtgtggg   1080
gaagcgggta agctgccaca gcaattaatg cacaacattt aacctacatt cttccttatc   1140
ggatcctcaa aacccttaaa aacatatgcc tcaccctaac atattttcca attaaccctc   1200
aatatttctc tgtcacccgg cctctatttt ccattttctt ctttacccgc cacgcgtttt   1260
tttctttcaa attttttttct tctttcttct ttttcttcca cgtcctcttg cataaataaa   1320
taaaccgttt tgaaaccaaa ctcgcctctc tctctccttt ttgaaatatt tttgggtttg   1380
tttgatcctt tccttcccaa tctctcttgt ttaatatata ttcatttata tcacgctctc   1440
tttttatctt cctttttttc ctctctcttg tattcttcct tcccctttct actcaaacca   1500
agaagaaaaa gaaaaggtca atctttgtta aagaatagga tcttctacta catcagcttt   1560
tagattttc acgcttactg cttttttctt cccaagatcg aaaatttact gaattaacaa   1620
tggtgagcaa gggcgaggag ctgttcaccg gggtggtgcc catcctggtc gagctggacg   1680
gcgacgtaaa cggccacaag ttcagcgtgt ccggcgaggg cgagggcgat gccacctacg   1740
gcaagctgac cctgaagttc atctgcacca ccggcaagct gcccgtgccc tggcccaccc   1800
tcgtgaccac cttgacctac ggcgtgcagt gcttcgcccg ctaccccgac cacatgaagc   1860
agcacgactt cttcaagtcc gccatgcccg aaggctacgt ccaggagcgc accatcttct   1920
tcaaggacga cggcaactac aagacccgcg ccgaggtgaa gttcgagggc gacaccctgg   1980
tgaaccgcat cgagctgaag ggcatcgact tcaaggagga cggcaacatc ctggggcaca   2040
agctggagta caactacaac agccacaagg tctatatcac cgccgacaag cagaagaacg   2100
gcatcaaggt gaacttcaag acccgccaca acatcgagga cggcagcgtg cagctcgccg   2160
accactacca gcagaacacc cccatcggcg acggccccgt gctgctgccc gacaaccact   2220
acctgagcac ccagtccgcc ctgagcaaag accccaacga gaagcgcgat cacatggtcc   2280
tgctggagtt cgtgaccgcc gccgggatca ctctcggcat ggacgagctg tacaagtaac   2340
```

-continued

```
tcgagaagct tgatccggct gcgaatttct tatgatttat gatttttatt attaaataag   2400

ttataaaaaa aataagtgta tacaaatttt aaagtgactc ttaggtttta aaacgaaaat   2460

tcttattctt gagtaactct ttcctgtagg tcaggttgct ttctcaggta tagcatgagg   2520

tcgctcttat tgaccacacc tctaccggca tgccgagcat gatgaacaat gggactacaa   2580

aatgaaataa agaaaaaata gaaatagaat agaagatcaa ttattaatcg ccctattctt   2640

ccttattacc tacacaaaat aaagcagcaa cataagaaac aaaaacaaaa tgaaaacaaa   2700

ccaaataaat ctatgtaagc atactcattt caatttgata ttcattactt gactttttg   2760

tccttatttg aggctccata agcgcgccat tttcccctac tccctttttt cgtaaatagt   2820

aataatgtgc tgaaaagaac aatgaagtag ttatcataca tattccgtcg tgtcgatatg   2880

aggggaggtg tctctttctt tcatcccttg tcgcaacctc caatatataa gagcataagc   2940

aactgatctt actttagtaa ttaacttagc atacctggcc cgaaggaaga aaaaaaattc   3000

acctcaacaa catggttcct aagttttaca aactttcaaa cggcttcaaa atcccaagca   3060

ttgctttggg aacctaccgg tgtttaaacc ccagcgcctg gcggggatat tccaagatcg   3120

caaacagccg aaattgtgta tgaaggtgtc aagtgcggct accgtcattt cgatactgct   3180

gttctttatg gtaatgagaa ggaagttggc gatggtatca ttaaatggtt gaacgaagat   3240

ccagggaacc ataaacgtga ggaaatcttc tacactacta aattatggaa ttcgcaaaac   3300

ggatataaaa gagctaaagc tgccattcag caatgtttga atgaagtctc gggcttgcaa   3360

tacatcgatc ttcttttgat tcattcgcca ctggaaggtt ctaaattaag gttggaaact   3420

tggcgcgcca tgcaagaagc ggttgatgaa ggattggtta agtctatagg ggtttccaac   3480

tatgggaaaa agcacattga tgaacttttg aactggccag aactgaagca caagccagtg   3540

gtcaaccaaa tcgagatatc accttggatt atgagacaag aattag                  3586


<210> SEQ ID NO 59
<211> LENGTH: 4300
<212> TYPE: DNA
<213> ORGANISM: Artificial Sequence
<220> FEATURE:
<223> OTHER INFORMATION: Synthetic: ADE2_YJR030C donor cassette

<400> SEQUENCE: 59

ggaactttat gaacatatta agtctgcttg atgaaatgtc atgtgcaggt gccgttggca     60

caaaatggga acaaaattat gaaaattcag tcgaggatgg gtgtgaagca cctgaatcca    120

atccataccg ttctattatt gatctttcta gtcgttccat taatataact gcagacctac    180

tttcgactgt tgggaggagt aattcagcac tcaacaagaa tgagattata gctgctattc    240

aaggtctcgc ccatcaatgc ctcaatccct gtgacgaact aggtatgcaa gcattgcaag    300

cattagagaa cattctgtta tctcgagcaa gtcaactacg tacggaaaaa gttgcggtgg    360

ataacctact agagacagga ttattaccga tttttgagtt ggatgaaatc caagatgtca    420

agatgaaacg aattactagc attttatccg ttctttctaa aatgacggca cggccacgcg    480

tttaaaccgc ccttcttggg tcaacttgtg gaaggcgtaa caagtaacga aacttttttg    540

agagtgctta acgtatttaa caagtatgta gatgatccta cggtggaaag gcagttgcaa    600

gagttgatta tttctaagag ggaaatcgag aaggagtaga ccaacgataa tgtaactata    660

ccaagaaact tagtatgatg gaattttttc aaggagtcgt aaattagatt ttcgcaggta    720

ataatgcgat atataagcaa tctcatttaa atatcgacgg tggcatttat accatcattt    780

actgttatat ttatctaacg cgtcgcgacg cgttagataa aatacaacaa gatttttttt    840
```

-continued

```
tcgtgtcacc aatggcatga aagcttcgag aataatttga aggaaatttc acttaatggg    900
aaaaataaaa atgtaccctt atcgagatta ctcttttacc ctcagttcaa ttaaaattca    960
tcatgaacca agtaaaagtt cctctaatta cgaacgagca agcaaattag tattgtgtgg   1020
gagacgggtt cttgaataat acataacttt tcttaaaaga atcaaagaca gataaaattt   1080
aagagatatt aaatattagt gagaagccga gaattttgta acaccaacat aacactgaca   1140
tctttaacaa cttttaatta tgatacattt cttacgtcat gattgattat tacagctatg   1200
ctgacaaatg actcttgttg catggctacg aaccgggtaa tactaagtga ttgactcttg   1260
ctgacctttt attaagaact aaatggacaa tattatggag catttcatgt ataaattggt   1320
gcgtaaaatc gttggatctc tcttctaagt acatcctact ataacaatca agaaaaacaa   1380
gaaaatcgga caaaacaatc aagtatggat tctagaacag ttggtatatt aggaggggga   1440
caattgggac gtatgattgt tgaggcagca aacaggctca acattaagac ggtaatacta   1500
gatgctgaaa attctcctgc caaacaaata agcaactcca atgaccacgt taatggctcc   1560
ttttccaatc ctcttgatat cgaaaaacta gctgaaaaat gtgatgtgct aacgattgag   1620
attgagcatg ttgatgttcc tacactaaag aatcttcaag taaaacatcc caaattaaaa   1680
atttaccctt ctccagaaac aatcagattg atacaagaca aatatattca aaaagagcat   1740
ttaatcaaaa atggtatagc agttacccaa agtgttcctg tggaacaagc cagtgagacg   1800
tccctattga atgttggaag agatttgggt tttccattcg tcttgaagtc gaggactttg   1860
gcatacgatg gaagaggtaa cttcgttgta aagaataagg aaatgattcc ggaagctttg   1920
gaagtactga aggatcgtcc tttgtacgcc gaaaaatggg caccatttac taaagaatta   1980
gcagtcatga ttgtgaggtc tgttaacggt ttagtgtttt cttacccaat tgtagagact   2040
atccacaagg acaatatttg tgacttatgt tatgcgcctg ctagagttcc ggactccgtt   2100
caacttaagg cgaagttgtt ggcagaaaat gcaatcaaat cttttcccgg ttgtggtata   2160
tttggtgtgg aaatgttcta tttagaaaca ggggaattgc ttattaacga aattgcccca   2220
aggcctcaca actctggaca ttataccatt gatgcttgcg tcacttctca atttgaagct   2280
catttgagat caatattgga tttgccaatg ccaaagaatt tcacatcttt ctccaccatt   2340
acaacgaacg ccattatgct aaatgttctt ggagacaaac atacaaaaga taaagagcta   2400
gaaacttgcg aaagagcatt ggcgactcca ggttcctcag tgtacttata tggaaaagag   2460
tctagaccta acagaaaagt aggtcacata aatattattg cctccagtat ggcggaatgt   2520
gaacaaaggc tgaactacat tacaggtaga actgatattc caatcaaaat ctctgtcgct   2580
caaaagttgg acttggaagc aatggtcaaa ccattggttg gaatcatcat gggatcagac   2640
tctgacttgc cggtaatgtc tgccgcatgt gcggttttaa aagattttgg cgttccattt   2700
gaagtgacaa tagtctctgc tcatagaact ccacatagga tgtcagcata tgctatttcc   2760
gcaagcaagc gtggaattaa aacaattatc gctggagctg gtggggctgc tcacttgcca   2820
ggtatggtgg ctgcaatgac accacttcct gtcatcggtg tgcccgtaaa aggttcttgt   2880
ctagatggag tagattcttt acattcaatt gtgcaaatgc ctagaggtgt tccagtagct   2940
accgtcgcta ttaataatag tacgaacgct gcgctgttgg ctgtcagact gcttggcgct   3000
tatgattcaa gttatacaac gaaaatggaa cagtttttat taaagcaaga agaagaagtt   3060
cttgtcaaag cacaaaagtt agaaactgtc ggttacgaag cttatctaga aaacaagtaa   3120
tatataagtt tattgatata cttgtacagc aaataattat aaaatgatat acctattttt   3180
taggctttgt tatgattaca tcaaatgtgg acttcataca tagaaatcaa cgcttacagg   3240
```

-continued

```
tgtccttttt taagaatttc atacataaga tcatgttgag ataattgttg ggattccatt   3300

gttgataaag gctataatat taggtataca gaatatacta gaagttctcc tcgaggatat   3360

aggaatcctc aaaatggaat ctatatttct acatactaat attacgatta ttcctcattc   3420

cgttttatat gtttatattc attgatccta ttacattatc aatccttgcg tttcagcttc   3480

ctctaacttc gatgacagct tctcataact tatgtcatca tcttaacacc gtatatgata   3540

atatattgat aatataacta ttagttgata gacgatagtg gatttttatt ccaacatacc   3600

acccataatg taatagatct aatgaatcca tttgtttgtt aatagtttga atgtttttat   3660

cggaagaggt ttggtcatta cgtctgcaat attctttttg gtttcgatat agcatacgtg   3720

cagatgattt cctgatactt catctctcaa tctcattgct ttagtaccaa aaaatctgtt   3780

cctaaatttc cggtgtttaa accccagcgc ctggcgggtc ttcattattg gatataatta   3840

tactgattgt agatttactg tcggttagta atcctttggt aattggtttc ttgtcaagtt   3900

cttgtatcag gtaacttaga ttatttaata atgggacaga ttcacttatc gcgtgtattt   3960

ctgcttccgt agttgaagta catgttaatg aagccttggt ggactttcct ccaattacct   4020

ttccattaag taaatatatg ttgccaattt gtgatttata atacggttgg ttgccatacg   4080

aggcatcgct tataacaact aatttatttg ttggcttaac aggtttgctt ttgtgccata   4140

ttaattgctt atctctcgta ttccatatga actgtatcaa ttcatatgtc atatctaaca   4200

cttgcttgga cggaaatagt atatgttgtg caagtgtgtt gatgtagtat aataggtcaa   4260

atctaaattt atatccaaca tatgatgcta gacctatcag                         4300
```

<210> SEQ ID NO 60
<211> LENGTH: 3586
<212> TYPE: DNA
<213> ORGANISM: Artificial Sequence
<220> FEATURE:
<223> OTHER INFORMATION: Synthetic: GFP_YJR030C donor cassette

<400> SEQUENCE: 60

```
ggaactttat gaacatatta agtctgcttg atgaaatgtc atgtgcaggt gccgttggca     60

caaaatggga acaaaattat gaaaattcag tcgaggatgg gtgtgaagca cctgaatcca    120

atccataccg ttctattatt gatctttcta gtcgttccat taatataact gcagacctac    180

tttcgactgt tgggaggagt aattcagcac tcaacaagaa tgagattata gctgctattc    240

aaggtctcgc ccatcaatgc ctcaatccct gtgacgaact aggtatgcaa gcattgcaag    300

cattagagaa cattctgtta tctcgagcaa gtcaactacg tacggaaaaa gttgcggtgg    360

ataacctact agagacagga ttattaccga tttttgagtt ggatgaaatc caagatgtca    420

agatgaaacg aattactagc attttatccg ttctttctaa aatgacggca cggccacgcg    480

tttaaaccgc ccttcttggg tcaacttgtg gaaggcgtaa caagtaacga aactttttttg    540

agagtgctta acgtatttaa caagtatgta gatgatccta cggtggaaag gcagttgcaa    600

gagttgatta tttctaagag ggaaatcgag aaggagtaga ccaacgataa tgtaactata    660

ccaagaaact tagtatgatg gaattttttc aaggagtcgt aaattagatt ttcgcaggta    720

ataatgcgat atataagcaa tctcatttaa atatcgacgg tggcatttat accatcattt    780

actgttatat ttatctaacg cgtcgcgacg cgttagataa aatacaacaa gatttttttt    840

tcgtgtcacc aatggcatga aagcttcgag aataatttga aggaaatttc acttaatggg    900

aaaaataaaa atgtaccctt atcgagatta ctcttttacc ctcagttcaa ttaaaattca    960

tcatgaacca agtaaaagtt cctctaatta cgaacgagca agcaaattag tattgtgtgg   1020
```

-continued

```
gagacgggac acaattacag taacaataac aagaggacag atactaccaa aatgtgtggg   1080
gaagcgggta agctgccaca gcaattaatg cacaacattt aacctacatt cttccttatc   1140
ggatcctcaa aacccttaaa aacatatgcc tcaccctaac atattttcca attaaccctc   1200
aatatttctc tgtcacccgg cctctatttt ccattttctt ctttacccgc cacgcgtttt   1260
tttctttcaa attttttttct tctttcttct ttttcttcca cgtcctcttg cataaataaa   1320
taaaccgttt tgaaaccaaa ctcgcctctc tctctccttt ttgaaatatt tttgggtttg   1380
tttgatcctt tccttcccaa tctctcttgt ttaatatata ttcatttata tcacgctctc   1440
tttttatctt cctttttttc ctctctcttg tattcttcct tcccctttct actcaaacca   1500
agaagaaaaa gaaaaggtca atctttgtta aagaatagga tcttctacta catcagcttt   1560
tagatttttc acgcttactg cttttttctt cccaagatcg aaaatttact gaattaacaa   1620
tggtgagcaa gggcgaggag ctgttcaccg gggtggtgcc catcctggtc gagctggacg   1680
gcgacgtaaa cggccacaag ttcagcgtgt ccggcgaggg cgagggcgat gccacctacg   1740
gcaagctgac cctgaagttc atctgcacca ccggcaagct gcccgtgccc tggcccaccc   1800
tcgtgaccac cttgacctac ggcgtgcagt gcttcgcccg ctaccccgac cacatgaagc   1860
agcacgactt cttcaagtcc gccatgcccg aaggctacgt ccaggagcgc accatcttct   1920
tcaaggacga cggcaactac aagacccgcg ccgaggtgaa gttcgagggc gacaccctgg   1980
tgaaccgcat cgagctgaag ggcatcgact tcaaggagga cggcaacatc ctggggcaca   2040
agctggagta caactacaac agccacaagg tctatatcac cgccgacaag cagaagaacg   2100
gcatcaaggt gaacttcaag acccgccaca acatcgagga cggcagcgtg cagctcgccg   2160
accactacca gcagaacacc cccatcggcg acggccccgt gctgctgccc gacaaccact   2220
acctgagcac ccagtccgcc ctgagcaaag accccaacga gaagcgcgat cacatggtcc   2280
tgctggagtt cgtgaccgcc gccgggatca ctctcggcat ggacgagctg tacaagtaac   2340
tcgagaagct tgatccggct gcgaatttct tatgatttat gatttttatt attaaataag   2400
ttataaaaaa aataagtgta tacaaatttt aaagtgactc ttaggtttta aaacgaaaat   2460
tcttattctt gagtaactct ttcctgtagg tcaggttgct ttctcaggta tagcatgagg   2520
tcgctcttat tgaccacacc tctaccggca tgccgagcat gttgagataa ttgttgggat   2580
tccattgttg ataaaggcta taatattagg tatacagaat atactagaag ttctcctcga   2640
ggatatagga atcctcaaaa tggaatctat atttctacat actaatatta cgattattcc   2700
tcattccgtt ttatatgttt atattcattg atcctattac attatcaatc cttgcgtttc   2760
agcttcctct aacttcgatg acagcttctc ataacttatg tcatcatctt aacaccgtat   2820
atgataatat attgataata taactattag ttgatagacg atagtggatt tttattccaa   2880
cataccaccc ataatgtaat agatctaatg aatccatttg tttgttaata gtttgaatgt   2940
ttttatcgga agaggtttgg tcattacgtc tgcaatattc tttttggttt cgatatagca   3000
tacgtgcaga tgatttcctg atacttcatc tctcaatctc attgctttag taccaaaaaa   3060
tctgttccta aatttccggt gtttaaaccc cagcgcctgg cgggtcttca ttattggata   3120
taattatact gattgtagat ttactgtcgg ttagtaatcc tttggtaatt ggtttcttgt   3180
caagttcttg tatcaggtaa cttagattat ttaataatgg gacagattca cttatcgcgt   3240
gtatttctgc ttccgtagtt gaagtacatg ttaatgaagc cttggtggac tttcctccaa   3300
ttacctttcc attaagtaaa tatatgttgc caatttgtga tttataatac ggttggttgc   3360
catacgaggc atcgcttata acaactaatt tatttgttgg cttaacaggt ttgcttttgt   3420
```

gccatattaa ttgcttatct ctcgtattcc atatgaactg tatcaattca tatgtcatat 3480
ctaacacttg cttggacgga aatagtatat gttgtgcaag tgtgttgatg tagtataata 3540
ggtcaaatct aaatttatat ccaacatatg atgctagacc tatcag 3586

<210> SEQ ID NO 61
<211> LENGTH: 43
<212> TYPE: DNA
<213> ORGANISM: Artificial Sequence
<220> FEATURE:
<223> OTHER INFORMATION: Synthetic: Recognition sequence for ZFN.YJR030C

<400> SEQUENCE: 61
cccggtatca gcaacccccc atgacgataa cgttgatgaa acg 43

<210> SEQ ID NO 62
<211> LENGTH: 40
<212> TYPE: DNA
<213> ORGANISM: Artificial Sequence
<220> FEATURE:
<223> OTHER INFORMATION: Synthetic: Recognition sequence for ZFN.SFC1

<400> SEQUENCE: 62
cacctttacc gtttatgaat atgtaaggga gcatttagaa 40

<210> SEQ ID NO 63
<211> LENGTH: 27
<212> TYPE: DNA
<213> ORGANISM: Artificial Sequence
<220> FEATURE:
<223> OTHER INFORMATION: Synthetic: Primer CUT351

<400> SEQUENCE: 63
gcgaatgagc catgaattat taaccgc 27

<210> SEQ ID NO 64
<211> LENGTH: 33
<212> TYPE: DNA
<213> ORGANISM: Artificial Sequence
<220> FEATURE:
<223> OTHER INFORMATION: Synthetic: Primer CUT350

<400> SEQUENCE: 64
agatgaaacg aattactagc attttatccg ttc 33

<210> SEQ ID NO 65
<211> LENGTH: 47
<212> TYPE: DNA
<213> ORGANISM: Artificial Sequence
<220> FEATURE:
<223> OTHER INFORMATION: Synthetic: Primer CUT371

<400> SEQUENCE: 65
taactaccat tactcagtgt acttgattgt tttgtccgat tttcttg 47

<210> SEQ ID NO 66
<211> LENGTH: 22
<212> TYPE: DNA
<213> ORGANISM: Artificial Sequence
<220> FEATURE:
<223> OTHER INFORMATION: Synthetic: Primer HJ788

<400> SEQUENCE: 66
gccgggtgac agagaaatat tg 22